US008252743B2

(12) United States Patent
Guyon et al.

(10) Patent No.: US 8,252,743 B2
(45) Date of Patent: Aug. 28, 2012

(54) MODIFIED ERYTHROPOIETIN POLYPEPTIDES AND USES THEREOF FOR TREATMENT

(75) Inventors: Thierry Guyon, Palaiseau (FR); Gilles Borrelly, Combs la Ville (FR); Xavier Gallet, Champhol (FR); Lila Drittanti, Bahia Blanca (AR); Manuel Vega, Bahia Blanca (AR)

(73) Assignee: HanAll BioPharma Co., Ltd., Seoul (KR)

( * ) Notice: Subject to any disclaimer, the term of this patent is extended or adjusted under 35 U.S.C. 154(b) by 836 days.

(21) Appl. No.: 11/998,387

(22) Filed: Nov. 28, 2007

(65) Prior Publication Data

US 2009/0238789 A1  Sep. 24, 2009

Related U.S. Application Data

(60) Provisional application No. 60/861,615, filed on Nov. 28, 2006.

(51) Int. Cl.
*A61K 38/18* (2006.01)
*C07K 14/505* (2006.01)

(52) U.S. Cl. .................. 514/7.7; 530/397
(58) Field of Classification Search .............. None
See application file for complete search history.

(56) References Cited

U.S. PATENT DOCUMENTS

| | | | |
|---|---|---|---|
| 4,044,126 A | 8/1977 | Cook et al. ............... 514/180 |
| 4,364,923 A | 12/1982 | Cook et al. ................... 424/46 |
| 4,377,513 A | 3/1983 | Sugimoto et al. ........... 530/395 |
| 4,397,840 A | 8/1983 | Takezawa et al. ........... 530/399 |
| 4,414,209 A | 11/1983 | Cook et al. ............... 514/180 |
| 4,667,016 A | 5/1987 | Lai et al. ................... 530/397 |
| 4,677,195 A | 6/1987 | Hewick et al. ................. 514/8 |
| 4,703,008 A | 10/1987 | Lin ........................... 435/360 |
| 4,835,260 A | 5/1989 | Shoemaker ................ 530/397 |
| 4,892,538 A | 1/1990 | Aebischer et al. ......... 604/891.1 |
| 5,013,718 A | 5/1991 | Adamson et al. ............... 514/8 |
| 5,052,558 A | 10/1991 | Carter ........................ 206/439 |
| 5,283,187 A | 2/1994 | Aebischer et al. ........... 435/182 |
| 5,323,907 A | 6/1994 | Kalvelage ................... 206/531 |
| 5,441,868 A | 8/1995 | Lin ........................... 435/69.4 |
| 5,457,089 A | 10/1995 | Fibi et al. ...................... 514/8 |
| 5,547,933 A | 8/1996 | Lin ............................... 514/8 |
| 5,580,853 A | 12/1996 | Sytkowski ...................... 514/8 |
| 5,614,184 A | 3/1997 | Sytkowski et al. .......... 424/85.1 |
| 5,614,195 A | 3/1997 | Bumstead et al. .......... 424/191.1 |
| 5,618,698 A | 4/1997 | Lin ........................... 435/69.4 |
| 5,621,080 A | 4/1997 | Lin ........................... 530/350 |
| 5,641,670 A | 6/1997 | Treco et al. ................ 435/325 |
| 5,688,679 A | 11/1997 | Powell ........................ 435/352 |
| 5,731,168 A | 3/1998 | Carter et al. ................ 435/69.1 |
| 5,733,761 A | 3/1998 | Treco et al. ................ 435/463 |
| 5,747,446 A | 5/1998 | Sytkowski ...................... 514/8 |
| 5,756,349 A | 5/1998 | Lin ........................... 435/325 |
| 5,773,569 A | 6/1998 | Wrighton et al. ........... 530/300 |
| 5,854,049 A | 12/1998 | Reed ........................... 435/216 |
| 5,856,298 A | 1/1999 | Strickland ....................... 514/8 |
| 5,888,772 A | 3/1999 | Okasinski ................. 435/69.5 |
| 5,955,422 A | 9/1999 | Lin ................................ 514/8 |
| 6,001,800 A | 12/1999 | Mehta et al. ................... 514/8 |
| 6,048,524 A | 4/2000 | Selden et al. .............. 424/93.21 |
| 6,048,971 A | 4/2000 | Sytkowski et al. ......... 536/23.51 |
| 6,099,830 A | 8/2000 | Kaushansky ................. 424/85.1 |
| 6,165,476 A | 12/2000 | Strom et al. ............. 424/195.11 |
| 6,274,158 B1 | 8/2001 | Czeizler ....................... 424/423 |
| 6,335,176 B1 | 1/2002 | Inglese et al. ................ 435/7.72 |
| 6,426,094 B2 | 7/2002 | Piver et al. ................... 424/649 |
| 6,489,293 B1 | 12/2002 | Sytkowski et al. ............... 514/8 |
| 6,548,653 B1 | 4/2003 | Young et al. ................ 536/23.4 |
| 6,555,343 B1 | 4/2003 | DeSauvage et al. ......... 435/69.1 |
| 6,583,272 B1 | 6/2003 | Bailon ........................ 530/387 |
| 6,608,183 B1 | 8/2003 | Cox ............................ 530/399 |
| 6,613,319 B2 | 9/2003 | Leiden ....................... 424/93.2 |
| 6,645,522 B2 | 11/2003 | Naeff et al. .................. 424/450 |
| 6,682,910 B2 | 1/2004 | Powell ........................ 435/69.1 |
| 6,726,924 B2 | 4/2004 | Keller ........................ 424/450 |
| 6,777,205 B1 | 8/2004 | Carcagno et al. ........... 435/69.1 |
| 6,831,060 B2 | 12/2004 | DeSauvage et al. ............... 514/8 |
| 6,833,351 B2 | 12/2004 | Dieterich ...................... 514/2 |
| 6,930,086 B2 | 8/2005 | Tischer ......................... 514/2 |
| 6,987,006 B2 | 1/2006 | Fleer et al. .................. 435/69.7 |
| 6,992,174 B2 | 1/2006 | Gillies et al. ............... 530/387.3 |
| 7,012,130 B1 | 3/2006 | Carcagno et al. ........... 530/350 |
| 7,041,794 B2 | 5/2006 | Escary ........................ 530/350 |

(Continued)

FOREIGN PATENT DOCUMENTS

CA  2021528  1/1991

(Continued)

OTHER PUBLICATIONS

Stettner et al. Hypoxic and hypercapnic challenges unveil respiratory vulnerability of Surf1 knockout mice, an animal model of Leigh syndrome. Mitochondrion 11:413-420 (2011).*
Abuchowski et al., "Alteration of the circulating life and antigenic properties of bovine adenosine deaminase in mice by attachment of polyethylene glycol," Clin Exp Immunol 46:649-652 (1981).
Agnello et al., "Erythropoietin exerts an anti-inflammatory effect on the CNS in a model of experimental autoimmune encephalomyelitis," Brain Res 952:128-134 (2002).
Alderuccio et al., "Animal models of human disease: experimental autoimmune gastritis—a model for autoimmune gastritis and pernicious anemia," Clin. Immun 102(1):48-58 (2002).
Altschul et al., "Basic local alignment search tool," J. Molec. Biol. 215:403-410 (1990).
Ando, et al., "Regulation of G 1/S transition by cyclins D2 and D3 in hematopoietic cells," Proc. Natl. Acad. Sci. USA 90:9571-9575 (1993).

(Continued)

*Primary Examiner* — Elizabeth C Kemmerer
*Assistant Examiner* — Regina M Deberry
(74) *Attorney, Agent, or Firm* — McKenna Long & Aldridge LLP; Stephanie Seidman

(57) ABSTRACT

Modified erythropoietin (EPO) polypeptides and other modified therapeutic polypeptides are provided. The EPO polypeptides and other therapeutic polypeptides are modified to exhibit physical properties and activities that differ from the unmodified EPO polypeptides and other unmodified therapeutic polypeptides, respectively. Nucleic acid molecules encoding these polypeptides also are provided. Also provided are methods of treatment and diagnosis using the polypeptides.

27 Claims, 1 Drawing Sheet

U.S. PATENT DOCUMENTS

| | | | |
|---|---|---|---|
| 7,101,971 B2 | 9/2006 | Meade et al. | 530/350 |
| 7,611,700 B2 | 11/2009 | Gantier et al. | 424/85.7 |
| 7,647,184 B2 | 1/2010 | Vega et al. | 702/19 |
| 7,650,243 B2 | 1/2010 | Gantier et al. | 702/19 |
| 2002/0086816 A1 | 7/2002 | Brines et al. | 514/8 |
| 2003/0064480 A1 | 4/2003 | Lauffer et al. | 435/69.7 |
| 2003/0072737 A1 | 4/2003 | Brines et al. | 424/85.1 |
| 2003/0104988 A1 | 6/2003 | Brines et al. | 514/8 |
| 2003/0120045 A1 | 6/2003 | Bailon | 530/397 |
| 2003/0129203 A1 | 7/2003 | Vega et al. | 424/233.1 |
| 2003/0129584 A1 | 7/2003 | Vega et al. | 435/5 |
| 2003/0134351 A1 | 7/2003 | Vega et al. | 435/69.1 |
| 2003/0175694 A1 | 9/2003 | Vega | 435/5 |
| 2003/0224404 A1 | 12/2003 | Vega et al. | 435/6 |
| 2004/0063635 A1 | 4/2004 | Yu et al. | 514/12 |
| 2004/0063917 A1 | 4/2004 | Carr et al. | 530/397 |
| 2004/0082039 A1 | 4/2004 | Gillies et al. | 435/69.7 |
| 2004/0091961 A1 | 5/2004 | Evans et al. | 435/69.1 |
| 2004/0115768 A1 | 6/2004 | Follstad | 435/69.1 |
| 2004/0122216 A1 | 6/2004 | Nielsen et al. | 530/351 |
| 2004/0132977 A1 | 7/2004 | Gantier et al. | 530/351 |
| 2004/0137557 A1 | 7/2004 | DeFrees et al. | 435/68.1 |
| 2004/0157293 A1 | 8/2004 | Evans et al. | 435/69.1 |
| 2005/0107591 A1 | 5/2005 | Cox | 530/351 |
| 2005/0137329 A1 | 6/2005 | Holmes et al. | 525/54.1 |
| 2005/0170457 A1 | 8/2005 | Pool et al. | 435/69.1 |
| 2005/0176627 A1 | 8/2005 | Cerami et al. | 514/8 |
| 2005/0181359 A1 | 8/2005 | Optelten et al. | 435/5 |
| 2005/0192211 A1 | 9/2005 | Gillies et al. | 514/8 |
| 2005/0202438 A1 | 9/2005 | Gantier et al. | 435/6 |
| 2005/0220800 A1 | 10/2005 | Scott et al. | 424/184.1 |
| 2005/0288220 A1 | 12/2005 | Burg et al. | 514/8 |
| 2006/0008872 A1 | 1/2006 | Chung et al. | 435/69.1 |
| 2006/0019877 A1 | 1/2006 | Conradt et al. | 514/8 |
| 2006/0020116 A1 | 1/2006 | Gantier et al. | 530/351 |
| 2006/0020396 A1 | 1/2006 | Gantier et al. | 702/19 |
| 2006/0035322 A1 | 2/2006 | Baker et al. | 435/69.1 |
| 2006/0058236 A1 | 3/2006 | Hutchins et al. | 514/12 |
| 2006/0073563 A1 | 4/2006 | Marshall | 435/69.1 |
| 2006/0088906 A1 | 4/2006 | DeFrees et al. | 435/68.1 |
| 2006/0100150 A1 | 5/2006 | Cheung et al. | 514/12 |
| 2006/0121611 A1 | 6/2006 | Yallop | 435/456 |
| 2006/0135754 A1 | 6/2006 | Christensen | 530/399 |
| 2006/0153860 A1 | 7/2006 | Cho et al. | 424/185.1 |
| 2006/0195268 A1 | 8/2006 | Vega | 702/19 |
| 2006/0233744 A1 | 10/2006 | Shultz et al. | 424/85.1 |
| 2006/0247170 A1 | 11/2006 | Guyon et al. | 514/12 |
| 2006/0251619 A1 | 11/2006 | Borrelly et al. | 424/85.6 |
| 2007/0100133 A1 | 5/2007 | Beals et al. | 530/350 |
| 2007/0129293 A1 | 6/2007 | Coleman et al. | 514/12 |
| 2007/0154922 A1 | 7/2007 | Collier et al. | 435/6 |
| 2007/0172459 A1 | 7/2007 | Gantier et al. | 424/85.5 |
| 2007/0190610 A1 | 8/2007 | Fares et al. | 435/69.1 |
| 2007/0224665 A1 | 9/2007 | Gantier et al. | 435/69.1 |
| 2007/0249532 A9 | 10/2007 | Guyon et al. | 514/12 |
| 2007/0254838 A1 | 11/2007 | Gantier et al. | 514/12 |
| 2008/0260820 A1 | 10/2008 | Borrelly et al. | 424/463 |
| 2009/0131318 A1 | 5/2009 | Gantier et al. | 514/12 |

FOREIGN PATENT DOCUMENTS

| | | |
|---|---|---|
| EP | 0409113 | 1/1991 |
| EP | 0 427 189 | 5/1991 |
| EP | 0640619 | 3/1995 |
| JP | 03072885 | 3/1991 |
| JP | 08151398 | 6/1996 |
| JP | 08269096 | 10/1996 |
| JP | 11155584 | 6/1999 |
| WO | WO 85/02610 | 6/1985 |
| WO | WO 86/03520 | 6/1986 |
| WO | WO 90/12874 | 11/1990 |
| WO | WO 91/05867 | 5/1991 |
| WO | WO 94/10308 | 5/1994 |
| WO | WO 94/12638 | 6/1994 |
| WO | WO 94/12639 | 6/1994 |
| WO | WO 94/24160 | 10/1994 |
| WO | WO 94/25055 | 11/1994 |
| WO | WO 95/05465 | 2/1995 |
| WO | WO 95/21197 | 8/1995 |
| WO | WO 95/21254 | 8/1995 |
| WO | WO 97/12977 | 4/1997 |
| WO | WO 97/12978 | 4/1997 |
| WO | WO 97/12979 | 4/1997 |
| WO | WO 97/12985 | 4/1997 |
| WO | 99/03887 | 1/1999 |
| WO | WO 99/03887 | 1/1999 |
| WO | 99/38890 | 8/1999 |
| WO | WO 00/24893 | 5/2000 |
| WO | WO 01/36489 | 5/2001 |
| WO | WO 01/61344 | 8/2001 |
| WO | WO 01/81405 | 11/2001 |
| WO | 02/062843 | 8/2002 |
| WO | WO 02/062843 | 8/2002 |
| WO | WO 02/085940 | 10/2002 |
| WO | WO 03/055526 | 7/2003 |
| WO | WO 2004/003176 | 1/2004 |
| WO | 2004/022593 | 3/2004 |
| WO | WO 2004/089973 | 10/2004 |
| WO | WO 2005/084364 | 9/2005 |
| WO | WO 2005/103076 | 11/2005 |
| WO | 2006/029094 | 3/2006 |
| WO | WO 2006/024547 | 3/2006 |
| WO | WO 2006/029094 | 3/2006 |
| WO | WO 2006/035322 | 4/2006 |
| WO | 2006/048777 | 5/2006 |
| WO | WO 2006/072773 | 7/2006 |
| WO | 2008/065372 | 6/2008 |
| WO | 2009/152944 | 12/2009 |

OTHER PUBLICATIONS

Ashwell, G. and J. Harford, "Carbohydrate-specific receptors of the liver," Ann. Rev. Biochem. 51:531-554 (1982).

Babitzke, P. and S. Kushner, "The Ams (altered mRNA stability) protein and ribonuclease E are encoded by the same structural gene of *Escherichia coli*," Proc. Natl. Acad. Sci. USA 88:1-5 (1991).

Bain et al., "Biosynthetic site-specific incorporation of a non-natural amino acid into a polypeptide," J. Am. Chem. Soc. 111:8013-8014 (1989).

Banks et al., "Passage of erythropoietic agents across the blood-brain barrier: a comparison of human and murine erythropoietin and the analog darbepoetin alfa," Eur J Pharmacology 505:93-101 (2004).

Bauminger, S. and M. Wilchek, "The use of carbodiimides in the preparation of immunizing conjugates," Meth. Enzymol. 70:151-159 (1980).

Besarab, A., "Optimizing anaemia management with subcutaneous administration of epoetin," Nephrol Dial Transplant 20:vi10-vi15 (2005).

Bill et al., "Expression and mutagenesis of recombinant human and murine erythropoietins in *Escherichia coli*," Biochim Biophys Acta 1261:35-43 (1995).

Binkley et al., "Epoetin alfa:Clinical Trial Therapy," ANNA Journal 16(5):344-348 (1989).

Bittorf et al. "Structural and functional characterisation of recombinant human erythropoietin analogues," FEBS Lett. 336(1):133-136 (1993).

Bohl et al., "Control of erythropoietin delivery by doxycycline in mice after intramuscular injection of adeno-associated vector," Blood 2(5):1512-1517 (1998).

Bohl et al., "Improvement of erythropoiesis in beta-thalassemic mice by continuous erythropoietin delivery from muscle," Blood 95:2793-2798 (2000).

Boissel et al. "Erythropoietin structure-function relationships. Mutant proteins that test a model of tertiary structure," J. Biol. Chem. 268(21):15983-15993 (1993).

Boissel et al., "Erythropoietin:mammalian sequences and scanning deletions support a four alpha-helical bundle structural model," Ann NY Acad Sci 718:203-212 (1994).

Boogaert et al., "Beyond Anaemia Management: Evolving Role of Erythropoietin Therapy in Neurological Disorders, Multiple Myeloma and Tumour Hypoxia Models," Oncology 69 Suppl 2:22-30 (2005).

Borkakoti, N., "Matrix metalloproteases:variations on a theme," Prog. Biophys. Mol. Biol. 70(1):73-94 (1998).

Brines et al., "Erythropoietin crosses the blood-brain barrier to protect against experimental brain injury," PNAS 97:10526-10531 (2000).

Brines, M. and A. Cerami, "Discovering erythropoietin's extra-hematopoietic functions: biology and clinical promise," Kidney Int. 70:246-50 (2006).

Browne et al., "Erythropoietin: gene cloning, protein structure, and biological properties," Cold Spring Harb Symp Quant Biol 51:693-702 (1986).

Brunner, J., "Biosynthetic incorporation of non-natural amino acids into proteins," Chem.. Soc. Rev. 22:183-189 (1993).

Budisa et al., "Toward the experimental codon reassignment in vivo: protein building with an expanded amino acid repertoire," FASEB J. 13:41 (1999).

Buemi et al., "Intravenous recombinant erythropoietin does not lead to an increase in cerebrospinal fluid erythropoietin concentration," Nephrol Dial Transplant 15:422-423 (2000).

Burns et al. "Purification and characterization of the yeast-expressed erythropoietin mutant Epo (R103A), a specific inhibitor of human primary hematopoietic cell erythropoiesis," Blood 99(12):4400-4405 (2002).

Carillo, H. and D. Lipman, "The multiple sequence alignment problem in biology," SIAM Journal of Applied Mathematics, 48:1073-1082, (1988).

Carter et al., "The significance of carbohydrates on G-CSF: differential sensitivity of G-CSFs to human neutrophil elastase degradation," J Leukoc. Biol. 75:515-522 (2004).

Casadevall et al., "Pure red-cell aplasia and antierythropoietin antibodies in patients treated with recombinant erythropoietin," N. Engl. J. Med. 346:469-475 (2002).

Chamorey et al., "Impact of glycosylation on the effect of cytokines. A special focus on oncology," European Cytokine Network 13:154-160 (2002).

Chen et al., "Synthetic erythropoietic proteins: tuning biological performance by site-specific polymer attachment," Chem and Biol 12:371-383 (2005).

Chen et al., "Growth inhibitory effects of celecoxib in human umbilical vein endothelial cells are mediated through G1 arrest via multiple signaling mechanisms," Blood 104:1671-1678 (2004).

Chen, J., "Animal models for acquired bone marrow failure syndromes," Clin. Med. Res. 3:102-108 (2005).

Chern et al., "Potentiation of the erythropoietin response by dimethyl sulfoxide priming of erythroleukemia cells: evidence for interaction of two signaling pathways," Blood 76(11): 2204-2209 (1990).

Cointe et al., "Unusual N-glycosylation of a recombinant human erythropoietin expressed in a human lymphoblastoid cell line does not alter its biological properties," Glycobiology 10:511-519 (2000).

Cotes, P. and D. Bangham, "Bio-assay of erythropoietin in mice made polycythaemic by exposure to air at a reduced pressure," Nature 191:1065 (1961).

Cummings, R., "Use of lectins in analysis of glycoconjugates," (1994) Methods in Enzymol. 230:66-86.

Cuzner and Opdenakker, "Plasminogen activators and matrix metalloproteases, mediators of extracellular proteolysis in inflammatory demyelination of the central nervous system," J. Neuroimmunol. 94(1-2):1-14 (1999).

D'Andrea et al., "Expression cloning of the murine erythropoietin receptor," Cell 57:277-285 (1989).

Dame, C. and H. Fahnenstitch, "Don't give up on erythropoietin as a neuroprotective agent," Pediatrics 116:521-522 (2005).

Darling et al., "Glycosylation of erythropoietin affects receptor binding kinetics: role of electrostatic interactions," Biochemistry 41:14524-14531 (2002).

David et al. "Protein iodination with solid state lactoperoxidase," Biochemistry 13:1014 (1974).

Davis et al. "Adenovirus-mediated erythropoietin production by airway epithelia is enhanced by apical localization of the coxsackie-adenovirus receptor in vivo," Mol Ther 10(3):500-506 (2004).

Dawson, P. and S. Kent, "Synthesis of native proteins by chemical ligation," Annu. Rev. Biochem. 69:923 (2000).

Delorme et al., "Role of glycosylation on the secretion and biological activity of erythropoietin," Biochemistry 31(41):9871-9876 (1992).

Devereux, et al., "A comprehensive set of sequence analysis programs for the VAX," Nucleic Acids Research 12(I):387-399 (1984).

Dexter et al., "Growth of factor-dependent hemopoietic precursor cell lines," J. Exp. Med. 152:1036-1047 (1980).

Dougherty, D., "Unnatural amino acids as probes of protein structure and function," Curr. Opin. Chem. Biol. 4:645 (2000).

Dube et al. "Glycosylation at specific sites of erythropoietin is essential for biosynthesis, secretion, and biological function," J. Biol. Chem. 263(33):17516-17521 (1988).

Dusanter-Fourt, et al. "Erythropoietin induces the tyrosine phosphorylation of its own receptor in human erythropoietin-responsive cells," J. Biol. Chem. 287:10670-10678 (1992).

Egrie et al., "Characterization and biological effects of recombinant human erythropoietin," Immunbiology 172: 213-224 (1986).

Eisenstaedt et al. "Anemia in the elderly: current understanding and emerging concepts," (2006) Blood Rev. 20(4):213-226 (2006).

Elliott et al. "Fine-structure epitope mapping of antierythropoietin monoclonal antibodies reveals a model of recombinant human erythropoietin structure," Blood 87(7):2702-2713 (1996).

Elliott et al., "Isolation and characterization of conformation sensitive antierythropoietin monoclonal antibodies: effect of disulfide bonds and carbohydrate on recombinant human erythropoietin structure," Blood 87(7):2714-2722 (1996).

Elliott et al. "Structural requirements for addition of O-linked carbohydrate to recombinant erythropoietin," Biochemistry 33(37):11237-11245 (1994).

Elliott et al., "Enhancement of therapeutic protein in vivo activities through glycoengineering," Nat. Biotechnol. 21:414-421 (2003).

Elliott et al., "Structural requirements for additional N-linked carbohydrate on recombinant human erythropoietin," J. Biol. Chem. 279(16):16854-16862 (2004).

Erbayraktar et al., "Carbamylated erythropoietin reduces radiosurgically-induced brain injury," Mol Med 12:74-80 (2006).

Fagan et al., "Tactics for vascular protection after acute ischemic stroke," Pharmacotherapy 25:387-395 (2005).

Fan et al., "Immunization via hair follicles by topical application of naked DNA to normal skin," Nat. Biotech. 17:870-872 (1999).

Fenjves et al., "Adenoviral gene transfer of erythropoietin confers cytoprotection to isolated pancreatic islets," Transplantation 77(1):13-18 (2004).

Fitch, W., "An improved method of testing for evolutionary homology," Journal of Molecular Evolution 16(1):9-16 (1966).

Friedler et al., "Development of a functional backbone cyclic mimetic of the HIV-1 Tat arginine-rich motif," J. Biol. Chem. 275:23783-23789 (2000).

Gascon, P., "Evaluating erythropoietic agents for the treatment of anaemia in the oncology setting," Eur J Cancer 41(17): 2601-2612 (2005).

Goldman, S. and M. Nedergaard, "Erythropoietin strikes a new cord," Nature Medicine 8:785-787 (2002).

Goldwasser et al., "On the mechanism of erythropoietin-induced differentiation. 13. The role of sialic acid in erythropoietin action," J. Biol. Chem. 249:4202-4206 (1974).

Gonnet et al., "Exhaustive matching of the entire protein sequence database," Science 256:1433-1445 (1992).

Goto et al., "Production of Recombinant Human Erythropoietin in Mammalian Cells: Host?Cell Dependency of the Biological Activity of the Cloned Glycoprotein," Bio/technology 6:67-71 (1988).

Gramer, M., "Detecting and minimizing glycosidase activities that can hydrolyze sugars from cell culture-produced glycoproteins," Mol Biotechnol 15:69-75 (2000).

Grantham, R., "Amino acid difference formula to help explain protein evolution," Science 185:862-864 (1974).

Grasso et al., "Amelioration of spinal cord compressive injury by pharmacological preconditioning with erythropoietin and a nonerythropoietic erythropoietin derivative," J Neurosurg:Spine 4:310-318 (2006).

Grasso et al., "Erythropoietin as a tissue-protective cytokine in brain injury: what do we know and where do we go?" The Neuroscientist 10:93-98 (2004).

Greenberger et al., "Demonstration of permanent factor-dependent multipotential (erythroid/neutrophil/basophil) hematopoietic progenitor cell lines," Proc. Natl. Acad. Sci. USA 80:2931-2935 (1983).

Gribskov et al., "Sigma factors from *E. coli, B. subtilis*, phage SP01, and phage T4 are homologous proteins," Nucl. Acids Res. 14: 6745 (1986).

Grodberg et al., "Alanine scanning mutagenesis of human erythropoietin identifies four amino acids which are critical for biological activity," Eur. J. Biochem. 218(2):597-601 (1993).

Gross, A. and H. Lodish, "Cellular trafficking and degradation of erythropoietin and novel erythropoiesis stimulating protein (NESP)," J Biol Chem 281:2024-2032 (2006).

Hakansson et al., "Crystal structure of the trimeric alpha-helical coiled-coil and the three lectin domains of human lung surfactant protein D," Structure 7:255-264 (1999).

Halstenson et al., "Comparative pharmacokinetics and pharmacodynamics of epoetin alfa and epoetin beta," Clin Pharmacol Ther 50:702-712 (1991).

Hanisch et al., "Evidence for glycosylation-dependent activities of polypeptide N-acetylgalactosaminyltransferases rGalNAc-T2 and -T4 on mucin glycopeptides," Glycobiology 11:731-740 (2001).

Haniu et al., "Recombinant human erythropoietin (rHuEPO): cross-linking with disuccinimidyl esters and identification of the interfacing domains in EPO," Protein Science 2:1441-1451 (1993).

Harbury et al., "A switch between two-, three-, and four-stranded coiled coils in GCN4 leucine zipper mutants," Science 262:1401-1405 (1993).

Harbury et al., "Crystal structure of an isoleucine-zipper trimer," Nature 371:80-83 (1994).

Haupt, K. and K. Mosbauch, "Plastic antibodies: developments and applications," TIBTech 16:468-475 (1998).

Henikoff et al., "Amino acid substitution matrices from protein blocks," Proc. Nat. Acad. Sci. USA 89:10915-10919 (1992).

Holten et al., "Interferon-beta for treatment of rheumatoid arthritis?," (2002), Arthritis Research, 4: 346-352 (2002).

Hunter et al., "Preparation of Iodine-131 Labelled Human Growth Hormone of High Specific Activity," Nature 144:945 (1962).

Inoue et al., "The production of recombinant human erythropoietin," Biotechnol. Annu. Rev.1:297-313 (1995).

IUPAC-IUB, "Abbreviated nomenclature of synthetic poypeptides-polymerized amino acids-revised recommendations," Commission on Biochemical Nomenclature, Biochemistry 11:942-944 (1972).

IUPAC-IUB, "Abbreviated nomenclature of synthetic poypeptides-polymerized amino acids-revised recommendations," Commission on Biochemical Nomenclature, Biochemistry 11:1726-1731 (1972).

Jacobs et al., "Isolation and characterization of genomic and cDNA clones of human erythropoietin" Nature 313(6005):806-810 (1985).

Jelkmann, W., "Effects of erythropoietin on brain function," Current Pharmaceutical Biotechnology 6:65-79 (2005).

Johnson, M. and J. Overington, "A structural basis for sequence comparisons-an evaluation of scoring methodologies," Journal of Molecular Biology 233:716-738 (1993).

Jones et al., "The rapid generation of mutation data matrices from protein sequences," Comput. Appl. Biosci. 8: 275-282 (1992).

Juul et al., "Erytropoietin concentrations in cerebrospinal fluid of nonhuman primates and fetal sheep following high-dose recombinant erythropoietin," Biology of the Neonate 85:138-144 (2004).

Kagawa et al., "Comparative study of the asparagine-linked sugar chains of natural human interferon-beta 1 and recombinant human interferon-beta 1 produced by three different mammalian cells," JBC 263:17508-17515 (1988).

Kaiho, S. and K. Miuno, "Sensitive assay systems for detection of hemoglobin with 2,7-diaminofluorene: histochemistry and colorimetry for erythrodifferentiation," Anal. Biochem. 149:117-120 (1985).

Kaltwasser et al., "Effect of recombinant human erythropoietin and intravenous iron on anemia and disease activity in rheumatoid arthritis," J Rheumatol. 28(11):2430-2436 (2001).

Kanaan et al., "Exogenous erythropoietin provides neuroprotection of grafted dopamine neurons in a rodent model of Parkinson's disease," Brain Research 1068:221-229 (2006).

Katre et al., "Chemical modification of recombinant interleukin 2 by polyethylene glycol increases its potency in the murine Meth A sarcoma model," PNAS USA 84:1487-1491 (1987).

Kawamura et al., "Effect of purified recombinant human erythropoietin on anemia in rats with experimental renal failure induced by five-sixth nephrectomy," (1990) Biotherapy 2(1):77-85 (1990).

Ketner et al., "Efficient manipulation of the human adenovirus genome as an infectious yeast artificial chromosome clone," Proc. Natl. Acad. Sci. USA 91:6186-6190 (1994).

Khalizzadeh et al., J. Ind. Microbiol. Biotechnol. 31(2):63-69 (2004).

Kitagawa et al,. "N-glycosylation of erythropoietin is critical for apical secretion by Madin-Darby canine kidney cells," Exp. Cell. Res. 213(2):449-457 (1994).

Kitamura et al., "Establishment and characterization of a unique human cell line that proliferates dependently on GM-CSF, IL-3, or erythropoietin," J. Cellular Physiol. 140:323-334 (1989).

Kochendoerfer et al., "Design and chemical synthesis of a homogeneous polymer-modified erythropoiesis protein," Science 299(5608):884-887 (2003).

Korhonen et al., "Expression of bovine beta-lactoglobulin/human erythropoietin fusion protein in the milk of transgenic mice and rabbits, "Eur. J. Biochem. 245:482-489 (1997).

Krebs et al., "Neuroprotective agents in schizophrenia and affective disorders," Expert Opin Pharmacother. 7(7):837-848 (2006).

Krstenansky et al., "Antithrombin properties of C-terminus of hirudin using synthetic unsulfated N alpha-acetyl-hirudin45-65," FEBS Lett. 211:10-16 (1987).

Krystal, "A simple microassay for erythropoietin based on 3H-thymidine incorporation into spleen cells from phenylhydrazine treated mice," Exp. Hematol. 11:649-660 (1983).

Kuehl A. and S. Noormohamed, "Recombinant erythropoietin for zidovudine-induced anemia in AIDS," Ann Pharmacother. 29(7-8):778-779 (1995).

Kwon et al., "Dynamic control of oligosaccharide modification in the mammary gland: linking recombinant human erythropoietin functional analysis of transgenic mouse milk-derived hEPO," Transgenic Res. 15(1):37-55 (2006).

Lai et al., "Structural characterization of human erythropoietin," J Biological Chem 261:3116-3121 (1986).

Lappin et al. "Structure-function relationships of the erythropoietin molecule," Ann. N. Y. Acad. Sci. 718:191-201; discussion 201-202 (1994).

Lee et al., "The prolonged half-lives of new erythropoietin derivatives via peptide addition," Biochemical and Biophysical Research Communications 339:380-385 (2006).

Leist et al., "Derivatives of erythropoietin that are tissue protective but not erythropoietic," Science 305:239-242 (2004).

Leonard, et al., " Dynamics of GATA transcription factor expression during erythroid differentiation," Blood 82:1071-1079 (1993).

Leppert et al., "Matrix metalloproteinases: multifunctional effectors of inflammation in multiple sclerosis and bacterial meningitis," Brain Res. Rev. 36(2-3):249-257 (2001).

Lin et al. "The molecular biology of erythropoietin" In Molecular and Cellular Aspects of Erythropoietin and Erythropoiesis, I. N. Rich, Ed. Springer Verlag, Berlin, pp. 23-36 (1987).

Lin et al., "Cloning and expression of the human erythropoietin gene," Proc Nat Acad Sci USA 82:7580-7584 (1985).

Lindenbaum et al., "A mammalian artificial chromosome engineering system (ACE System) applicable to biopharmaceutical protein production, transgenesis and gene-based cell therapy," Nucleic Acids Res. 32(21):e172 (2004).

Lipsic et al., "Protective effects of erythropoietin in cardiac ischemia: from bench to bedside," Journal of the American College of Cardiology 48(11):2161-2167 (2006).

Little et al., "Combination erythropoietin-hydroxyurea therapy in sickle cell disease: experience from the National Institutes of Health and a literature review," Haematologica 91(8):1076-1083 (2006).

Locatelli, F. and L. Del Vecchio, "Pure red cell aplasia secondary to treatment with erythropoietin," J. Nephrol. 16:461-466 (2003).

Lodish et al., "The erythropoietin receptor: biogenesis, dimerization, and intracellular signal transduction," Cold Spring Harb Symp Quant Biol 60:93-104 (1995).

Loo, T. and D. Clarke, "Quality control by proteases in the endoplasmic reticulum. Removal of a protease-sensitive site enhances expression of human P-glycoprotein," J Biol Chem 273:32373-32376 (1998).

Lovejoy et al., "Crystal structure of a synthetic triple-stranded alpha-helical bundle," Science 259:1288-1293 (1993).

Lu et al., " Erythropoietin enhances neurogenesis and restores spatial memory in rats after traumatic brain injury," J of Neurotrauma 22(9):1011-1017 (2005).

Lukowsky, W. and R. Painter, "Studies on the role of sialic acid in the physical and biological properties of erythropoietin," Can. J. Biochem. 60:909-917 (1972).

Macdougall et al., "Pharmacokinetics of novel erythropoiesis stimulating protein compared with epoetin alfa in dialysis patients," J Am Soc Nephrol 10:2392-2395 (1999).

Macdougall, I., "Darbepoetin alfa: a new therapeutic agent for renal anemia," Kidney Int Suppl. 80:55-61 (2002).

Macdougall, I., "Pure red cell aplasia with anti-erythropoietin antibodies occurs more commonly with one formulation of epoetin alfa than another," Curr. Med. Res. Opin. 20:83-86 (2004).

Macmillan et al., "Selective in vitro glycosylation of recombinant proteins: semi-synthesis of novel homogeneous glycoforms of human erythropoietin," Chem. Biol. 8(2):133-45 (2001).

Marini et al., "Recombinant human granulocyte-macrophage colony-stimulating factor: effect of glycosylation on pharmacokinetic parameters," Electronic Journal of Biotechnology 10:271-278 (2007).

Marsden, J., "Erythropoietin—measurement and clinical applications," Ann Clin Biochem 43:97-104 (2006).

Martin, P., "Next Generation Products and Prospects for the Oral Delivery of Proteins" (Meeting Abstract) Fourth Annual Protein Process Development (Jan. 11, 2007) http://www.chi-peptalk.com/06_Ppd.asp.

Martin, P., "The Market for Therapeutic Proteins: New Business Opportunities" (Meeting Abstract) Second Annual Advancing Protein Therapeutics, Engineering the Next Generation of Proteins for Therapeutics (Jan. 13, 2006) http://www.chi-peptalk.com/pttn2006.asp.

Martinez-Estrada et al., "Erythropoietin protects the in vitro blood-brain barrier against VEGF-induced permeability," Eur J Neurosci 18:2538-2544 (2003).

Matthews et al., "A sequential dimerization mechanism for erythropoietin receptor activation," Proc. Natl.Acad. Sci. U. S. A. 93(18):9471-9476 (1996).

Mayfield et al., "Expression and assembly of a fully active antibody in algae," PNAS 100:438-442 (2003).

McGuire, et al., "Interaction of Huntingtin-associated protein-1 with kinesin light change," Journal of Biological Chemistry, 243:3552-3559 (1969).

McLachlan, A., "Tests for comparing related amino-acid sequences. Cytochrome c and cytochrome c 551 ," J. Mol. Biol. 61:409-424 (1971).

McMahon et al., "Pharmacokinetics and effects of recombinant human erythropoietin after intravenous and subcutaneous injections in healthy volunteers," Blood 76(9):1718-1722 (1990).

McMullin et al., "Serum erythropoietic activity in acute anemia—an animal model," Biochem Med Metab Biol. 41(1):30-35 (1989).

Merrifield, R., "Solid Phase Peptide Synthesis. I. The Synthesis of a Tetrapeptide," J. Amer. Chem. Soc. 85:2149-2154 (1963).

Mi et al., "Screening of carbohydrate-specific phage antibodies against recombinant human erythropoietin (rhuEPO) using a phage display antibody library: preliminary study," (2006) J. Immunoassay Immunochem. 27(2):115-128 (2006).

Mikus et al., "Generation and phenotypic analysis of a transgenic line of rabbits secreting active recombinant human erythropoietin in the milk," Transgenic Res. 13(5):487-498 (2004).

Minamitake et al., "Structure of recombinant human interleukin 5 produced by Chinese hamster ovary cells," J. Biochem. 107:2:292-297 (1990).

Miyake et al., "Purification of human erythropoietin," J. Biol. Chem. 252(15):5558-5564 (1977).

Miyata et al., "Two types of amino acid substitutions in protein evolution," J. Mol. Evol. 12:219-236 (1979).

Moon et al., "Erythropoietin, modified to not stimulate red blood cell production, retains its cardioprotective properties," The Journal of Pharmacology and Experimental Therapeutics 316:999-1005 (2006).

Mosmann, T., "Rapid colorimetric assay for cellular growth and survival: application to proliferation and cytotoxicity assays," J. Immunol. Meth. 65:55-63 (1983).

Nagel, R., "A knockout of a transgenic mouse—animal models of sickle cell anemia," N. Engl J Med. 339(3):194-195 (1998).

Narhi et al., "Asn to Lys mutations at three sites which are N-glycosylated in the mammalian protein decrease the aggregation of *Escherichia coli*-derived erythropoietin," Protein Eng. 14(2):135-140 (2001).

Needleman, S. and C. Wunsch, "A general method applicable to the search for similarities in the amino acid sequence of two proteins," J. Mol. Biol. 48:443-453 (1970).

Nelissen et al., "Gelatinase B/matrix metalloproteinase-9 cleaves interferon-beta and is a target for immunotherapy," Brain 126:1371-1381 (2003).

Noren et al., "A general method for site-specific incorporation of unnatural amino acids into proteins," Science 244:182-188 (1989).

Nowak et al., "Nicotinic receptor binding site probed with unnatural amino acid incorporation in intact cells," Science 268:439-442 (1995).

Nurko, S., "Anemia in chronic kidney disease: causes, diagnosis, treatment," Cleveland Clin. J. Med. 73(3):289-297 (2006).

Nygren, H., "Conjugation of horseradish peroxidase to Fab fragments with different homobifunctional and heterobifunctional cross-linking reagents. A comparative study," Histochem. and Cytochem. 30:407-412 (1982).

Ohls, R. and A. Dai, "Long-acting erythropoietin: clinical studies and potential uses in neonates," Clin Perinatol. 77-89 (2004).

Olsson et al., "Erythropoietin treatment in metastatic breast cancer—effects on Hb, quality of life and need for transfusion," Acta Oncol. 41(6):517-524 (2002).

Opdenakker et al., "Cells regulate the activities of cytokines by glycosylation," FASEB J 9:453-457 (1995).

Opdenakker, G., "On the roles of extracellular matrix remodeling by gelatinase B,"Verh. K. Acad. Geneeskd. Belg. 59(6):489-514 (1997).

Pain et al., "Preparation of protein A-peroxidase monoconjugate using a heterobifunctional reagent, and its use in enzyme immunoassays," (1981) J. Immunol. Meth., 40:219-230 (1981).

Pascual et al., "Recombinant erythropoietin and analogues:a challenge for doping control," Ther Drug Monit 26:175-179 (2004).

Patel, et al., "Activation of two discrete signaling pathways by erythropoietin," J. Biol. Chem. 267:21300-21302 (1992).

Pearson, W. and D. Lipman, "Improved tools for biological sequence comparison," Proc. Natl. Acad. Sci. USA 85:2444-2448 (1988).

Pestka et al., "Interferons, interferon-like cytokines, and their receptors," Immunological Reviews 202:8-32 (2004).

Pham et al., "Large-scale transient transfection of serum-free suspension-growing HEK293 EBNA1 cells: peptone additives improve cell growth and transfection efficiency," Biotechnol. Bioeng. 84:332-342 (2003).

Pichierri, F., "The electronic structure of human erythropoietin as an aid in the design of oxidation-resistant therapeutic proteins," Bioorg Med Chem Lett. 16(3):587-591 (2006).

Platis, D. and G. Foster, "High yield expression, refolding, and characterization of recombinant interferon alpha2/alpha8 hybrids in *Escherichia coli*," Protein Expression and Purification 31(2):222-230 (2003).

Powell et al., "Human erythropoietin gene: high level expression in stably transfected mammalian cells and chromosome localization," PNAS 83:6465-6469 (1986).

Qiu et al., "Homodimerization restores biological activity to an inactive erythropoietin mutant," J Biol Chem 273:11173-11176 (1998).

Quelle et al., "Phosphorylatable and epitope-tagged human erythropoietins: utility and purification of native baculovirus-derived forms," Protein Expr. Purif. 3(6):461-469 (1992).

Quelle, et al., "Interleukin 3, granulocyte-macrophage colony-stimulating factor, and transfected erythropoietin receptors mediate tyrosine phosphorylation of a common cytosolic protein (pp100) in FDC-ER cells," J. Biol. Chem. 267:17055-17060 (1992).

Quelle, F. and D. Wojchowski, "Proliferative action of erythropoietin is associated with rapid protein tyrosine phosphorylation in responsive B6SUt.EP cells," J. Biol. Chem. 266:609-614 (1991).

Rao, J., "New scoring matrix for amino acid residue exchanges based on residue characteristic physical parameters," International Journal of Peptide and Protein Research 29:276-281 (1987).

Recny et al., "Structural characterization of natural human urinary and recombinant DNA-derived erythropoietin. Identification of des-arginine 166 erythropoietin," J Biol Chem 262:17156-17163 (1987).

Regnier, L., "Erythropoietin used in renal failure complicated by paroxysmal nocturnal hemoglobinuria," Anna J. (7):512-513 (1989).

Rendahl et al., "Tightly regulated long-term erythropoietin expression in vivo using tet-inducible recombinant adeno-associated viral vectors," Human Gene Therapy 13(2):335-342 (2002).

Risler et al., "Amino acid substitutions in structurally related proteins. A pattern recognition approach. Determination of a new and efficient scoring matrix," J. Mol. Biol. 204:1019-1029 (1988).

Ritz, E. and V. Haxsen, "Diabetic nephropathy and anaemia," Eur J Clin Invest. 35 Suppl 3:66-74 (2005).

Rizzuto et al., "Efficient and regulated erythropoietin production by naked DNA injection and muscle electroporation," Proc Natl Acad Sci USA 96:6417-6422 (1999).

Rodgers, G. and L. Lessin, "Recombinant erythropoietin improves the anemia associated with Gaucher's disease," Blood 73(8):2228-2229 (1989).

Romanowski, R. and A. Sytkowski, "The molecular structure of human erythropoietin," Hematol Oncol Clin North Am. 8(5):885-894 (1994).

Sasaki et al., "Isolation of human erythropoietin with monoclonal antibodies," Methods Enzymol. 147:328-340 (1987).

Satake et al., "Chemical modification of erythropoietin: an increase in in vitro activity by guanidination," Biochimica et Biophysica Acta 1038:125-129 (1990).

Schwartz and Dayhoff, eds., Atlas of Protein Sequence and Structure, National Biomedical Research Foundation, pp. 353-358 (1979).

Serguera et al., "Control of erythropoietin secretion by doxycycline or mifepristone in mice bearing polymer-encapsulated engineered cells," Human Gene Therapy 10(3):375-383 (1999).

Sethuraman, N. and T. Stadheim, "Challenges in therapeutic glycoprotein production," Curr. Opin. Biotech. 17:341-346 (2006).

Setoguchi et al., "Stimulation of erythropoiesis by in vivo gene therapy: physiologic consequences of transfer of the human erythropoietin gene to experimental animals using an adenovirus vector," Blood 84(9):2946-2953 (1994).

Sinclair, A. and S. Elliott, "Glycoengineering: the effect of glycosylation on the properties of therapeutic proteins," J of Pharmaceut. Sciences 94:1626-1635 (2005).

Singer et al., "Single and combination drug therapy for fetal hemoglobin augmentation in hemoglobin E-beta 0-thalassemia: Considerations for treatment," Ann N Y Acad Sci. 1054: 250-256 (2005).

Skoko et al., "Expression and characterization of human interferon-beta1 in the methylotrophic yeast *Pichia pastoris*," Biotechnol. Appl. Biochem. 38(Pt3):257-265 (2003).

Smith, T. and M. Waterman, "Comparison of biosequences," Advances in Applied Mathematics 2:482-489 (1981).

Smith, D. and K. Johnson, "Single-step purification of polypeptides expressed in *Escherichia coli* as fusions with glutathione S-transferase," Gene 67:31-40 (1988).

Spivak et al., "Erythropoietin: isolation by affinity chromatography with lectin-agarose derivatives," Proc. Natl. Acad. Sci. USA 74(10):4633-4635 (1977).

Spivak, J. and B., "The in vivo metabolism of recombinant human erythropoietin in the rat," Blood 73(1):90-99 (1989).

Storring et al., "Epoetin alfa and beta differ in their erythropoietin isoform compositions and biological properties," Br J Haematol 100:79-89 (1998).

St-Pierre et al., "Emerging features in the regulation of MMP-9 gene expression for the development of novel molecular targets and therapeutic strategies," Curr. Drug Targets Inflamm. Allergy 2(3):206-215 (2003).

Svensson et al., "Long-term erythropoietin expression in rodents and non-human primates following intramuscular injection of a replication-defective adenoviral vector," (1997) Hum Gene Ther 8: 1797-1806.

Syed et al., "Efficiency of signalling through cytokine receptors depends critically on receptor orientation," Nature 395:511-516 (1998).

Sytkowski et al., "An erythropoietin fusion protein comprised of identical repeating domains exhibits enhanced biological properties," J. Biol. Chem. 274(35):24773-24778 (1999).

Takeuchi, M. and A. Kobata, "Structures and functional roles of the sugar chains of human erythropoietins," Glycobiology 1(4):337-346 (1991).

Takeuchi et al., "Comparative study of the asparagine-linked sugar chains of human erythropoietins purified from urine and the culture medium of recombinant Chinese hamster ovary cells," J. Biol. Chem. 263(8):3657-3663 (1988).

Takeuchi et al., "Role of sugar chains in the in vitro biological activity of human erythropoietin produced in recombinant Chinese hamster ovary cells," J Biol Chem 265:12127-12130 (1990).

Tangri et al., "Rationally engineered therapeutic proteins with reduced immunogenicity," Jour. of Immun. 174:3187-3196 (2005).

Ten Hagen et al., "All in the family: the UDP-GalNAc:polypeptide N-acetylgalactosaminyltransferases," Glycobiology 13:1R-16R (2003).

Ten Hagen et al., "Characterization of a UDP-GalNAc:polypeptide N-acetylgalactosaminyltransferase that displays glycopeptide N-acetylgalactosaminyltransferase activity," J. Biol. Chem. 274:27867-27874 (1999).

Tipathy et al. "Stable delivery of physiologic levels of recombinant erythropoietin to the systemic circulation by intramuscular injection of replication-defective adenovirus," Proc Natl. Acad Sci U S A. 91(24):11557-11561 (1994).

Tsao et al., "Optimization of a roller bottle process for the production of recombinant erythropoietin," Ann N Y Acad Sci. 665:127-136 (1992).

Vega, M., "Improving the Delivery and Pharmacokinetics of Therapeutic Proteins by Increased Resistance to Proteolysis" (Meeting Abstract) Second Annual Advancing Protein Therapeutics, Engineering the Next Generation of Proteins for Therapeutics (Jan. 12, 2006). http://www.chi-peptalk.com/pttn2006.asp.

Vega, M., "Next-Generation Protein Therapeutics for Oral Delivery" (Meeting Abstract) Third Annual Optimizing Protein and Antibody Therapeutics, Pioneering New Frontiers (Jan. 9, 2007). http://www.chi-peptalk.com/06_PTT.asp.

Verhelst et al., "Treatment of erythropoietin-induced pure red cell aplasia: a retrospective study," Lancet 363:1768-1771 (2004).

Wang et al., "Erythropoietin production from CHO cells grown by continuous culture in a fluidized-bed bioreactor," Biotechnol Bioeng. 77:194-203 (2002).

Watson et al., "Structure determination of the intact major sialylated oligosaccharide chains of recombinant human erythropoietin expressed in Chinese hamster ovary cells," Glycobiology 4(2):227-237 (1994).

Way et al., "Improvement of Fc-erythropoietin structure and pharmacokinetics by modification at a disulfide bond," Protein Eng Des Sel. 18:111-118 (2005).

Weiner et al., "Liposome-collagen gel matrix: a novel sustained drug delivery system," J Pharm Sci. 74(9):922-925 (1985).

Wen et al., "Erythropoietin structure-function relationships. Identification of functionally important domains," J. Biol. Chem. 269(36):22839-22846 (1994).

Wen et al., "Erythropoietin structure-function relationships: high degree of sequence homology among mammals," Blood 82:1507-1516 (1993).

Wingard et al., "Efficacy of oral iron therapy in patients receiving recombinant human erythropoietin," Am J Kidney Dis 25:433-439 (1995).

Witthuhn, et al., "JAK2 associates with the erythropoietin receptor and is tyrosine phosphorylated and activated following stimulation with erythropoietin," Cell 74:227-236 (1993).

Worthington et al., "Quantitation of erythroid differentiation in vitro using a sensitive colorimetric assay for hemoglobin," Exp. Hematol. 15:85-92 (1987).

Yamaguchi et al., "Effects of site-directed removal of N-glycosylation sites in human erythropoietin on its production and biological properties," J. Biol. Chem. 266(30):20434-20439 (1991).

Yoon et al., "Enhancement of recombinant erythropoietin production in CHO cells in an incubator without CO2 addition," Biomed. Life Sci. 37(2):119-132 (2001).

Zola, Monoclonal Antibodies: A Manual of Techniques, CRC Press, Inc. 147-158 (1987).

Bork et al., "Powers and pitfalls in sequence analysis: the 70% hurdle," Genome Res. 10:398-400 (2000).

Bork et al., "Go hunting in sequence databases but watch out for the traps," Trends in Genetics 12:425-427 (1996).

Brenner S.E., "Errors in genome annotation," Trends in Genetics 15:153-133 (1999).

Doerks et al., "Protein annotation: detective work for function prediction," Trends in Genetics 14:248-250 (1998).

Ngo et al., "Computational complexity, protein structure and the Levinthal paradox," in the Protein Folding Problem and Tertiary Structure Prediction, K. Merz Jr and Le grands (eds), Birkenhauser, Boston, 492-495 (1994).

Skolnick et al., "From genes to protein structure and function: novel applications of computational approaches in the genomic era," Trends Biotechnol. 18:34-39 (2000).

Smith et al., "The challenges of genome sequence annotation or "The devil is in the details,"" Nature Biotechnol. 15:1222-1223 (1997).

Wells et al., "Additivity of mutational effects in proteins," Biochem. 29:8509-8517 (1990).

Wen et al., "Erythropoietin structure-function relationships," J. Biol. Chem. 269(36):22839-22846 (1994).

Boissel, J. and H. Bunn, "Erythropoietin structure-function relationships," in *The Biology of Hematopoiesis*, Wiley-Liss, Inc., New York, pp. 227-232 (1990).

Collard, R. and A. Gearing (eds.), "IFNγ," in *The Cytokine FactsBook*, Academic Press, Inc., San Diego, CA, pp. 157-158 (1994).

Charbonneau, N., "Kidney hormone protects oxygen-starved brain cells," retrieved from the Internet:<URL:mult-sclerosis.org/news/Aug2001/KidneyHormoneBrainCells.html [retrieved on Dec. 7, 2007.10] [2 pages].

Cheetham et al., "NMR structure of human erythropoietin and a comparison with its receptor bound conformation," Nature Struct. Biol. 5(10):861-866 (1998).

Christensen, D., "Old drug, new uses?" Science News 162(19):296-298 (2002).

ClinicalTrials.gov, "Erythropoietin therapy for subarachnoid hemorrhage," retrieved from the Internet:<URL:clinicaltrials.gov/ct/show/NCT00140010 [retrieved on Dec. 7, 2010] [4 pages].

Cornish et al., "Probing protein structure and function with an expanded genetic code," Angew. Chem. Int. Ed. Engl. 34(6):621-633 (1995).

Dayhoff et al., "A model of evolutionary change in proteins," in Atlas of Protein Sequence and Structure, vol. 5, Supp. 3, The National Biomedical Research Foundation, Silver Spring, MD, pp. 345-352 (1979).

Ehrenreich et al., "Erythropoietin: a candidate compound for neuroprotection in schizophrenia," Mol. Psych. 9:42-54 (2004).

Elliott et al., "Mapping of the active site of recombinant human erythropoietin," Blood 89(2):493-502 (1997).

Feng et al., "Aligning amino acid sequences: comparison of commonly used methods," J. Mol. Evol. 12:112-125 (1985).

Hammerling et al., "In vitro bioassay for human erythropoietin based on proliferative stimulation of an erythroid cell line and analysis of carboydrate-dependent microheterogeneity," J. Pharm. Biomed. Anal. 14(11):1455-1469 (1996).

InfoBioGen online database, "Proteol: proteolytic digestion of a protein," retrieved from the Internet:<URL:clinicaltrials bioinfo.hku.hk/services/analyseq/cgi-bin/proteol_in.pl [retrieved on Jan. 4, 2006] [2 pages].

Keil, B., "Specificity of Proteolysis," Springer Verlag: New York, pp. 1, 2, 6, 102-104, 107-108, 201 (1992).

NIH Clinical Research Studies, "Protocol No. 06-H-0054: Evaluation of a synergy of combining hydroxyurea with recombinant human erythropoietin glycoform alpha (rhu-erythropoietin-alpha) on fetal hemoglobin synthesis in patients with sickle cell anemia," retrieved from the Internet:<URL:clinicalstudies.info.nih.gov/cgi/wais/bold032001.pl?B_06-H-0054.html@erythropoietin [retrieved on Jan. 4, 2011] [4 pages].

Examination Report, issued Sep. 22, 2010, in connection with European Patent Application Serial No. 07 824 714.5.

Office Action, issued Nov. 1, 2010, in connection with U.S. Appl. No. 12/157,150.

International Preliminary Report on Patentability, issued Nov. 30, 2010, in connection with International Patent Application Serial No. PCT/EP09/003862.

Gibrat et al., "Surprising similarities in structure comparison," Curr. Opionion in Structural Biology 6(3):377-385 (1996).

Holm et al., "Mapping the protein Universe," Science 273(2):595-603 (1996).

Ohta et al., "Selective glycopeptide mapping of erythropoietin by on-line high-performance liquid chromotography-electrospray ionization mass spectrometry," Journal of Chromatography 910:1-11 (2001).

\* cited by examiner

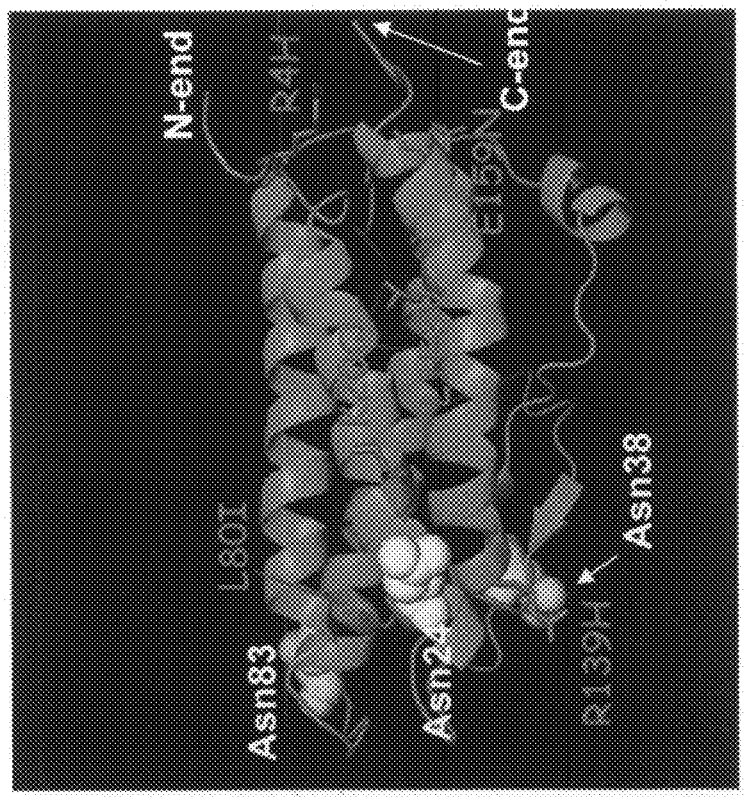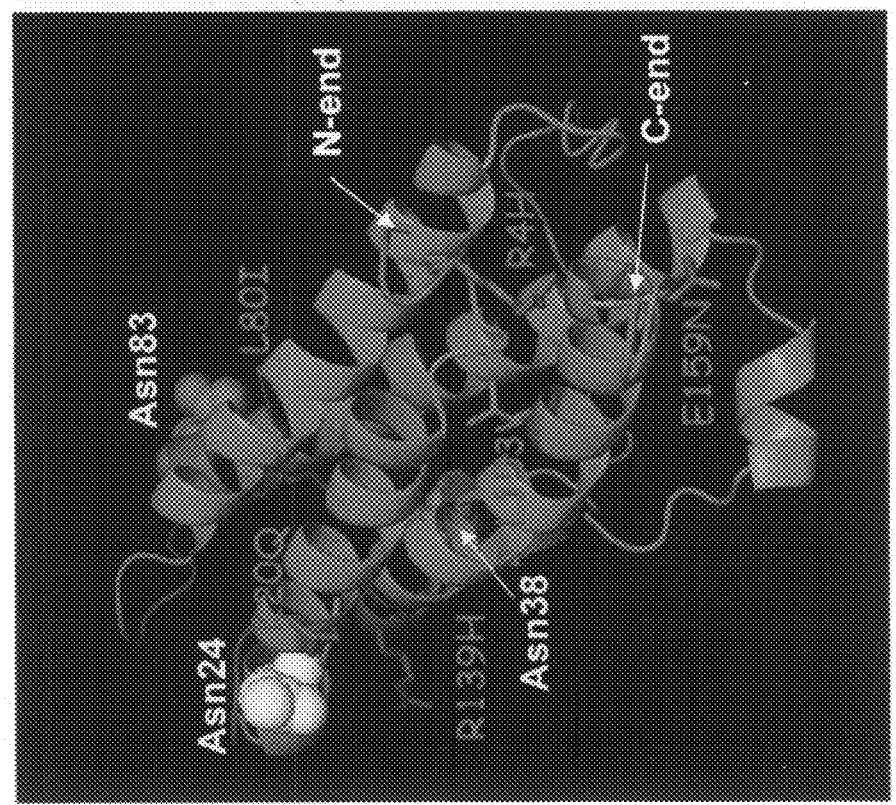

US 8,252,743 B2

MODIFIED ERYTHROPOIETIN POLYPEPTIDES AND USES THEREOF FOR TREATMENT

RELATED APPLICATIONS

Benefit of priority is claimed under 35 U.S.C. §119(e) to U.S. provisional application Ser. No. 60/861,615, to Thierry Guyon, Giles Borrelly, Xavier Gallet, Lila Drittanti and Manuel Vega, entitled "MODIFIED ERYTHROPOIETIN POLYPEPTIDES AND USES THEREOF," filed Nov. 28, 2006.

This application is related to corresponding International Application No. PCT/GB07/004520 to Thierry Guyon, Giles Borrelly, Xavier Gallet, Lila Drittanti and Manuel Vega, entitled "MODIFIED ERYTHROPOIETIN POLYPEPTIDES AND USES THEREOF," which also claims priority to U.S. Provisional Application Ser. No. 60/861,615.

This application is related to U.S. application Ser. No. 11/176,830, to Rene Gantier, Thierry Guyon, Manuel Vega and Lila Drittanti, entitled "RATIONAL EVOLUTION OF CYTOKINES FOR HIGHER STABILITY, THE CYTOKINES AND ENCODING NUCLEIC ACID MOLECULES," filed Jul. 6, 2005 and published as U.S. Application No. US 2006-0020116, which is a continuation of U.S. application Ser. No. 10/658,834, to Rene Gantier, Thierry Guyon, Manuel Vega and Lila Drittanti entitled "RATIONAL EVOLUTION OF CYTOKINES FOR HIGHER STABILITY, THE CYTOKINES AND ENCODING NUCLEIC ACID MOLECULES," filed Sep. 8, 2003 and published as U.S. Application No. US-2004-0132977-A1. This application also is related to U.S. application Ser. No. 11/196,067, to Rene Gantier, Thierry Guyon, Hugo Cruz Ramos, Manuel Vega and Lila Drittanti entitled "RATIONAL DIRECTED PROTEIN EVOLUTION USING TWO-DIMENSIONAL RATIONAL MUTAGENESIS SCANNING," filed Aug. 2, 2005 and published as U.S. Application No. US-2006-0020396-A1, which is a continuation of U.S. application Ser. No. 10/658,355, to Rene Gantier, Thierry Guyon, Hugo Cruz Ramos, Manuel Vega and Lila Drittanti entitled "RATIONAL DIRECTED PROTEIN EVOLUTION USING TWO-DIMENSIONAL RATIONAL MUTAGENESIS SCANNING", filed Sep. 8, 2003 and published as U.S. Application No. US 2005-0202438.

This application also is related to U.S. application Ser. No. 10/658,834, filed Sep. 8, 2003, and to published International PCT Application WO 2004/022593, to Rene Gantier, Thierry Guyon, Manuel Vega and Lila Drittanti entitled, "RATIONAL EVOLUTION OF CYTOKINES FOR HIGHER STABILITY, THE CYTOKINES AND ENCODING NUCLEIC ACID MOLECULES." This application also is related to U.S. application Ser. No. 10/658,355, filed Sep. 8, 2003, and to International PCT Application WO 2004/022747, to Rene Gantier, Thierry Guyon, Hugo Cruz Ramos, Manuel Vega and Lila Drittanti entitled "RATIONAL DIRECTED PROTEIN EVOLUTION USING TWO-DIMENSIONAL RATIONAL MUTAGENESIS SCANNING."

The subject matter of each of the above-referenced applications is incorporated by reference in its entirety.

INCORPORATION BY REFERENCE OF SEQUENCE LISTING PROVIDED ON COMPACT DISCS

An electronic version on compact disc (CD-R) of the Sequence Listing is filed herewith in duplicate (labeled Copy #1 Replacement Feb. 19, 2009 and Copy #2 Replacement Feb. 19, 2009), the contents of which are incorporated by reference in their entirety. The computer-readable file on each of the aforementioned compact discs, created on Feb. 19, 2009, is identical, 464 kilobytes in size, and titled 931SEQ.002.txt.

FIELD OF INVENTION

Modified erythropoietin (EPO) polypeptides and other modified therapeutic polypeptides are provided. The EPO polypeptides and other modified therapeutic polypeptides are modified to exhibit physical properties and activities that differ from the corresponding unmodified EPO polypeptides and other unmodified therapeutic polypeptides, respectively. Nucleic acid molecules encoding these polypeptides also are provided. Also provided are methods of treatment and diagnosis using the polypeptides.

BACKGROUND

Effective delivery of therapeutic proteins for clinical use is a challenge to pharmaceutical science. Once in the blood stream, these proteins are constantly eliminated from circulation within a short time by different physiological processes, involving metabolism as well as clearance using normal pathways for protein elimination, such as filtration in the kidneys (e.g., glomerular) or proteolysis in blood. Once in the luminal gastrointestinal tract, these proteins are constantly digested by luminal proteases. The latter can be a limiting process affecting the half-life of proteins used as therapeutic agents in per-oral administration or subcutaneous, intravenous or intramuscular injection. The problems associated with these routes of administration of proteins are known and various strategies have been used in attempts to solve them. In addition, many therapeutic proteins are glycosylated, and production of glycosylated therapeutic proteins can be costly, highly variable and often difficult to achieve. Production of non-glycosylated forms of such proteins is often not possible due to protein degradation.

A protein family that has been the focus of clinical work and effort to improve its administration and bio-assimilation is the cytokine family, which includes erythropoietin (EPO). Recombinantly produced EPO polypeptides have been approved for treatment of variety of anemias, such those caused by renal failure, chronic inflammation, cancer, and AIDS; however, there is still an urgent need for more stable forms of erythropoietin for therapy. Erythropoietin has a relatively short plasma half-life (Spivak, J. L. and Hogans, B. B., Blood 73(1): 90-99 (1989); McMahon, F. G., et al., Blood 76(9): 1718-1722 (1990)); therefore, therapeutic plasma levels are rapidly lost, and repeated intravenous administrations must be made. Since naturally occurring variants can have undesirable side effects in addition to the problems of administration, bioavailability, and short half-life, there is a need to improve properties of EPO for its use as a biotherapeutic agent. Therefore, among the objects herein, it is an object to provide modified EPO polypeptides and other therapeutic polypeptides that have improved therapeutic properties.

SUMMARY

Provided herein are pharmaceutical compositions of modified erythropoietin (EPO) polypeptides and other modified therapeutic polypeptides that exhibit increased protein stability compared to the corresponding unmodified therapeutic polypeptides. The modified EPO polypeptides and other modified therapeutic polypeptides provided herein exhibit increased resistance to proteases compared to the corresponding unmodified therapeutic polypeptides. Modified EPO polypeptides and other therapeutic polypeptides provided herein exhibiting increased protein stability display increased protein half-life in vivo or in vitro compared to the corresponding unmodified therapeutic polypeptide. For example, modified EPO polypeptides and other therapeutic polypeptides provided herein exhibit increased stability, in the bloodstream, following oral administration or injection, and/or under storage conditions. Increased resistance to digestion by proteases can be manifested as increased protein statability. Such resistance includes that assessed by resistance to blood, intestinal or any other proteases.

Provided herein are pharmaceutical compositions of non-glycosylated modified therapeutic polypeptides. The non-glycosylated modified therapeutic polypeptides exhibit increased resistance to proteases compared to the unmodified therapeutic polypeptides. Included among modified therapeutic polypeptides that are non-glycosylated and that exhibit increased protease resistance are modified erythropoietin (EPO) polypeptides that are non-glycosylated and that exhibit increased protease resistance. Other exemplary therapeutic polypeptides include, but are not limited to, cytokines, such as, but not limited to, interleukin-1β (IL-1), interleukin-2 (IL-2), interleukin-3 (IL-3), interleukin-4 (IL-4), interleukin-5 (IL-5), interleukin-6 (IL-6) interleukin-9 (IL-9), interferon-beta (IFN-β), interferon-gamma (IFN-γ), granulocyte-colony stimulating factor (G-CSF), granulocyte macrophage-colony stimulating factor (GM-CSF), macrophage-colony stimulating factor (M-CSF), thrombopoietin (TPO), leukemia inhibitory factor (LIF), stem cell factor (SCF), oncostatin M (OSM) and vascular endothelial growth factor (VEGF).

Provided herein are pharmaceutical compositions of modified therapeutic polypeptides or active fragments of the modified therapeutic polypeptides wherein the unmodified therapeutic polypeptide contains at least one glycosylation site, and glycosylation is required for therapeutic activity of the unmodified therapeutic polypeptide, and the modified therapeutic polypeptide (i) contains one or more amino acid replacements, insertions and/or deletions compared to the unmodified therapeutic polypeptide, (ii) exhibits increased resistance to proteolysis compared to the unmodified therapeutic polypeptide by virtue of one or more amino acid replacements, insertions and/or deletions, (iii) is not glycosylated and exhibits therapeutic activity, and (iv) if the polypeptide is an active fragment, the active fragment includes the modification resulting in increased resistance to proteolysis.

Also provided are pharmaceutical compositions of modified therapeutic polypeptides or active fragments of the modified therapeutic polypeptides wherein the unmodified therapeutic polypeptide contains at least one glycosylation site, and the modified therapeutic polypeptide (i) contains one or more amino acid replacements, insertions and/or deletions compared to the unmodified therapeutic polypeptide, (ii) exhibits increased resistance to proteolysis compared to the unmodified therapeutic polypeptide by virtue of one or more amino acid replacements, insertions and/or deletions, (iii) the modified therapeutic polypeptide is not glycosylated and is not an interferon-α, and (iv) if the polypeptide is an active fragment, the active fragment includes the modification resulting in increased resistance to proteolysis.

Also provided are pharmaceutical compositions of modified therapeutic polypeptides or active fragments of the modified therapeutic polypeptides wherein the unmodified therapeutic polypeptide contains at least one glycosylation site, and the modified therapeutic polypeptide contains two or more amino acid replacements, insertions and/or deletions compared to the unmodified therapeutic polypeptide, where at least one of the amino acid replacements renders the modified therapeutic polypeptide more resistant to proteolysis compared to the therapeutic polypeptide without the replacement and at least one of the amino acid replacements removes a native glycosylation site in the therapeutic protein.

The modified therapeutic polypeptides can contain one or more modifications that eliminates all glycosylation sites. In some examples, the modified therapeutic polypeptides also can contain a modification that introduces a non-native glycosylation site. In some examples, the polypeptides are produced in a prokaryotic host, such as E. coli, whereby the polypeptide is not glycosylated. In some examples, the modified therapeutic polypeptide is a cytokine. Exemplary modified therapeutic polypeptides include, but are not limited to, erythropoietin (EPO), interleukin-1β (IL-1), interleukin-2 (IL-2), interleukin-3 (IL-3), interleukin-4 (IL-4), interleukin-5 (IL-5), interleukin-6 (IL-6) interleukin-9 (IL-9), interferon-beta (IFN-β), interferon-gamma (IFN-γ), granulocyte-colony stimulating factor (G-CSF), granulocyte macrophage-colony stimulating factor (GM-CSF), macrophage-colony stimulating factor (M-CSF), thrombopoietin (TPO), leukemia inhibitory factor (LIF), stem cell factor (SCF), oncostatin M (OSM) and vascular endothelial growth factor (VEGF).

The modified therapeutic polypeptides can be precursor forms or mature forms of the therapeutic polypeptide. Typically, the modified therapeutic polypeptides retain one or more activities of the unmodified therapeutic polypeptide under the same conditions as the modified therapeutic polypeptide. The modified therapeutic polypeptides can also retain one or more activities of the unmodified therapeutic polypeptide that is fully glycosylated. The one or more activities of the modified therapeutic polypeptides can be increased or decreased compared to the unmodified therapeutic polypeptide. The modified therapeutic polypeptides can be an active fragment of a therapeutic polypeptide, where the active fragment includes the modification resulting in increased resistance to proteolysis. In some examples, the modified therapeutic polypeptides contain an active portion or fragment of the therapeutic polypeptide, wherein the active portion or fragment retains one or more activities of the unmodified therapeutic polypeptide and contains the one or more amino acid replacements that increase protease resistance compared to the unmodified therapeutic polypeptide. Modified therapeutic polypeptides provided herein include polypeptides modified at 1, 2, 3, 4, 5, 6, 7, 8, 9, 10, 11, 12, 13, 14, 15, 16, 17, 18, 19, 20 or more positions as compared to an unmodified modified therapeutic polypeptide.

The modified therapeutic polypeptides provided herein exhibit increased protein stability compared to the unmodified therapeutic polypeptides. The modified therapeutic polypeptides exhibit increased resistance to proteolysis by one or more proteases compared to the unmodified polypeptide. In some cases, the modified therapeutic polypeptides exhibit increased resistance to proteolysis by one or more proteases in serum, blood, saliva, digestive fluids or in vitro. For example, the proteases can be any of pepsin, trypsin, chymotrypsin, elastase, aminopeptidase, gelatinase B, gelatinase A, α-chymotrypsin, carboxypeptidase, endoproteinase Arg-C, endoproteinase Asp-N, endoproteinase Glu-C, endoproteinase Lys-C, luminal pepsin, microvillar endopeptidase, dipeptidyl peptidase, enteropeptidase, hydrolase, NS3, factor Xa, Granzyme B, thrombin, plasmin, urokinase, tPA and PSA. The increased resistance to proteolysis is exhibited by the modified polypeptide when it is administered orally, intravenously, nasally, pulmonarily, or is present in the digestive tract. In some examples, the modified therapeutic polypeptides are further modified and the modification is one or more of carboxylation, hydroxylation, hasylation, carbamylation, sulfation, phosphorylation, albumination, oxidation or conjugation to a polyethylene glycol (PEG) moiety. The modified therapeutic polypeptides can also contain one or more additional amino acid modifications that contributes to altered immunogenicity, carboxylation, hydroxylation, hasylation, carbamylation, sulfation, phosphorylation, oxidation, PEGylation or protease resistance of the modified therapeutic polypeptide.

In some examples, the pharmaceutical compositions provided contain modified therapeutic polypeptides that are erythropoietin (EPO) polypeptides. The modified EPO polypeptides can be precursor forms or mature forms of an EPO polypeptide. The mature form of the unmodified therapeutic polypeptide that is EPO can have the amino acid sequence set forth in SEQ ID NO: 2 or 237 or an allelic or species variant or other variant thereof. In some examples, the allelic, species variant or other variant at least or at least about 40%, 50%, 60%, 70%, 80%, 90%, 91%, 92%, 93%, 94%, 95%, 96%, 97%, 98%, or 99% sequence identity to the polypeptide set forth in SEQ ID NO: 2 or 237, excluding the amino acid modification(s). Where the modified EPO polypeptide is a precursor form of the polypeptide, the sequence identity is compared along the portion of the modified polypeptide that corresponds to the mature form of the EPO polypeptide. In some examples, the unmodified EPO polypeptide the unmodified EPO polypeptide contains the sequence of amino acids set forth in any of SEQ NOS: 2, 227, 228, 237, 309 and 310 or allelic or species variants thereof. The modified EPO polypeptide can contain one or more amino acid replacements correspond to any selected from among P2S, P2A, P3S, P3A, R4H, R4Q, L5I, L5V, C7S, C7V, C7A, C7I, C7T, D8Q, D8H, D8N, R10H, R10Q, L12V, L12I, E13Q, E13H, E13N, R14H, R14Q, Y15H, Y15I, L16I, L16V, L17I, L17V, E18Q, E18H, E18N, E21Q, E21H, E21N, E23Q, E23H, E23N, C29S, C29V, C29A, C29I, C29T, E31Q, E31H, E31N, L35V, L35I, E37Q, E37H, E37N, K20Q, K20T, K20N, P42S, P42A, D43Q, D43H, D43N, K45Q, K45T, K45N, F48I, F48V, Y49H, Y49I, W51S, W51H, K52Q, K52T, K52N, R53H, R53Q, M54V, M54I, E55Q, E55H, E55N, E62Q, E62H, E62N, W64S, W64H, L67I, L67V, L69V, L69I, L70I, L70V, E72Q, E72H, E72N, L75V, L75I, R76H, R76Q, L80V, L80I, L81I, L81V, P87S, P87A, W88S, W88H, E89Q, E89H, E89N, P90S, P90A, L91I, L91V, L93V, L93I, D96Q, D96H, D96N, K97Q, K97T, K97N, L102V, L102I, R103H, R103Q, L105I, L105V, L108I, L108V, L109I, L109V, R110H, R110Q, L112V, L112I, K116Q, K116T, K116N, E117Q, E117H, E117N, P121S, P121A, P122S, P122A, D123Q, D123H, D123N, P129S, P129A, L130V, L130I, R131H, R131Q, D136Q, D136H, D136N, F138I, F138V, R139H, R139Q, K140N, K140Q, L141I, L141V, F142I, F142V, R143H, R143Q, Y145H, Y145I, F148I, F148V, L149I, L149V, R150H, R150Q, K152Q, K152T, K152N, L153I, L153V, K154Q, K154T, K154N, L155V, L155I, Y156H, Y156I, E159Q, E159H, E159N, R162H, R162Q, D165Q, D165H, D165N, R166H, and R166Q. The modified EPO polypeptide can be an active fragment of an EPO polypeptide, where the active fragment retains one or more activities of the unmodified EPO polypeptide and contains the one or more modifications that confer protease resistance of the EPO polypeptide. Such activities can be, for example, erythrocyte proliferation, promotion of cell survival or inhibition of tissue damage. The EPO polypeptides can contain amino acid modifications at one or more glycosylation sites, such as the N-glycosylation sites N24, N38 and N83, where the modification eliminates glycosylation at the site. For example, such EPO polypeptides can contain amino acid replacements selected from among N24H, N38H, N83H, N24K, N38K and N83K. The modified EPO polypeptides can be 166 amino acids in length or can be shorter, such as, for example, 160, 161, 162, 163, 164, 165 amino acids in length.

Provided herein are modified EPO polypeptides containing one or more amino acid modifications corresponding to amino acid positions 2, 3, 4, 5, 7, 8, 10, 12, 13, 14, 15, 16, 17, 18, 20, 21, 23, 29, 31, 35, 37, 42, 43, 45, 48, 49, 51, 52, 53, 54, 55, 62, 64, 67, 69, 70, 72, 75, 76, 80, 81, 87, 88, 89, 90, 91, 93, 96, 97, 102, 103, 105, 108, 109, 110, 112, 116, 117, 121, 122, 123, 129, 130, 131, 136, 138, 139, 140, 141, 142, 143, 145, 148, 149, 150, 152, 153, 154, 155, 156, 159, 162, 165, and 166 where the amino acid position that is modified corresponds to a mature human EPO polypeptide having the sequence set forth in SEQ ID NO: 2 or 237 or is at a corresponding position in an allelic or species variant or other variant of a mature human EPO polypeptide, an EPO polypeptide having at least or at least about 60%, 70%, 75%, 80%, 85%, 90%, 91%, 92%, 93%, 94%, 95%, 96%, 97%, 98%, 99%, or more sequence identity to a mature human EPO polypeptide, or a fragment thereof that includes the recited one or more amino acid modifications and retains at least one activity of the full-length EPO or exhibits an EPO activity. For example, amino acid replacements at any one of the one or more amino acid positions can include replacements of any of P2, P3, R4, L5, C7, D8, R10, L12, E13, R14, Y15, L16, L17, E18, K20, E21, E23, C29, E31, L35, E37, P42, D43, K45, F48, Y49, W51, K52, R53, M54, E55, E62, W64, L67, L69, L70, E72, L75, R76, L80, L81, P87, W88, E89, P90, L91, L93, D96, K97, L102, R103, L105, L108, L109, R110, L112, K116, E117, P121, P122, D123, P129, L130, R131, D136, F138, R139, K140, L141, F142, R143, Y145, F148, L149, R150, K152, L153, K154, L155, Y156, E159, R162, D165, and R166.

Provided herein are modified EPO polypeptides, including active fragments thereof, containing one or more amino acid modifications in an unmodified EPO polypeptide, where the one or more amino acid modifications correspond to an amino acid replacement selected from among P2S, P2A, P3S, P3A, R4H, R4Q, L5I, L5V, C7S, C7V, C7A, C7I, C7T, D8Q, D8H, D8N, R10H, R10Q, L12V, L12I, E13Q, E13H, E13N, R14H, R14Q, Y15H, Y15I, L16I, L16V, L17I, L17V, E18Q, E18H, E18N, K20Q, K20T, K20N, E21Q, E21H, E21N, E23Q, E23H, E23N, C29S, C29V, C29A, C29I, C29T, E31Q, E31H, E31N, L35V, L35I, E37Q, E37H, E37N, P42S, P42A, D43Q, D43H, D43N, K45Q, K45T, K45N, F48I, F48V, Y49H, Y49I, W51S, W51H, K52Q, K52T, K52N, R53H, R53Q, M54V, M54I, E55Q, E55H, E55N, E62Q, E62H, E62N, W64S, W64H, L67I, L67V, L69V, L69I, L70I, L70V, E72Q, E72H, E72N, L75V, L75I, R76H, R76Q, L80V, L80I, L81I, L81V, P87S, P87A, W88S, W88H, E89Q, E89H, E89N, P90S, P90A, L91I, L91V, L93V, L93I, D96Q, D96H, D96N, K97Q, K97T, K97N, L102V, L102I, R103H, R103Q, L105I, L105V, L108I, L108V, L109I, L109V, R110H, R110Q, L112V, L112I, K116Q, K116T, K116N, E117Q, E117H, E117N, P121S, P121A, P122S, P122A, D123Q, D123H, D123N, P129S, P129A, L130V, L130I, R131H, R131Q, D136Q, D136H, D136N, F138I, F138V, R139H, R139Q, K140N, K140Q, L141I, L141V, F142I, F142V, R143H, R143Q, Y145H, Y145I, F148I, F148V, L149I, L149V, R150H, R150Q, K152Q, K152T, K152N, L153I, L153V, K154Q, K154T, K154N, L155V, L155I, Y156H, Y156I, E159Q, E159H, E159N, R162H, R162Q, D165Q, D165H, D165N, R166H, and R166Q, where the amino acid position that is modified corresponds to a mature human EPO polypeptide having the sequence set forth in SEQ ID NO: 2 or 237 or is at a corresponding position in an allelic or species variant or other variant of a mature human EPO polypeptide, an EPO polypeptide having at least or at least about 60%, 70%, 75%, 80%, 85%, 90%, 91%, 92%, 93%, 94%, 95%, 96%, 97%, 98%, 99%, or more sequence identity to a mature human EPO polypeptide, or a fragment thereof that includes the recited one or more amino acid modifications and retains at least one activity of the full-length EPO or exhibits an EPO activity.

In a particular example, the modifications in an EPO polypeptide are selected from among P2S, P2A, P3S, P3A, R4H, R4Q, L5I, L5V, C7V, C7I, C7T, D8Q, D8H, D8N, R10H, R10Q, L12V, L12I, E13H, E13N, R14H, Y15H, L16I, L16V, L17I, L17V, E18Q, E18H, E18N, K20Q, K20T, K20N, E21Q, E21H, E21N, E23Q, E23H, E23N, C29I, C29T, E31Q, E31H, E31N, L35V, L35I, E37Q, E37H, E37N, P42S, D43H, K45T, W51H, K52T, E62Q, E62H, E62N, W64S, W64H, L67I, L67V, L69V, L69I, L70I, L70V, L80V, L80I, L81I, L81V, P87A, W88S, W88H, E89Q, E89H, E89N, P90S, L91I, L91V, L93V, L93I, D96Q, D96H, D96N, K97Q, K97T, K97N, L102V, L102I, L105I, L105V, L108I, L108V, L109I, L109V, R110H, R110Q, L112V, L112I, K116Q, K116T, K116N, E117Q, E117H, E117N, D123H, D136Q, D136H, D136N, R139H, R139Q, K140N, K140Q, L141I, L141V, R143H, R143Q, Y145H, F148I, L149I, L149V, R150H, K152Q, K152T, K152N, L153I, L153V, K154Q, K154N, L155V, L155I, Y156H, E159Q, E159H, E159N, D165H, R166H, and R166Q.

Provided herein are modified EPO polypeptides containing two or more amino acid modifications corresponding to modifications at any two or more positions, where the amino acid position that is modified corresponds to a mature human EPO polypeptide having the sequence set forth in SEQ ID NO: 2 or 237 or is at a corresponding position in an allelic or species variant or other variant of a mature human EPO polypeptide, an EPO polypeptide having at least or at least about 60%, 70%, 75%, 80%, 85%, 90%, 91%, 92%, 93%, 94%, 95%, 96%, 97%, 98%, 99%, or more sequence identity to a mature human EPO polypeptide, or a fragment thereof that includes the recited two or more amino acid modifications and retains at least one activity of the full-length EPO or exhibits an EPO activity. For example, amino acid replacements at any two or more of the amino acid positions can include replacements of any of P2S, P2A, P3S, P3A, R4H, R4Q, L5I, L5V, C7S, C7V, C7A, C7I, C7T, D8Q, D8H, D8N, R10H, R10Q, L12V, L12I, E13Q, E13H, E13N, R14H, R14Q, Y15H, Y15I, L16I, L16V, L17I, L17V, E18Q, E18H, E18N, K20Q, K20T, K20N, E21Q, E21H, E21N, E23Q, E23H, E23N, C29S, C29V, C29A, C29I, C29T, E31Q, E31H, E31N, L35V, L35I, E37Q, E37H, E37N, P42S, P42A, D43Q, D43H, D43N, K45Q, K45T, K45N, F48I, F48V, Y49H, Y49I, W51S, W51H, K52Q, K52T, K52N, R53H, R53Q, M54V, M54I, E55Q, E55H, E55N, E62Q, E62H, E62N, W64S, W64H, L67I, L67V, L69V, L69I, L70I, L70V, E72Q, E72H, E72N, L75V, L75I, R76H, R76Q, L80V, L80I, L81I, L81V, P87S, P87A, W88S, W88H, E89Q, E89H, E89N, P90S, P90A, L91I, L91V, L93V, L93I, D96Q, D96H, D96N, K97Q, K97T, K97N, L102V, L102I, R103H, R103Q, L105I, L105V, L108I, L108V, L109I, L109V, R110H, R110Q, L112V, L112I, K116Q, K116T, K116N, E117Q, E117H, E117N, P121S, P121A, P122S, P122A, D123Q, D123H, D123N, P129S, P129A, L130V, L130I, R131H, R131Q, D136Q, D136H, D136N, F138I, F138V, R139H, R139Q, K140N, K140Q, L141I, L141V, F142I, F142V, R143H, R143Q, Y145H, Y145I, F148I, F148V, L149I, L149V, R150H, R150Q, K152Q, K152T, K152N, L153I, L153V, K154Q, K154T, K154N, L155V, L155I, Y156H, Y156I, E159Q, E159H, E159N, R162H, R162Q, D165Q, D165H, D165N, R166H, and R166Q.

Provided herein are any of the above modified EPO polypeptides above that are further modified at one or more positions corresponding to amino acid positions P2, P3, R4, L5, C7, D8, R10, L12, E13, R14, Y15, L16, L17, E18, K20, E21, E23, C29, E31, L35, E37, P42, D43, K45, F48, Y49, W51, K52, R53, M54, E55, E62, W64, L67, L69, L70, E72, L75, R76, L80, L81, P87, W88, E89, P90, L91, L93, D96, K97, L102, R103, L105, L108, L109, R110, L112, K116, E117, P121, P122, D123, P129, L130, R131, D136, F138, R139, K140, L141, F142, R143, Y145, F148, L149, R150, K152, L153, K154, L155, Y156, E159, R162, D165, and R166. For example, amino acid replacements at any one of the one or more further amino acid positions can include amino acid replacements of any of P2S, P2A, P3S, P3A, R4H, R4Q, L5I, L5V, C7S, C7V, C7A, C7I, C7T, D8Q, D8H, D8N, R10H, R10Q, L12V, L12I, E13Q, E13H, E13N, R14H, R14Q, Y15H, Y15I, L16I, L16V, L17I, L17V, E18Q, E18H, E18N, K20Q, K20T, K20N, E21Q, E21H, E21N, E23Q, E23H, E23N, C29S, C29V, C29A, C29I, C29T, E31Q, E31H, E31N, L35V, L35I, E37Q, E37H, E37N, P42S, P42A, D43Q, D43H, D43N, K45Q, K45T, K45N, F48I, F48V, Y49H, Y49I, W51S, W51H, K52Q, K52T, K52N, R53H, R53Q, M54V, M54I, E55Q, E55H, E55N, E62Q, E62H, E62N, W64S, W64H, L67I, L67V, L69V, L69I, L70I, L70V, E72Q, E72H, E72N, L75V, L75I, R76H, R76Q, L80V, L80I, L81I, L81V, P87S, P87A, W88S, W88H, E89Q, E89H, E89N, P90S, P90A, L91I, L91V, L93V, L93I, D96Q, D96H, D96N, K97Q, K97T, K97N, L102V, L102I, R103H, R103Q, L105I, L105V, L108I, L108V, L109I, L109V, R110H, R110Q, L112V, L112I, K116Q, K116T, K116N, E117Q, E117H, E117N, P121S, P121A, P122S, P122A, D123Q, D123H, D123N, P129S, P129A, L130V, L130I, R131H, R131Q, D136Q, D136H, D136N, F138I, F138V, R139H, R139Q, K140N, K140Q, L141I, L141V, F142I, F142V, R143H, R143Q, Y145H, Y145I, F148I, F148V, L149I, L149V, R150H, R150Q, K152Q, K152T, K152N, L153I, L153V, K154Q, K154T, K154N, L155V, L155I, Y156H, Y156I, E159Q, E159H, E159N, R162H, R162Q, D165Q, D165H, D165N and R166H.

Provided herein are modified EPO polypeptides or active fragments thereof that contain a modification corresponding to amino acid replacement of K20Q and/or R139H in a mature EPO polypeptide, having a sequence of amino acids set forth in SEQ ID NO:2 or 237, or in a corresponding residue in an allelic or species variant thereof or other variant thereof that has at least or at least about 60%, 70%, 75%, 80%, 85%, 90%, 91%, 92%, 93%, 94%, 95%, 96%, 97%, 98%, 99% or more sequence identity with the polypeptide having the sequence set forth in SEQ ID NO: 2 or 237, wherein if the polypeptide is an active fragment, the active fragment contains the modifications. In some examples, K20Q or R139H is the only modification. In other examples, one or more additional modifications at one or more amino acid positions, such as by amino acid replacement, deletion and/or insertion, also are incorporated into the modified EPO polypeptide. For example, the modification can be at one or more of amino acid positions 2, 3, 4, 5, 7, 8, 10, 12, 13, 14, 15, 16, 17, 18, 20, 21, 23, 29, 31, 35, 37, 42, 43, 45, 48, 49, 51, 52, 53, 54, 62, 64, 67, 69, 70, 72, 75, 76, 80, 81, 87, 88, 89, 90, 91, 93, 96, 97, 102, 103, 105, 108, 109, 110, 112, 116, 117, 121, 122, 123, 129, 130, 131, 136, 138, 139, 140, 141, 142, 143, 145, 148, 149, 150, 152, 153, 154, 155, 156, 159, 162, 165, and 166, wherein said amino acid positions reference the positions in a mature human EPO polypeptide having the sequence set forth in SEQ ID NO:2 or 237. The additional modifications at such positions can be amino acid replacements, such as P2S, P2A, P3S, P3A, R4H, R4Q, L5I, L5V, C7S, C7V, C7A, C7I, C7T, D8Q, D8H, D8N, R10H, R10Q, L12V, L12I, E13Q, E13H, E13N, R14H, R14Q, Y15H, Y15I, L16I, L16V, L17I, L17V, E18Q, E18H, E18N, K20Q, K20T, K20N, E21Q, E21H, E21N, E23Q, E23H, E23N, C29S, C29V, C29A, C29I, C29T, E31Q, E31H, E31N, L35V, L35I, E37Q, E37H, E37N, P42S, P42A, D43Q, D43H, D43N, K45Q, K45T, K45N, F48I, F48V, Y49H, Y49I, W51S, W51H, K52Q, K52T, K52N, R53H, R53Q, M54V, M54I, E55Q, E55H, E55N, E62Q, E62H, E62N, W64S, W64H, L67I, L67V, L69V, L69I, L70I, L70V, E72Q, E72H, E72N, L75V, L75I, R76H, R76Q, L80V, L80I, L81I, L81V, P87S, P87A, W88S, W88H, E89Q, E89H, E89N, P90S, P90A, L91I, L91V, L93V, L93I, D96Q, D96H, D96N, K97Q, K97T, K97N, L102V, L102I, R103H, R103Q, L105I, L105V, L108I, L108V, L109I, L109V, R110H, R110Q, L112V, L112I, K116Q, K116T, K116N, E117Q, E117H, E117N, P121S, P121A, P122S, P122A, D123Q, D123H, D123N, P129S, P129A, L130V, L130I, R131H, R131Q, D136Q, D136H, D136N, F138I, F138V, R139H, R139Q, K140N, K140Q, L141I, L141V, F142I, F142V, R143H, R143Q, Y145H, Y145I, F148I, F148V, L149I, L149V, R150H, R150Q, K152Q, K152T, K152N, L153I, L153V, K154Q, K154T, K154N, L155V, L155I, Y156H, Y156I, E159Q, E159H, E159N, R162H, R162Q, D165Q, D165H, D165N, R166H, and R166Q.

Examples of the modified EPO polypeptides provided herein include, but are not limited to, those that contain more than one mutation, such as R139H/R4H, R139H/L93I, R139H/K20Q, R139H/E159N, R139H/K52N, R139H/L153V, R139H/L93V, R139H/L80I, R139H/L93I, K20Q/L80I/R139H, K20Q/L93I/R139H, K20Q/L93V/R139H, R4H/K20Q/R139H/L80I, E159N/K20Q/R139H/L93I, K20Q/R139H/L153V, L153V/K20Q/R139H/L80I and E159N/K20Q/R139H/L80I.

Provided herein are modified EPO polypeptides that contain one or more additional amino acid modifications such as A30N, H32T, P87V, W88N and/or P90T. Any of the modified EPO polypeptides provided herein can contain additional amino acid modifications, such as A30N, H32T, P87V, W88N and/or P90T.

The modified EPO polypeptides provided herein can be glycosylated or de-glycosylated. A de-glycosylated EPO polypeptide can be produced in a prokaryotic host, such as *E. coli*. In some examples, the modified EPO polypeptide has one or more modifications that eliminates one, two, three or four native glycosylation sites or all glycosylation sites. The modifications can be at an O-glycoslyation site, such as S126, and/or at an N-glycoslyation site, such as N24, N38 and/or N83. For example, the modified EPO polypeptide can contain an one or more of the amino acid replacements selected from among N24H, N38H, N83H, N24K, N38K and N83K. Thus, provided herein are EPO polypeptides containing modifications N38H/R139H, N38H/R139H/R4H, N38H/R139H/L93I, N38H/R139H/K20Q, N38H/R139H/E159N, N38H/R139H/K52N, N38H/R139H/L153V, N38H/N83H/R139H, K20Q/N38H/N83H/R139H, N38H/N83H/R139H/L93V, N38H/N83H/R139H/L80I, N38H/N83H/R139H/L93I, K20Q/N38H/L80I/N83H/R139H, K20Q/N38H/N83H/L93I/R139H, K20Q/N38H/N83H/L93V/R139H, N24H/N38H/N83H/R139H/L80I, N24H/N38H/N83H/R139H/L93I, N24H/N38H/N83H/R139H/L93V, K20Q/N24H/N38H/N83H/R139H/L80I, K20Q/N24H/N38H/N83H/R139H/L93I, K20Q/N24H/N38H/N83H/R139H/L93V, R4H/K20Q/N24H/N38H/N83H/R139H/L80I, E159N/K20Q/N24H/N38H/N83H/R139H/L93I, K20Q/N24H/N38H/N83H/R139H/L153V, L153V/K20Q/N24H/N38H/N83H/R139H/L80I and E159N/K20Q/N24H/N38H/N83H/R139H/L80I.

The modified EPO polypeptides provided herein include precursor forms and mature forms, such as modification of a wild-type human EPO polypeptide having a sequence of amino acids set forth in SEQ ID NO: 1 (precursor form) or SEQ ID NO: 2 (mature form). Exemplary modified EPO polypeptides have a sequence of amino acids set forth in any of SEQ ID NOS: 3-201. It also is understood that amino acid modification of a EPO polypeptide can be in an allelic, species, or other variant of SEQ ID NO: 2 or 237, where the variant has 40%, 50%, 60%, 70%, 80%, 90%, 91%, 92%, 93%, 94%, 95%, 96%, 97%, 98%, or 99% sequence identity to the polypeptide set forth in SEQ ID NO: 2 or 237, excluding the modified positions. A modified EPO polypeptide can be a human polypeptide or a non-human polypeptide. Modified loci are identified with reference to the amino acid numbering of a known unmodified mature EPO polypeptide having a sequence of amino acids set forth in SEQ ID NO: 2 or 237. One of skill in the art can readily determine corresponding positions on a particular polypeptide, such as by alignment of unchanged residues. Furthermore, shortened or lengthened variants with insertions or deletions of amino acids, particularly at either terminus that retain an activity readily can be prepared and the loci for corresponding mutations identified. Exemplary EPO polypeptides, include but are not limited to, EPO polypeptides that are 160, 161, 162, 163, 164, 165 or 166 amino acids in length.

Modified EPO polypeptides provided herein include polypeptides modified at 1, 2, 3, 4, 5, 6, 7, 8, 9, 10, 11, 12, 13, 14, 15, 16, 17, 18, 19, 20 or more positions as compared to an unmodified EPO polypeptide. The modified EPO polypeptides provided herein exhibit increased protein stability compared to the unmodified EPO polypeptide. Provided herein are modified EPO polypeptides in which increased protein stability of the modified polypeptide is the result of modification to the primary sequence of the EPO polypeptide. The increased protein stability exhibited by a modified EPO polypeptide can be manifested as increased protease resistance. In some cases, increased protein stability of a modified EPO polypeptide can be due to increased resistance of the modified polypeptide to proteolysis in serum, blood, saliva, digestive fluids, or in vitro when exposed to one or more proteases. The increased resistance to proteolysis can be exhibited by the modified EPO polypeptide when it is administered intravenously, orally, nasally, pulmonarily, or is present in the digestive tract. Such modified EPO polypeptides exhibit increased resistance to proteolysis by one or more proteases compared to the unmodified EPO polypeptide. For example, the proteases can by any of pepsin, trypsin, chymotrypsin, elastase, aminopeptidase, gelatinase B, gelatinase A, α-chymotrypsin, carboxypeptidase, endoproteinase Arg-C, endoproteinase Asp-N, endoproteinase Glu-C, endoproteinase Lys-C, luminal pepsin, microvillar endopeptidase, dipeptidyl peptidase, enteropeptidase, hydrolase, NS3, factor Xa, Granzyme B, thrombin, plasmin, urokinase, tPA and PSA.

Modified EPO polypeptides provided herein can be naked polypeptides chains or can be post-translationally modified. Exemplary post-translational modifications include glycosylation, carboxylation, hydroxylation, hasylation, carbamylation, sulfation, phosphorylation, or conjugated to albumin or a polyethylene glycol (PEG) moiety. The modified EPO polypeptides provided herein can be further modified at one or more amino acid positions, where the modification contributes to altered immunogenicity, glycosylation, carboxylation, hydroxylation, hasylation, carbamylation, sulfation, phosphorylation, PEGylation or protease resistance of the modified EPO polypeptide. Exemplary amino acid modifications include replacement with natural amino acids, non-natural amino acids and combinations of natural and non-natural amino acids. Such modifications can increase the stability of the EPO polypeptide. Also provided herein are any of the above modified therapeutic polypeptides or EPO polypeptides, further containing one or more pseudo-wild type mutations. In one embodiment, the pseudo-wild-type mutations include, but are not limited to, one or more of insertions, deletions or replacements of the amino acid residue(s) of the unmodified therapeutic polypeptide or EPO polypeptide.

Typically, the modified EPO polypeptides provided herein exhibit increased protein stability compared to the unmodified EPO polypeptide and retain one or more activities of the unmodified EPO polypeptide. Provided herein are any of the above modified EPO polypeptides exhibiting increased activity compared to the unmodified polypeptides. Provided herein are any of the above modified EPO polypeptides exhibiting decreased activity compared to the unmodified polypeptides. Activity of EPO polypeptides can be assessed, for example, by measuring erythropoietic activity or tissue protective activity in vitro or in vivo. The results of such assays correlate with an in vivo activity and hence a biological activity. In some examples, the modified EPO polypeptide promotes erythropoiesis. In some examples, the modified EPO polypeptide attenuates or prevents tissue injury. In some examples, the modified EPO polypeptide promotes erythropoiesis and attenuates or prevents tissue injury.

Provided herein are any of the above modified therapeutic polypeptides or EPO polypeptides, in which the increased protein stability is manifested as an increased half-life in vivo or in vitro. In one example, the increased stability is manifested as an increased half-life when administered to a subject. In another example, the modified polypeptide has a half-life increased by at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more compared to the half-life of unmodified polypeptide. In yet another example, the modified polypeptide also has a half-life increased by at least 1.5 times, 2 times, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times and 1000 times, or more times when compared to the half-life of unmodified therapeutic polypeptides or EPO.

Provided herein are any of the above modified therapeutic polypeptides or EPO polypeptides that is a precursor polypeptide containing a signal peptide. In one example, the signal sequence is amino acids 1-27 of the sequence of amino acids for a precursor EPO molecule set forth in SEQ ID NO: 1. Provided herein are any of the above modified therapeutic polypeptides or EPO polypeptides that do not have a signal peptide. Modified therapeutic polypeptides or EPO polypeptides without a signal peptide are referred to herein as mature therapeutic polypeptides or EPO polypeptides. In some cases, the modified therapeutic polypeptides or EPO polypeptides provided herein are secreted. Such a secreted polypeptide has a signal sequence that is processed prior to secretion. Such secreted therapeutic polypeptides or EPO polypeptides can contain other post-translational modifications, such as for example, glycosylation, carboxylation, hydroxylation, sulfation or phosphorylation. In some examples, the C-terminal amino acid (e.g., R166) is removed or proteolytically cleaved. In other examples, the modified therapeutic polypeptides or EPO polypeptide further truncated at the C-terminus by 1, 2, 3, 4, 5, 6 or more amino acids.

Provided herein are collections (or libraries) of therapeutic polypeptides or modified EPO polypeptides containing two, three, four, five, 10, 50, 100, 500, 1000, $10^3$, $10^4$ or more modified therapeutic polypeptides or modified EPO polypeptides as described herein.

Provided herein are nucleic acid molecules containing a sequence of nucleotides encoding modified therapeutic polypeptides or EPO polypeptides as described herein. Provided herein are collections (or libraries) of nucleic acid molecules comprising a plurality of the molecules as described herein.

Provided herein are vectors containing the nucleic acid molecules encoding modified therapeutic polypeptides or EPO polypeptides as described herein. Exemplary vectors include, but are not limited to, a prokaryotic vector, a viral vector, or a eukaryotic vector. Exemplary viral vectors include adenovirus, adeno-associated-virus, retrovirus, herpes virus, vaccinia virus, lentivirus, poxvirus and cytomegalovirus vectors. In some examples, the nucleic acid in the vector is operably linked to a promoter, such as a viral promoter or a eukaryotic promoter. Such promoters can be constitutive promoters or inducible promoters. Provided herein are collections (or libraries) of such vectors containing two, three, four, five, 10, 50, 100, 500, 1000, $10^3$, $10^4$ or more vectors containing the nucleic acid molecules encoding modified therapeutic polypeptides or EPO polypeptides as described herein.

Provided herein are cells containing nucleic acid molecules encoding modified therapeutic polypeptides or EPO polypeptides as described herein. Provided herein are cells containing vectors that contain the nucleic acid molecules encoding modified therapeutic polypeptides or EPO polypeptides as described herein. Such cells can be prokaryotic or eukaryotic cells, and can express the modified therapeutic polypeptides or EPO polypeptides.

Provided herein are antibodies that are specific for a modified EPO polypeptide provided herein.

Provided herein are methods for expressing a modified therapeutic polypeptide or EPO polypeptide. Such methods can include the steps of: i) introducing a nucleic acid encoding a modified therapeutic polypeptide or EPO polypeptide or a vector containing a nucleic acid encoding a modified therapeutic polypeptide or EPO polypeptide into a cell, and ii) culturing the cell under conditions in which the encoded modified therapeutic polypeptides or EPO polypeptides is expressed. In one embodiment, cells are eukaryotic cells. In another embodiment, the cells are prokaryotic cells. In one embodiment, the modified therapeutic polypeptide or EPO polypeptide is post-translationally modified. In another method for expression of a modified therapeutic polypeptide or EPO polypeptide, a nucleic acid molecule encoding a modified therapeutic polypeptide or EPO or a vector containing a nucleic acid encoding a modified therapeutic polypeptide or EPO is introduced into a cell-free translation system, whereby the encoded modified therapeutic polypeptide or EPO polypeptide is expressed. In such expression methods above, the method can further include detection of the modified therapeutic polypeptide or EPO polypeptide.

Provided herein are non-human transgenic animals containing an exogenous nucleic acid encoding a modified therapeutic polypeptide or a modified EPO polypeptide. Exemplary non-human transgenic animals include pigs, goats, sheep, rabbits, rats and cows. Provided herein are methods of expressing modified polypeptides in non-human transgenic animals and detecting the expressed modified polypeptides. Modified polypeptides can be isolated from tissues or fluids of the non-human transgenic animals, such as in serum, milk or eggs. Such expressed modified polypeptides can be post-translationally modified. For example, the modified polypeptides can be glycosylated, carboxylated, hydroxylated, hasylated, carbamylated, sulfated, phosphorylated albuminated, or conjugated to a polyethylene glycol (PEG) moiety.

Provided herein are pharmaceutical compositions including any of the modified therapeutic polypeptides or EPO polypeptides described herein. In some examples, the modified EPO polypeptides are any of amino acids set forth in SEQ ID NOS: 3-201 and 247-272.

Provided herein are the pharmaceutical compositions formulated for local, systemic or topical administration. For example the pharmaceutical compositions provided herein can be formulated for oral, nasal, pulmonary, buccal, mucosal, transdermal, subcutaneous, intraduodenal, enteral, parenteral, intravenous or intramuscular administration. In a particular example, the pharmaceutical compositions are formulated for oral administration.

Provided herein are pharmaceutical compositions of a modified EPO polypeptide, where the polypeptide is modified by replacement of one or more amino acids in its primary structure to be resistant to a protease and the composition is formulated for oral administration. Provided herein are pharmaceutical compositions of a modified EPO polypeptide, in which the modified EPO polypeptide comprises at least 1, 2, 3, 4, 5, 6, 7, 8, 9, 10, 11, 12, 13, 14, 15, 16, 17, 18, 19, or 20 or more modifications. Provided herein are pharmaceutical compositions of a modified EPO polypeptide, in which only the primary sequence of the polypeptide is modified, and the polypeptide exhibits increased protein stability. Such pharmaceutical compositions of a modified EPO polypeptide can include removal of proteolytic digestion sites.

Provided herein are pharmaceutical compositions of an EPO polypeptide, in which increased protein stability is manifested as increased resistance to proteolysis. In some instances, the modified EPO polypeptide in the pharmaceutical formulation exhibits increased protein stability in the gastrointestinal tract under conditions selected from exposure to saliva, exposure to proteases in the gastrointestinal tract and exposure to low pH conditions compared to an unmodified EPO polypeptide. In some instances, the modified EPO polypeptide exhibits increased resistance to proteolysis in serum, blood, saliva, digestive fluids or in vitro when exposed to one or more proteases. Proteases include, but are not limited to one or more of a luminal pepsin, trypsin, chymotrypsin, elastase, aminopeptidase, gelatinase B, gelatinase A, α-chymotrypsin, carboxypeptidase, endoproteinase Arg-C, endoproteinase Asp-N, endoproteinase Glu-C, endoproteinase Lys-C, luminal pepsin, microvillar endopeptidase, dipeptidyl peptidase, enteropeptidase, hydrolase, NS3, factor Xa, Granzyme B, thrombin, plasmin, urokinase, tPA and PSA. In some instances, the modified EPO polypeptide in the pharmaceutical formulation exhibits increased protease resistance when it is administered orally or is present in the digestive tract.

Provided herein are pharmaceutical compositions of a modified EPO polypeptide that is a naked EPO polypeptide, or a post-translationally modified polypeptide, such as a modified EPO polypeptide that is glycosylated, carboxylated, hydroxylated, hasylated, carbamylated, sulfated, phosphorylated albuminated, or conjugated to a polyethylene glycol (PEG) moiety.

Provided herein are pharmaceutical compositions of a modified EPO polypeptide that further contain one or more additional amino acid modifications that contribute to altered immunogenicity, glycosylation, carboxylation, hydroxylation, hasylation, carbamylation, sulfation, phosphorylation, PEGylation or protease resistance of the modified EPO polypeptide. Provided herein are pharmaceutical compositions of a modified EPO polypeptide, in which one or more additional amino acid modifications are selected from natural amino acids, non-natural amino acids or a combination of natural and non-natural amino acids. Provided herein are pharmaceutical compositions of a modified EPO polypeptide, in which one or more additional amino acid modifications increase stability of the polypeptide.

Provided herein are pharmaceutical compositions of a modified EPO polypeptide that further contain one or more pseudo-wild type mutations, including insertions, deletions, and replacements of the amino acid residue(s) of the unmodified polypeptide.

Provided herein are pharmaceutical compositions of a modified EPO polypeptide that exhibits increased protein stability compared to the unmodified therapeutic polypeptide or EPO polypeptide and retains one or more activities of the unmodified therapeutic polypeptide or EPO polypeptide. Provided herein are pharmaceutical compositions of a modified EPO polypeptide that promote proliferation of red blood cells or inhibit tissue damage.

Provided herein are pharmaceutical compositions of a modified EPO polypeptide in which increased protein stability of the EPO polypeptide leads to increased protein half-life of the EPO polypeptide in vivo or in vitro. Increased protein stability can lead to increased protein half-life following administration to a subject. Protein half-life can be increased in an amount of at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more compared to the half-life of the unmodified EPO polypeptide. Alternatively, protein half-life can be increased in an amount of at least 6 times, at least 7 times, at least 8 times, at least 9 times, at least 10 times, at least 20 times, at least 30 times, at least 40 times, at least 50 times, at least 60 times, at least 70 times, at least 80 times, at least 90 times, at least 100 times, at least 200 times, at least 300 times, at least 400 times, at least 500 times, at least 600 times, at least 700 times, at least 800 times, at least 900 times or at least 1000 times or more compared to the unmodified EPO polypeptide. In one example, the modified EPO polypeptide in the pharmaceutical composition exhibits increased protein half-life or bioavailability in the gastrointestinal tract.

Provided herein are pharmaceutical compositions of a modified therapeutic polypeptide or modified EPO polypeptide containing composition that also contains a pharmaceutically acceptable carrier, diluent or excipient. Provided herein are pharmaceutical compositions of a modified therapeutic polypeptide or modified EPO polypeptide, in which the excipient is a binding agent, a filler, a lubricant, a disintegrant or a wetting agent. In a particular example, the excipient is anhydrous crystalline maltose or magnesium stearate. Provided herein are pharmaceutical compositions of a modified therapeutic polypeptide or modified EPO polypeptide, in which the additive is a suspending agent, an emulsifying agent, a non-aqueous vehicle, or a preservative.

Provided herein are pharmaceutical compositions of a modified therapeutic polypeptide or modified EPO polypeptide, in which the pharmaceutical composition is formulated for administration in a form selected from among liquid, a pill, a tablet, a lozenge, and a capsule. In particular pharmaceutical compositions, the modified therapeutic polypeptide or modified EPO polypeptide is delivered orally to the gastrointestinal tract. Typically, such oral formulations are ingested and delivered to the lower gastrointestinal tract. Exemplary pill, tablet or capsule pharmaceutical compositions include an enteric coating. In other pharmaceutical compositions, the pill or tablet is chewable or dissolves when exposed to saliva on the tongue or in the mouth. In other pharmaceutical compositions the capsule is in liquid form. Exemplary liquid pharmaceutical compositions include a solution, syrup or a suspension. In some pharmaceutical compositions, the modified therapeutic polypeptide or modified EPO polypeptide is formulated for controlled-release.

Provided herein are pharmaceutical compositions prepared without the use of protease inhibitors, such as a Bowman-Birk inhibitor, a conjugated Bowman-Birk inhibitor, aprotinin and camostat. Provided herein are pharmaceutical compositions formulated without protective compounds.

Provided herein are pharmaceutical compositions of nucleic acid molecules encoding any of the modified therapeutic polypeptide or modified EPO polypeptides described herein or a vector containing a nucleic acid molecule encoding any of the modified therapeutic polypeptide or modified EPO polypeptides described herein and a pharmaceutically acceptable excipient.

Provided herein are methods of treating a subject that has a disease or condition that is amenable to treatment with the therapeutic polypeptides. Provided herein are methods of treating a subject exhibiting symptoms of or having EPO-mediated disease or condition by administering any of the pharmaceutical compositions described herein. For example, such pharmaceutical compositions can contain modified EPO polypeptides having a sequence of amino acids set forth in any one of SEQ ID NOS: 3-201 and 247-272. In some examples, the EPO-mediated disease or condition is treated by administration of an active EPO polypeptide. Typically, treatment with the pharmaceutical composition ameliorates or alleviates the symptoms associated with the disease or condition. Provided herein are methods of monitoring the subject for changes in the symptoms associated with the EPO-mediated disease or condition.

In one example, the EPO-mediated disease or condition includes, but is not limited to anemia, such as an anemia that is caused by renal failure, AIDS, malignancy and chronic inflammation. In such an example where the disease to be treated is anemia, the disease or condition can be congenital or acquired. In cases where increased red blood cell proliferation is desired (e.g., for anemia), modified EPO polypeptides that promote cell proliferation are administered.

In one example, the EPO-mediated disease or condition includes, but is not limited to diseases or conditions which utilize the tissue protective activities of an EPO polypeptide for protection against an injury or restoration of function following the injury to responsive mammalian cells, tissues or organs. Examples of such diseases or conditions include, but are not limited to, a seizure disorder, multiple sclerosis, stroke, hypotension, cardiac arrest, ischemia, myocardial infarction, inflammation, age-related loss of cognitive function, radiation damage, cerebral palsy, a neurodegenerative disease, Alzheimer's disease, Parkinson's disease, Leigh disease, AIDS dementia, memory loss, amyotrophic lateral sclerosis, alcoholism, mood disorder, anxiety disorder, attention deficit disorder, schizophrenia, autism, Creutzfeld-Jakob disease, brain or spinal cord trauma or ischemia, heart-lung bypass, chronic head failure, macular degeneration, toxin induced neuropathy, diabetic neuropathy, diabetic retinopathy, glaucoma, retinal ischemia, or retinal trauma.

Provided herein are methods of treating a subject exhibiting symptoms of or having EPO-mediated disease or condition by administering modified EPO polypeptides with additional factors.

Provided herein are uses for compositions of modified therapeutic polypeptides and modified EPO polypeptides. Such uses include treating a disease or condition that is amenable to treatment with the therapeutic polypeptide or EPO polypeptide, and formulating a medicament for treatment of a disease or condition that is amenable to treatment with the therapeutic polypeptide or EPO polypeptide.

Provided herein are combinations of one or more modified EPO polypeptides with one or more additional factors for the treatment of an EPO-mediated disease or condition.

Provided herein are articles of manufacture including, but not limited to, packaging material and a pharmaceutical composition of a modified EPO polypeptide described herein contained within the packaging material. In a particular embodiment, the pharmaceutical composition packaged within the article of manufacture is effective for treatment of an EPO-mediated disease or disorder, and the packaging material includes a label that indicates that the modified EPO is used for treatment of an EPO-mediated disease or disorder.

Provided herein are kits including a pharmaceutical composition of a modified therapeutic polypeptide or EPO polypeptide as described herein, a device for administration of the modified therapeutic polypeptide or EPO polypeptide and optionally instructions for administration. Provided herein are kits including combinations of one or more modified EPO polypeptides with one or more additional factors for the treatment of an EPO-mediated disease or condition and optionally instructions for administration.

Provided herein are methods for producing a modified EPO polypeptide, having an evolved predetermined property, wherein the evolved predetermined property is increased protein stability manifested as increased protease resistance. In such examples, the increased protein stability of the EPO polypeptide that is evolved is due to amino acid modifications, such that only the primary sequence of the polypeptide is modified to confer the property. In some examples, the methods include modifications of one or more additional amino acids that contribute to altered immunogenicity, glycosylation, carboxylation, hydroxylation, hasylation, carbamylation, sulfation, phosphorylation or PEGylation of the modified EPO polypeptide.

Provided herein are methods for increasing the protease resistance of a non-glycosylated or deglycosylated therapeutic polypeptide that is glycosylated in its native form by modifying protease sensitive sites that are exposed in the non-glycosylated or de-glycosylated therapeutic polypeptide compared to the fully glycosylated therapeutic polypeptide.

BRIEF DESCRIPTION OF THE FIGURES

FIG. 1 displays two views (A and B) of the structure of erythropoietin in ribbon representation. The three N-linked glycosylation sites, N24, N38 and N83 and representative corresponding residues selected for modification for protease resistance (K20Q, R139H and L80I, respectively) are in space filling representation. Additional residues selected for protease resistance are also shown in space filling representation (e.g., R4H, L153V, E159N).

DETAILED DESCRIPTION

Outline
A. Definitions
B. Erythropoietin (EPO)
C. Exemplary methods for modifying EPO polypeptides and other modified therapeutic polypeptides 1. Non-Restricted Rational Mutagenesis One-Dimensional (1D)-Scanning
2. Two dimensional (2D) rational scanning (restricted rational mutagenesis)
   a. Identifying in-silico HITs
   b. Identifying replacing amino acids
   c. Construction of mutant proteins and biological assays
3. Three dimensional (3D) scanning
   a. Homology
   b. 3D-scanning (structural homology) methods
4. Super-LEADs and additive directional mutagenesis (ADM)
5. Multi-overlapped primer extensions D. Modified EPO polypeptides exhibiting increased protein stability
1. Protease resistance
   a. Serine Proteases
   b. Matrix Metalloproteinases
   c. Increased resistance to proteolysis by removal of proteolytic sites
   d. Modified EPO polypeptides exhibiting increased protease resistance
   e. Assessment of EPO variants with increased resistance to proteolysis
2. Super-LEADs
3. Other EPO modifications
   a. Immunogenicity
   b. Glycosylation
   c. Additional modifications E. Modifications for increased resistance to proteolysis in non-glycosylated or partially glycosylated forms of glycosylated therapeutic polypeptides
1. Modification of protease sensitive sites
2. Production of non-glycosylated modified therapeutic polypeptides
3. Exemplary glycosylated therapeutic polypeptides for modification
4. Other modifications
   a. Modifications to increase solubility
5. Methods for increasing protease resistance of a partially glycosylated or non-glycosylated therapeutic polypeptide by targeted modification
   a. Targeted modification of protease sensitive sites exposed by deglycosylation F. Production of EPO polypeptides and other modified therapeutic polypeptides
1. Expression systems
   a. Prokaryotic expression
   b. Yeast
   c. Insects and insect cells
   d. Mammalian cells
   e. Plants
2. Purification
3. Fusion proteins
4. Polypeptide modification
5. Nucleotide sequences G. Assessing modified EPO polypeptide properties and activities
1. In vitro assays
2. Non-human animal models
3. Clinical Assays H. Formulation/Packaging/Administration
1. Administration of modified EPO polypeptides and other modified therapeutic polypeptides
2. Administration of nucleic acids encoding modified EPO polypeptides or other modified therapeutic polypeptides (gene therapy)

I. Therapeutic Uses
1. Anemias
2. Tissue protective therapies

J. Diagnostic Uses

K. Combination Therapies

L. Articles of manufacture and kits

M. Antibodies to modified EPO polypeptides and other modified therapeutic polypeptides

N. EXAMPLES

A. Definitions

Unless defined otherwise, all technical and scientific terms used herein have the same meaning as is commonly understood by one of skill in the art to which the invention(s) belong. All patents, patent applications, published applications and publications, GenBank sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, a "therapeutic polypeptide" is a polypeptide that is administered to an animal, such as a human subject, for treatment of a disease or disorder. Therapeutic polypeptides are known to those of skill in the art, and typically are polypeptides that have activity in vivo, such as cytokines (e.g., erythropoietin (EPO)), and that can be exploited to treat a disease or disorder (i.e., ameliorate the symptoms of the disease or disorder). Such polypeptides can be prepared by any methods, and hence, include, but are not limited to, a recombinantly produced polypeptides, synthetically produced polypeptides, therapeutic polypeptides extracted from cells or tissues and other sources. As isolated from any sources or as produced, mature therapeutic polypeptides can be heterogeneous in length. Heterogeneity of therapeutic polypeptides can differ depending on the source of the therapeutic polypeptides. Hence reference to therapeutic polypeptides refers to the heterogeneous population as produced or isolated. When a homogeneous preparation is intended, it will be so-stated. References to therapeutic polypeptides herein are to their monomeric, dimeric or other multimeric forms, as appropriate.

Human therapeutic polypeptides include allelic variant isoforms, synthetic molecules produced from encoding nucleic acid molecules, proteins isolated from human tissue and cells, synthetic proteins, and modified forms thereof. Exemplary unmodified mature human therapeutic polypeptides include, but are not limited to, unmodified and native (i.e., wild-type) therapeutic polypeptides and the unmodified and native precursor therapeutic polypeptides that include a signal peptide and/or propeptide, and polymorphic native therapeutic polypeptides. Other exemplary human therapeutic polypeptides are those that are truncated at the N- or C-terminus.

Reference to therapeutic polypeptides also includes allelic or species variants of therapeutic polypeptides, and truncated forms or fragments thereof and forms that contain modifications in addition to those that increase protease resistance. Therapeutic polypeptides include homologous polypeptides from different species including, but not limited to animals, including humans and non-human species, such as other mammals. As with human therapeutic polypeptides, non-human therapeutic polypeptides also include heterogeneous lengths or fragments or portions of therapeutic polypeptides that are of sufficient length or include appropriate regions to retain at least one activity of full-length mature polypeptide.

Non-human therapeutic polypeptides include therapeutic polypeptides, allelic variant isoforms, synthetic molecules prepared from nucleic acids, protein isolated from non-human tissue and cells, and modified forms thereof. Therapeutic polypeptides of non-human origin include, but are not limited to, bovine, ovine, porcine, equine, murine, leporine, canine, feline, avian and other primate, such as chimpanzee and macaque, therapeutic polypeptides.

As used herein, "native therapeutic polypeptide" refers to a therapeutic polypeptide encoded by a naturally occurring gene that is present in an organism in nature, including a human or other animal. Included among native therapeutic polypeptides are the encoded precursor polypeptide, fragments thereof, and processed forms thereof, such as a mature form lacking the signal peptide as well as any pre- or post-translationally processed or modified form thereof. Also included among native therapeutic polypeptides are those that are post-translationally modified, including, but not limited to, modification by glycosylation, carboxylation, hydroxylation, hasylation, carbamylation, sulfation, and phosphorylation.

As used herein, non-glycosylated polypeptide is a polypeptide that has no glycosylation (i.e., does not contain carbohydrate moieties attached to glycosylation sites in the protein). The non-glycosylated polypeptide is produced by virtue of its expression in a host, such as prokaryotic host, that does not glycosylate the polypeptide, or by elimination of all glycosylation sites (e.g., mutation of the glycosylation sites).

As used herein, a glycosylation site refers to an amino position in a polypeptide to which a carbohydrate moiety can be attached. Typically, a glycosylated protein contains one or more amino acid residues, such as asparagine or serine, for the attachment of the carbohydrate moieties.

As used herein, a fully glycosylated polypeptide is a polypeptide that is glycosylated at all native glycosylation sites in the polypeptide.

As used herein, a deglycosylated polypeptide has reduced glycosylation compared to the native glycosylated protein because it has fewer carbohydrate moieties attached to the polypeptide, such as by virtue of fewer up to all glycosylation sites removed by mutation. Deglycosylated polypeptides also include polypeptides that have one or more carbohydrate moieties removed or partially removed by chemical or enzymatic cleavage.

As used herein, a native glycosylation site refers to an amino position, which is attached to a carbohydrate moiety, in a native polypeptide when the native polypeptide is produced in nature.

As used herein, "native polypeptide" refers to a polypeptide encoded by a naturally occurring gene that is present in an organism in nature, including a human or other animal.

As used herein, the phrase "produced under the same conditions" refers to the production of two or more polypeptides using the same production method for generating each polypeptide.

As used herein, an "erythropoietin" polypeptide (also referred to herein as EPO) refers to any erythropoietin polypeptide, including but not limited to, a recombinantly produced polypeptide, a synthetically produced polypeptide, a native EPO polypeptide, and a erythropoietin polypeptide extracted from cells as tissues including, but not limited to, kidneys, liver, urine, and blood. Alternative names that are used interchangeably for erythropoietin include epoietin. Abbreviations for erythropoietin include EPO, hEPO (human erythropoietin), and rhuEPO (recombinant human erythropoietin). Erythropoietin includes related polypeptides from different species including, but not limited to animals of human and non-human origin. Human erythropoietin (hEPO) includes erythropoietin, allelic variant isoforms, synthetic molecules from nucleic acids, protein isolated from human tissue and cells, and modified forms thereof. Exemplary unmodified mature human erythropoietin polypeptides include, but are not limited to, unmodified and wild-type native erythropoietin polypeptides (such as the polypeptide containing a sequence set forth in SEQ ID NO: 2 or 237) and the unmodified and wild-type precursor erythropoietin polypeptide that includes a signal peptide (e.g., the precursor EPO polypeptide that has the sequence set forth in SEQ ID NO: 1). One of skill in the art would recognize that the referenced positions of the mature erythropoietin polypeptide (SEQ ID NO: 2) differ by 27 amino acid residues when compared to the precursor EPO polypeptide SEQ ID NO: 1, which is the erythropoietin polypeptide containing the signal peptide sequence. Thus, the first amino acid residue of SEQ ID NO: 2 "corresponds to" the twenty-eighth ($28^{th}$) amino acid residue of SEQ ID NO: 1. The term "erythropoietin" also encompasses an erythropoietin polypeptide produced from a mature EPO polypeptide (SEQ ID NO: 2) by proteolytic cleavage of the C-terminal Arginine amino acid residue or a recombinant EPO polypeptide where the C-terminal arginine has been removed (e.g., as set forth in SEQ ID NOS: 236 (precursor) and 237 (mature)). The EPO polypeptides provided herein can be further modified, such as by chemical modification, or post-translational modification. Such modifications include, but are not limited to, pegylation, albumination, glycosylation, farnysylation, carboxylation, hydroxylation, hasylation, carbamylation, sulfation, phosphorylation, and other polypeptide modifications known in the art. The EPO polypeptides provided herein can be further modified by modification of the primary amino acid sequence, by deletion, addition, or substitution of one or more amino acids.

Erythropoietin includes erythropoietin from any species (as used herein, species variant), including human and non-human species. EPO polypeptides of non-human origin include, but are not limited to, murine, canine, feline, leporine, avian, bovine, ovine, porcine, equine, piscine, ranine, and other primate erythropoietin polypeptides. Exemplary EPO polypeptides of non-human origin include, for example, rhesus macaque (*Macaca mulatta*, e.g., SEQ ID NO: 202), mouse (*Mus musculus*, e.g., SEQ ID NO: 203), rat (*Rattus norvegicus*, e.g., SEQ ID NO: 204), pig (*Sus scrofa*, e.g., SEQ ID NO: 205), dog (*Canis familiaris*, e.g., SEQ ID NO: 206), cat (*Felis catus*, e.g., SEQ ID NO: 207), rabbit (*Oryctolagus cuniculus*, e.g., SEQ ID NO: 208), bull (*Bos taurus*, e.g., SEQ ID NO: 209), horse (*Equus caballus*, e.g., SEQ ID NO: 210), sheep (*Ovis aries*, e.g., SEQ ID NO: 211), chimpanzee (Pan troglodytes, e.g., SEQ ID NO: 212), zebrafish (*Danio rerio*, e.g., SEQ ID NO: 213), Japanese pufferfish (*Takifugu rubripes*, e.g., SEQ ID NO: 214), orangutan (*Pongo pygmaeus*, e.g., SEQ ID NO: 225), gorilla (*Gorilla gorilla*, e.g., SEQ ID NO: 226) among others (e.g., SEQ ID NOS: 215-224). Typically, species variants of a human EPO polypeptide have at least 40%, 50%, 60%, 70%, 80%, 90%, 91%, 92%, 93%, 94%, 95%, 96%, 97%, 98%, 99% or greater amino acid identity compared to the human EPO polypeptide.

Human and non-human EPO polypeptides include EPO polypeptides, allelic variant isoforms, tissue-specific isoforms and allelic variants thereof, synthetic variants with one more amino acid mutations, replacements, deletions, insertions, or additions, synthetic molecules prepared by translation of nucleic acids, proteins isolated from human and non-human tissue and cells, chimeric EPO polypeptides and modified forms thereof. Human and non-human EPO also include fragments or portions of EPO that are of sufficient length or include appropriate regions to retain at least one activity of the full-length mature polypeptide. In addition, as used herein, fragments or portions of modified EPO polypeptides provided also comprise one or more of the amino acid modifications set forth herein (e.g., amino acid modifications set forth in Table 3).

As used herein, "mature erythropoietin" refers to an EPO polypeptide that lacks a signal sequence. Typically, a signal sequence targets a protein for secretion via the endoplasmic reticulum (ER)-golgi pathway and is cleaved following insertion into the ER during translation. Thus, a mature EPO polypeptide is typically a secreted protein. In one example, a mature human EPO polypeptide is set forth in SEQ ID NO: 2. The amino acid sequence set forth in SEQ ID NO: 2 differs from that of the precursor polypeptide set forth in SEQ ID NO: 1 in that SEQ ID NO: 2 is lacking the signal sequence, which includes residues 1-28 of SEQ ID NO: 1.

As used herein, "native erythropoietin" refers to an EPO polypeptide encoded by a naturally occurring EPO gene that is present in an organism in nature, including a human or other animal. Included among native EPO polypeptides are the encoded precursor polypeptide, fragments thereof, and processed forms thereof, such as a mature form lacking the signal peptide as well as any pre- or post-translationally processed or modified form thereof. For example, humans express EPO. Exemplary native human EPO sequences are set forth in SEQ ID NO: 1 (precursor EPO with a signal peptide) and SEQ ID NO: 2 (mature EPO lacking a signal peptide). Also included among native EPO polypeptides are those that are post-translationally modified, including, but not limited to, modification by glycosylation, carboxylation, hydroxylation, hasylation, carbamylation, sulfation, and phosphorylation. Native EPO polypeptides also include those that have been proteolytically cleaved at R166 of SEQ ID NO: 2. Other animals produce native EPO, and include, but are not limited to, primates, mice, rats, pigs, dogs, cats, rabbits, chickens, cows, sheep, frogs, and fish. Exemplary native EPO sequences from other animals are provided in SEQ ID NOS: 202-226.

As used herein, a "protease-resistant polypeptide" is a protein that contains one or more modifications in its primary sequence of amino acids compared to a native or wild-type polypeptide and exhibits increased resistance to proteolysis compared to the native or wild-type polypeptide without the one or more amino acid modifications.

As used herein, a polypeptide modified to be protease resistant by changes in primary structure refers to a polypeptide that has been modified at one or more amino acid residues in the primary sequence of the polypeptide, which confers protease resistance. Among these are changes that do not result in changes in post-translational modification at that site.

Increased resistance to proteases can be assessed by testing for activity following exposure to particular proteases present in the gastrointestinal tract and/or serum. Typically the increase in protease resistance is at least about 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more compared to the same polypeptide, absent the changes in amino acid sequence that confer the resistance. In other embodiments, the resistance to proteases of the variant polypeptides for use in oral formulations provided herein is increased by an amount of at least, 2 time, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, or more, compared to the same polypeptide, absent the changes in amino acid sequence that confer the resistance.

As used herein, "resistance to proteolysis" refers to any amount of decreased cleavage of polypeptide by a proteolytic agent, such as a protease. This can be achieved by modifying particular amino acid residues in a polypeptide that are susceptible to cleavage by a particular protease to render the polypeptide less susceptible to cleavage compared to cleavage of the polypeptide without the modification, by the same protease under the same conditions. A modified polypeptide that exhibits increased resistance to proteolysis exhibits, for example, 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more resistance to proteolysis compared to the same polypeptide, absent the amino acid modification(s).

As used herein, "proteases," "proteinases" or "peptidases" are interchangeably used to refer to enzymes that catalyze the hydrolysis of covalent peptide bonds. Proteases include, for example, serine proteases and matrix metalloproteinases. Serine protease or serine endopeptidases constitute a class of peptidases, which are characterized by the presence of a serine residue in the active center of the enzyme. Serine proteases participate in a wide range of functions in the body, including blood clotting, inflammation as well as digestive enzymes in prokaryotes and eukaryotes. The mechanism of cleavage by "serine proteases," is based on nucleophilic attack of a targeted peptide bond by a serine. Cysteine, threonine, or water molecules associated with aspartate or metals also can play this role. Aligned side chains of serine, histidine, and aspartate form a catalytic triad common to most serine proteases. The active site of serine proteases is shaped as a cleft where the polypeptide substrate binds. Amino acid residues are labeled from N to C termini of a polypeptide substrate (Pi, . . . , P3, P2, P1, P1', P2', P3', . . . , Pj). The respective binding sub-sites are labeled (Si, . . . , S3, S2, S1, S1', S2', S3', . . . , Sj). The cleavage is catalyzed between P1 and P1'.

As used herein, a matrix metalloproteinases (MMP) refers to any of a family of metal-dependent, such as $Zn^{2+}$-dependent, endopeptidases that degrade components of the extracellular matrix (ECM). MMPs include four classes: collagenases, stromelysin, membrane-type metalloproteinases, and gelatinases. Proteolytic activities of MMPs and plasminogen activators, and their inhibitors, are important for maintaining the integrity of the ECM. Cell-ECM interactions influence and mediate a wide range of processes including proliferation, differentiation, adhesion, and migration of a variety of cell types. MMPs also process a number of cell-surface cytokines, receptors and other soluble proteins and are involved in tissue remodeling processes such as wound healing, pregnancy and angiogenesis. Under physiological conditions in vivo, MMPs are synthesized as inactive precursors (zymogens) and are cleaved to produce an active form. Additionally, the enzymes are specifically regulated by endogenous inhibitors called tissue inhibitors of matrix metalloproteinases (TIMPs).

As used herein, corresponding residues refer to residues compared among or between two polypeptides that are allelic or species variants or other isoforms. One of skill in the art can readily identify residues that correspond between or among such polypeptides. For example, by aligning the sequences of EPO polypeptides, one of skill in the art can identify corresponding residues, using conserved and identical amino acid residues as guides. For example, A1 of SEQ ID NO: 2 (mature erythropoietin) corresponds to A28 of SEQ ID NO: 1 (precursor erythropoietin with a signal peptide sequence). In other instances, corresponding regions can be identified. One skilled in the art also can employ conserved amino acid residues as guides to find corresponding amino acid residues between and among human and non-human sequences. For example, residue P148 in the precursor human EPO of SEQ ID NO: 1 (residue P121 of mature human EPO of SEQ ID NO: 2) corresponds to residue P147 in the precursor mouse EPO of SEQ ID NO: 203.

As used herein, an "active portion or fragment" of an erythropoietin (EPO) polypeptide or other therapeutic polypeptide refers to a portion of the polypeptide that includes at least one modification provided herein and exhibits an activity, such as one or more activities of a full-length polypeptide or possesses another activity. For example, for an EPO polypeptide, such activities include, but are not limited to, erythropoietic or tissue protective activity. Activity can be any percentage of activity (more or less) of the full-length polypeptide, including but not limited to, 1% of the activity, 2%, 3%, 4%, 5%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more activity compared to the full polypeptide. Such activities can be empirically determined. Assays to determine function or activity of modified forms of EPO polypeptides or other modified therapeutic polypeptides include those known to those of skill in the art, and exemplary assays are included herein. Assays for an EPO polypeptide include, for example, but are not limited to, erythrocyte proliferation assays, cell survival assays, or clinical assays to measure a therapeutic benefit. Activity also includes activities possessed by a fragment or modified form of an EPO polypeptide or other modified therapeutic polypeptide that are not possessed by the full length polypeptide or unmodified EPO polypeptide.

As used herein, "unmodified target protein," "unmodified protein," "unmodified polypeptide," "unmodified EPO," "unmodified therapeutic polypeptide" and grammatical variations thereof refer to a starting polypeptide that is selected for modification as provided herein. The starting target polypeptide can be a naturally-occurring, wild-type form of a polypeptide. In addition, the starting target polypeptide can be altered or mutated, such that it differs from a native wild type isoform but is nonetheless referred to herein as a starting unmodified target protein relative to the subsequently modified polypeptides produced herein. Thus, existing proteins known in the art that have been modified to have a desired increase or decrease in a particular activity or property compared to an unmodified reference protein can be selected and used as the starting unmodified target protein. For example, a protein that has been modified from its native form by one or more single amino acid changes and possesses either an increase or decrease in a desired property, such as reduced immunogenicity (see e.g., U.S. Patent Publication Nos. 2004-0063917, 2005-0220800, 2006-035322, and 2006-0073563) or a change in an amino acid residue or residues to alter glycosylation, can be a target protein, referred to herein as unmodified, for further modification of either the same or a different property. Exemplary modified EPO polypeptides known in the art include any EPO polypeptide described in, for example, U.S. Pat. Nos. 4,703,008, 4,835, 260, 5,457,089, 5,614,184, 5,856,298, 6,831,060, 6,555,343, 6,831,060, and 7,041,794; U.S. Patent Publication Nos. 2004-0063917, 2005-0107591, 2005-0176627, 2006-029094, and 2006-0008872; and International Patent Publication Nos. WO8603520, EP0640619, WO04003176, EP1228214, WO05103076, WO9424160 WO9012874.

Existing proteins known in the art that previously have been modified to have a desired alteration, such as an increase or decrease, in a particular biological activity or property compared to an unmodified or reference protein can be selected and used as provided herein for identification of structurally homologous loci on other structurally homologous target proteins. For example, a protein that has been modified by one or more single amino acid changes and possesses either an increase or decrease in a desired property or activity, such as for example resistance to proteolysis, can be utilized with the methods provided herein to identify on structurally homologous target proteins, corresponding structurally homologous loci that can be replaced with suitable replacing amino acids and tested for either an increase or decrease in the desired activity.

As used herein, an "activity" or a "functional activity" of an EPO polypeptide or other therapeutic polypeptide refers to any activity exhibited by the polypeptide. Such activities can be empirically determined. For an EPO polypeptide, such activities include, but are not limited to, erythropoietic or tissue protective activity. Activity can be assessed in vitro or in vivo using recognized assays. For example, for an EPO polypeptide, activities can be assessed by measuring erythrocyte proliferation in vitro or in vivo. The results of such assays that indicate that a polypeptide exhibits an activity can be correlated to activity of the polypeptide in vivo, in which in vivo activity can be referred to as therapeutic activity, or biological activity. Activity of a modified polypeptide can be any level of percentage of activity of the unmodified polypeptide, including but not limited to, 1% of the activity, 2%, 3%, 4%, 5%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more of activity compared to the unmodified polypeptide. Assays to determine functionality or activity of modified forms of EPO are known to those of skill in the art. Exemplary assays to assess the activity of an EPO polypeptide include erythropoietic assays that measure erythrocyte cell proliferation and are described in the Examples.

As used herein. "therapeutic activity" refers to the in vivo activity of a therapeutic polypeptide. Generally, the therapeutic activity is the activity that is used to treat a disease or condition. Therapeutic activity of a modified polypeptide can be any level of percentage of therapeutic activity of the unmodified polypeptide, including but not limited to, 1% of the activity, 2%, 3%, 4%, 5%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more of therapeutic activity compared to the unmodified polypeptide.

As used herein, the recitation the glycosylation is required for therapeutic activity" or "important for therapeutic activity" means that the glycosylated form of the polypeptide has greater therapeutic activity (activity in vivo when administered) than a deglycosylated or non-glycosylated form of the therapeutic polypeptide (i.e., form of the polypeptide that is not glycosylated, such as a polypeptide expressed in a bacterial host). For example, glycosylation is required for therapeutic activity if therapeutic activity of the glycosylated polypeptide is greater than the non-glycosylated form, particularly such that the non-glycosylated form cannot be used therapeutically. Such difference in activity depends upon the protein, but those of skill in the art can recognize whether a particular protein is suitable for therapeutic use. Exemplary of such proteins is erythropoietin (EPO), which is a glycosylated protein, and is administered therapeutically as a glycosylated protein. The difference in activity between a form of a therapeutic protein that is glycosylated and one that is not glycosylated, is as noted, dependent upon the protein, but can be 15%, 25%, 30%, 50% or 100% greater, including at least or about 1 time, at least or about 2 times, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, or more times greater than the therapeutic activity of the deglycosylated or non-glycosylated form of the therapeutic polypeptide.

As used herein, "exhibits at least one activity" or "retains at least one activity" refers to the activity exhibited by a modified polypeptide, such as a modified, EPO polypeptide or other therapeutic polypeptide, compared to the polypeptide that does not contain the modification. A modified polypeptide that retains an activity of an unmodified polypeptide can exhibit improved activity or maintains the activity (e.g., erythropoietic or tissue protective activity for an EPO polypeptide) of the unmodified polypeptide. In some instances, a modified polypeptide can retain an activity that is increased compared to an unmodified polypeptide. In some cases, a modified polypeptide can retain an activity that is decreased compared to an unmodified polypeptide. Activity of a modified polypeptide can be any level of percentage of activity of the unmodified polypeptide, including but not limited to, 1% of the activity, 2%, 3%, 4%, 5%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more activity compared to the unmodified polypeptide. For example, a modified EPO polypeptide retains at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, or at least 99% of the activity of the unmodified polypeptide. In other embodiments, the change in activity is at least about 2 times, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, or more times greater than unmodified polypeptide. Assays for retention of an activity depend on the activity to be retained. Such assays can be performed in vitro or in vivo. Activity can be measured, for example, using assays known in the art and described in the Examples below for activities such as but not limited to cell proliferative and cell survival activity. Activities of a modified polypeptide compared to an unmodified polypeptide also can be assessed in terms of an in vivo therapeutic or biological activity or result following administration of the polypeptide. For example, for an EPO polypeptide, such activities include, but are not limited to, changes in the hematocrit levels, reticulocyte count, erythrocyte mass, plasma iron turnover rates, marrow transit time, or hemoglobin concentration (i.e., stimulation of hemoglobin C synthesis), or stimulation of reticulocyte response.

As used herein, a "property" of an erythropoietin polypeptide or other therapeutic polypeptide refers to any property exhibited by an erythropoietin polypeptide or therapeutic polypeptide. Such properties include, but are not limited to, protein stability, resistance to proteolysis, conformational stability, thermal tolerance, and tolerance to pH conditions. Changes in properties can alter an "activity" of the polypeptide. For example, a change in the protease resistance of the therapeutic polypeptide can alter the in vivo therapeutic polypeptide.

As used herein, "protein stability" refers to increased protein-half-life under one or more conditions including, but not limited to, exposure to proteases, increased temperature, particular pH conditions and/or exposure to denaturing ingredients. Increased protein stability exhibited by a polypeptide can be manifested as increased protease resistance, or increased conformational stability such as increased tolerance to temperature, pH, or tolerance to other denaturing ingredients. A modified polypeptide that exhibits increased protein stability in vitro or in vivo is, for example, 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more stable than an unmodified polypeptide. The protein stability of a polypeptide, for example, can be assessed in assays of protease resistance or conformational stability (e.g., resistance to temperature changes) to determine if an activity of the polypeptide is altered, such as is described in the Examples below. For example, the resistance of the modified polypeptides compared to wild-type polypeptides against enzymatic cleavage by proteases (e.g., α-chymotrypsin, carboxypeptidase, endoproteinase Arg-C, endoproteinase Asp-N, endoproteinase Glu-C, endoproteinase Lys-C, and trypsin) can be empirically tested by treating the polypeptides with proteases over time and then testing the polypeptides for residual functional activity such as for example, erythropoietic or tissue protective activities.

As used herein, "serum stability" refers to protein stability in serum.

As used herein, "resistance to proteolysis" refers to any amount of decreased cleavage of polypeptide by a proteolytic agent, such as a protease. This can be achieved by modifying particular amino acid residues that are susceptible to cleavage by a particular protease to render them less susceptible to cleavage compared to cleavage by the same protease under the same conditions. A modified polypeptide that exhibits increased resistance to proteolysis exhibits, for example, 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more resistance to proteolysis than an unmodified polypeptide.

As used herein, a "protease sensitive sites" are amino acid positions in a polypeptide that are susceptible to cleavage by a particular protease. Protease sensitive site is used herein interchangeably with protease recognition site or protease cleavage site.

As used herein, "conformational stability" refers to any amount of increased tolerance of a polypeptide to denaturation. This can be achieved by modifying particular amino acid residues that are susceptible to denaturation conditions to render them less susceptible to denaturation under the same conditions. Conformational stability can be determined by assessing the resistance or susceptibility of a polypeptide to denaturation conditions, such as resistance to temperature or pH. A modified polypeptide that exhibits increased conformational stability exhibits, for example, 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more resistance to denaturation than an unmodified polypeptide.

As used herein, "denaturation" refers to any noncovalent change in the structure of a protein. This change can alter the secondary, tertiary and/or quaternary structure of the polypeptide molecule. Denaturation of a polypeptide can occur by, for example but not limited to, exposure to chaotropic agents such as urea and guanidine hydrochloride, detergents, temperature, pH, and reagents which cleave disulfide bridges such as dithiothreitol or dithiothreitol.

As used herein, "thermal tolerance" refers to any temperature affected or dependent change the stability of a protein. For example, a change, such as an increased thermal tolerance, can be reflected in a decreased amount of denaturation of a polypeptide after exposure to altered (particularly increased) temperatures or compared to the unmodified protein under the same conditions. A modified polypeptide that exhibits increased thermal tolerance exhibits, for example, 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more stability at varied temperatures compared to the unmodified polypeptide. For example, a modified polypeptide can exhibit increased thermal tolerance in vivo when administered to a subject compared to an unmodified polypeptide, and thereby exhibit increased serum half-life.

As used herein, "$EC_{50}$" refers to the effective concentration of a therapeutic polypeptide necessary to give one-half of a maximum response. For purposes herein, the response measured is any activity of an EPO polypeptide, such as but not limited to, activity in an erythropoietic or tissue protection assay.

As used herein, "half-life" refers to the time required for a measured parameter, such the potency, activity and effective concentration of a polypeptide, molecule to fall to half of its original level, such as half of its original potency, activity, or effective concentration at time zero. Thus, the parameter, such as potency, activity, or effective concentration of a polypeptide molecule is generally measured over time. For purposes herein, half-life can be measured in vitro or in vivo. For example, the half-life of a therapeutic polypeptide or a modified therapeutic polypeptide can be measured in vitro by assessing its activity (e.g., erythropoietic or tissue protective activity) following incubation over increasing time under certain conditions, such as for example, after exposure to proteases, or denaturing conditions such as temperature or pH. In another example, the half-life of a therapeutic polypeptide or a modified therapeutic polypeptide can be measured in vivo following administration (e.g., intravenous, subcutaneous, intraduodenal, oral) of the polypeptide to a human or other animal, followed by sampling of the blood over time to determine the remaining effective concentration and/or activity of the polypeptide in the blood sample.

As used herein, "therapeutic polypeptide-mediated disease or disorder" refers to any disease or disorder in which treatment with the therapeutic polypeptide (or modified therapeutic polypeptide) ameliorates any symptom or manifestation of the disease or disorder.

As used herein, "erythropoietin- or EPO-mediated disease or disorder" refers to any disease or disorder in which treatment with an erythropoietin (or modified erythropoietin) ameliorates any symptom or manifestation of the disease or disorder. Exemplary erythropoietin-mediated diseases and disorders include, but are not limited to, anemias, such as anemias of chronic inflammation, renal failure, AIDS, and malignancy or diseases or conditions which utilize the tissue protective activities of an EPO polypeptide for protection against an injury or restoration of function following the injury to responsive mammalian cells, tissues, or organs.

As used herein, "treating" a subject with a disease or condition means that the subject's symptoms are partially or totally alleviated, or remain static following treatment. Hence treatment encompasses prophylaxis, therapy and/or cure. Prophylaxis refers to prevention of a potential disease or condition and/or a prevention of worsening of symptoms or progression of a disease or condition. Prevention of a disease or condition encompasses alleviation or elimination of one or more risk factors for development of the disease or condition. Treatment also encompasses any pharmaceutical use of a modified therapeutic polypeptide and oral compositions provided herein.

As used herein, treatment encompasses prophylaxis, therapy, and/or cure. For example, treatment encompasses any pharmaceutical use of a modified erythropoietin or other therapeutic polypeptide provided and compositions thereof provided herein.

As used herein, prophylaxis refers to prevention of a potential disease and/or a prevention of worsening of symptoms or progression of a disease.

As used herein, prevention refers to absolute prevention of a particular disease or disorder. Since it generally is not possible to ascertain whether a disease or disorder never developed, prevention also includes reduction in the risk of developing or having a disease or disorder.

As used herein, a composition that does not include exogenously added proteases is a composition formulated without the addition of proteases. Any additional proteases present in the composition would originate from the method of formulation.

As used herein, "therapeutically effective amount administered" or "therapeutically effective dose," refers to an amount of an agent, compound, material, in a dosage formulation that is at least sufficient to produce a therapeutic effect in a subject. Typically, the amount is high enough to reach a therapeutically effective amount in the blood. The therapeutically effective amount in the blood to be achieved is known for many of the therapeutic polypeptides employed in the methods and dosage formulations effective dosages have been established for the unmodified proteins. For the modified proteins the dosages can be selected to achieve the same effect. The therapeutically effective amount of a protease-resistant polypeptide for use for treatment will vary with the particular condition being treated, the age and physical condition of the patient being treated, the severity of the condition, the duration of the treatment, the nature of concurrent therapy, the particular protease-resistant polypeptide being employed, the particular pharmaceutically-acceptable excipients and/or factors within the knowledge and expertise of the attending physician.

As used herein term "pharmaceutically-acceptable excipients" includes any physiologically inert, pharmacologically inactive material known to one skilled in the art, which is compatible with the physical and chemical characteristics of the particular protease-resistant polypeptide selected for use. Pharmaceutically-acceptable excipients include, but are not limited to, polymers, resins, plasticizers, fillers, lubricants, solvents, co-solvents, buffer systems, surfactants, preservatives, sweetening agents, flavoring agents, pharmaceutical grade dyes or pigments, and viscosity agents. All or part of the pharmaceutically-acceptable excipients contained in the pharmaceutically compositions described herein can be part of the enteric coating.

As used herein, "oral administration" or "oral delivery" of a therapeutic polypeptide refers to administration of a therapeutic polypeptide to the gastrointestinal tract by ingestion. Typically the compositions for oral administration provided herein differ from mucosal delivery in that the therapeutic polypeptide is delivered to the lower intestinal tract for absorption into the bloodstream.

As used herein, the term "lower gastrointestinal tract" means the small intestine and the large intestine.

As used herein, "mucosal administration" or "mucosal delivery" of a therapeutic polypeptide refers to administration of a therapeutic polypeptide to a mucosal surface, including nasal, pulmonary, vaginal, rectal, urethral, and sublingual or buccal delivery.

As used herein, "oromucosal" refers to refers to the mucosa lining the oral and/or nasopharyngeal cavities.

As used herein, the term "enteric-coating" relates to a mixture of pharmaceutically-acceptable excipients which is applied to, combined with, mixed with or otherwise added to the protease-resistant polypeptide. The enteric coating effects release of the protease-resistant polypeptide in the lower intestinal tract and prevents early digestion or degradation of the tablet, capsule or other oral dosage form. The coating can be applied to a compressed tablet, a gelatin capsule, and/or the beads, granules, particles, or a lyophilized powder of the protease-resistant polypeptide, which are encapsulated into starch or gelatin capsules or compressed into tablets.

Accordingly, an enteric coating can be applied to a compressed tablet which contains granules, particles, or a lyophilized powder of the protease-resistant-polypeptide; however, in the event the granules or particles are themselves enterically-coated before being compressed into a tablet, then the enteric coating of the compressed tablet itself is optional. The enteric coating also can applied to the beads or small particles of the therapeutic polypeptide, which can be encapsulated into a starch or gelatin capsule. The capsule can then be coated with an enteric coating, if desired. Because of their enteric coating, these oral formulations will prohibit the undesirable delivery of the protease-resistant polypeptide to the mucosal and epithelial tissues of the upper gastrointestinal tract, especially the mouth, pharynx and esophagus. The coating also achieves the delivery of the active to the lower gastrointestinal tract at a point which can be manipulated by one skilled in the art by choosing the excipients which make up the coating, its type, and/or its thickness.

As used herein, the term "delayed-release" refers to a delivery of a protease-resistant polypeptide, which is effected by formulating the protease-resistant polypeptide in a pharmaceutical composition so that the release will be accomplished at some generally predictable location in the lower intestinal tract more distal to that which would have been accomplished if there had been no alteration in the delivery of the therapeutic polypeptide. An exemplary method for effecting the delayed-release of the active ingredient involves coating (or otherwise encapsulating) the active ingredient with a substance which is not absorbed, or otherwise broken down, by the gastrointestinal fluids to release the active ingredient until a specific desired point in the intestinal tract is reached. An exemplary type of delayed-release formulation for use herein is achieved by coating the tablet, capsule, or particles, granules, or beads of active ingredient with a substance which is pH-dependent, i.e., broken down at a pH which is generally present in the small intestine, but not broken down at a pH which is generally present in the mouth, pharynx, esophagus or stomach. However, if it is desired to effect the topical delivery via the oral administration of a pharmaceutical composition containing the protease-resistant polypeptide to only the large intestine, or to the entire length of the intestinal tract beginning with the small intestine, then the selection of the coating material and/or the method of coating or otherwise combining the protease-resistant polypeptide with the selected coating material or other pharmaceutically-acceptable excipients can be varied or altered as is described herein or by any method known to one skilled in the art.

As used herein, a "therapeutic effect" or "therapeutic benefit" refers to a positive outcome of treating a symptom and can include, for example, a beneficial change in a clinical index such as, for example, in the case of treatment with an EPO polypeptide, red blood cell count (RBC), platelet count, hematocrit (HCT), hemoglobin level (hemoglobin C), as well as subjective indices such as reduced pain, reduced fatigue, improved vigor or betterment in sense of well being.

As used herein, "responsive cell" refers to a mammalian cell whose function or viability can be maintained, promoted, enhanced, regenerated, or in any other way benefited, by exposure to a modified therapeutic polypeptide.

As used herein, "subject" to be treated includes humans and human or non-human animals. Mammals include, primates, such as humans, chimpanzees, gorillas and monkeys; a domesticated animals, such as dogs, horses, cats, pigs, goats, cows, and rodents, such as mice, rats, hamsters and gerbils.

As used herein, "patient" or "subject" to be treated includes humans or non-human animals. Mammals include primates, such as humans, chimpanzees, a gorillas and monkeys; domesticated animals, such as dogs, horses, cats, pigs, goats, cows; and rodents such as mice, rats, hamsters and gerbils.

As used herein, "a directed evolution method" refers to methods that "adapt" either proteins, including natural proteins, synthetic proteins or protein domains to have changed proportions, such as the ability to act in different or existing natural or artificial chemical or biological environments and/or to elicit new functions and/or to increase or decrease a given activity, and/or to modulate a given feature. Exemplary directed evolution methods include, among others, rational directed evolution methods described in U.S. Published Application Nos. US 2003-0134351 A1 and US-2004-0132977 A1.

As used herein, "two dimensional rational mutagenesis scanning (2-D scanning)" refers to the processes provided herein in which two dimensions of a particular protein sequence are scanned: (1) one dimension is to identify specific amino acid residues along the protein sequence to replace with different amino acids, referred to as is-HIT target positions, and (2) the second dimension is the amino acid type selected for replacing the particular is-HIT target, referred to as the replacing amino acid.

As used herein, "in silico" refers to research and experiments performed using a computer. In silico methods include, but are not limited to, molecular modeling studies and biomolecular docking experiments.

As used herein, "is-HIT" refers to an in silico identified amino acid position along a target protein sequence that has been identified based on i) the particular protein properties to be evolved, ii) the protein's sequence of amino acids, and/or iii) the known properties of the individual amino acids. These is-HIT loci on the protein sequence are identified without use of experimental biological methods. For example, once the protein feature(s) to be optimized is (are) selected, diverse sources of information or previous knowledge (i.e., protein primary, secondary or tertiary structures, literature, patents) are exploited to determine those amino acid positions that are amenable to improved protein fitness by replacement with a different amino acid. This step uses protein analysis "in silico." All possible candidate amino acid positions along a target protein's primary sequence that might be involved in the feature being evolved are referred to herein as "in silico HITs" ("is-HITs"). The collection (library), of all is-HITs identified during this step represents the first dimension (target residue position) of the two-dimensional scanning methods provided herein.

As used herein, "amenable to providing the evolved predetermined property or activity" in the context of identifying is-HITs refers to an amino acid position on a protein that is contemplated, based on in silico analysis, to possess properties or features that when replaced result in the desired activity being evolved. The phrase "amenable to providing the evolved predetermined property or activity" in the context of identifying replacement amino acids refers to a particular amino acid type that is contemplated, based on in silico analysis, to possess properties or features that when used to replace the original amino acid in the unmodified starting protein result in the evolution of a desired or preselected activity.

As used herein, "high-throughput screening" (HTS) refers to processes that test a large number of samples, such as samples of test proteins or cells containing nucleic acids encoding the proteins of interest to identify structures of interest or to identify test compounds that interact with the variant proteins or cells containing them. HTS operations are amenable to automation and are typically computerized to handle sample preparation, assay procedures, and the subsequent processing of large volumes of data.

As used herein, the term "restricted," in the context of the identification of is-HIT amino acid positions along the amino acid residues in a protein selected for amino acid replacement and/or the identification of replacing amino acids, means that fewer than all amino acids on the protein-backbone are selected for amino acid replacement and/or fewer than all of the remaining 19 amino acids available to replace the original amino acid present in the unmodified starting protein are selected for replacement. In particular embodiments of the methods provided herein, the is-HIT amino acid positions are restricted such that fewer than all amino acids on the protein-backbone are selected for amino acid replacement. In other embodiments, the replacing amino acids are restricted such that fewer than all of the remaining 19 amino acids available to replace the native amino acid present in the unmodified starting protein are selected as replacing amino acids. In an exemplary embodiment, both of the scans to identify is-HIT amino acid positions and the replacing amino acids are restricted such that fewer than all amino acids on the protein-backbone are selected for amino acid replacement and fewer than all of the remaining 19 amino acids available to replace the native amino acid are selected for replacement.

As used herein, "candidate LEADs" are mutant proteins that are designed to have an alteration in property, activity or other attribute, typically a predetermined or preselected property, activity or other attribute, such as a, chemical, physical or biological property or activity in which such alteration is sought. The alteration can add, alter, remove or otherwise change a property, activity or other attribute of a polypeptide. In the methods herein, candidate LEADs are generally generated by systematically replacing is-HITS loci in a protein or a domain thereof with typically a restricted subset, or all, of the remaining 19 amino acids, such as obtained using PAM analysis. Candidate LEADs can be generated by other methods known to those of skill in the art tested by the high throughput methods herein.

As used herein, "LEADs" are "candidate LEADs" whose property, activity or other attribute has been changed, optimized, improved, added or eliminated. For purposes herein a "LEAD" typically has activity with respect to a property or activity of interest in an unmodified polypeptide that exhibits such activity or property that differs by at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more from the unmodified and/or wild type (native) protein.

In certain embodiments, the change in activity is at least about 2 times, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, or more times greater than the activity of the unmodified and/or wild type (native) protein. The desired alteration, which can be either an increase or a reduction in activity, depends upon the function or property of interest (e.g., at least about or 10%, at least about or 20%, etc.). The LEADs can be further optimized by replacement of a plurality (2 or more) of "is-HIT" target positions on the same protein molecule to generate "super-LEADs."

As used herein, the term "super-LEAD" refers to protein mutants (variants) obtained by adding the single mutations present in two or more of the LEAD molecules in a single protein molecule. Accordingly, in the context of the modified proteins provided herein, the phrase "proteins comprising one or more single amino acid replacements" encompasses addition of two or more of the mutations described herein for one respective protein. For example, the modified proteins provided herein containing one or more single amino acid replacements can have any of 2, 3, 4, 5, 6, 7, 8, 9, 10, 11, 12, 13, 14, 15, 16, 17, 18, 19, 20 or more of the amino acid replacements at the disclosed replacement positions. The collection of super-LEAD mutant molecules is generated, tested, and phenotypically characterized one-by-one in addressable arrays. Super-LEAD mutant molecules are molecules containing a variable number and type of LEAD mutation. Those molecules displaying further improved fitness for the particular feature being evolved, are referred to as super-LEADs. Super-LEADs can be generated by other methods known to those of skill in the art and tested by the high throughput methods herein. For purposes herein, a super-LEAD typically has activity with respect to the function of interest that differs from the altered activity (or the new activity or eliminated activity) of a LEAD by a desired amount, such as at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more from the LEAD mutant from which it is derived. As with LEADs, the change in the activity for super-LEADs is dependent upon the activity that is being "evolved." The desired alteration, which can be either an increase or a reduction in activity, depends upon the function or property of interest. The desired alteration also can be an addition or elimination of a property or activity.

As used herein, the phrase "altered loci" refers to the is-HIT amino acid positions in the LEADs or super-LEADs that are replaced with different replacing amino acids resulting in the desired altered phenotype or activity.

As used herein, an "exposed residue" presents more than 15% of its surface exposed to the solvent.

As used herein, the phrase "structural homology" refers to the degree of coincidence in space between two or more protein backbones. Protein backbones that adopt the same protein structure, fold and show similarity upon three-dimensional structural superposition in space can be considered structurally homologous. Structural homology is not based on sequence homology, but rather on three-dimensional homology. Two amino acids in two different proteins said to be homologous based on structural homology between those proteins do not necessarily need to be in sequence-based homologous regions. For example, protein backbones that have a root mean squared (RMS) deviation of less than 3.5, 3.0, 2.5, 2.0, 1.7 or 1.5 angstroms at a given space position or defined region between each other can be considered to be structurally homologous in that region and are referred to herein as having a "high coincidence" between their backbones. It is contemplated herein that substantially equivalent (e.g., "structurally related") amino acid positions that are located on two or more different protein sequences that share a certain degree of structural homology have comparable functional tasks; also referred to herein as "structurally homologous loci." These two amino acids then can be said to be "structurally similar" or "structurally related" with each other, even if their precise primary linear positions on the sequences of amino acids, when these sequences are aligned, do not match with each other. Amino acids that are "structurally related" can be far away from each other in the primary protein sequences, when these sequences are aligned following the rules of classical sequence homology.

As used herein, a "structural homolog" is a protein that is recognized by structural homology. Exemplary EPO structural homologs include many other cytokines, including, for example, granulocyte-macrophage colony stimulating factor (GM-CSF), interleukin-2 (IL-2), interleukin-3 (IL-3), interleukin-4 (IL-4), interleukin-5 (IL-5), interleukin-13 (IL-13), Flt3 ligand and stem cell factor (SCF).

As used herein, "corresponding to structurally-related" positions on two or more polypeptides, such as two EPO polypeptides or other polypeptides that are EPO structural homologs, refers to those amino acid positions determined based upon structural homology to maximize tri-dimensional overlapping between or among polypeptides.

As used herein, "variant," "therapeutic polypeptide variant," "modified therapeutic polypeptide" and "modified therapeutic protein" refer to a therapeutic polypeptide that has one or more mutations compared to an unmodified therapeutic polypeptide. An "erythropoietin variant," "modified erythropoietin polypeptides" and "modified erythropoietin proteins" refers to an EPO polypeptide that has one or more mutations compared to an unmodified erythropoietin polypeptide. The one or more mutations can be one or amino acid replacements, insertions or deletions and any combination thereof. Typically, a modified polypeptide has one or more modifications in primary sequence compared to the unmodified polypeptide. For example, a modified polypeptide provided herein can have 1, 2, 3, 4, 5, 6, 7, 8, 9, 10, 11, 12, 13, 14, 15, 16, 17, 18, 19, 20, or more mutations compared to an unmodified polypeptide. Any length polypeptide is contemplated as long as the resulting polypeptide exhibits at least one activity associated with a native polypeptide.

As used herein, a "single amino acid replacement" refers to the replacement of one amino acid by another amino acid. The replacement can be by a natural amino acid or non-natural amino acids. When one amino acid is replaced by another amino acid in a protein, the total number of amino acids in the protein is unchanged.

As used herein, the phrase "only one amino acid replacement occurs on each target protein" refers to the modification of a target protein, such that it differs from the unmodified form of the target protein by a single amino acid change. For example, in one embodiment, mutagenesis is performed by the replacement of a single amino acid residue at only one is-HIT target position on the protein backbone (e.g., "one-by-one" in addressable arrays), such that each individual mutant generated is the single product of each single mutagenesis reaction. The single amino acid replacement mutagenesis reactions are repeated for each of the replacing amino acids selected at each of the is-HIT target positions. Thus, a plurality of mutant protein molecules are produced, whereby each mutant protein contains a single amino acid replacement at only one of the is-HIT target positions.

As used herein, the phrase "pseudo-wild type," in the context of single or multiple amino acid replacements, are those amino acids that, while different from the original (e.g., such as native) amino acid at a given amino acid position, can replace the native one at that position without introducing any measurable change in a particular protein activity.

A population (library) of sets of nucleic acid molecules encoding a collection of mutant molecules is generated and phenotypically characterized such that proteins with sequences of amino acids different from the original amino acid, but that still elicit substantially the same level (i.e., at least about or 10%, 50%, 80%, 90%, 91%, 92%, 93%, 94%, 95%, 96%, 97%, 98%, 99%, or 100%, depending upon the protein) and type of desired activity as the original protein are selected. A collection (or library), contains two, three, four, five, 10, 50, 100, 500, 1000, $10^3$, $10^4$ or more modified therapeutic polypeptides.

As used herein, "in a position or positions corresponding to an amino acid position" of a protein, refers to amino acid positions that are determined to correspond to one another based on sequence and/or structural alignments with a specified reference protein. For example, in a position corresponding to an amino acid position of human EPO set forth as SEQ ID NO: 2 can be determined empirically by aligning the sequence of amino acids set forth in SEQ ID NO: 2 with a particular EPO polypeptide of interest. Corresponding positions can be determined by such alignment by one of skill in the art using manual alignments or by using the numerous alignment programs available (for example, BLASTP). Corresponding positions also can be based on structural alignments, for example by using computer simulated alignments of protein structure. Recitation that amino acids of a polypeptide correspond to amino acids in a disclosed sequence refers to amino acids identified upon alignment of the polypeptide with the disclosed sequence to maximize identity or homology (where conserved amino acids are aligned) using a standard alignment algorithm, such as the GAP algorithm.

As used herein, "at a position corresponding to" refers to a position of interest (i.e., base number or residue number) in a nucleic acid molecule or protein relative to the position in another reference nucleic acid molecule or protein. The position of interest to the position in another reference protein can be in, for example, a precursor protein, an allelic variant, a heterologous protein, an amino acid sequence from the same protein of another species (i.e., species variant), etc. Corresponding positions can be determined by comparing and aligning sequences to maximize the number of matching nucleotides or residues, for example, such that identity between the sequences is greater than 95%, preferably greater than 96%, more preferably greater than 97%, even more preferably greater than 98% and most preferably greater than 99%. The position of interest is then given the number assigned in the reference nucleic acid molecule.

As used herein, the terms "homology" and "identity" are used interchangeably, but homology for proteins can include conservative amino acid changes. In general to identify corresponding positions the sequences of amino acids are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis*

*Primer*, Gribskov, M. and Devereux, J., eds., M Stockton Press, New York, 1991; Carillo et al. (1988) *SIAM J Applied Math* 48:1073).

As use herein, "sequence identity" refers to the number of identical amino acids (or nucleotide bases) in a comparison between a test and a reference polypeptide or polynucleotide. Homologous polypeptides refer to a pre-determined number of identical or homologous amino acid residues. Homology includes conservative amino acid substitutions as well identical residues. Sequence identity can be determined by standard alignment algorithm programs used with default gap penalties established by each supplier. Homologous nucleic acid molecules refer to a pre-determined number of identical or homologous nucleotides. Homology includes substitutions that do not change the encoded amino acid (i.e., "silent substitutions") as well identical residues. Substantially homologous nucleic acid molecules hybridize typically at moderate stringency or at high stringency all along the length of the nucleic acid or along at least about 70%, 80%, 85%, 90%, 91%, 92%, 93%, 94%, 95%, 96%, 97%, 98%, or 99% of the full-length nucleic acid molecule of interest. Also contemplated are nucleic acid molecules that contain degenerate codons in place of codons in the hybridizing nucleic acid molecule. (For determination of homology of proteins, conservative amino acids can be aligned as well as identical amino acids; in this case, percentage of identity and percentage homology vary). Whether any two nucleic acid molecules have nucleotide sequences (or any two polypeptides have amino acid sequences) that are at least 70%, 80%, 85%, 90%, 91%, 92%, 93%, 94%, 95%, 96%, 97%, 98% or 99% "identical" can be determined using known computer algorithms such as the "FASTA" program, using for example, the default parameters as in Pearson et al. *Proc. Natl. Acad. Sci. USA* 85: 2444 (1988) (other programs include the GCG program package (Devereux, J., et al., *Nucleic Acids Research* 12(I): 387 (1984)), BLASTP, BLASTN, FASTA (Atschul, S. F., et al., *J Molec. Biol.* 215:403 (1990); *Guide to Huge Computers*, Martin J. Bishop, ed., Academic Press, San Diego (1994), and Carillo et al. *SIAM J Applied Math* 48: 1073 (1988)). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)). Percent homology or identity of proteins and/or nucleic acid molecules can be determined, for example, by comparing sequence information using a GAP computer program (e.g., Needleman et al. *J. Mol. Biol.* 48: 443 (1970), as revised by Smith and Waterman (*Adv. Appl. Math.* 2: 482 (1981)). Briefly, a GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and 0 for non identities) and the weighted comparison matrix of Gribskov et al. *Nucl. Acids Res.* 14: 6745 (1986), as described by Schwartz and Dayhoff, eds., *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps.

Therefore, as used herein, the term "identity" represents a comparison between a test and a reference polypeptide or polynucleotide. In one non-limiting example, "at least 90% identical to" refers to percent identities from 90 to 100% relative to the reference polypeptides. Identity at a level of 90% or more is indicative of the fact that, assuming for exemplification purposes a test and reference polynucleotide length of 100 amino acids are compared, no more than 10% (i.e., 10 out of 100) of amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often without relying on software.

As used herein, the phrase "sequence-related proteins" refers to proteins that have at least 50%, at least 60%, at least 70%, at least 80%, at least 90%, at least 91%, at least 92%, at least 93%, at least 94%, at least 95%, at least 96%, at least 97%, at least 98% or at least 99% amino acid sequence identity or homology with each other.

As used herein, families of non-related proteins or "sequence-non-related proteins" refer to proteins having less than 50%, less than 40%, less than 30%, less than 20% amino acid identity, or homology with each other.

As used herein, it also is understood that the terms "substantially identical" or "similar" varies with the context as understood by those skilled in the relevant art.

As used herein, "a naked polypeptide chain" refers to a polypeptide that is not post-translationally modified or otherwise chemically modified, but contains only covalently linked amino acids.

As used herein, a polypeptide complex includes polypeptides produced by chemical modification or post-translational modification. Such modifications include, but are not limited to, pegylation, albumination, glycosylation, farnysylation, hasylation, carbamylation, sulfation, carboxylation, hydroxylation, phosphorylation, and other polypeptide modifications known in the art.

As used herein, "output signal" refers to parameters that can be followed over time and, optionally, quantified. For example, when a recombinant protein is introduced into a cell, the cell containing the recombinant protein undergoes a number of changes. Any such change that can be monitored and used to assess the transformation or transfection is an output signal, and the cell is referred to as a reporter cell; the encoding nucleic acid is referred to as a reporter gene; and the construct that includes the encoding nucleic acid is a reporter construct. Output signals include, but are not limited to, enzyme activity, fluorescence, luminescence, amount of product produced, and other such signals. Output signals include expression of a gene or gene product, including heterologous genes (transgenes) inserted into the plasmid virus. Output signals are a function of time ("t") and are related to the amount of protein used in the composition. For higher concentrations of protein, the output signal can be higher or lower. For any particular concentration, the output signal increases as a function of time until a plateau is reached. Output signals also can measure the interaction between cells, expressing heterologous genes and biological agents.

As used herein, a population of sets of nucleic acid molecules encoding a collection (or library) of mutants refers to a collection of plasmids or other vehicles that carry (i.e., encode) the gene variants. Thus, individual plasmids or other individual vehicles carry individual gene variants. Each element (or member) of the collection is physically separated from the others in an appropriate addressable array and has been generated as the single product of an independent mutagenesis reaction. When a collection (or library) of such proteins is contemplated, it will be so-stated. A collection (or library), contains three, four, five, 10, 50, 100, 500, 1000, $10^3$, $10^4$ or more modified EPO polypeptides or modified therapeutic polypeptides.

As used herein, a "reporter cell" is the cell that undergoes the change in response to a condition. For example, in response to exposure to a protein or a virus or to a change in its external or internal environment, the reporter cell "reports" (i.e., displays or exhibits the change).

As used herein, "reporter" or "reporter moiety" refers to any moiety that allows for the detection of a molecule of interest, such as a protein expressed by a cell. Reporter moieties include, but are not limited to, fluorescent proteins (e.g., red, blue, and green fluorescent proteins), LacZ and other detectable proteins and gene products. For expression in cells, nucleic acids encoding the reporter moiety can be expressed as a fusion protein with a protein of interest or under to the control of a promoter of interest.

As used herein, phenotype refers to the physical, physiological, or other manifestation of a genotype (a sequence of a gene). In methods herein, phenotypes that result from alteration of a genotype are assessed.

As used herein, culture medium is any medium suitable for supporting the viability, growth, and/or differentiation of mammalian cells ex vivo. Any such medium known to those of skill in the art. Examples of culture medium include, but are not limited to, X-Vivo15 (BioWhittaker), RPMI 1640, DMEM, Ham's F12, McCoys 5A and Medium 199. The medium can be supplemented with additional ingredients including serum, serum proteins, growth suppressing and growth promoting substances, such as mitogenic monoclonal antibodies and selective agents for selecting genetically engineered or modified cells.

As used herein, the amino acids that occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide comprises two or more amino acids. For purposes herein, amino acids include the twenty naturally-occurring amino acids, non-natural amino acids and amino acid analogs (e.g., amino acids wherein the α-carbon has a side chain).

As used herein, the abbreviations for any protective groups, amino acids and other compounds are, unless indicated otherwise, in accord with their common usage, recognized abbreviations, or the IUPAC-IUB Commission on Biochemical Nomenclature (1972) *Biochem.* 11: 1726. Each naturally occurring L-amino acid is identified by the standard three letter code (or single letter code) or the standard three letter code (or single letter code) with the preEPO "L-;" the preEPO "D-" indicates that the stereoisomeric form of the amino acid is D.

As used herein, "amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide.

"$NH_2$" refers to the free amino group present at the amino terminus of a polypeptide. "COOH" refers to the free carboxy group present at the carboxyl terminus of a polypeptide. In keeping with standard polypeptide nomenclature described in *J. Biol. Chem.*, 243: 3552-3559 (1969), and adopted 37 C.F.R. §§1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, the term "non-natural amino acid" refers to an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally occurring amino acids and include, but are not limited to, the D-isostereomers of amino acids. Exemplary non-natural amino acids are described herein and are known to those of skill in the art.

As used herein, nucleic acids include DNA, RNA and analogs thereof, including protein nucleic acids (PNA) and mixtures thereof. Nucleic acids can be single- or double-stranded. When referring to probes or primers (optionally labeled with a detectable label, e.g., a fluorescent or a radio-label), single-stranded molecules are contemplated. Such molecules are typically of a length such that they are statistically unique of low copy number (typically less than 5, generally less than 3) for probing or priming a library. Generally a probe or primer contains at least 10, 15, 20, 25 or 30 contiguous of sequence complementary to, or identical to, a gene of interest. Probes and primers can be 5, 6, 7, 8, 9, 10 or more, 20 or more, 30 or more, 50 or more, 100 or more nucleic acids long.

As used herein, heterologous or foreign nucleic acid, such as DNA and RNA, are used interchangeably and refer to DNA or RNA that does not occur naturally as part of the genome in which it occurs or is found at a locus or loci in a genome that differs from that in which it occurs in nature. Heterologous nucleic acid includes nucleic acid not endogenous to the cell into which it is introduced, but that has been obtained from another cell or prepared synthetically. Generally, although not necessarily, such nucleic acid encodes RNA and proteins that are not normally produced by the cell in which it is expressed. Heterologous DNA herein encompasses any DNA or RNA that one of skill in the art recognizes or considers as heterologous or foreign to the cell or locus in or at which it is expressed. Heterologous DNA and RNA also can encode RNA or proteins that mediate or alter expression of endogenous DNA by affecting transcription, translation, or other regulatable biochemical processes. Examples of heterologous nucleic acid include, but are not limited to, nucleic acid that encodes traceable marker proteins (e.g., a protein that confers drug resistance), nucleic acid that encodes therapeutically effective substances (e.g., anti-cancer agents), enzymes and hormones, and DNA that encodes other types of proteins (e.g., antibodies). Hence, herein heterologous DNA or foreign DNA includes a DNA molecule not present in the exact orientation and position as the counterpart DNA molecule found in the genome. It also can refer to a DNA molecule from another organism or species (i.e., exogenous).

As used herein, "isolated with reference to a nucleic acid molecule or polypeptide or other biomolecule" means that the nucleic acid or polypeptide has separated from the genetic environment from which the polypeptide or nucleic acid was obtained. It also can mean altered from the natural state. For example, a polynucleotide or a polypeptide naturally present in a living animal is not "isolated," but the same polynucleotide or polypeptide separated from the coexisting materials of its natural state is "isolated," as the term is employed herein. Thus, a polypeptide or polynucleotide produced and/ or contained within a recombinant host cell is considered isolated. Also intended as an "isolated polypeptide" or an "isolated polynucleotide" are polypeptides or polynucleotides that have been partially or substantially purified from a recombinant host cell or from a native source. For example, a recombinantly produced version of a compound can be substantially purified by the one-step method described in Smith et al., *Gene*, 67:31-40 (1988). The terms isolated and purified can be used interchangeably.

Thus, by "isolated" it is meant that the nucleic acid is free of coding sequences of those genes that, in the naturally-occurring genome of the organism (if any), immediately flank the gene encoding the nucleic acid of interest. Isolated DNA can be single-stranded or double-stranded, and can be genomic DNA, cDNA, recombinant hybrid DNA or synthetic DNA. It can be identical to a starting DNA sequence or can differ from such sequence by the deletion, addition or substitution of one or more nucleotides.

"Purified" preparations made from biological cells or hosts mean cell extracts containing the indicated DNA or protein, including a crude extract of the DNA or protein of interest. For example, in the case of a protein, a purified preparation can be obtained following an individual technique or a series of preparative or biochemical techniques, and the DNA or protein of interest can be present at various degrees of purity in these preparations. The procedures can include, but are not limited to, ammonium sulfate fractionation, gel filtration, ion exchange chromatography, affinity chromatography, density gradient centrifugation and electrophoresis.

A preparation of DNA or protein that is "substantially pure" or "isolated" refers to a preparation substantially free from naturally-occurring materials with which such DNA or protein is normally associated in nature and generally contains 5% or less of the other contaminants.

A cell extract that contains the DNA or protein of interest refers to a homogenate preparation or cell-free preparation obtained from cells that express the protein or contain the DNA of interest. The term "cell extract" is intended to include culture medium, especially spent culture medium from which the cells have been removed.

As used herein, "a targeting agent" refers to any molecule that can bind another target-molecule, such as an antibody, receptor or ligand.

As used herein, "receptor" refers to a biologically active molecule that specifically binds to (or with) other molecules. The term "receptor protein" can be used to more specifically indicate the proteinaceous nature of a specific receptor.

As used herein, "recombinant" refers to any progeny formed as the result of genetic engineering.

As used herein, a "promoter region" refers to the portion of DNA of a gene that controls transcription of the DNA to which it is operatively linked. The promoter region includes specific sequences of DNA sufficient for RNA polymerase recognition, binding and transcription initiation. This portion of the promoter region is referred to as the "promoter". In addition, the promoter region includes sequences that modulate this recognition, binding and transcription initiation activity of the RNA polymerase. Promoters, depending upon the nature of the regulation, can be constitutive or regulated by cis acting or trans acting factors.

As used herein, the phrase "operatively linked" with reference to a nucleic acid molecule generally means the sequences or segments have been covalently joined into one piece of DNA, whether in single- or double-stranded form, whereby control or regulatory sequences on one segment control or permit expression or replication or other such control of other segments. The two segments are not necessarily contiguous. For gene expression, a DNA sequence and a regulatory sequence(s) are connected in such a way to control or permit gene expression when the appropriate molecular, e.g., transcriptional activator proteins, are bound to the regulatory sequence(s).

As used herein, "production by recombinant means by using recombinant DNA methods" means the use of the well-known methods of molecular biology for expressing proteins encoded by cloned DNA, including cloning expression of genes and methods.

As used herein, a splice variant refers to a variant produced by differential processing of a primary transcript of genomic DNA that results in more than one type of mRNA.

As used herein, a composition refers to any mixture of two or more products or compounds (e.g., agents, modulators, regulators, etc.). It can be a solution, a suspension, liquid, powder, a paste, aqueous, non-aqueous formulations or any combination thereof.

As used herein, a combination refers to any association between two or more items. Items of a combination for administration to a subject can be administered separately or together, used simultaneously or sequentially, or packaged together or packaged separately.

As used herein, an "article of manufacture" is a product that is made and sold. As used throughout this application, the term is intended to encompass pharmaceutical compositions of modified EPO polypeptides or other modified therapeutic polypeptides and/or nucleic acids as described herein contained in articles of packaging.

As used herein, a "kit" refers to a combination of modified polypeptides or nucleic acid molecules as described herein provided in pharmaceutical compositions and another item for a purpose including, but not limited to, administration, diagnosis, and assessment of an activity or property of the polypeptides described herein. Kits, optionally, include instructions for use.

As used herein, "substantially identical to a product" means sufficiently similar so that the property of interest is sufficiently unchanged so that the substantially identical product can be used in place of the product.

As used herein, the term "vector" refers to a nucleic acid molecule capable of transporting another nucleic acid to which it has been linked. One type of exemplary vector is an episome, i.e., a nucleic acid capable of extra-chromosomal replication. Exemplary vectors are those capable of autonomous replication and/or expression of nucleic acids to which they are linked; such vectors typically include origins of replication. Vectors also can be designed for integration into host chromosomes. Vectors capable of directing the expression of genes to which they are operatively linked are referred to herein as "expression vectors." Expression vectors are often in the form of "plasmids," which refer generally to circular double-stranded DNA loops which, in their vector form are not bound to the chromosome. "Plasmid" and "vector" are used interchangeably as the plasmid is the most commonly used form of vectors. Other such other forms of expression vectors that serve equivalent functions and that become known in the art subsequently hereto.

As used herein, vector also includes "virus vectors" or "viral vectors." Viral vectors are engineered viruses that are operatively linked to exogenous genes to transfer (as vehicles or shuttles) the exogenous genes into cells.

As used herein, "allele," which is used interchangeably herein with "allelic variant" refers to alternative forms of a gene or portions thereof among a population. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide or several nucleotides, and can include substitutions, deletions and insertions of nucleotides. An allele of a gene also can be a form of a gene containing a mutation. Typically, allelic variants, have at least 80%, 90%, 91%, 92%, 93%, 94%, 95%, 96%, 97%, 98%, 99% or greater amino acid identity with a wild-type and/or predominant form from the same species.

As used herein, the terms "gene" or "recombinant gene" refer to a nucleic acid molecule containing an open reading frame and including at least one exon and, optionally, an intron-encoding sequence. A gene can be either RNA or DNA. Genes can include regions preceding and following the coding region (leader and trailer).

As used herein, "intron" refers to a DNA fragment that occurs in a gene, but is spliced out during mRNA maturation.

As used herein, "nucleotide sequence complementary to the nucleotide sequence encoding the amino acid sequence set forth in SEQ ID NO: 1" refers to the nucleotide sequence of the complementary strand of a nucleic acid strand encoding a polypeptide that includes an amino acid sequence having the particular SEQ ID NO: 1.

The term "complementary strand" is used herein interchangeably with the term "complement." The complement of a nucleic acid strand can be the complement of a coding strand or the complement of a non-coding strand. When referring to double-stranded nucleic acids, the complement of a nucleic acid encoding a polypeptide containing amino acid residues having a sequence set forth in a particular SEQ ID NO: 1 refers to the complementary strand of the strand encoding the amino acid sequence set forth in the particular SEQ ID NO: 1 or to any nucleic acid molecule containing the nucleotide sequence of the complementary strand of the particular nucleic acid sequence. When referring to a single-stranded nucleic acid molecule containing a nucleotide sequence, the complement of this nucleic acid is a nucleic acid having a nucleotide sequence which is complementary to that of the particular nucleic acid sequence.

As used herein, the term "coding sequence" refers to that portion of a gene that encodes a sequence of amino acids present in a protein.

As used herein, the term "sense strand" refers to that strand of a double-stranded nucleic acid molecule that has the sequence of the mRNA that encodes the sequence of amino acids encoded by the double-stranded nucleic acid molecule.

As used herein, the term "antisense strand" refers to that strand of a double-stranded nucleic acid molecule that is the complement of the sequence of the mRNA that encodes the sequence of amino acids encoded by the double-stranded nucleic acid molecule.

As used herein, an "array" refers to a collection of elements, such as nucleic acid molecules, containing three or more members. An addressable array is one in which the members of the array are identifiable, typically by position on a solid phase support or by virtue of an identifiable or detectable label, such as by color, fluorescence, electronic signal (e.g., RF, microwave or other frequency that does not substantially alter the interaction of the molecules of interest), bar code or other symbology, chemical or other such label. In certain embodiments, the members of the array are immobilized to discrete identifiable loci on the surface of a solid phase or directly or indirectly linked to or otherwise associated with the identifiable label, such as affixed to a microsphere or other particulate support (herein referred to as beads) and suspended in solution or spread out on a surface.

As used herein, a "support" (e.g., a matrix support, a matrix, an insoluble support or solid support, etc.) refers to any solid or semisolid or insoluble support to which a molecule of interest (e.g., a biological molecule, organic molecule or biospecific ligand) is linked or contacted. Such materials include any materials that are used as affinity matrices or supports for chemical and biological molecule syntheses and analyses, such as, but are not limited to: polystyrene, polycarbonate, polypropylene, nylon, glass, dextran, chitin, sand, pumice, agarose, polysaccharides, dendrimers, buckyballs, polyacrylamide, silicon, rubber, and other materials used as supports for solid phase syntheses, affinity separations and purifications, hybridization reactions, immunoassays and other such applications. The matrix herein can be particulate or can be in the form of a continuous surface, such as a microtiter dish or well, a glass slide, a silicon chip, a nitrocellulose sheet, nylon mesh, or other such materials. When particulate, typically the particles have at least one dimension in the 5-10 mm range or smaller. Such particles, referred collectively herein as "beads," are often, but not necessarily, spherical. Such reference, however, does not constrain the geometry of the matrix, which can be any shape, including random shapes, needles, fibers, and elongated. Roughly spherical "beads," particularly microspheres that can be used in the liquid phase, also are contemplated. The "beads" can include additional components, such as magnetic or paramagnetic particles (see, for example, Dynabeads (Dynal, Oslo, Norway)) for separation using magnets as long as the additional components do not interfere with the methods and analyses herein.

As used herein, matrix or support particles refer to matrix materials that are in the form of discrete particles. The particles have any shape and dimensions, but typically have at least one dimension that is 100 mm or less, 50 mm or less, 10 mm or less, 1 mm or less, 100 µm or less, 50 µm or less and typically have a size that is 100 mm$^3$ or less, 50 mm$^3$ or less, 10 mm$^3$ or less, and 1 mm$^3$ or less, 100 µm$^3$ or less and can be order of cubic microns. Such particles are collectively called "beads."

As used herein, the abbreviations for any protective groups, amino acids and other compounds are, unless indicated otherwise, in accord with their common usage, recognized abbreviations, or the IUPAC-IUB Commission on Biochemical Nomenclature (1972) *Biochem.*, 11: 942-944.

B. Erythropoietin (EPO)

Erythropoietin (EPO) is a member of the hematopoietic growth factor family that acts as a hormone. It is responsible for the regulation of red blood cell (erythrocyte) production (erythropoiesis) and maintaining the body's red blood cell mass at an optimum level. EPO production is stimulated by reduced oxygen content in the renal arterial circulation, mediated by a transcription factor that is oxygen-sensitive. EPO is produced primarily by cells of the peritubular capillary endothelium of the kidney. Secreted EPO binds to EPO receptors on the surface of bone marrow erythroid precursors, resulting in their rapid replication and maturation to functional red blood cells. This stimulation results in a rapid rise in erythrocyte counts and a consequent rise in hematocrit (% of red blood cells in blood) (D'Andrea et al. (1989) *Cell* 57: 277-285; Lodish et al. (1995) *Cold Spring Harb Symp Quant Biol* 60: 93-104).

Human EPO was first cloned and amino acid sequence reported by Lin et al. (1985) *Proc Nat Acad Sci USA* 82: 7582-4 and Jacobs et al. (1985) *Nature* 313: 806-810. Human EPO is an acidic glycoprotein with a molecular weight of approximately 30,400 Daltons. It is composed of a 165 amino acid single polypeptide chain containing four cysteine residues (at positions 7, 29, 33 and 161), which form internal disulphide bonds (Lai et al. (1986) *J Biol Chem* 261: 3116-3121; Recny et al. (1987) *J Biol Chem* 262: 17156-17163). The disulphide bridge between cysteine 7 and 161 is important for erythropoietic activity. The structure of human EPO has been reported and described in Cheetham et al. (1988) *Nat Struct Biol* 5:861-866 and Syed et al. (1998) *Nature* 395:511-516. Human EPO is a four helix bundle, typical of members of the hematopoietic growth factor family.

In vivo, EPO is post-translationally modified by glycosylation. The carbohydrate portion of EPO consists of three N-linked sugars chains at Asn 24, 38 and 83, and one O-linked sugar at Ser 126 (see e.g., Browne et al. (1986) *Cold Spring Harb Symp Quant Biol* 51: 693-702; Egrie et al. (1986) *Immunbiology* 172: 213-224). The carbohydrate structures that are attached to EPO are variable, a feature referred to as microheterogeneity. The differences in carbohydrate moieties, in terms of the branching pattern, complexity size and charge have profound effects on the pharmacokinetics and pharmacodynamics of EPO. The effects of different glycosylation patterns have been well studied (see e.g., Darling et al. (2002) *Biochemistry* 41: 14524-14531; Storring et al. (1998) *Br J Haematol* 100: 79-89; Halstenson et al. (1991 *Clin Pharmacol Ther* 50: 702-712; Takeuchi et al. (1990) *J Biol Chem* 265: 12127-12130).

The following EPO polypeptides have the same amino acid sequence as recombinant human EPO (rhEPO) and variations in the methods of production and glycosylation distinguish these products. Epoetin α (generated from genomic DNA) and epoetin β (generated from cDNA) are described in U.S. Pat. Nos. 4,703,008 and 5,955,422. These polypeptides have the same amino acid sequence as human EPO and are produced in Chinese hamster ovary (CHO) cells. Epoetin α is available under the trade names Procrit® (Ortho Biotech), Eprex® (Johnson & Johnson), Epogin® (Chugai) or Epogen® (Amgen). Epoetin β is available under the trade name Neorecormon® or Recormon® (Hoffmann-La Roche). It was developed by the Genetics Institute for the treatment of anemia associated with renal disease. Epoetin ω, described in U.S. Pat. No. 5,688,679, has the same amino acid sequence as human EPO and is produced in baby hamster kidney cells (BHK-21). Epoetin ω is available under the trade names Epomax® (Elanex).

Darbepoetin α (also known as Novel Erythropoiesis Stimulating Protein, NESP) was developed by Amgen and is available under the trade name Aranesp® (Macdougall (2002) *Kidney Int Suppl.* 80:55-61). It was designed to contain five N-linked carbohydrate chains (two more than rhEPO). The amino acid sequence of Aranesp® differs from that of rhEPO at five amino acid substitutions (A30N, H32T, P87V, W88N, P90T (SEQ ID NO: 228)), thus allowing for additional oligosaccharide attachment at asparagine residues at positions 30 and 88. Due to its increased carbohydrate content, Aranesp® differs from rhEPO as a result of a higher molecular weight (37,100 compared to 30,400 Daltons), sialic acid content (22 compared to 14 sialic acid residues), and increased negative charge. The increased carbohydrate content of Aranesp® accounts for its distinct biochemical and biological properties, in particular a 3-fold longer circulating half-life than other existing erythropoietins when administered via the intravenous (i.v.) or subcutaneous (s.c.) route. However, the relative EPO receptor binding affinity was inversely correlated with the carbohydrate content, with Aranesp® displaying a 4.3-fold lower relative affinity for the EPO receptor than that of rhEPO. Following s.c. administration, the absorption of Aranesp® is slow and rate-limiting, serum levels reaching a maximum at a mean of 54 h. The time to maximum concentration is longer than that reported for rhEPO, probably because of the increased molecular size of Aranesp®. However currently, the extended circulating half-life gives Aranesp® a significant clinical advantage over Procrit® due to its less frequent dosing.

Dynepo (Epoetin δ; developed by Transkaryotic Therapies (in conjunction with Aventis Pharma)) is a gene-activated human erythropoietin, produced in human cell culture, for the treatment of anemia in patients with renal failure. Continuous erythropoietin receptor activator (CERA; developed by Roche), or R-744, is a second-generation erythropoietin, for the potential treatment of anemia associated with chemotherapy. CERA contains a single methoxypolyethylene glycol polymer of approximately 30 Kda that extends the half life of this agent.

EPO is a major biopharmaceutical product with worldwide sales topping US $3 billion. It is used primarily to boost erythrocyte and red blood cell formation in patients to treat anemia associated with chronic renal failure, cancer chemotherapy, HIV infection, pediatric use, premature infants and to reduce the need for blood transfusions in anemic patients undergoing elective non-cardiac and non-vascular surgery. In humans, treatment with doses of EPO has been found to be safe and well-tolerated.

Recently, several lines of evidence suggest that erythropoietin, as a member of the cytokine superfamily, performs other important physiologic functions which are mediated through interaction with the erythropoietin receptor (EPOR). These actions include mitogenesis, modulation of calcium influx into smooth muscle cells and neural cells, production of erythrocytes, hyperactivation of platelets, production of thrombocytes, and effects on intermediary metabolism. It is believed that erythropoietin provides compensatory responses that serve to improve hypoxic cellular microenvironments as well as modulate programmed cell death caused by metabolic stress. Hence, in addition to its erythropoietic activity, EPO exhibits tissue protective capabilities. Further, such tissue protective activities appear to be independent of its hematopoietic function.

EPO can be administered orally, systemically, buccally, transdermally, intravenously, intramuscularly and subcutaneously and, typically, multiple administrations are used in treatment regimens. The formulations are typically stored in refrigerated (2-8° C.) conditions to ensure retention of activity. Hence, improved EPO stability (half-life) in administered conditions (in vivo), such as stability in serum, and in vitro (e.g., during production, purification and storage conditions) can improve its utility and efficiency as a drug.

Provided herein are variants of the EPO polypeptide that display improved stability as assessed by resistance to proteases (blood, intestinal, etc) and/or increased thermal tolerance and/or pH conditions, wherein the mutant variants exhibit increased protein half-life. The EPO variants that exhibit improved stability possess increased stability in administration conditions such as in the bloodstream, gastrointestinal tract, under low pH conditions (e.g., the stomach), mouth, throat, and/or under storage conditions.

C. Exemplary Methods for Evolving or Modifying EPO Polypeptides and Other Therapeutic Polypeptides Provided herein are methods for increasing stability and half-life of an EPO polypeptide and other therapeutic polypeptides by increasing resistance to proteolysis. Any method for such modification can be employed including directed evolution methods, such as those in published U.S. application Serial Nos. US-2004-0132977-A1 and US-2005-0202438-A1. Exemplary methods of modifying EPO polypeptides and other therapeutic polypeptides to increase resistance to proteolysis by proteases (blood, serum, gastrointestinal, etc.), whereby the modified polypeptide exhibits increased half-life in vitro and/or in vivo. Provided herein are modified EPO polypeptides and other therapeutic polypeptides in which the primary amino acid sequence is modified to confer increased resistance to proteases. Among the amino acid modifications provided herein are such modifications including replacement of amino acids in the primary sequence of the EPO polypeptide and other therapeutic polypeptides in order to decrease proteolytic cleavage of the polypeptide.

Any EPO polypeptide or variants thereof, including species and allelic variants, can be modified as described herein. The positions of such mutations are described with reference to SEQ ID NOS: 2 and 237, but can effected in any variant EPO polypeptide such as, but not limited to those set forth in SEQ ID NOS: 227, 228, 238-243, 309 and 310.

Other modifications of the modified EPO polypeptide or other therapeutic polypeptides can be included, such as, but not limited to, addition of carbohydrate, phosphate, sulfur, hydroxyl, carboxyl and polyethylene glycol (PEG) moieties. Thus, the modified EPO polypeptides and other therapeutic polypeptides provided herein can be further modified, for example, by glycosylation, phosphorylation, sulfation, hydroxylation, carboxylation and/or PEGylation. Such modifications can be effected in vivo or in vitro.

Provided herein are methods of modifying therapeutic polypeptides to increase resistance to proteolysis by proteases and contacting proteolytic enzymes with peptide inhibitors, thereby inhibiting activity of the proteases. Also provided herein are the modified polypeptides generated by said methods. Provided herein are EPO polypeptides and other therapeutic polypeptides that display improved stability as assessed by resistance to proteases; the modified EPO polypeptides and other therapeutic polypeptides exhibiting these properties possess, thereby, increased protein half-life in vitro or in vivo.

The modified EPO polypeptides and other therapeutic polypeptides (also referred to herein as variants) are more stable compared to unmodified EPO polypeptides or other unmodified therapeutic polypeptides. Increasing stability (i.e., the half-life of proteins in vivo) can result in a decrease in the frequency of injections needed to maintain a sufficient drug level in serum, thus leading to: i) higher comfort to, and acceptance by, treated subjects, particularly human subjects, ii) lower doses necessary to achieve comparable biological effects, and iii) as a consequence, an attenuation of the (dose-dependent) secondary effects.

Increased stability of EPO polypeptides and other therapeutic polypeptides can be achieved, for example, by destruction of protease target residues or sequences and/or by modification of residues that contribute to conformational stability and are susceptible to denaturation by temperature, pH or other denaturing agent. Modification of EPO polypeptides and other therapeutic polypeptides to increase stability can be accomplished while keeping activity unchanged compared to the unmodified or wild-type therapeutic polypeptide. Alternatively, modification of EPO or other therapeutic polypeptide stability can be accomplished while increasing activity compared to the unmodified or wild-type therapeutic polypeptide. Any methods known in the art can be used to create modified EPO polypeptides and other modified therapeutic polypeptides. In the methods described herein, modifications are chosen using the method of 2D-scanning mutagenesis as described, for example, in PCT published applications WO 2004/022747 and WO 2004/022593.

Any of a variety of general approaches described for protein-directed evolution based on mutagenesis can be employed. Any of these methods or other suitable method, alone or in combination, can be used to produce modified EPO polypeptides and other therapeutic polypeptides to achieve increased stability and/or resistance to proteolysis. Such methods include, but are not limited to, random mutagenesis, where the amino acids in the starting protein sequence are replaced by all (or a group) of the 20 amino acids either in single or multiple replacements at different amino acid positions are generated on the same molecule, at the same time. Another method, restricted random mutagenesis, introduces either all of the 20 amino acids or DNA-biased residues. The bias is based on the sequence of the DNA and not on that of the protein in a stochastic or semi-stochastic manner, respectively, within restricted or predefined regions of the protein known in advance to be involved in the activity being "evolved." Additionally, methods of rational mutagenesis including 1D-scanning, 2D-scanning and 3D-scanning can be used alone or in combination to construct modified EPO variants.

1. Non-Restricted Rational Mutagenesis One-Dimensional (1D)-Scanning

Rational mutagenesis, also termed 1D-scanning, is a two-step process and is described in co-pending U.S. application Ser. No. 10/022,249 (U.S. Publication No. 2003/0134351-A1). 1D-scanning can be used to modify EPO polypeptides and other therapeutic polypeptides and, additionally, to identify positions for further modification by other methods such as 2D- and 3D-scanning. Briefly, in the first step, full-length amino acid scanning is performed where all and each amino acid in the starting therapeutic polypeptide sequence (for example, the EPO polypeptide of SEQ ID NO: 2) is replaced by a designated reference amino acid (e.g., alanine). Only a single amino acid is replaced on each protein molecule at a time. A collection of protein molecules having a single amino acid replacement is generated such that molecules differ from each other by the amino acid position at which the replacement has taken place. Mutant DNA molecules are designed, generated by mutagenesis and cloned individually, such as in addressable arrays, such that they are physically separated from each other and such that each one is the single product of an independent mutagenesis reaction. Mutant protein molecules derived from the collection of mutant nucleic acid molecules also are physically separated from each other, such as by formatting in addressable arrays. Activity assessment on each protein molecule allows for the identification of those amino acid positions that result in a drop in activity when replaced, thus indicating the involvement of that particular amino acid position in the protein's biological activity and/or conformation that leads to fitness of the particular feature being evolved. Those amino acid positions are referred to as HITs.

At the second step, a new collection of molecules is generated such that each molecule differs from each of the others by the amino acid present at the individual HIT positions identified in step 1. All 20 amino acids (19 remaining) are introduced at each of the HIT positions identified in step 1; while each individual molecule contains, in principle, one and only one amino acid replacement. Mutant DNA molecules are designed, generated by mutagenesis and cloned individually, such as in addressable arrays, such that they are physically separated from each other and such that each one is the single product of an independent mutagenesis reaction. Mutant protein molecules derived from the collection of mutant DNA molecules also are physically separated from each other, such as by formatting in addressable arrays. Activity assessment then is individually performed on each individual mutant molecule. The newly generated mutants that lead to a desired alteration (such as an improvement) in a protein activity are referred to as LEADs. This method permits an indirect search for property or activity alteration, such as improved stability (e.g., improved resistance to proteases) based on one rational amino acid replacement and sequence change at a single amino acid position at a time, in search of a new, unpredicted amino acid sequence at some unpredicted regions along a protein to produce a protein that exhibits a desired activity or altered activity, such as better performance than the starting protein.

In this approach, neither the amino acid position nor the replacing amino acid type are restricted. Full length protein scanning is performed during the first step to identify HIT positions, and then all 20 amino acids are tested at each of the HIT positions, to identify LEAD sequences; while, as a starting point, only one amino acid at a time is replaced on each molecule. The selection of the target region (HITs and surrounding amino acids) for the second step is based upon experimental data on activity obtained in the first step. Thus, no prior knowledge of protein structure and/or function is necessary. Using this approach, LEAD sequences have been found on proteins that are located at regions of the protein not previously known to be involved in the particular biological activity being modified; thus emphasizing the power of this approach to discover unpredictable regions (HITs) as targets for fitness improvement.

2. Two Dimensional (2D) Rational Scanning (Restricted Rational Mutagenesis)

The 2D-scanning (or restricted rational mutagenesis) methods for protein rational evolution (see, co-pending U.S. Published Application Nos. US 2005-0202438 A1 and US-2004-0132977-A1 and published International applications WO 2004/022593 and WO 2004/022747) are based on scanning over two dimensions. The first dimension is the amino acid position along the protein sequence, in order to identify is-HIT target positions. The second dimension is scanning the amino acid type selected for replacing a particular is-HIT amino acid position. An advantage of the 2D-scanning methods provided herein is that at least one, and typically the amino acid position and/or the replacing amino acid, can be restricted such that fewer than all amino acids on the protein-backbone are selected for amino acid replacement; and/or fewer than all of the remaining 19 amino acids available to replace an original, such as native, amino acid are selected for replacement.

In particular embodiments, based on i) the particular protein properties to be evolved (e.g., resistance to proteolysis), ii) sequence of amino acids of the protein, and iii) the known properties of the individual amino acids, a number of target positions along the protein sequence are selected, in silico, as "is-HIT target positions." This number of is-HIT target positions is as large as reasonably possible such that all reasonably possible target positions for the particular feature being evolved are included. In particular, embodiments where a restricted number of is-HIT target positions are selected for replacement, the amino acids selected to replace the is-HIT target positions on the particular protein being optimized can be either all of the remaining 19 amino acids or, more frequently, a more restricted group comprising selected amino acids that are contemplated to have the desired effect on protein activity. In another embodiment, so long as a restricted number of replacing amino acids are used, all of the amino acid positions along the protein backbone can be selected as is-HIT target positions for amino acid replacement. Mutagenesis then is performed by the replacement of single amino acid residues at specific is-HIT target positions on the protein backbone (e.g., "one-by-one," such as in addressable arrays), such that each individual mutant generated is the single product of each single mutagenesis reaction. Mutant DNA molecules are designed, generated by mutagenesis and cloned individually, such as in addressable arrays, such that they are physically separated from each other and that each one is the single product of an independent mutagenesis reaction. Mutant protein molecules derived from the collection of mutant DNA molecules also are physically separated from each other, such as by formatting in addressable arrays. Thus, a plurality of mutant protein molecules is produced. Each mutant protein contains a single amino acid replacement at only one of the is-HIT target positions. Activity assessment is then individually performed on each individual protein mutant molecule, following protein expression and measurement of the appropriate activity. An example of practice of this method is shown in the Examples in which mutant EPO molecules are produced.

The newly generated proteins that lead to altered, typically improved, target protein activity are referred to as LEADs.

This method relies on an indirect search for protein improvement for a particular activity, such as increased resistance to proteolysis, based on amino acid replacement and sequence change at single or, in another embodiment, a limited number of amino acid positions at a time. As a result, optimized proteins, which have modified sequences of amino acids at some regions along the protein that perform better (at a particular target activity or other property) than or different from the starting protein, are identified and isolated.

2D-scanning on EPO was used to generate variants improved in protein stability, including improved resistance to proteolysis. To effect such modifications, amino acid positions were selected using in silico analysis of EPO.

a. Identifying In-Silico HITS

The 2D-scanning method for directed evolution of proteins includes identifying and selecting (using in silico analysis) specific amino acids and amino acid positions (referred to herein as is-HITs) along the protein sequence that are contemplated to be directly or indirectly involved in the feature being evolved. As noted, the 2D-scanning methods provided include the following two steps. The first step is an in silico search of a target sequence of amino acids of the protein to identify all possible amino acid positions that can be targets for the activity being evolved. This is effected, for example, by assessing the effect of amino acid residues on the property or properties to be altered on the protein, using any known standard software. The particulars of the in silico analysis is a function of the property to be modified.

Once identified, these amino acid positions or target sequences are referred to as "is-HITs" (in silico HITs). In silico HITs are defined as those amino acid positions (or target positions) that potentially are involved in the "evolving" feature, such as increased resistance to proteolysis. The discrimination of the is-HITs among all the amino acid positions in a protein sequence can be made based on the amino acid type at each position in addition to the information on the protein secondary or tertiary structure. In silico HITs constitute a collection of mutant molecules such that all possible amino acids, amino acid positions or target sequences potentially involved in the evolving feature are represented. No strong theoretical discrimination among amino acids or amino acid positions is made at this stage. In silico HIT positions are spread over the full length of the protein sequence. Single or a limited number of is-HIT amino acids are replaced at a time on the target EPO polypeptide or other therapeutic polypeptide.

A variety of parameters can be analyzed to determine whether or not a particular amino acid on a protein might be involved in the evolving feature, typically a limited number of initial premises (typically no more than 2) are used to determine the in silico HITs. For example, as described herein, to increase the stability of EPO polypeptides and other therapeutic polypeptides, the first condition is the nature of the amino acids linked to stability of the molecule such as its participation in directing proteolytic cleavage. A second premise, for example, can be related to the specific position of those amino acids along the protein structure.

During the first step of identification of is-HITs according to the methods provided herein, each individual amino acid along the protein sequence is considered individually to assess whether it is a candidate for is-HIT. This search is done one-by-one and the decision on whether the amino acid is considered to be a candidate for a is-HIT is based on (1) the amino acid type; (2) the position in the protein and protein structure if known; and (3) the predicted interaction between that amino acid and its neighbors in sequence and space.

Is-HITs were identified for a number of properties of EPO that contribute to protein stability, such as removal/modification of protease sensitive sites. Such modifications contribute to protein stability and thereby, to increasing the half-life of an EPO polypeptide and other therapeutic polypeptides provided in vitro, in vivo or ex vivo.

b. Identifying Replacing Amino Acids

Once the is-HITs target positions are selected, the next step is identifying those amino acids that will replace the original, such as native, amino acid at each is-HIT position to alter the activity level for the particular feature being evolved. The set of replacing amino acids to be used to replace the original, such as native, amino acid at each is-HIT position can be different and specific for the particular is-HIT position. The choice of the replacing amino acids takes into account the need to preserve the physicochemical properties such as hydrophobicity, charge and polarity of essential (e.g., catalytic, binding, etc.) residues and alter some other property of the protein (e.g., protein stability). The number of replacing amino acids of the remaining 19 non-native (or non-original) amino acids that can be used to replace a particular is-HIT target position ranges from 1 up to about 19, and anywhere in between, depending on the properties for the particular modification.

Numerous methods of selecting replacing amino acids (also referred to herein as "replacement amino acids") are well known in the art. Protein chemists determined that certain amino acid substitutions commonly occur in related proteins from different species. As the protein still functions with these substitutions, the substituted amino acids are compatible with protein structure and function. Often, these substitutions are to a chemically similar amino acid, but other types of changes, although relatively rare, also can occur.

Knowing the types of changes that are most and least common in a large number of proteins can assist with predicting alignments and amino acid substitutions for any set of protein sequences. Amino acid substitution matrices are used for this purpose. A number of matrices are available. A detailed presentation of such matrices can be found in the co-pending U.S. Published Application Nos. US 2005-0202438 A1 and US-2004-0132977-A1 and published International applications WO 2004/022593 and WO 2004/022747, each of which is incorporated herein in their entirety. Such matrices also are known and available in the art, for example in the reference listed below.

In amino acid substitution matrices, amino acids are listed horizontally and vertically, and each matrix position is filled with a score that reflects how often one amino acid would have been paired with the other in an alignment of related protein sequences. The probability of changing amino acid "A" into amino acid "B" is assumed to be identical to the reverse probability of changing "B" into "A". This assumption is made because, for any two sequences, the ancestor amino acid in the phylogenetic tree is usually not known. Additionally, the likelihood of replacement should depend on the product of the frequency of occurrence of the two amino acids and on their chemical and physical similarities. A prediction of this model is that amino acid frequencies will not change over evolutionary time (Dayhoff et al., *Atlas of Protein Sequence and Structure,* 5(3): 345-352, 1978). Several exemplary amino acid substitution matrices, including, but not limited to block substitution matrix (BLOSUM) (Henikoff et al., *Proc. Nat. Acad. Sci. USA,* 89: 10915-10919 (1992)), Jones et al. (*Comput. Appl. Biosci.,* 8: 275-282 (1992)), Gonnet et al. (*Science,* 256: 1433-1445 (1992)), Fitch (*J. Mol. Evol.,* 16(1): 9-16 (1966)), Feng et al. (*J. Mol. Evol.,* 21: 112-125 (1985)), McLachlan (*J. Mol. Biol.,* 61:

409-424 (1971)), Grantham (*Science,* 185: 862-864 (1974)), Miyata (*J. Mol. Evol.,* 12: 219-236 (1979)), Rao (*J. Pept. Protein Res.,* 29: 276-281 (1987)), Risler (*J. Mol. Biol.,* 204: 1019-1029 (1988)), Johnson et al (*J. Mol. Biol.,* 233: 716-738 (1993)), and Point Accepted Mutation (PAM) (Dayhoff et al., *Atlas Protein Seq. Struct.* 5: 345-352 (1978)).

Dayhoff and coworkers developed a model of protein evolution that resulted in the development of a set of widely used replacement matrices (Dayhoff et al., *Atlas of Protein Sequence and Structure,* 5(3):345-352 (1978)) termed percent accepted mutation matrices (PAM). In deriving these matrices, each change in the current amino acid at a particular site is assumed to be independent of previous mutational events at that site. Thus, the probability of change of any amino acid A to amino acid B is the same, regardless of the previous changes at that site and also regardless of the position of amino acid A in a protein sequence.

In the Dayhoff approach, replacement rates are derived from alignments of protein sequences that are at least 85% identical; this constraint ensures that the likelihood of a particular mutation being the result of a set of successive mutations is low. Because these changes are observed in closely related proteins, they represent amino acid substitutions that do not significantly change the function of the protein. Hence, they are called "accepted mutations," as defined as amino acid changes that are accepted by natural selection.

The outcome of the two steps set forth above, which is performed in silico is that: (1) the amino acid positions that are the target for mutagenesis are identified (referred to as is-HITs); and (2) the replacing amino acids for the original, such as native, amino acids at the is-HITs are identified, to provide a collection of candidate LEAD mutant molecules that are expected to perform differently from the native molecule. These are assayed for a desired optimized, improved or altered activity.

c. Construction of Modified Proteins and Biological Assays

Once is-HITs are selected as set forth above, replacing amino acids are introduced. Mutant proteins typically are prepared using recombinant DNA methods and assessed in appropriate biological assays for the particular activity (feature) optimized. An exemplary method of preparing the mutant proteins is by mutagenesis of the original, such as native, gene using methods well known in the art. Mutant molecules are generated one-by-one, such as in addressable arrays, such that each individual mutant generated is the single product of each single and independent mutagenesis reaction. Individual mutagenesis reactions are conducted separately, such as in addressable arrays where they are physically separated from each other. Once a population of sets of nucleic acid molecules encoding the respective mutant proteins is prepared, each is separately introduced one-by-one into appropriate cells for the production of the corresponding mutant proteins. This also can be performed, for example, in addressable arrays where each set of nucleic acid molecules encoding a respective mutant protein is introduced into cells confined to a discrete location, such as in a well of a multi-well microtiter plate. Each individual mutant protein is individually phenotypically characterized and performance is quantitatively assessed using assays appropriate for the feature being optimized (i.e., feature being evolved). Again, this step can be performed in addressable arrays. Those mutants displaying a desired increased or decreased performance compared to the original, such as native molecules are identified and designated LEADs. From the beginning of the process of generating the mutant DNA molecules up through the readout and analysis of the performance results, each candidate LEAD mutant is generated, produced and analyzed individually, such as from its own address in an addressable array. The process is amenable to automation.

3. Three Dimensional (3D) Scanning 3D scanning, as described in co-pending U.S. Published Application Nos. US 2005-0202438 A1 and US-2004-0132977-A1 and published PCT applications WO 2004/022747 and WO 2004/022593, is an additional method of rational evolution of proteins based on the identification of potential target sites for mutagenesis (is-HITs). The method uses comparison of patterns of protein backbone folding between structurally related proteins, irrespective of the underlying sequences of the compared proteins. Once the structurally related amino acid positions are identified on the protein of interest, then suitable amino acid replacement criteria, such as PAM analysis, can be employed to identify candidate LEADs for construction and screening.

For example, analysis of "structural homology" between and among a number of related cytokines can be used to identify on various members of the cytokine family, those amino acid positions and residues that are structurally similar or structurally related. For example, 3D scanning can be used to identify amino acid positions on EPO that are structurally similar or structurally related to those found in cytokine mutants, for example, that have been modified for improved stability. Exemplary cytokines include, but are not limited to, granulocyte-macrophage colony stimulating factor (GM-CSF), interleukin-2 (IL-2), interleukin-3 (IL-3), interleukin-4 (IL-4), interleukin-5 (IL-5), interleukin-13 (IL-13), Flt3 ligand and stem cell factor (SCF).

Using the 3D-scanning methods described herein, once one protein within a family of proteins (e.g., EPO within cytokine family) is modified using the methods provided herein for generating LEAD mutants, is-HITs can be identified for other or all proteins within a particular family by identifying the corresponding amino acid positions therein using structural homology analysis (based upon comparisons of the 3D structures of the family members with original protein to identify corresponding residues for replacement) as described hereinafter. The is-HITs for the family members identified in this manner then can be subjected to the next step of identifying replacing amino acids and further assayed to obtain LEADs or super-LEADs as described herein. Similarly, information from 2D-scanning performed on other cytokines such as, for example, granulocyte-macrophage colony stimulating factor (GM-CSF), interleukin-2 (IL-2), interleukin-3 (IL-3), interleukin-4 (IL-4), interleukin-5 (IL-5), interleukin-13 (IL-13), Flt3 ligand, and stem cell factor (SCF), can be used to optimize EPO polypeptides.

This method can be applied to any desired phenotype using any protein, such as a cytokine, as the starting material to which an evolution procedure, such as the rational directed evolution procedure of U.S. Published Application No. US 2003-0134351 A1 or the 2-dimensional scanning method described herein. The structurally corresponding residues are then altered on members of the family to produce additional cytokines with similar phenotypic alterations.

a. Homology

Typically, homology between proteins is compared at the level of their amino acid sequences, based on the percent or level of coincidence of individual amino acids, amino acid per amino acid, when sequences are aligned starting from a reference, generally the residue encoded by the start codon. For example, two proteins are said to be "homologous" or to bear some degree of homology whenever their respective amino acid sequences show a certain degree of matching upon alignment comparison. Comparative molecular biology is primarily based on this approach. From the degree of homology or coincidence between amino acid sequences, conclusions can be made on the evolutionary distance between or among two or more protein sequences and biological systems.

The concept of "convergent evolution" is applied to describe the phenomena by which phylogenetically-unrelated organisms or biological systems have evolved to share features related to their anatomy, physiology and structure as a response to common forces, constraints and evolutionary demands from the surrounding environment and living organisms. Alternatively, "divergent evolution," is applied to describe the phenomena by which strongly phylogenetically related organisms or biological systems have evolved to diverge from identity or similarity as a response to divergent forces, constraints and evolutionary demands from the surrounding environment and living organisms.

In the typical traditional analysis of homologous proteins there are two conceptual biases corresponding to: i) "convergent evolution," and ii) "divergent evolution." Whenever the aligned amino acid sequences of two proteins do not match well with each other, these proteins are considered "not related" or "less related" with each other and have different phylogenetic origins. There is no (or low) homology between these proteins and their respective genes are not homologous (or show little homology). If these two "non-homologous" proteins under study share some common functional features (e.g., interaction with other specific molecules, or activity), they are determined to have arisen by "convergent evolution," (i.e., by evolution of their non-homologous amino acid sequences, in such a way that they end up generating functionally "related" structures).

On the other hand, whenever the aligned amino acid sequences of two proteins do match with each other to a certain degree, these proteins are considered to be "related" and to share a common phylogenetic origin. A given degree of homology is assigned between these two proteins and their respective genes likewise share a corresponding degree of homology. During the evolution of their initial highly homologous amino acid sequence, enough changes can be accumulated in such a way that they end up generating "less-related" sequences and less related function. The divergence from perfect matching between these two "homologous" proteins under study is said come from "divergent evolution."

b. 3D-Scanning (Structural Homology) Methods

Structural homology refers to homology between the topology and three-dimensional structure of two proteins. Structural homology is not necessarily related to "convergent evolution" or to "divergent evolution," nor is it related to the underlying amino acid sequence. Rather, structural homology is likely driven (through natural evolution) by the need of a protein to fit specific conformational demands imposed by its environment. Particular structurally homologous "spots" or "loci" would not be allowed to structurally diverge from the original structure, even when its own underlying sequence does diverge. This structural homology is exploited herein to identify loci for mutation.

Within the amino acid sequence of a protein resides the appropriate biochemical and structural signals to achieve a specific spatial folding in either an independent or a chaperon-assisted manner. Indeed, this specific spatial folding ultimately determines protein traits and activity. Proteins interact with other proteins and molecules in general through their specific topologies and spatial conformations. In principle, these interactions are not based solely on the precise amino acid sequence underlying the involved topology or conformation. If protein traits, activity (behavior and phenotypes) and interactions rely on protein topology and conformation, then evolutionary forces and constraints acting on proteins can be expected to act on topology and conformation. Proteins sharing similar functions will share comparable characteristics in their topology and conformation, despite the underlying amino acid sequences that create those topologies and conformations.

4. Super-LEADs and Additive Directional Mutagenesis (ADM)

Modification of EPO polypeptides and other therapeutic polypeptides also can include combining two or more mutations. For example, Additive Directional Mutagenesis (ADM) can be used to assemble on a single mutant protein multiple mutations present on the individual LEAD molecules, so as to generate super-LEAD mutant proteins (see co-pending U.S. Published Application Nos. US 2005-0202438 A1 and US-2004-0132977-A1 and published PCT applications WO 2004/022747 and WO 2004/022593). ADM is a repetitive multi-step process where at each step after the creation of the first LEAD mutant protein a new LEAD mutation is added onto the previous LEAD mutant protein to create successive super-LEAD mutant proteins. ADM is not based on genetic recombination mechanisms, nor on shuffling methodologies; instead, it is a simple one-mutation-at-a-time process, repeated as many times as necessary until the total number of desired mutations is introduced on the same molecule. To avoid the exponentially increasing number of all possible combinations that can be generated by putting together on the same molecule a given number of single mutations, a method is provided herein that, although it does not cover all the combinatorial possible space, still captures a big part of the combinatorial potential. "Combinatorial" is used herein in its mathematical meaning (i.e., subsets of a group of elements, containing some of the elements in any possible order) and not in the molecular biological or directed evolution meaning (i.e., generating pools, or mixtures, or collections of molecules by randomly mixing their constitutive elements).

A population of sets of nucleic acid molecules encoding a collection of new super-LEAD mutant molecules is generated tested and phenotypically characterized one-by-one in addressable arrays. Super-LEAD mutant molecules are such that each molecule contains a variable number and type of LEAD mutations. Those molecules displaying further improved fitness for the particular feature being evolved are referred to as super-LEADs. Super-LEADs can be generated by other methods known to those of skill in the art and tested by the high throughput methods herein. For purposes herein a super-LEAD typically has activity with respect to the function or biological activity of interest that differs from the improved activity of a LEAD by a desired amount, such as at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more from at least one of the LEAD mutants from which it is derived. In yet other embodiments, the change in activity is at least about 2 times, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, or more greater than at least one of the LEAD molecules from which it is derived. As with LEADs, the change in the activity for super-LEADs is dependent upon the property that is being "evolved." The desired alteration, which can be either an increase or a reduction in a feature or property, will depend upon the function or property of interest.

In one embodiment, the ADM method employs a number of repetitive steps, such that at each step a new mutation is added on a given molecule. Although numerous different ways are possible for combining each LEAD mutation onto a super-LEAD protein, an exemplary way the new mutations (e.g., mutation 1 (m1), mutation 2 (m2), mutation 3 (m3), mutation 4 (m4), mutation 5 (m5), mutation n (mn)) can be added corresponds to the following diagram:

m1
m1+m2
m1+m2+m3
m1+m2+m3+m4
m1+m2+m3+m4+m5
m1+m2+m3+m4+m5+ . . . +mn
m1+m2+m4
m1+m2+m4+m5
m1+m2+m4+m5+ . . . +mn
m1+m2+m5
m1+m2+m5+ . . . +mn
m2
m2+m3
m2+m3+m4
m2+m3+m4+m5
m2+m3+m4+m5+ . . . +mn
m2+m4
m2+m4+m5
m2+m4+m5+ . . . +mn
m2+m5
m2+m5+ . . . +mn
. . . , etc. . . .

5. Multi-Overlapped Primer Extensions

Another method that can be employed to generate combinations of two or more mutations is using oligonucleotide-mediated mutagenesis referred to as "multi overlapped primer extensions". This method can be used for the rational combination of mutant LEADs to form super-LEADS. This method allows the simultaneous introduction of several mutations throughout a small protein or protein-region of known sequence. Overlapping oligonucleotides of typically around 70 bases in length (since longer oligonucleotides lead to increased error) are designed from the DNA sequence (gene) encoding the mutant LEAD proteins in such a way that they overlap with each other on a region of typically around 20 bases. Although typically about 70 bases are used to create the overlapping oligonucleotides, the length of additional overlapping oligonucleotides for use can range from about 30 bases up to about 100 bases. Likewise, although typically the overlapping region of the overlapping oligonucleotides is about 20 bases, the length of other overlapping regions for use herein can range from about 5 bases up to about 40 bases. These overlapping oligonucleotides (including or not point mutations) act as template and primers in a first step of PCR (using a proofreading polymerase, e.g., Pfu DNA polymerase, to avoid unexpected mutations) to create small amounts of full-length gene. The full-length gene resulting from the first PCR is then selectively amplified in a second step of PCR using flanking primers, each one tagged with a restriction site in order to facilitate subsequent cloning. One multi overlapped extension process yields a full-length (multi-mutated) nucleic acid molecule encoding a candidate super-LEAD protein having multiple mutations therein derived from LEAD mutant proteins.

D. Modified EPO Polypeptides Exhibiting Increased Protein Stability

Provided herein are modified EPO polypeptides (also referred to herein as EPO variants) that display improved protein stability (e.g., increased protease resistance, or increased conformational stability that, for example, renders a polypeptide more resistant to denaturation by temperature or pH changes). A modified EPO polypeptide provided herein exhibiting increased protein stability can lead to an increased half-life of the polypeptide in vitro (e.g., during production, purification and storage) or in vivo (e.g., after administration to a subject). For example, increased half-life can occur following administration of the polypeptide to a subject, such as a human subject. The increased half-life of the modified EPO polypeptide can be increased by an amount that is at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more compared to the half-life of the unmodified EPO polypeptide. In some examples, the increased half-life of the modified EPO polypeptide can be increased by an amount that is at least 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, or more times when compared to the half-life of the unmodified EPO polypeptide. Hence, the modified EPO polypeptides provided herein offer EPO with advantages including a decrease in the frequency of injections needed to maintain a sufficient drug level in serum, thus leading to, for example, higher comfort and acceptance by subjects, lower doses necessary to achieve comparable biological effects and attenuation of secondary effects.

Provided herein are modified EPO polypeptides containing modifications that alter any one or more of the properties of EPO that contribute to increased protein stability, such as increased protease resistance, and any combinations of the modifications thereof. Increased protein stability can be accomplished by amino acid replacement, such that resistance to proteases by amino acid or replacements can be achieved by direct destruction of the protease target residue or sequence. Generally, modified EPO polypeptides retain one or more activities of an unmodified EPO polypeptide. For example, the modified EPO polypeptides provided herein exhibit at least one activity that is substantially unchanged (less than 1%, 5% or 10% changed) compared to the unmodified or wild-type EPO. In other examples, the activity of a modified EPO polypeptide is increased or is decreased as compared to an unmodified EPO polypeptide. Activity includes, for example, but not limited erythropoietic or tissue protective activity. Activity can be assessed in vitro or in vivo and can be compared to the unmodified EPO polypeptide, such as for example, the mature, wild-type native EPO polypeptide (SEQ ID NO: 2 or 237), the wild-type precursor EPO polypeptide (SEQ ID NO: 1), or any other EPO polypeptide known to one of skill in the art that is used as the starting material.

Modified EPO polypeptides provided herein can be modified at one or more amino acid positions corresponding to amino acid positions of a mature EPO polypeptide, for example, a mature EPO polypeptide having an amino acid sequence set forth in SEQ ID NO: 2 or 237. EPO polypeptides can be modified compared to a precursor or mature EPO polypeptide having an amino acid sequence set forth in SEQ ID NO: 1 or 2, respectively. EPO polypeptides can be modified compared to a precursor or mature EPO polypeptide in which the C-terminal arginine is removed, for example, having an amino acid sequence set forth in SEQ ID NO: 236 or 237, respectively. Modified EPO polypeptides provided herein also include naturally occurring human EPO (hEPO) variants. Exemplary hEPO variants include, but are not limited to, variants that occur at amino acid positions C7, Y15, D43, Y49, G77, S120, Y145 of the mature hEPO polypeptide, wherein the amino acid modification is C7H, Y15F, D43N, Y49F, G77S, S120C, Y145F (see e.g., U.S. Pat. Nos. 4,703,008 and 7,041,794; SEQ ID NOS: 238-243). Any of the modified EPO polypeptide provided here can contain such modifications. The hEPO polypeptide can be of any human tissue or cell-type origin. Modified EPO polypeptides provided herein also include variants of EPO of non-human origin. Such alignments and selection of positions can be performed with any EPO polypeptide by aligning it with hEPO and selecting corresponding positions for modification. For example, modified EPO polypeptides can be variants of a non-human EPO, including, but not limited to, mouse, rat, guinea pig, cow, sheep, dog, cat, chicken, pig, rabbit, fish and chimpanzee EPO. Exemplary unmodified non-human EPO polypeptides have amino acid sequences set forth in SEQ ID NOS: 202-226. Modified EPO polypeptides also include polypeptides that are synthetic EPO polypeptides prepared recombinantly, or synthesized or constructed by other methods known in the art based upon known polypeptides.

Typically, modifications include replacement (i.e., substitution), addition, deletion or a combination thereof, of amino acid residues as described herein. Modified EPO polypeptides include those with 1, 2, 3, 4, 5, 6, 7, 8, 9, 10, 11, 12, 13, 14, 15, 16, 17, 18, 19, 20 or more modified positions. Generally, the modification results in increased stability without losing at least one activity, such as erythropoietic or tissue protective activity (i.e., retains at least one activity as defined herein) of an unmodified EPO polypeptide. A modified EPO exhibiting increased protein stability containing a single amino acid change at an is-HIT position as compared to an unmodified EPO is called a LEAD. EPO polypeptide candidate LEAD polypeptides can include amino acid replacement or replacements at any one or more of the is-HIT positions selected using methods described herein or known in the art, such as obtained using PAM analysis. Exemplary amino acid modifications corresponding to amino acid positions of a mature EPO polypeptide that can contribute to an increase in protein stability with respect to protease resistance are set forth in Table 3. In Table 3 below, the sequence identifier (SEQ ID NO) is in parenthesis next to each substitution.

Also among the variants provided herein are modified EPO polypeptides with two or more modifications compared to native or wild-type EPO. Modified EPO polypeptides include those with 2, 3, 4, 5, 6, 7, 8, 9, 10, 11, 12, 13, 14, 15, 16, 17, 18, 19, 20 or more modified positions. The two or more modifications can include two or more modifications of the same property, e.g., two modifications that modify resistance to proteases (blood, intestinal, etc.). In another embodiment, the two or more modifications include combinations of properties that each contribute to EPO stability. For example, an EPO variant can include one or more modifications that remove a protease sensitive site and one or more modifications that alter EPO conformational stability. EPO variants carrying replacements at more than one is-HIT sites and displaying improved stability are called super-LEADs. A EPO super-LEAD can for example, contain 2, 3, 4, 5, 6, 7, 8, 9, 10 or more than 10 amino acid changes compared to wild-type or unmodified EPO. In one example, a modified EPO polypeptide candidate super-LEAD can contain two or more amino acid modifications selected from among modifications set forth in Table 3.

1. Protease Resistance

The delivery of stable peptide and protein drugs to patients is a major challenge for the pharmaceutical industry. These types of drugs in the human body are constantly eliminated or taken out of circulation by different physiological processes including internalization, glomerular filtration and proteolysis. The latter is often the limiting process affecting the half-life of proteins used as therapeutic agents in per-oral administration and either intravenous or intramuscular injections. Hence, of interest are therapeutic proteins that increase protein stability manifested as an increased resistance to digestion by proteases. Among modifications for therapeutic proteins are those that increase protection against protease digestion without destroying or eliminating a therapeutic or the therapeutic activity. Such changes are useful for producing longer-lasting therapeutic proteins. Thus, in one aspect, the EPO polypeptides provided herein have been modified to increase resistance to proteolysis, thereby increasing the half-life of the modified EPO polypeptide in vitro (e.g., production, processing, storage, assay, etc.) or in vivo (e.g., serum stability). Thus, the modified EPO polypeptides provided herein are useful as longer-lasting therapeutic proteins.

Proteases, proteinases or peptidases catalyze the hydrolysis of covalent peptide bonds. Modified EPO polypeptides provided herein exhibit increased resistance to proteolysis by proteases, including those that occur, for example, in body fluids and tissues, such as those that include, but are not limited to, saliva, blood, serum, intestinal, stomach, blood, cell lysates, cells and others. These include proteases of all types, such as, for example, serine proteases and matrix metalloproteinases.

Modifications of EPO polypeptides include, but are not limited to, resistance to one or more proteases including, but not limited to, pepsin, trypsin, chymotrypsin, elastase, aminopeptidase, gelatinase B, gelatinase A, α-chymotrypsin, carboxypeptidase, endoproteinase Arg-C, endoproteinase Asp-N, endoproteinase Glu-C, endoproteinase Lys-C, luminal pepsin, microvillar endopeptidase, dipeptidyl peptidase, enteropeptidase, hydrolase, NS3, factor Xa, Granzyme B, thrombin, plasmin, urokinase, tPA and PSA.

Modified EPO polypeptides provided herein exhibit increased resistance to proteolysis, particularly by enzymes present in serum, blood, the gut, the mouth and other body fluids. Such increase in resistance is manifested as increased half-life of the EPO polypeptide by an amount that is at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more compared to the unmodified or wild-type EPO polypeptide in either in vivo (human blood, human serum, saliva, digestive fluid, the intestinal tract, etc.), or an in vitro mixture containing one or more proteases. Typically, the half-life in vitro or in vivo of the modified EPO polypeptides provided herein is increased by an amount selected from at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more when compared to the half-life of unmodified or wild-type EPO in either blood, serum, or in an in vitro preparation or an in vitro mixture containing one or more proteases.

Typically, the modified EPO polypeptides provided herein exhibit at least one activity that is substantially unchanged (less than 1%, 5% or 10% changed) compared to the unmodified or wild-type EPO. In some examples, the activity is increased compared to the unmodified EPO. In other examples, the activity is decreased compared to the unmodified EPO polypeptide. Activity includes, for example, erythropoietic or tissue protective activity, and can be compared to the unmodified polypeptide, such as for example, the mature, wild-type native EPO polypeptide (SEQ ID NO: 2 or 237), the wild-type precursor EPO polypeptide (SEQ ID NO: 1 or 236), or any other EPO polypeptide used as the starting material.

a. Serine Proteases

Serine proteases participate in a range of functions in the body, including blood clotting, inflammation as well as digestive enzymes in prokaryotes and eukaryotes. Serine proteases are sequence specific. While cascades of protease activations control blood clotting and complement, other proteases are involved in signaling pathways, enzyme activation and degradative functions in different cellular or extracellular compartments.

Serine proteases include, but are not limited, to chymotrypsin, trypsin, elastase, NS3, factor Xa, Granzyme B, thrombin, plasmin, urokinase, tPA and PSA. Chymotrypsin, trypsin and elastase are synthesized by the pancreatic acinar cells, secreted in the small intestine and are responsible for catalyzing the hydrolysis of peptide bonds. All three of these enzymes are similar in structure, as shown through their X-ray structures. Each of these digestive serine proteases targets different regions of the polypeptide chain, based upon the amino acid residues and side chains surrounding the site of cleavage. The active site of serine proteases is shaped as a cleft where the polypeptide substrate binds. Amino acid residues are labeled from N to C term of the polypeptide substrate (Pi, ..., P3, P2, P1, P1', P2', P3', ..., Pj) and their respective binding sub-sites (Si, ..., S3, S2, S1, S1', S2', S3', ..., Sj). The cleavage is catalyzed between P1 and P1'. Chymotrypsin hydrolyzes peptide bonds flanked with bulky hydrophobic amino acid residues. Particular residues include phenylalanine, tryptophan and tyrosine, which fit into a snug hydrophobic pocket. Trypsin hydrolyzes peptide bonds flanked with positively charged amino acid residues. Instead of having the hydrophobic pocket of the chymotrypsin, trypsin possesses an aspartic acid residue at the back of the pocket, which can interact with positively charged residues such as arginine and lysine. Elastase hydrolyzes peptide bonds flanked with small neutral amino acid residues, such as alanine, glycine and valine. In contrast to trypsin and chymotrypsin, elastase contains a pocket that is lined with valine and threonine, rendering it a mere depression, which can accommodate the smaller amino acid residues. Serine proteases are ubiquitous in prokaryotes and eukaryotes and serve important and diverse biological functions such as hemostasis, fibrinolysis, complement formation and the digestion of dietary proteins.

Elastases that belong to the serine protease family display extensive sequence homology to other known serine proteases, including trypsin and chymotrypsin. Serine elastases preferentially cleave polypeptides adjacent to aliphatic amino acids residues, typically alanine, valine and methionine, and to a lesser extent, leucine and isoleucine. Humans have six elastase genes which encode the structurally similar proteins, elastase 1 (ELA-1, also known as pancreatic elastase, PE), elastase 2 (neutrophil elastase, NE, also known as PMN elastase, bone marrow serine protease, medullasin, human leukocyte elastase, HLE), elastase 2A (ELA-2A), elastase 2B (ELA-2B), elastase 3A (ELA-3A, elastase IIIA, Protease E), and elastase-3B (ELA-3B, elastase IIIB, protease E). Other serine proteases with elastase activity include, but are not limited to, proteinase-3 (PR-3), endogenous vascular elastase (EVE), and endothelial cell elastase (ECE).

Neutrophil primary azurophil granules carry NE (ELA-2) and PR-3, which are released upon neutrophil activation. NE is involved in degradation of the extracellular matrix and (ECM), including degradation of elastin, cartilage proteoglycans, collagens, and fibronectin, and digestion of material taken into the cell by phagocytosis. NE also helps in degradation of proteins, such as immunoglobulins and surfactant apoproteins. NE preferentially cleaves Val-X bonds and to a lesser extent Ala-X bonds. Abnormal or excessive release of NE has been linked to defects in connective tissue turnover, arthritis and inflammation. Like NE, PR-3 also functions to activate proenzymes, such as metalloproteinases, and cytokines, such as TNF-α, IL-1β, and interleukin-8 (IL-8).

Pancreatic elastase (ELA-1) preferentially cleaves Ala-X bonds and is expressed primarily in skin keratinocytes. Expression of ELA is not normally found in the adult pancreas though it is often expressed in and used as a marker for pancreatic cancers. Elastase activity of the normal pancreas is attributable to ELA-2A and ELA-2B. ELA-2A and ELA-2B preferentially cleaves Leu-X, Met-X and Phe-X bonds.

Some pathological conditions are believed to result at least in part from an imbalance between the elastases and their endogenous inhibitors. Uncontrolled proteolytic degradation by neutrophil elastases, especially ELA-2 has been implicated in a number of pathological conditions like pulmonary emphysema, acute respiratory distress syndrome, septic shock, multiple organ failure, rheumatoid arthritis and cystic fibrosis.

High concentrations of elastases can be found in the gastrointestinal tract and blood stream. Hence, effective therapeutics to be administered via these routes can be achieved through modification of elastase cleavage sites.

b. Matrix Metalloproteinases

Matrix metalloproteinases (MMPs) are a family of $Zn^{2+}$- and calcium-dependent endopeptidases that degrade components of the extracellular matrix (ECM). In addition, MMPs also can process a number of cell-surface cytokines, receptors and other soluble proteins. They are involved in normal tissue remodeling processes such as wound healing, pregnancy and angiogenesis. Under physiological conditions, MMPs are made as inactive precursors (zymogens) and are processed to their active form. Additionally, the enzymes are specifically regulated by endogenous inhibitors called tissue inhibitors of matrix metalloproteinases (TIMPs). The proteolytic activity of MMPs acts as an effector mechanism of tissue remodeling in physiologic and pathologic conditions, and as modulator of inflammation. The excess synthesis and production of these proteins lead to accelerated degradation of the ECM which is associated with a variety of diseases and conditions such as, for example, bone homeostasis, arthritis, cancer, multiple sclerosis and rheumatoid arthritis. In the context of neuroinflammatory diseases, MMPs have been implicated in processes such as (a) blood-brain barrier (BBB) and blood-nerve barrier opening, (b) invasion of neural tissue by blood-derived immune cells, (c) shedding of cytokines and cytokine receptors, and (d) direct cellular damage in diseases of the peripheral and central nervous system (Leppert et al. *Brain Res. Rev.* 36(2-3): 249-57 (2001); Borkakoti et al. *Prog. Biophys. Mol. Biol.* 70(1): 73-94 (1998)).

Members of the MMP family include collagenases, gelatinases, stromelysins, matrilysin and membrane-bound MMPs. Most MMPs are secreted in the inactive proenzyme form. The secreted proenzyme MMPs can be activated by several proinflammatory agents such as oxidants, proteinases including elastase, plasmin, and trypsin, and other MMPs (Cuzner and Opdenakker. *J Neuroimmunol.* 94(1-2): 1-14 (1999)). In tissues, physiological MMP activators include tissue or plasma proteinases or opportunistic bacterial proteinases. For example, the plasminogen activator/plasmin system, including ubiquitous plasminogen by urokinase (u-Pa) and tissue-type plasminogen activator (t-Pa), is an important activator of pro-MMP in pathological situations. MMP activity can be inhibited by tissue inhibitors of metalloproteinases (TIMPs), by serine proteinase inhibitors (serpins), and by nonspecific proteinase inhibitors, such as α2-macroglobulin. TIMPs inhibit the MMP activity through noncovalent binding of the active zinc-binding sites of MMPs. Proteolytic activities of MMPs and plasminogen activators, and their inhibitors, are important in maintaining the integrity of the ECM as cell-ECM interactions influence and mediate a wide range of processes including proliferation, differentiation, adhesion and migration of a variety of cell types. Excessive production of matrix metalloproteinases has been implicated in tissue damage and wound healing, inflammatory disorders, proliferative disorders and autoimmune diseases (St-Pierre et al. *Curr. Drug Targets Inflamm. Allergy* 2(3): 206-215 (2003); Opdenakker, G. Verh. K. Acad. Geneeskd. Belg. 59(6): 489-514 (1997)).

c. Increased Resistance to Proteolysis by Removal of Proteolytic Sites

The 2D-scanning methodology was used to identify the amino acid changes on hEPO that lead to an increase in stability when challenged either with proteases (blood, intestinal, etc.), blood lysate or serum. Increasing protein stability to proteases (blood, lysate, intestinal serum, etc.), is contemplated herein to provide a longer in vivo half-life for the particular protein molecules and, thus, a reduction in the frequency of necessary administrations to subjects.

The first step in the design of hEPO mutants resistant to proteolysis includes identifying sites vulnerable to proteolysis along the protein sequence. Based on a list of selected blood, intestinal or any other type of proteases considered (Table 2), the complete list of all amino acids and sequences of amino acids in hEPO that can be targeted by those proteases was first determined in silico. The protease targets (amino acids or sequences of amino acids along the hEPO polypeptide) are named in silico HITs (is-HITs). Since protease mixtures in the body are quite complex in composition, it can be expected that the majority of the residues in a given protein sequence can be targeted for proteolysis.

The second step in the design of hEPO mutants that are resistant to proteolysis includes identifying the appropriate replacing amino acids such that if they replaced the natural amino acids in hEPO at is-HITs, the protein (i) becomes resistant to proteolysis; and (ii) elicits a level of activity at least comparable to the wild-type hEPO polypeptide. The choice of the replacing amino acids must consider the broad target specificity of certain proteases and the need to preserve the physicochemical properties such as hydrophobicity, charge and polarity of essential (e.g., catalytic, binding, etc.) residues in hEPO.

"Point Accepted Mutation" (PAM; Dayhoff et al., 1978) can be used as part of the 2D scanning approach. PAM values, originally developed to produce alignments between protein sequences, are available in the form of probability matrices that reflect an evolutionary distance between amino acids. Conservative substitutions of a residue in a reference sequence are those substitutions that are physically and functionally similar to the corresponding reference residues, i.e., that have a similar size, shape, electric charge, and/or chemical properties, including the ability to form covalent or hydrogen bonds and other such interactions. Conservative substitutions show the highest scores fitting with the PAM matrix criteria in the form of accepted point mutations. The PAM250 matrix is used in the frame of 2D-scanning to identify candidate replacing amino acids for the is-HITs in order to generate conservative mutations without affecting protein function. At least two amino acids with the highest values in PAM250 matrix corresponding to conservative substitutions or accepted point mutations were chosen for replacement at each is-HIT. The replacement of amino acids by cysteine residues is explicitly avoided since this change can lead to the formation of intermolecular disulfide bonds.

Briefly, using the algorithm PROTEOL (on-line at infobiogen.fr and at bioinfo.hku.hk/services/analyseq/cgi-bin/proteol_in.pl), a list of residues along the mature hEPO polypeptide of 166 amino acids (SEQ ID NO: 2), which can be recognized as substrate for proteases (blood, intestinal, etc.) in Table 2 was established. The algorithm generates a proteolytic digestion map based on a list of proteases, the proteolytic specificity of the proteases, and the polypeptide amino acid sequence that is entered. Table 2 shows the in silico identification of amino acid positions that are targets for proteolysis using selected proteases and chemical treatment.

TABLE 2

| Abbreviation | Amino Acid Position | Protease or Chemical Treatment |
| --- | --- | --- |
| AspN | D | Endoproteinase Asp-N |
| Chymo | (F, W, Y, M, L)~P | Chymotrypsin |
| Clos | R | Clostripain |
| CnBr | M | Cyanogen Bromide |
| IBzO | W | Iodosobenzoate |
| Myxo | K | Myxobacter |
| NH₂OH | N G | Hydroxylamine |
| pH2.5 | D P | pH 2.5 |
| ProEn | P | Proline Endopeptidase |
| Staph | E | Staphylococcal Protease |
| Tryp | (K, R)~P | Trypsin |
| TrypK | K~P | Trypsin (Arg blocked) |
| TrypR | R~P | Trypsin (Lys blocked) |

Is-HITS were identified and LEADS created for higher resistance to proteolysis of hEPO. The native amino acids at each of the is-HIT positions and replacing amino acids for increased resistance to proteolysis can include, but are not limited to replacing any of Y, A, L, S, T, I, V, F, Q and M by any of E, D, K, R, N, Q, S and T. Is-HITS and LEADs can include modifications at regions susceptible to proteolysis.

d. Modified EPO Polypeptides Exhibiting Increased Protease Resistance

Using methods described herein and in U.S. Patent Publication No. US 2005-0202438, the following is-HIT positions were identified to eliminate protease sensitive sites of EPO polypeptide: 2, 3, 4, 5, 7, 8, 10, 12, 13, 14, 15, 16, 17, 18, 20, 21, 23, 29, 31, 35, 37, 42, 43, 45, 48, 49, 51, 52, 53, 54, 55, 62, 64, 67, 69, 70, 72, 75, 76, 80, 81, 87, 88, 89, 90, 91, 93, 96, 97, 102, 103, 105, 108, 109, 110, 112, 116, 117, 121, 122, 123, 129, 130, 131, 136, 138, 139, 140, 141, 142, 143, 145, 148, 149, 150, 152, 153, 154, 155, 156, 159, 162, 165, and 166. The amino acid replacement or replacements can be at any one or more positions corresponding to any of the following positions: P2, P3, R4, L5, C7, D8, R10, L12, E13, R14, Y15, L16, L17, E18, K20, E21, E23, C29, E31, L35, E37, P42, D43, K45, F48, Y49, W51, K52, R53, M54, E55, E62, W64, L67, L69, L70, E72, L75, R76, L80, L81, P87, W88, E89, P90, L91, L93, D96, K97, L102, R103, L105, L108, L109, R110, L112, K116, E117, P121, P122, D123, P129, L130, R131, D136, F138, R139, K140, L141, F142, R143, Y145, F148, L149, R150, K152, L153, K154, L155, Y156, E159, R162, D165, and R166 of a mature EPO polypeptide set forth in SEQ ID NO: 2 or 237 or is at a corresponding position in an allelic or species variant or other variant of a mature human EPO polypeptide, an EPO polypeptide having at least or at least about 60%, 70%, 75%, 80%, 85%, 90%, 91%, 92%, 93%, 94%, 95%, 96%, 97%, 98%, 99%, or more sequence identity to a mature human EPO polypeptide set forth in SEQ ID NO: 2 or 237.

In one embodiment, positions are typically replaced as follows: replacement of D with N or Q, replacement of E with H, Q or N, replacement of F with I or V, replacement of K with Q or N, replacement of L with I or V, replacement of M with I or V, replacement of N with Q or S, replacement of P with A or S, replacement of R with H or Q, replacement of W with H or S, replacement of Y with I or H, replacement of A, G, I, S, T, or V with Q, H, or N.

In one embodiment, positions corresponding to hEPO are selected (is-HITS) and amino acid replacements are made (LEADs) with increased resistance to proteolysis that include, but are not limited to replacements corresponding to those set forth in Table 3 where the replacements are made compared to the sequence of amino acids set forth in SEQ ID NO: 2. Table 3 provides non-limiting examples of amino acid replacements, corresponding to amino acid positions of a mature EPO polypeptide, that increase resistance to proteolysis and, thereby, protein stability.

In reference to such mutants, the first amino acid (one-letter abbreviation) corresponds to the amino acid that is replaced, the number corresponds to position in the hEPO polypeptide sequence with reference to SEQ ID NO: 2, and the second amino acid (one-letter abbreviation) corresponds to the amino acid selected that replaces the first amino acid at that position. In Table 3, the sequence identifier (SEQ ID NO.) is in parenthesis next to each substitution. The EPO polypeptides employed for modification can be any EPO polypeptide, including other mammalian EPO polypeptides. Corresponding positions, as assessed by appropriate alignment, are identified and modified as described herein.

(e.g., SEQ ID NO: 2)), P2A, P3S, P3A, R4H, R4Q, L5I, L5V, C7S, C7V, C7A, C7I, C7T, D8Q, D8H, D8N, R10H, R10Q, L12V, L12I, E13Q, E13H, E13N, R14H, R14Q, Y15H, Y15I, L61I, L16V, L17I, L17V, E18Q, E18H, E18N, K20Q, K20T, K20N, E21Q, E21H, E21N, E23Q, E23H, E23N, C29S, C29V, C29A, C29I, C29T, E31Q, E31H, E31N, L35V, L35I, E37Q, E37H, E37N, P42S, P42A, D43Q, D43H, D43N, K45Q, K45T, K45N, F48I, F48V, Y49H, Y49I, W51S, W51H, K52Q, K52T, K52N, R53H, R53Q, M54V, M54I, E55Q, E55H, E55N, E62Q, E62H, E62N, W64S, W64H, L67I, L67V, L69V, L69I, L70I, L70V, E72Q, E72H, E72N, L75V, L75I, R76H, R76Q, L80V, L80I, L81I, L81V, P87S, P87A, W88S, W88H, E89Q, E89H, E89N, P90S, P90A, L91I, L91V, L93V, L93I, D96Q, D96H, D96N, K97Q, K97T, K97N, L102V, L102I, R103H, R103Q, L105I, L105V, L108I, L108V, L109I, L109V, R110H, R110Q, L112V, L112I, K116Q, K116T, K116N, E117Q, E117H, E117N, P121S, P121A, P122S, P122A, D123Q, D123H, D123N, P129S, P129A, L130V, L130I, R131H, R131Q, D136Q, D136H, D136N, F138I, F138V, R139H, R139Q, K140N, K140Q, L141I, L141V, F142I, F142V, R143H, R143Q, Y145H, Y145I, F148I, F148V, L149I, L149V, R150H, R150Q, K152Q, K152T, K152N, L153I, L153V, K154Q, K154T, K154N, L155V, L155I, Y156H, Y156I, E159Q, E159H, E159N, R162H, R162Q, D165Q, D165H, D165N, R166H, and R166Q where the modified polypeptide exhibits increased resistance to proteolysis. In some examples, the modifications are in an unmodified EPO polypeptide, such as an EPO having a sequence of amino acids set forth in SEQ ID NO: 2 or 237. In other examples, the modifications are in an

TABLE 3

List of Human EPO Modifications to Increase Resistance to Proteolysis

| | | | | | | |
|---|---|---|---|---|---|---|
| P2S (3) | P2A (4) | P3S (5) | P3A (6) | R4H (7) | R4Q (8) | C7S (9) |
| C7V (10) | D8Q (11) | D8H (12) | R10H (13) | R10Q (14) | L12V (15) | L12I (16) |
| E18Q (17) | E18H (18) | K20Q (19) | K20T (20) | E21Q (21) | E21H (22) | E23Q (23) |
| E23H (24) | C29S (25) | C29V (26) | E31Q (27) | E31H (28) | L35V (29) | L35I (30) |
| E37Q (31) | E37H (32) | P42S (33) | P42A (34) | D43Q (35) | D43H (36) | K45Q (37) |
| K45T (38) | F48I (39) | F48V (40) | Y49H (41) | Y49I (42) | W51S (43) | W51H (44) |
| K52Q (45) | K52T (46) | R53H (47) | R53Q (48) | M54V (49) | M54I (50) | E55Q (51) |
| E55H (52) | E62Q (53) | E62H (54) | W64S (55) | W64H (56) | L69V (57) | L69I (58) |
| E72Q (59) | E72H (60) | L75V (61) | L75I (62) | R76H (63) | R76Q (64) | L80V (65) |
| L80I (66) | P87S (67) | P87A (68) | W88S (69) | W88H (70) | E89Q (71) | E89H (72) |
| P90S (73) | P90A (74) | L93V (75) | L93I (76) | D96Q (77) | D96H (78) | K97Q (79) |
| K97T (80) | L102V (81) | L102I (82) | R110H (83) | R110Q (84) | L112V (85) | L112I (86) |
| K116Q (87) | K116T (88) | P121S (89) | P121A (90) | P122S (91) | P122A (92) | D123Q (93) |
| D123H (94) | P129S (95) | P129A (96) | L130V (97) | L130I (98) | R131H (99) | R131Q (100) |
| D136Q (101) | D136H (102) | R143H (103) | R143Q (104) | Y145H (105) | Y145I (106) | R150H (107) |
| R150Q (108) | K152Q (109) | K152T (110) | K154Q (111) | K154T (112) | L155V (113) | L155I (114) |
| E159Q (115) | E159H (116) | R162H (117) | R162Q (118) | C29A (119) | C29I (120) | C29T (121) |
| C7A (122) | C7I (123) | C7T (124) | D123N (125) | D136N (126) | D43N (127) | D96N (128) |
| E159N (129) | E18N (130) | E21N (131) | E23N (132) | E31N (133) | E37N (134) | E55N (135) |
| E62N (136) | E72N (137) | E89N (138) | K116N (139) | K152N (140) | K154N (141) | K20N (142) |
| K45N (143) | K52N (144) | K97N (145) | D8N (146) | D165Q (147) | D165H (148) | D165N (149) |
| R166H (150) | R166Q (151) | L5I (152) | L5V (153) | E13Q (154) | E13H (155) | E13N (156) |
| R14H (157) | R14Q (158) | Y15H (159) | Y15I (160) | L16I (161) | L16V (162) | L17I (163) |
| L17V (164) | L67I (165) | L67V (166) | L70I (167) | L70V (168) | L81I (169) | L81V (170) |
| L91I (171) | L91V (172) | R103H (173) | R103Q (174) | L105I (175) | L105V (176) | L108I (177) |
| L108V (178) | L109I (179) | L109V (180) | E117Q (181) | E117H (182) | E117N (183) | F138I (184) |
| F138V (185) | R139H (186) | R139Q (187) | K140N (188) | K140Q (189) | L141I (190) | L141V (191) |
| F142I (192) | F142V (193) | F148I (194) | F148V (195) | L149I (196) | L149V (197) | L153I (198) |
| L153V (199) | Y156H (200) | Y156I (201) | | | | |

A modified EPO polypeptide provided herein that exhibits increased protease resistance can contain one or more amino acid modifications corresponding to any one or more modifications of P2S (i.e., replacement of P by S at a position corresponding to amino acid position 2 of mature human EPO in an unmodified EPO polypeptide that is an allelic or species variant or other variant of a mature human EPO polypeptide having at least or at least about 60%, 70%, 75%, 80%, 85%, 90%, 91%, 92%, 93%, 94%, 95%, 96%, 97%, 98%, 99%, or more sequence identity to a mature human EPO polypeptide set forth in SEQ ID NO: 2 or 237. Exemplary modified EPO LEAD candidate polypeptides are set forth in any one of SEQ ID NOS: 3-201.

Additionally, a modified EPO polypeptide as set forth above can contain a further modification compared to an unmodified EPO polypeptide. Generally, the resulting modified EPO polypeptide retains one or more activities of the unmodified EPO polypeptide.

e. Assessment of EPO Variants with Increased Resistance to Proteolysis

Increased resistance to proteolysis of EPO variants can be assessed by any methods known in the art to assess protein stability, thermal tolerance, protease sensitivity, and resistance and/or EPO activity. In one example, protease resistance is measured by incubating a modified EPO polypeptide with one or more proteases and then assessing residual activity compared to an untreated control. A modified EPO can be compared with an unmodified and/or wild-type native EPO treated under similar conditions to determine if the particular variant retains more activity than the unmodified EPO. Activity can be assessed by any methods known in the art, for example by measuring erythropoietic or tissue protective activities.

Kinetic studies of protease resistance also can be used to assess a modified EPO polypeptide. For example, a modified EPO polypeptide is incubated with one or more proteases and samples are taken over a series of time-points. At each time point, the proteases are inactivated and the samples are then tested for EPO activity. In one embodiment, the modified polypeptide is at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more resistant to proteolysis.

In one exemplary embodiment, EPO variants are assessed for protease resistance with a mixture of proteases and proteolytic conditions including pepsin, trypsin, chymotrypsin, elastase, aminopeptidase, gelatinase B, gelatinase A, α-chymotrypsin, carboxypeptidase, endoproteinase Arg-C, endoproteinase Asp-N, endoproteinase Glu-C, endoproteinase Lys-C, luminal pepsin, microvillar endopeptidase, dipeptidyl peptidase, enteropeptidase, hydrolase, NS3, factor Xa, Granzyme B, thrombin, plasmin, urokinase, tPA and PSA. For example, a cell proliferation assay can be used to assess erythropoietic activity of modified EPO polypeptides compared to unmodified EPO polypeptides. Specifically, erythrocyte cell proliferation activity of EPO can be determined by the capacity of the modified EPO polypeptides to induce cell proliferation in an erythrocyte cell proliferation assay, such as a TF-1 proliferative assay. The resistance of the modified EPO polypeptides compared to wild-type EPO against enzymatic cleavage can be analyzed by mixing EPO polypeptides with proteases. After exposure to proteases, erythropoietic or tissue protective activities can be assessed.

In one example, erythropoietic activity of modified EPO is assessed in an assay by measuring the capacity of the modified EPO to modulate cell proliferation when added to the sample. Prior to the measurement of activity, EPO polypeptides can be challenged with proteases (e.g., blood, intestinal, etc.) including conditions mimicking administered conditions, such as serum, blood, saliva, or digestive assays (i.e., in vitro assays), and/or administered to a subject such as a mouse or human (i.e., in vivo assays) during different incubation or post-injection times. The activity measured, corresponds then to the residual activity following exposure to the proteolytic mixtures. Activity can be compared with an unmodified EPO as a measurement of the effect of the modification on protease stability and on the activity. In one example, the unmodified EPO is a wild-type native EPO. In another example, the unmodified EPO is a variant form of EPO that was used as a starting material to introduce further modifications. Modified EPO polypeptides also can be compared with any known EPO polypeptide in any assay known in the art to compare protease sensitivity, thermal tolerance and/or any other activity.

2. Super-LEADs

Modification of EPO polypeptides also can include combining two or more modifications as set forth above. Modified EPO super-LEAD polypeptides are a combination of single amino acid mutations present in two or more of the respective modified EPO LEAD polypeptides. Thus, modified EPO super-LEAD polypeptides have two or more of the single amino acid replacements derived from two or more of the respective modified EPO LEAD polypeptides. As described above and in detail below, modified EPO polypeptides provided herein exhibit increased protein stability manifested as an increased resistance to proteolysis. Typically, modified EPO LEAD polypeptides created are those whose performance has been optimized with respect to the unmodified polypeptide by modification of a single amino acid replacement at one is-HIT position. Modified EPO super-LEAD polypeptides are created such that the polypeptide contains two or more EPO LEAD modifications, each at a different is-HIT position. Modifications that increase proteolysis resistance can be added to other modifications provided herein or known in the art to increase proteolysis resistance. In one example, modifications that increase stability can be added to other modifications provided herein or known in the art to increase protein stability. In another example, modifications that increase stability can be added to modifications provided herein or known in the art to increase proteolysis resistance. Modifications that increase protease resistance and/or stability also can be added to modifications to EPO that alter other functionalities including activity, modifications that affect post-translation protein modifications and any other known modifications in the art.

Once the modified LEAD polypeptides have been identified using, for example, 2D-scanning methods, super-LEADs can be generated by combining two or more individual LEADs using methods well known in the art, such as recombination, mutagenesis and DNA shuffling, and by methods such as additive directional mutagenesis, 3D-scanning, and multi-overlapped primer extensions, as provided above.

Exemplary modified EPO super-LEAD polypeptides exhibiting increased protein stability can include EPO polypeptides containing two or more amino acid modifications as compared to an unmodified EPO polypeptide. In some examples, an EPO polypeptide can contain 2, 3, 4, 5, 6, 7, 8, 9, 10, 11, 12, 13, 14, 15, 16, 17, 18, 19, 20 or more modified positions. Generally, the resulting EPO polypeptide exhibits increased protein stability and retains at least one activity of an unmodified EPO polypeptide. A modified EPO polypeptide can include any two or more amino acid modifications set forth in Table 3 above. For example, the modified EPO polypeptide can contain two or more amino acid modifications corresponding to any two or more modifications selected from among P2S, P2A, P3S, P3A, R4H, R4Q, L5I, L5V, C7S, C7V, C7A, C7I, C7T, D8Q, D8H, D8N, R10H, R10Q, L12V, L12I, E13Q, E13H, E13N, R14H, R14Q, Y15H, Y15I, L16I, L16V, L17I, L17V, E18Q, E18H, E18N, K20Q, K20T, K20N, E21Q, E21H, E21N, E23Q, E23H, E23N, C29S, C29V, C29A, C29I, C29T, E31Q, E31H, E31N, L35V, L35I, E37Q, E37H, E37N, P42S, P42A, D43Q, D43H, D43N, K45Q, K45T, K45N, F48I, F48V, Y49H, Y49I, W51S, W51H, K52Q, K52T, K52N, R53H, R53Q, M54V, M54I, E55Q, E55H, E55N, E62Q, E62H, E62N, W64S, W64H, L67I, L67V, L69V, L69I, L70I, L70V, E72Q, E72H, E72N, L75V, L75I, R76H, R76Q, L80V, L80I, L81I, L81V, P87S, P87A, W88S, W88H, E89Q, E89H, E89N, P90S, P90A, L91I, L91V, L93V, L93I, D96Q, D96H, D96N, K97Q, K97T, K97N, L102V, L102I, R103H, R103Q, L105I, L105V, L108I, L108V, L109I, L109V, R110H, R110Q, L112V, L112I, K116Q, K116T, K116N, E117Q, E117H, E117N, P121S, P121A, P122S, P122A, D123Q, D123H, D123N, P129S, P129A, L130V, L130I, R131H, R131Q, D136Q, D136H, D136N, F138I, F138V, R139H, R139Q, K140N, K140Q, L141I, L141V, F142I, F142V, R143H, R143Q, Y145H, Y145I, F148I, F148V, L149I, L149V, R150H, R150Q, K152Q, K152T, K152N, L153I, L153V, K154Q, K154T, K154N, L155V, L155I, Y156H, Y156I, E159Q, E159H, E159N, R162H, R162Q, D165Q, D165H, D165N, R166H, and R166Q of a mature EPO polypeptide set forth in SEQ ID NO: 2. In some examples, the modifications are in an unmodified EPO polypeptide having a sequence of amino acids set forth in SEQ ID NO: 237. In other examples, the modifications are in an in an unmodified EPO polypeptide that is an allelic or species variant or other variant of a mature human EPO polypeptide having at least or at least about 60%, 70%, 75%, 80%, 85%, 90%, 91%, 92%, 93%, 94%, 95%, 96%, 97%, 98%, 99%, or more sequence identity to a mature human EPO polypeptide set forth in SEQ ID NO: 2 or 237.

Exemplary modified EPO polypeptides provided herein that contain more than one modification, include, but are not limited to, R139H/R4H, R139H/L93I, R139H/K20Q, R139H/E159N, R139H/K52N, R139H/L153V, R139H/L93V, R139H/L80I, R139H/L93I, K20Q/L80I/R139H, K20Q/L93I/R139H, K20Q/L93V/R139H, R4H/K20Q/R139H/L80I, E159N/K20Q/R139H/L93I, K20Q/R139H/L153V, L153V/K20Q/R139H/L80I and E159N/K20Q/R139H/L80I.

3. Other EPO Modifications

In addition to any one or more amino acid modifications provided herein, a modified EPO polypeptide also can contain one or more additional modifications, including those known to those of skill in the art, including, but not limited to, PEGylation, hyperglycosylation, deimmunization, and others (see e.g., U.S. Pat. No. 5,856,298; U.S. Patent Publication Nos. 2003-0120045, 2004-0063917, 2005-0220800, 2005-0107591, 2006-0035322, and 2006-0073563; and International PCT Publication No.: WO 01/81405). Generally, the modification results in increased stability without losing at least one activity, such as erythropoietic or tissue protective activity (i.e., retains at least one activity as defined herein) of an unmodified EPO polypeptide. For example, other further modifications in an EPO polypeptide include one or more additional amino acid modifications and/or one or more chemical modifications. Such modifications include, but are not limited to, those that alter the immunogenicity, glycosylation, activity, or any other known property of an EPO polypeptide. In another example, chemical modifications include post-translational modifications of a protein, such as for example, glycosylation by a carbohydrate moiety, acylation (e.g., acetylation or succinylation), methylation, phosphorylation, hasylation, carbamylation, sulfation, prenylation, oxidation, guanidination, amidination, carbamylation (i.e., carbamoylation), trinitrophenylation, nitration, PEGylation, or a combination thereof. In addition, protein modifications also can include modification to facilitate the detection, purification and assay development of a polypeptide, such as for example, modification of a polypeptide with a Sulfo-NHS-LC-biotin for covalent attachment to a primary amine on a protein, or other similar modification for florescent, non-isotopic or radioactive labels. Exemplary further modifications in an EPO polypeptide are described below. Modified polypeptides that are conjugates and/or labeled also are provided. For example, provided herein are modified polypeptides that are conjugated to a PEG moiety or contain a carbohydrate moiety covalently linked to one or more glycosylation sites on the polypeptide.

In another embodiment, other known properties of an EPO polypeptide can be modified in addition to any one or more amino acid modifications provided herein. Such modifications include, but are not limited to, alteration of the erythropoietic or tissue protective activity of an EPO polypeptide. Resulting modified EPO polypeptides can be tested for one or more parameters to assess polypeptide properties, such as protein stability (e.g., increased resistance to proteases), or polypeptide activities, such as erythropoietic or tissue protective activity, using any of the assays described herein.

a. Immunogenicity

There are many instances where the efficacy of a therapeutic protein is limited by an unwanted immune reaction to the therapeutic protein. An immune response to a therapeutic protein, such as EPO, proceeds via the MHC class II peptide presentation pathway. Here, exogenous proteins are engulfed and processed for presentation in association with MHC class II molecules of the DR, DQ or DP type. MHC class II molecules are expressed by professional antigen presenting cells (APCs), such as macrophages and dendritic cells, amongst others. Engagement of a MHC class II peptide complex by a cognate T-cell receptor on the surface of the T cell, together with the cross binding of certain other co-receptors, such as the CD4 molecule, can induce an activated state within the T cell. Activation leads to the release of cytokines, further activating other lymphocytes such as B cells to produce antibodies or activating T killer cells as a full cellular immune response.

The ability of a peptide (T cell epitope) to bind a given MHC class II molecule for presentation on the surface of an APC is dependent on a number of factors, most notably its primary sequence. This will influence its propensity for proteolytic cleavage and also its affinity for binding within the peptide binding cleft of the MHC class II molecule. The MHC class II/peptide complex on the APC surface presents a binding face to a particular T cell receptor (TCR) able to recognize determinants provided by exposed residues of the peptide and the MHC class II molecule.

Formation of inhibitory antibodies to therapeutic EPO polypeptides is known in the art (see e.g., Casadevall et al. (2002) *N. Engl. J. Med.* 346: 469-475; Macdougall (2004) *Curr. Med. Res. Opin.* 20: 83-86; Verhelst et al. (2004) *Lancet* 363: 1768-1771; Locatelli and Del Vecchio (2003) *J. Nephrol.* 16: 461-466). Hence, the combination modified EPO polypeptides provided herein with modifications to decrease overall immunogenicity of the modified EPO polypeptides can improve the therapeutic properties of the EPO polypeptide. The identification of T cell epitopes can be carried out according to methods known in the art (see e.g., U.S. Patent Publication Nos. 2004-0063917, 2005-0220800, 2006-0035322, and 2006-0073563) and can be used to identify the binding propensity of EPO peptides to an MHC class II molecule.

Further modifications to a modified EPO polypeptide provided herein can include modifications of at least one amino acid residue resulting in a substantial reduction in activity of or elimination of one or more T cell epitopes from the protein, i.e., deimmunization of the polypeptide. One or more amino acid modifications at particular positions within any of the MHC class II ligands can result in a deimmunized EPO polypeptide with a reduced immunogenicity when administered as a therapeutic to a host, such as for example, a human host.

Exemplary amino acid positions for modification of a T cell epitope, and thereby a deimmunized EPO polypeptide with a reduced immunogenic potential, include amino acid modifications at one or more positions corresponding to any of the following positions: R4, L5, I6, D8, S9, R10, V11, L12, E13, R14, Y15, L16, L17, E18, A19, K20, E21, A22, E23, N24, I25, T27, G28, A30, C33, L35, N38, I39, T40, V41, D43, V46, F48, Y49, W51, K52, R53, M54A, M54C, M54D, M54E, M54G, M54, E55, V56, G57, Q58, Q59, A60, V61, E62, V63, W64, Q65, G66, L67, A68, L69P, L70, S71, E72, A73Q, A73, V74, L75, R76, G77, A79, L80, L81, V82, W88, E89, L91, Q92, L93, H94, V95, D96, K97, A98, V99, S100, G101, L102, R103, S104, L105, T107, L108, L109, R110, L112, G113, A114, Q115, K116, E117, A118, A118K, I119, S120, A124, A125, A127, L130, I133, A135, D136, F138, R139, K140, L141, F142, R143, V144, Y145, S146, N147, F148, L149, R150, G151, K152, L153E, K154, L155, Y156, T157, G158, E159, A160, C161, R162, T163 and G164 of a mature EPO polypeptide set forth in SEQ ID NO: 2 or 237.

Exemplary amino acid substitution for modification of a T cell epitope, and thereby a deimmunized EPO polypeptide with a reduced immunogenic potential, include amino acid modifications including: R4A, R4C, R4G, R4P, L5A, L5C, L5D, L5E, L5G, L5H, L5K, L5N, L5P, L5Q, L5R, L5S, L5T, I6A, I6G, I6D, I6E, I6G, I6H, I6K, I6N, I6P, I6Q, I6R, I6S, I6T, I6M, I6W, D8A, D8C, D8G, D8P, S9P, S9T, R10A, R10C, R10G, R10P, V11A, V11C, V11D, V11E, V11G, V11H, V11K, V11N, V11P, V11Q, V11R, V11S, V11T, V11F, V11I, V11M, V11W, V11Y, L12A, L12C, L12D, L12E, L12G, L12H, L12K, L12N, L12P, L12Q, L12R, L12S, L12T, L12F, L12I, L12M, L12V, L12W, L12Y, E13A, E13C, E13G, E13P, R14A, R14C, R14G, R14H, R14P, R14T, Y15A, Y15C, Y15D, Y15E, Y15G, Y15H, Y15K, Y15N, Y15P, Y15Q, Y15R, Y15S, Y15T, L16A, L16C, L16D, L16E, L16G, L16H, L16K, L16N, L16P, L16Q, L16R, L16S, L16T, L16W, L16Y, L17A, L17C, L17D, L17E, L17G, L17H, L17K, L17N, L17P, L17Q, L17R, L17S, L17T, L17F, L17I, L17M, L17V, L17W, L17Y, E18A, E18C, E18G, E18P, E18T, A19H, A19P, A19T, K20H, K20P, K20T, E21A, E21C, E21G, E21P, A22C, A22D, A22E, A22G, A22H, A22K, A22N, A22P, A22Q, A22R, A22S, A22T, E23P, E23T, N24A, N24C, N24G, N24P, I25A, I25C, I25D, I25E, I25G, I25H, I25K, I25N, I25P, I25Q, I25R, I25S, I25T, T27A, T27C, T27G, T27P, G28H, G28T, A30D, A30H, A30P, C33H, C33T, L35A, L35C, L35D, L35E, L35G, L35H, L35K, L35N, L35P, L35Q, L35R, L35S, L35T, L35M, L35W, L35Y, N38T, I39A, I39C, I39D, I39E, I39G, I39H, I39K, I39N, I39P, I39Q, I39R, I39S, I39T, T40D, T40H, V41A, V41C, V41D, V41E, V41G, V41H, V41K, V41N, V41P, V41Q, V41R, V41S, V41T, V41I, V41Y, D43T, V46A, V46C, V46D, V46E, V46G, V46H, V46K, V46N, V46P, V46Q, V46R, V46S, V46T, V46M, V46W, V46Y, F48A, F48C, F48D, F48E, F48G, F48H, F48K, F48N, F48P, F48Q, F48R, F48S, F48T, F48M, F48W, Y49A, Y49C, Y49D, Y49E, Y49G, Y49H, Y49K, Y49N, Y49P, Y49Q, Y49R, Y49S, Y49T, Y49M, Y49W, W51A, W51C, W51D, W51E, W51G, W51H, W51K, W51N, W51P, W51Q, W51R, W51S, W51T, K52A, K52C, K52G, K52H, K52P, K52T, K52E, K52D, R53A, R53C, R53G, R53H, R53P, R53Q, R53N, R53H, R53S, R53E, R53A, R53D, M54A, M54P, M54Q, M54R, M54S, M54T, M54H, M54K, M54N, M54P, M54Q, M54R, M54S, M54T, M54F, M54I, M54L, M54V, M54W, M54Y, E55A, E55C, E55G, E55P, E55T, V56, V56A, V56C, V56D, V56E, V56G, V56H, V56K, V56N, V56P, V56Q, V56R, V56S, V56T, V56F, V56I, V56L, V56W, V56Y, G57C, G57D, G57E, G57H, G57K, G57N, G57P, G57Q, G57R, G57S, G57T, Q58A, Q58C, Q58G, Q58P, Q59A, Q59C, Q59G, Q59H, Q59P, Q59T, Q59K, Q59R, Q59M, Q59W, Q59L, Q59Y, Q59F, Q59N, Q59E, Q59I, Q59A, A60C, A60D, A60E, A60G, A60H, A60K, A60N, A60P, A60Q, A60R, A60S, A60T, V61A, V61C, V61D, V61E, V61G, V61H, V61K, V61N, V61P, V61Q, V61R, V61S, V61T, V61W, E62H, E62P, E62S, E62T, V63A, V63C, V63D, V63E, V63G, V63H, V63K, V63N, V63P, V63Q, V63R, V63S, V63T, V63F, V63I, V63M, V63W, V63Y, W64A, W64C, W64D, W64E, W64G, W64H, W64K, W64N, W64P, W64Q, W64R, W64S, W64T, Q65A, Q65C, Q65G, Q65P, G66D, G66E, G66H, G66K, G66N, G66P, G66Q, G66R, G66S, G66T, L67A, L67C, L67D, L67E, L67G, L67H, L67K, L67N, L67P, L67Q, L67R, L67S, L67T, L67F, L67I, L67H, L67V, L67W, L67Y, A68C, A68D, A68E, A68G, A68H, A68K, A68N, A68P, A68Q, A68R, A68S, A68T, L69A, L69C, L69D, L69E, L69G, L69H, L69K, L69N, L69P, L69Q, L69R, L69S, L69T, L69F, L69I, L69M, L69W, L69Y, L70A, L70C, L70D, L70E, L70G, L70H, L70K, L70N, L70P, L70Q, L70R, L70S, L70T, L70Y, S71A, S71C, S71G, S71H, S71P, S71T, E72H, E72P, E72T, A73E, A73H, A73P, A73Q, A73T, V74A, V74C, V74D, V74E, V74G, V74H, V74K, V74N, V74P, V74Q, V74R, V74S, V74T, V74F, V74I, V74W, V74Y, L75A, L75C, L75D, L75E, L75G, L75H, L75K, L75N, L75P, L75Q, L75R, L75S, L75T, L75F, L75I, L75V, L75W, L75Y, R76A, R76C, R76G, R76P, G77H, G77P, G77T, A79H, A79P, L80A, L80C, L80D, L80E, L80G, L80H, L80K, L80N, L80P, L80Q, L80R, L80S, L80T, L80F, L80I, L80Y, L81A, L81C, L81D, L81E, L81G, L81H, L81K, L81N, L81P, L81Q, L81R, L81S, L81T, V82A, V82C, V82D, V82E, V82G, V82H, V82K, V82N, V82P, V82Q, V82R, V82S, V82T, W88A, W88C, W88D, W88E, W88G, W88H, W88K, W88N, W88P, W88Q, W88R, W88S, W88T, E89A, E89C, E89G, E89P, L91A, L91C, L91D, L91E, L91G, L91H, L91K, L91N, L91P, L91Q, L91R, L91S, L91T, L91F, L91I, L91M, L91V, L91W, L91Y, Q92A, Q92C, Q92G, Q92P, L93A, L93C, L93D, L93E, L93G, L93H, L93K, L93N, L93P, L93Q, L93R, L93S, L93T, L93M, L93W, L93Y, H94P, H94T, V95A, V95C, V95D, V95E, V95G, V95H, V95K, V95N, V95P, V95Q, V95R, V95S, V95T, V95F, V95I, V95M, V95W, V95Y, D96A, D96C, D96G, D96H, D96P, D96T, K97A, K97C, K97G, K97P, A98C, A98D, A98E, A98H, A98K, A98N, A98P, A98Q, A98R, A98S, A98T, V99A, V99C, V99D, V99E, V99G, V99H, V99K, V99N, V99P, V99Q, V99R, V99S, V99T, V99W, V99Y, S100D, S100H, S100N, S100P, S100Q, G101D, G101E, G101H, G101K, G101N, G101P, G101Q, G101R, G101S, G101T, L102A, L102C, L102D, L102E, L102G, L102H, L102K, L102N, L102P, L102Q, L102R, L102S, L102T, L102F, L102I, L102W, L102W, L102Y, R103D, R103E, R103H, R103N, R103P, R103Q, R103S, R103T, R103K, R103I, R103M, S104H, S104P, S104A, S104T, L105A, L105C, L105D, L105E, L105G, L105H, L105K, L105N, L105P, L105Q, L105R, L105S, L105T, L105I, L105Y, L105V, T107H, T107 K, T107R, T107N, T107G, T107D, T107E, L108A, L108C, L108D, L108E, L108G, L108H, L108K, L108N, L108P, L108Q, L108R, L108S, L108T, L108W, L108Y, L109A, L109C, L109D, L109E, L109G, L109H, L109K, L109N, L109P, L109Q, L109R, L109S, L109T, L109F, L109I, L109M, L109V, L109W, L109Y, R110A, R110C, R110G, R110P, R110K, R110N, R110H, R110Q, R110T, R110D, R110Y, L112A, L112C, L112D, L112E, L112G, L112H, L112K, L112N, L112P, L112Q, L112R, L112S, L112T, L112F, L121I, L112M, L112V, L112W, L112Y, G113H, G113T, A114C, A114D, A114E, A114G, A114H, A114K, A114N, A114P, A114Q, A114R, A114S, A114T, Q115P, Q115T, K116A, K116C, K116G, K116P, E117H, E117P, E117T, A118C, A118D, A118E, A118G, A118H, A118K, A118N, A118P, A118Q, A118R, A118S, A118T, I119A, I119C, I119D, I119E, I119G, I119H, I119K, I119N, I119P, I119Q, I119R, I119S, I119T, I119W, I119Y, S120P, S120T, A124D, A124H, A124P, A125P, A125T, A127H, A127P, A127T, L130A, L130C, L130D, L130E, L130G, L130H, L130K, L130N, L130P, L130Q, L130R, L130S, L130T, L130M, L130W, L130Y, I133A, I133C, I133D, I133E, I133G, I133H, I133K, I133N, I133P, I133Q, I133R, I133S, I133T, I133W, I133Y, A135H, A135P, D136P, D136T, F138A, F138C, F138D, F138E, F138G, F138H, F138K, F138N, F138P, F138Q, F138R, F138S, F138T, F138M, F138W, F138Y, R139A, R139C, R139G, R139P, R139T, R139H, R139K, R139Q, R139N, R139D, R139E, R139D, R139S, R139A, K140A, K140C, K140G, K140P, K140 D, K140E, L141A, L141C, L141D, L141E, L141G, L141H, L141K, L141N, L141P, L141Q, L141R, L141S, L141T, L141F, L141I, L141H, L141V, L141W, L141Y, F142A, F142C, F142D, F142E, F142G, F142H, F142K, F142N, F142P, F142Q, F142R, F142S, F142T, F142W, R143A, R143C, R143G, R143H, R143P, R143M, R143L, R143K, R143Q, R143E, R143W, R143D, R143N, R143A, R143T, R143S, V144A, V144C, V144D, V144E, V144G, V144H, V144K, V144N, V144P, V144Q, V144R, V144S, V144T, Y145A, Y145C, Y145D, Y145E, Y145G, Y145H, Y145K, Y145N, Y145P, Y145Q, Y145R, Y145S, Y145T, Y145W, S146D, S146H, S146P, S146T, S146 F, S146L, S146Y, S146E, S146W, S146A, S146M, S146K, S146Q, S146G, S146N, N147P, N147T, N147D, F148A, F148C, F148D, F148E, F148G, F148H, F148K, F148N, F148P, F148Q, F148R, F148S, F148T, F148M, L149A, L149C, L149D, L149E, L149G, L149H, L149K, L149N, L149P, L149Q, L149R, L149S, L149T, L149F, L149I, L149H, L149V, L149W, L149Y, R150A, R150C, R150D, R150G, R150H, R150P, R150T, R150K, R150E, R150Q, G151E, G151H, G151N, G151P, G151Q, G151S, G151T, G151A, K152A, K152C, K152D, K152G, K152N, K152P, K152Q, K152S, K152T, L153A, L153C, L153D, L153E, L153G, L153H, L153K, L153N, L153P, L153Q, L153R, L153S, L153T, L153F, L153I, L153M, L153V, L153W, L153Y, K154A, K154C, K154D, K154E, K154G, K154H, K154N, K154P, K154Q, K154S, K154T, K154F, K154W, K154L, K154M, K154Y, L155A, L155C, L155D, L155E, L155G, L155H, L155K, L155N, L155P, L155Q, L155R, L155S, L155T, L155F, L155I, L155M, L155V, L155W, L155Y, Y156A, Y156C, Y156D, Y156E, Y156G, Y156H, Y156K, Y156N, Y156P, Y156Q, Y156R, Y156S, Y156T, Y156M, Y156W, Y156Y, T157A, T157C, T157F, T157G, T157I, T157L, T157M, T157P, T157V, T157W, T157Y, T157N, T157D, T157E, G158C, G158D, G158E, G158F, G158H, G158I, G158K, G158M, G158N, G158P, G158Q, G158R, G158S, G158T, G158V, G158W, G158Y, E159A, E159C, E159F, E159G, E159I, E159L, E159M, E159P, E159T, E159V, E159K, E159Y, A160D, A160F, A160H, A160I, A160L, A160P, A160V, A160W, A160Y, C161D, C161E, C161F, C161H, C161I, C161K, C161L, C161N, C161P, C161Q, C161R, C161S, C161T, C161V, C161W, C161Y, R162T, T163A, T163C, T163F, T163G, T163I, T163L, T163M, T163P, T163V, T163W, T163Y, G164F, G164H, G164I, G164N, G164P, G164Q, G164S, G164T, G164V, G164W, and G164Y, where the amino acid position that is modified corresponds to a mature human EPO polypeptide having the sequence set forth in SEQ ID NO: 2 or 237 or is at a corresponding position in an allelic or species variant or other variant of a mature human EPO polypeptide having at least or at least about 60%, 70%, 75%, 80%, 85%, 90%, 91%, 92%, 93%, 94%, 95%, 96%, 97%, 98%, 99%, or more sequence identity to a mature human EPO polypeptide set forth in SEQ ID NO: 2 or 237. Exemplary amino acids modifications that can contribute to reduced immunogenicity of a EPO polypeptide include any one or more amino acid modifications corresponding to any one or more modifications set forth on Table 4 corresponding to amino acid positions of a mature EPO polypeptide set forth in SEQ ID NO: 2 or 237.

TABLE 4

List of human EPO Modifications for Decreased Immunogenicity

| | | | | | | | | | |
|---|---|---|---|---|---|---|---|---|---|
| R4A | R4C | R4G | R4P | L5A | L5C | L5D | L5E | L5G | L5H |
| L5K | L5N | L5P | L5Q | L5R | L5S | L5T | I6A | I6C | I6D |
| I6E | I6G | I6H | I6K | I6N | I6P | I6Q | I6R | I6S | I6T |
| I6M | I6W | D8A | D8C | D8G | D8P | S9P | S9T | R10A | R10C |
| R10G | R10P | V11A | V11C | V11D | V11E | V11G | V11H | V11K | V11N |
| V11P | V11Q | V11R | V11S | V11T | V11F | V11I | V11M | V11W | V11Y |
| L12A | L12C | L12D | L12E | L12G | L12H | L12K | L12N | L12P | L12Q |
| L12R | L12S | L12T | L12F | L12I | L12M | L12V | L12W | L12Y | E13A |
| E13C | E13G | E13P | R14A | R14C | R14G | R14H | R14P | R14T | Y15A |
| Y15C | Y15D | Y15E | Y15G | Y15H | Y15K | Y15N | Y15P | Y15Q | Y15R |
| Y15S | Y15T | L16A | L16C | L16D | L16E | L16G | L16H | L16K | L16N |
| L16P | L16Q | L16R | L16S | L16T | L16W | L16Y | L17A | L17C | L17D |
| L17E | L17G | L17H | L17K | L17N | L17P | L17Q | L17R | L17S | L17T |
| L17F | L17I | L17M | L17V | L17W | L17Y | E18A | E18C | E18G | E18P |
| E18T | A19H | A19P | A19T | K20H | K20P | K20T | E21A | E21C | E21G |
| E21P | A22C | A22D | A22E | A22G | A22H | A22K | A22N | A22P | A22Q |
| A22R | A22S | A22T | E23P | E23T | N24A | N24C | N24G | N24P | I25A |
| I25C | I25D | I25E | I25G | I25H | I25K | I25N | I25P | I25Q | I25R |
| I25S | I25T | T27A | T27C | T27G | T27P | G28H | G28T | A30D | A30H |
| A30P | C33H | C33T | L35A | L35C | L35D | L35E | L35G | L35H | L35K |
| L35N | L35P | L35Q | L35R | L35S | L35T | L35M | L35W | L35Y | N38T |
| I39A | I39C | I39D | I39E | I39G | I39H | I39K | I39N | I39P | I39Q |
| I39R | I39S | I39T | T40D | T40H | V41A | V41C | V41D | V41E | V41G |
| V41H | V41K | V41N | V41P | V41Q | V41R | V41S | V41T | V41I | V41Y |
| D43T | V46A | V46C | V46D | V46E | V46G | V46H | V46K | V46N | V46P |
| V46Q | V46R | V46S | V46T | V46M | V46W | V46Y | F48A | F48C | F48D |
| F48E | F48G | F48H | F48K | F48N | F48P | F48Q | F48R | F48S | F48T |
| F48M | F48W | Y49A | Y49C | Y49D | Y49E | Y49G | Y49H | Y49K | Y49N |
| Y49P | Y49Q | Y49R | Y49S | Y49T | Y49M | Y49W | W51A | W51C | W51D |
| W51E | W51G | W51H | W51K | W51N | W51P | W51Q | W51R | W51S | W51T |

TABLE 4-continued

| List of human EPO Modifications for Decreased Immunogenicity | | | | | | | | | |
|---|---|---|---|---|---|---|---|---|---|
| K52A | K52C | K52G | K52H | K52P | K52T | K52E | K52D | R53A | R53C |
| R53G | R53H | R53P | R53Q | R53N | R53H | R53S | R53E | R53A | R53D |
| M54A | M54C | M54D | M54E | M54G | M54H | M54K | M54N | M54P | M54Q |
| M54R | M54S | M54T | M54F | M54I | M54L | M54V | M54W | M54Y | E55A |
| E55C | E55G | E55P | E55T | V56 | V56A | V56C | V56D | V56E | V56G |
| V56H | V56K | V56N | V56P | V56Q | V56R | V56S | V56T | V56F | V56I |
| V56L | V56W | V56Y | G57C | G57D | G57E | G57H | G57K | G57N | G57P |
| G57Q | G57R | G57S | G57T | Q58A | Q58C | Q58G | Q58P | Q59A | Q59C |
| Q59G | Q59H | Q59P | Q59T | Q59K | Q59R | Q59M | Q59W | Q59L | Q59Y |
| Q59F | Q59N | Q59E | Q59I | Q59A | A60C | A60D | A60E | A60G | A60H |
| A60K | A60N | A60P | A60Q | A60R | A60S | A60T | V61A | V61C | V61D |
| V61E | V61G | V61H | V61K | V61N | V61P | V61Q | V61R | V61S | V61T |
| V61W | E62H | E62P | E62S | E62T | V63A | V63C | V63D | V63E | V63G |
| V63H | V63K | V63N | V63P | V63Q | V63R | V63S | V63T | V63F | V63I |
| V63M | V63W | V63Y | W64A | W64C | W64D | W64E | W64G | W64H | W64K |
| W64N | W64P | W64Q | W64R | W64S | W64T | Q65A | Q65C | Q65G | Q65P |
| G66D | G66E | G66H | G66K | G66N | G66P | G66Q | G66R | G66S | G66T |
| L67A | L67C | L67D | L67E | L67G | L67H | L67K | L67N | L67P | L67Q |
| L67R | L67S | L67T | L67F | L67I | L67H | L67V | L67W | L67Y | A68C |
| A68D | A68E | A68G | A68H | A68K | A68N | A68P | A68Q | A68R | A68S |
| A68T | L69A | L69C | L69D | L69E | L69G | L69H | L69K | L69N | L69P |
| L69Q | L69R | L69S | L69T | L69F | L69I | L69M | L69W | L69Y | L70A |
| L70C | L70D | L70E | L70G | L70H | L70K | L70N | L70P | L70Q | L70R |
| L70S | L70T | L70Y | S71A | S71C | S71G | S71H | S71P | S71T | E72H |
| E72P | E72T | A73E | A73H | A73P | A73Q | A73T | V74A | V74C | V74D |
| V74E | V74G | V74H | V74K | V74N | V74P | V74Q | V74R | V74S | V74T |
| V74F | V74I | V74W | V74Y | L75A | L75C | L75D | L75E | L75G | L75H |
| L75K | L75N | L75P | L75Q | L75R | L75S | L75T | L75F | L75I | L75V |
| L75W | L75Y | R76A | R76C | R76G | R76P | G77H | G77P | G77T | A79H |
| A79P | L80A | L80C | L80D | L80E | L80G | L80H | L80K | L80N | L80P |
| L80Q | L80R | L80S | L80T | L80F | L80I | L80Y | L81A | L81C | L81D |
| L81E | L81G | L81H | L81K | L81N | L81P | L81Q | L81R | L81S | L81T |
| V82A | V82C | V82D | V82E | V82G | V82H | V82K | V82N | V82P | V82Q |
| V82R | V82S | V82T | W88A | W88C | W88D | W88E | W88G | W88H | W88K |
| W88N | W88P | W88Q | W88R | W88S | W88T | E89A | E89C | E89G | E89P |
| L91A | L91C | L91D | L91E | L91G | L91H | L91K | L91N | L91P | L91Q |
| L91R | L91S | L91T | L91F | L91I | L91M | L91V | L91W | L91Y | Q92A |
| Q92C | Q92G | Q92P | L93A | L93C | L93D | L93E | L93G | L93H | L93K |
| L93N | L93P | L93Q | L93R | L93S | L93T | L93M | L93W | L93Y | H94P |
| H94T | V95A | V95C | V95D | V95E | V95G | V95H | V95K | V95N | V95P |
| V95Q | V95R | V95S | V95T | V95F | V95I | V95M | V95W | V95Y | D96A |
| D96C | D96G | D96H | D96P | D96T | K97A | K97C | K97G | K97P | A98C |
| A98D | A98E | A98H | A98K | A98N | A98P | A98Q | A98R | A98S | A98T |
| V99A | V99C | V99D | V99E | V99G | V99H | V99K | V99N | V99P | V99Q |
| V99R | V99S | V99T | V99W | V99Y | S100D | S100H | S100N | S100P | S100Q |
| G101D | G101E | G101H | G101K | G101N | G101P | G101Q | G101R | G101S | G101T |
| L102A | L102C | L102D | L102E | L102G | L102H | L102K | L102N | L102P | L102Q |
| L102R | L102S | L102T | L102F | L102I | L102W | L102W | L102Y | R103D | R103E |
| R103H | R103N | R103P | R103Q | R103S | R103T | R103 K | R103I | R103M | S104H |
| S104P | S104A | S104T | L105A | L105C | L105D | L105E | L105G | L105H | L105K |
| L105N | L105P | L105Q | L105R | L105S | L105T | L105I | L105Y | L105V | T107H |
| T107K | T107R | T107N | T107G | T107D | T107E | L108A | L108C | L108D | L108E |
| L108G | L108H | L108K | L108N | L108P | L108Q | L108R | L108S | L108T | L108W |
| L108Y | L109A | L109C | L109D | L109E | L109G | L109H | L109K | L109N | L109P |
| L109Q | L109R | L109S | L109T | L109F | L109I | L109M | L109V | L109W | L109Y |
| R110A | R110C | R110G | R110P | R110K | R110N | R110H | R110Q | R110T | R110D |
| R110Y | L112A | L112C | L112D | L112E | L112G | L112H | L112K | L112N | L112P |
| L112Q | L112R | L112S | L112T | L112F | L112I | L112M | L112V | L112W | L112Y |
| G113H | G113T | A114C | A114D | A114E | A114G | A114H | A114K | A114N | A114P |
| A114Q | A114R | A114S | A114T | Q115P | Q115T | K116A | K116C | K116G | K116P |
| E117H | E117P | E117T | A118C | A118D | A118E | A118G | A118H | A118K | A118N |
| A118P | A118Q | A118R | A118S | A118T | I119A | I119C | I119D | I119E | I119G |
| I119H | I119K | I119N | I119P | I119Q | I119R | I119S | I119T | I119W | I119Y |
| S120P | S120T | A124D | A124H | A124P | A125P | A125T | A127H | A127P | A127T |
| L130A | L130C | L130D | L130E | L130G | L130H | L130K | L130N | L130P | L130Q |
| L130R | L130S | L130T | L130M | L130W | L130Y | I133A | I133C | I133D | I133E |
| I133G | I133H | I133K | I133N | I133P | I133Q | I133R | I133S | I133T | I133W |
| I133Y | A135H | A135P | D136P | D136T | F138A | F138C | F138D | F138E | F138G |
| F138H | F138K | F138N | F138P | F138Q | F138R | F138S | F138T | F138M | F138W |
| F138Y | R139A | R139C | R139G | R139P | R139T | R139 H | R139K | R139Q | R139N |
| R139D | R139E | R139D | R139S | R139A | K140A | K140C | | | | b. Glycosylation

Many proteins with therapeutic activity contain one or more glycosylation sites, i.e., amino acid sequences that are glycosylated by a eukaryotic cell. The degree of glycosylation of therapeutic proteins can be altered in order to achieve 1) reduced immunogenicity; 2) less frequent administration of the protein; 3) increased protein stability such as increased serum half-life; and 4) reduction in adverse side effects such as inflammation. The glycosylation site(s) provides a site for attachment of a carbohydrate moiety on the subject polypeptide, such that when the subject polypeptide is produced in a eukaryotic cell capable of glycosylation, the subject polypeptide is glycosylated. The further glycosylation of an EPO polypeptide confers one or more advantages including increased serum half-life; reduced immunogenicity; increased functional in vivo half-life; reduced degradation by gastrointestinal tract conditions such as gastrointestinal tract proteases; and increased rate of absorption by gut epithelial cells. An increased rate of absorption by gut epithelial cells and reduced degradation by gastrointestinal tract conditions is important for enteral (e.g., oral) formulations of an EPO polypeptide.

Glycosylation can increase serum-half-life of polypeptides by increasing the stability, solubility, and reducing the immunogenicity of a protein. Glycosylation can increase the stability of proteins by reducing the proteolysis of the protein and can protect the protein from thermal degradation, exposure to denaturing agents, damage by oxygen free radicals, and changes in pH. Glycosylation also can allow the target protein to evade clearance mechanisms that can involve binding to other proteins, including cell surface receptors. Carbohydrate moieties that contain sialic acid can affect the solubility of a protein. The sialic acid moieties are highly hydrophilic and can shield hydrophobic residues of the target protein. This decreases aggregation and precipitation of the target protein. Decreased aggregation also aids in the prevention of the immune response against the target protein. Carbohydrates can furthermore shield immunogenic sequences from the immune system. The volume of space occupied by the carbohydrate moieties can decrease the available surface area that is surveyed by the immune system. These properties lead to the reduction in immunogenicity of the target protein.

Glycosylation of proteins results in the formation of glycoproteins due to the covalent attachment of oligosaccharides to a polypeptide. The carbohydrate modifications found in glycoproteins are linked to the protein component through either O-glycosidic or N-glycosidic bonds. The predominant carbohydrate attachment in glycoproteins of mammalian cells is via N-glycosidic linkage. The N-glycosidic linkage is through the Nitrogen of the amide group of asparagines. The site of carbohydrate attachment to N-linked glycoproteins is found within a consensus sequence of amino acids, N-X-S/T, where X is any amino acid except proline. In N-linked glycosylation, the carbohydrate directly attached to the protein is a 14-residue oligosaccharide, N-acetylglucosamine (GlcNAc). Glycosyltransferases subsequently alter the attached oligosaccharide to form a mature N-glycan. N-linked oligosaccharides contain mannose, N-acetylglucosamine and typically have several branches of carbohydrates, each terminating with a negatively charged sialic acid residue. Protein secondary structure can affect the availability of consensus sites as targets for glycosylation. Since glycosylation is known to be highly host cell-dependent, the sugar chains associated with N-linked glycosylation of a protein can differ (Kagawa et al., (1988) JBC 263:17508-17515). The O-glycosidic linkage is to the hydroxyl of serine, threonine or hydroxylysine. In Ser- and Thr-type O-linked glycoproteins, the carbohydrate directly attached to the protein is a monosaccharide, such as N-acetylgalactosamine (GalNac) or galactose. Glycosyltransferases subsequently attach additional carbohydrate moieties to the modified residue to form a mature O-glycan, which typically contains one to four sugar residues. O-linked glycosylation typically occurs at sites defined by protein secondary structures, such as an extended beta turn. A number of O-linked glycosylation sites are known in the art and have been reported in the literature, see e.g., Ten Hagen et al. (1999) *J. Biol. Chem.*, 274:27867-74; Hanisch et al. (2001) *Glycobiology*, 11:731-740; and Ten Hagen et al., (2003) *Glycobiology*, 13:1R-16R.

Modified EPO polypeptides provided herein can further be glycosylated (i.e., hyperglycosylated) as compared to an unmodified EPO polypeptide due to a carbohydrate moiety covalently linked to at least one non-native glycosylation site not found in the unmodified EPO polypeptide or a carbohydrate moiety covalently linked to at least one native glycosylation site found but not glycosylated in the unmodified EPO polypeptide. An EPO polypeptide can be modified at one or more positions to affect glycosylation of the polypeptide. A hyperglycosylated EPO polypeptide can include O-linked glycosylation, N-linked glycosylation, and/or a combination thereof. In some examples, a hyperglycosylated EPO polypeptide can include 1, 2, 3, 4, 5 or more carbohydrate moieties, each linked to different glycosylation sites. The glycosylation site can be a native glycosylation site. In other examples, the hyperglycosylated polypeptide can be glycosylated at a single non-native glycosylation site. In still other examples, the hyperglycosylated polypeptide can be glycosylated at more than one non-native glycosylation site, for example, the hyperglycosylated EPO polypeptide can be glycosylated at 1, 2, 3, 4, 5 or more non-native glycosylation sites. Glycosylation sites in an EPO polypeptide can be created, altered, eliminated or rearranged. For example, native glycosylation sites can be modified to prevent glycosylation or enhance or decrease glycosylation, while other positions in the EPO polypeptide can be modified to create new glycosylation sites or enhance or decrease glycosylation of existing sites. In some examples, the carbohydrate content of the EPO polypeptide can be modified. For example, the number position, bond strength, structure and composition of the carbohydrate linkages (i.e., structure of the carbohydrate based on the nature of the glycosidic linkages or branches of the carbohydrate) of carbohydrate moieties added to the EPO polypeptide can be altered. Such properties vary between the different known recombinant erythropoietins, such as epoetin-α, epoetin-β, epoetin-ω and epoetin-δ, and between urinary human erythropoietin. In one example the number of sialic moieties of a modified EPO polypeptide provided herein is modified.

Changes in the carbohydrate content of the glycosylated EPO polypeptides provided herein, including sialic acid content, can be generated by any method known in the art including but not limited to modification of the primary sequence of the EPO polypeptide, enzymatic or chemical modification, production in different host cells, or modified host cells, to produce differences in the glycosylation pattern, and purification methods to enrich EPO polypeptides with specific glycosylation profiles. Such methods are known in the art and include, for example, modified EPO polypeptides as described in U.S. Patent Publication Nos. 2004-0137557, 2005-0153879, 2005-0181359, 2005-0192211, 2005-0288220, 2006-0088906, and 2006-0121611. Additionally, growth conditions (e.g., media composition) in which host cells express the modified EPO polypeptides can be altered to provided changes in glycosylation, in particular, sialic acid content (see e.g., U.S. Patent Publication No. 2004-0115768).

Commercial products that contain EPO polypeptides have been developed that differ in the glycosylation of the EPO polypeptide, such as by changing the number of glycosylation sites or altering the glycosylation pattern or content of the carbohydrate moieties attached to the EPO polypeptide. For example Epogen® (Amgen) is an α-glycosylated form produced in CHO cells with 22 sialic acid residues, having a molecular weight of 30,400 Da; Neorecormon® (or Recormon®; Roche) is a β-glycosylated form of EPO produced in CHO cells, which has a higher molecular weight and a lower number of sialylated glycan residues; Epomax® (Elanex), or epoetin-ω, is produced in BHK cells has a molecular 35 kDa and differs from α and β forms in the amounts of glycosylation, in particular, different amounts of sialylation.

In some instances, a hyperglycosylated EPO polypeptide is glycosylated at a native glycosylation site. For example, EPO, such as for example human EPO having an amino acid sequence set forth in SEQ ID NO: 2 or 237, contains N-linked glycosylation sites at N24, N38, and N83 and an O-linked glycosylation site at S126 (with respect to a mature EPO polypeptide as set forth in SEQ ID NO: 2 or 237). The EPO polypeptide can be glycosylated at a single native glycosylation site, or at more than one native glycosylation site, e.g., at 1, 2, 3, 4, 5, or more native glycosylation sites. A hyperglycosylated EPO polypeptide also can be glycosylated at a native glycosylation site and a non-native glycosylation site. A hyperglycosylated EPO polypeptide also can be glycosylated at multiple native and non-native glycosylation sites.

Modified EPO polypeptides provided herein can have at least one additional carbohydrate moiety not found in the unmodified EPO polypeptide when each is synthesized in a eukaryotic cell that is capable of N- and/or O-linked protein glycosylation. Thus, for example, compared to an unmodified EPO polypeptide, a hyperglycosylated modified EPO polypeptide can have at least 1, at least 2, at least 3, at least 4, at least 5, at least 6, at least 7, at least 8, at least 9, at least 10, or more additional carbohydrate moieties. For example, where an unmodified EPO polypeptide has one covalently linked carbohydrate moiety, a hyperglycosylated EPO polypeptide can have 2, 3, 4, 5, 6, 7, 8, 9, 10, or more covalently linked carbohydrate moieties. In some examples, a hyperglycosylated EPO polypeptide of a modified EPO polypeptide provided herein, lacks a carbohydrate moiety covalently linked to a non-native glycosylation site, and has instead at least 1, at least 2, at least 3, at least 4, at least 5, at least 6, at least 7, at least 8, at least 9, at least 10, or more additional carbohydrate moieties attached to native glycosylation sites. In other examples, a hyperglycosylated EPO polypeptide lacks a carbohydrate moiety covalently linked to a native glycosylation site, and has instead at least 2, at least 3, at least 4, at least 5, at least 6, at least 7, at least 8, at least 9, at least 10, or more carbohydrate moieties attached to non-native glycosylation sites.

Exemplary amino acid positions contemplated herein for modification of a glycosylation site, for attachment of a carbohydrate moiety, include positions corresponding to native positions, such as N24, N38, N83, and S126 of a mature EPO polypeptide set forth in SEQ ID NO: 2 or 237. In some examples, the modified EPO polypeptide has one or more modifications that eliminates one, two, three or four native glycosylation sites or all glycosylation sites. Amino acid replacement or replacements are known in the art that can be modified to prevent glycosylation, to create new glycosylation sites, enhance or decrease glycosylation of existing sites, or a combination thereof. For example, amino acid modifications can include one or more of the following non-limiting examples: N38H/R139H, N38H/R139H/R4H, N38H/R139H/L93I, N38H/R139H/K20Q, N38H/R139H/E159N, N38H/R139H/K52N, N38H/R139H/L153V, N38H/N83H/R139H, K20Q/N38H/N83H/R139H, N38H/N83H/R139H/L93V, N38H/N83H/R139H/L80I, N38H/N83H/R139H/L93I, K20Q/N38H/L80I/N83H/R139H, K20Q/N38H/N83H/L93I/R139H, K20Q/N38H/N83H/L93V/R139H, N24H/N38H/N83H/R139H/L80I, N24H/N38H/N83H/R139H/L93I, N24H/N38H/N83H/R139H/L93V, K20Q/N24H/N38H/N83H/R139H/L80I, K20Q/N24H/N38H/N83H/R139H/L93I, K20Q/N24H/N38H/N83H/R139H/L93V, R4H/K20Q/N24H/N38H/N83H/R139H/L80I, E159N/K20Q/N24H/N38H/N83H/R139H/L93I, K20Q/N24H/N38H/N83H/R139H/L153V, L153V/K20Q/N24H/N38H/N83H/R139H/L80I, E159N/K20Q/N24H/N38H/N83H/R139H/L80I, A30N, W51N, G57N, L69N, W88N, E89N, D136N, F138N, K52N/M54T, R53N/E55T, A30N/H32T/P87V/W88N/P90T, A30N/H32T/P87V/W88N/P90T/A125T, A30N/H32T/R53N/E55T/P87V/W88N/P90T, E55N/G57T, Q86N/P87V/W88T, P87A/W88N/P90T, P87V/W88N/P90S, P87V/W88N/E89G/P90T, A30N/H32T/R53N/E55T, A114N/K116T, A30N/H32T/A114N/K116T, A30N/H32T/R53N/E55T/P87V/W88N/P90T/A 114N/K116T, A30N/H32T/E55N/G57T, A30N/H32T/E55N/G57T/P87V/W88N/P90T, A30N/H32T/E55N/G57T/A114N/K116T, A30N/H32T/P87V/W88N/P90T/A114N/K116T, A30N/H32T/E55N/G57T/P87V/W88N/P90T/A114N/K116T, A30N/H32T/E55N/G57T/P87V/W88N/P90T/A124P/A125T/S126T, A30N/H32T/E55N/G57T/A114N/K116T/A124P/A125T/S126T, R4N/I6S, S9N/V11S, L69N, A124N, A125N/A127S, T163N/D165S, A125T, A125T/A124P, L69N/S71T, L69N/A68S/S71T, A125N/A127T, A125N/A127T/R131T, A125N/A124P/A127S, A125N/A124P/A127T, A125T/S126T, A125T/A124P/S126T/R131S, A30N/H32T, A30N/H32T/P87V/W88N/P90T, W51N/R53T, P87V/W88N/P90T, P87S/W88N/P90T, P87S/W88N/E89G/P90T, P87S/W88N/P90T/Q92T, P87S/W88N/P90T/R162A, L69N/S71T/P87S/W88N/P90T, L69N/S71T/P87V/W88N/P90T, E89N/P90I/L91T, P87S/E89N/P90I/L91T, D136N/F138T, F138N/K140T, A125T, A124P/A125T, N24Q/P87S/W88N/P90T, N38Q/P87S/W88N/P90T, N83Q/P87S/W88N/P90T of a mature EPO polypeptide set forth in SEQ ID NO: 2 or 237 (see e.g., U.S. Pat. No. 5,856,298, U.S. Patent Publication No. 2003-0120045; International Patent Publication No. EP 0640619). In some examples, amino acid modifications can include relocation of a native glycosylation site, such as N38 to another site, such as W51, G57, L69, W88, E89, D136, or F138 of a mature EPO (see e.g., PCT Publication No. WO 01/81405). In a particular embodiment, the amino acid replacement or replacements contributing to hyperglycosylation of modified EPO polypeptides is (are) replacement of amino acids by asparagines (N) or threonine (T). In another particular embodiment the amino acid modifications are selected from one or both of the following modifications: A30N/H32T and P87V/W88N/P90T (Elliot et al. (2004) *J. Biol. Chem.* 279(16): 16854-16862; Elliott et al. (2003) *Nat. Biotechnol.* 21: 414-421). Any of the modifications provided herein can be combined with any modifications that generate a hyperglycosylated erythropoietin analogue. One non-limiting hyperglycosylated erythropoietin analogue is the novel erythropoiesis stimulating protein (NESP), which contains the amino acid modifications A30N, H32T, P87V, W88N, P90T (see e.g., PCT publication WO 00/24893, available as Aranesp® (Amgen Inc); SEQ ID NO: 228).

Whether an EPO polypeptide has N-linked and/or O-linked glycosylation is readily determined using standard techniques, such as, for example, enzymatic treatment, electrophoresis analysis, isoelectric focusing, and immunohistochemistry (see e.g., "Techniques in Glycobiology" R. Townsend and A. Hotchkiss, eds. (1997) Marcel Dekker; and "Glycoanalysis Protocols (Methods in Molecular Biology, Vol. 76)" E. Hounsell, ed. (1998) Humana Press. The change in electrophoretic mobility of a protein before and after treatment with chemical or enzymatic deglycosylation (e.g., using endoglycosidases and/or exoglycosidases) is routinely used to determine the glycosylation status of a protein. Enzymatic deglycosylation can be carried out using any of a variety of enzymes, including, but not limited to, peptide-N4-(N-acetyl-β-D-glycosaminyl) asparagine amidase (PNGase F); endoglycosidase F1, endoglycosidase F2, endoglycosidase F3, α(2→3,6,8,9) neuraminidase, and the like. For example, sodium dodecyl sulfate-polyacrylamide gel electrophoresis (SDS-PAGE) analysis of the protein, either pre-treated with PNGaseF or untreated with PNGaseF, is conducted. A marked decrease in band width and change in migration position after treatment with PNGaseF is considered diagnostic of N-linked glycosylation. The carbohydrate content of a glycosylated protein also can be detected using lectin analysis of protein blots (e.g., proteins separated by SDS-PAGE and transferred to a support, such as a nylon membrane). Lectins, carbohydrate binding proteins from various plant tissues, have high affinity and narrow specificity for a wide range of defined sugar epitopes found on glycoprotein glycans (Cummings (1994) Methods in Enzymol. 230:66-86). Lectins can be detectably labeled (either directly or indirectly), allowing detection of binding of lectins to carbohydrates on glycosylated proteins. For example, when conjugated with biotin or digoxigenin, a lectin bound to a glycosylated protein can be easily identified on membrane blots through a reaction utilizing avidin or anti-digoxigenin antibodies conjugated with an enzyme such as alkaline phosphatase, β-galactosidase, luciferase or horse radish peroxidase, to yield a detectable product. Screening with a panel of lectins with well-defined specificity provides considerable information about a glycoprotein's carbohydrate complement.

As described above, glycosylated or hyperglycosylated EPO polypeptides have been developed, including commercially glycosylated or hyperglycosylated recombinant EPO forms. Such glycosylated forms have been found to have higher proliferation activity in vivo as compared to a non-glycosylated EPO polypeptide, most likely due to rapid clearance of the non-glycosylated form (see e.g., Lukowsky and Painter (1972) Can. J. Biochem. 60: 909-917; Goldwasser et al. (1974) J. Biol. Chem. 249, 4202-4206; Sasaki (1987) Methods Enzymol. 147: 328-340; Goto et al. (1988) Bio/technology 6: 67-71). Nevertheless, some forms of EPO polypeptides with decreased or no glycosylation, while exhibiting less proliferation activity in vivo, also have been reported to possess higher proliferation activity in in vitro assays and greater binding to an EPO receptor relative to wild-type glycosylated EPO and other glycosylated forms of EPO (see e.g., Yamaguchi et al. (1991) 266(30): 20434-20439). Accordingly, one can select an expression system (e.g., bacterial or various mammalian cells, such as CHO or BHK) for expression of a modified EPO polypeptide provided herein to generate a particular level of EPO glycosylation or no glycosylation, depending on the application of the EPO polypeptide. Non-glycosylated forms of modified EPO polypeptides can be particularly useful, for example, for in vitro assays as controls for EPO activity, for detection of EPO receptor concentration, or employed in assays or screens for EPO inhibitors.

c. Additional or Alternative Modifications

Additional or alternative modifications of polypeptides provided herein include chemical derivatization of polypeptides, including but not limited to, acetylation and carboxylation; changes in amino acid sequence that make the protein susceptible to PEGylation or other modification or that alter properties of the EPO polypeptide. Related moieties for modifying EPO polypeptides also are contemplated, including, but not limited to copolymers of polyethylene glycol and polypropylene glycol, carboxymethylcellulose, dextran, polyvinyl alcohol, polyvinylpyrrolidine or polyproline (Abuchowski et al. (1981); Newmark et al. (1982); and Katre et al. (1987)). A modified EPO polypeptide provided herein can be modified with one or more polyethylene glycol moieties (PEGylated). Activated PEG derivatives can be used to interact directly with the EPO polypeptides, and include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups can be used for the modification of sulfhydryl groups, and PEG reagents containing hydrazine or hydrazide groups can be used to modify aldehydes generated by periodate oxidation of carbohydrate groups. In some instances, a modified EPO polypeptide provided herein can contain one or more non-naturally occurring pegylation sites that are engineered to provide PEG-derivatized polypeptides with reduced serum clearance. Exemplary amino acid modification to create PEGylation can include, but are not limited to, A1C, P2C, P3C, R4C, D8C, S9C, N24C, I25C, T26C, T27C, G28C, A30C, E31C, H32C, S34C, N36C, N38C, I39C, T40C, D43C, T44C, K45C, N47C, A50C, K52C, E55C, G57C, Q58C, G77C, Q78C, A79C, N83C, S84C, S85C, Q86C, W88C, E89C, T107C, R110C, A111C, G113C, A114C, Q115C, K116C, E117C, A118C, S120C, P121C, P122C, D123C, A124C, A125C, A127C, A128C, T132C, K154C, T157C, G158C, E159C, A160C, T163C, G164C, and D165C of a mature EPO polypeptide (see e.g., U.S. Patent Publication No: 2005-0107591 and International Patent Publication No. WO 90/12874). In addition, N-terminal cysteine(s) can be added to the EPO polypeptide to produce free thiol groups for attachment of groups, such as PEG moieties (see e.g., U.S. Patent Publication No. 2005-0170457).

Also contemplated are modified EPO polypeptide sequences that have phosphorylated amino acid residues, e.g., phosphotyrosine, phosphoserine, or phosphothreonine (see e.g., U.S. Pat. No. 6,335,176).

Other suitable additional modifications of a modified EPO polypeptide provided herein are polypeptides that have been modified using ordinary chemical techniques so as to improve their resistance to proteolytic degradation, to optimize solubility properties, or to render them more suitable as a therapeutic agent. For example, the backbone of the peptide can be cyclized to enhance stability (see e.g., Friedler et al. (2000) J. Biol. Chem. 275:23783-23789). Another exemplary modification includes addition of hydroxyalkylstarch (HAS) moieties to the modified EPO polypeptides provided herein. Exemplary methods of hasylation of EPO polypeptides are known in the art and are described, for example, in U.S. Patent Publication No. 2006-0019877. Yet another exemplary modification includes carbamylation of the N-terminal amino acid or primary amines of amino acids of the modified EPO polypeptides provided herein. Exemplary methods of carbamylation of EPO polypeptides are known in the art and are described, for example, in U.S. Patent Publication No. 2006-0135754.

Non-natural amino acids can be incorporated into the modified EPO polypeptides provided herein. Non-natural amino acids also can be incorporated at sites identified herein for increased protease resistance. Analogs can be used that include residues other than naturally occurring L-amino acids, e.g., D-amino acids or non-naturally occurring synthetic amino acids. Exemplary non-naturally occurring synthetic amino acids include, but are not limited to, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a unnatural functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a α-amino acid; and a cyclic amino acid other than proline. For example, the unnatural amino acid can be, but is not limited to, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAc β-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, para-acetyl-phenylalanine (pAcF), L-difluoromethionine (DFM), and an isopropyl-L-phenylalanine.

Non-natural amino acids can be incorporated into the EPO polypeptides provided herein by any method known in the art including, but not limited to, derivatization of amino acids with reactive side-chains, chemical synthesis, enzymatic ligation, native chemical ligation, an in vitro biosynthetic method in which a suppressor tRNA is chemically or enzymatically acylated with an unnatural amino acid, an in vivo method, in which a suppressor tRNA is acylated with an unnatural amino acid by selective pressure incorporation, modification of synthetases that have proofreading mechanisms to allow incorporation of unnatural amino acids onto tRNAs, a microinjection technique of tRNAs to incorporate unnatural amino acids into proteins, or an in vivo method of generating modified orthogonal tRNAs carrying unnatural amino acids using orthogonal tRNA synthetases (see e.g., Dawson and Kent, (2000) *Annu. Rev. Biochem.* 69: 923; Cornish et al. (1995) *Chem. Int. Ed. Engl.* 34:621; Noren et al. (1989) *Science* 244: 182-188; Bain et al. (1989) *J. Am. Chem. Soc.* 111: 8013-8014; Budisa et al. (1999) *FASEB J,* 13:41; Nowak et al. (1995) Science 268: 439; Dougherty (2000) *Curr. Opin. Chem. Biol.* 4: 645; Brunner (19993) *Chem. Soc. Rev.* 22: 183-189; U.S. Patent Publication Nos. 2006-0233744 and 2006-0153860).

Modifications of EPO polypeptides provided herein also can be combined with modifications to improve post-translational processing of the EPO polypeptides. For example, EPO can be modified to improve proteolytic cleavage of the signal sequence or to improve post-translational modifications such as glycosylation, as discussed above.

Modifications of EPO polypeptides provided herein also can be combined with amino acid modifications to further improve stability, binding properties and serum half-life of the EPO polypeptides. For example further modifications can include mutations that affect the ability of EPO polypeptides to bind with its receptor, such as an EPO receptor (EPOR) or secondary receptor. For example, amino acid modifications can be made in the molecular contact areas between the EPO polypeptide and its receptor. Such modifications can increase or decrease the interaction with the receptor or increase or decrease activation of the receptor by EPO. Exemplary amino acid modifications that can affect EPO interactions with its receptor can include any of the following non-limiting examples: C7A, R14A/Y15A, L16A, P42A, D43A, F48A, Y49A, T132A, I133A, T134A, N147A, P148A, R150A, K152W, G151A, G158A, C161A, R162A, F48V, F138V, F142V, F148V D8S, S9A, S9N, R10A, E13A, R14L, Y15F, L16A, L16S, L17A, L17S, K20A, K20I, K20R, K45A, K45R, N47A, F48I, F48S, Y49F, Y49S, K52S, K52R, K52Q, Q78A, Q78E, Q78R, D96A, K97R, S100A, S103K, T107A, T107L, T107S, R110T, R131T, K140A, K140R, K140M, K140T, R143E, K154A, K154R, K154S, R10I, V11S, R14A, R14E, R14Q, Y15I, K20E, T44I, K45I, K45D, V46A, F48G, K52E, D96R, K97A, K97E, V99A, V99S, S100R, S100E, S100T, S103A, S103E, S103H, S103N, S103Q, S104A, S104I, L108A, L108K, R110E, R143A, N147A, N147K, R150A, R150Q, R150E, G151A, L155A, and L155N (see e.g., U.S. Patent Publication Nos. 2004-0122216, 2005-0176627, 2006-0008872; Syed (1998) Nature 395:511-516).

Modifications of EPO polypeptides provided herein also can be combined with extensions of the carboxy terminus that can improve the properties of an EPO polypeptide. One non-limiting example is an extension of the protein derived from C-terminal end of human chorionic gonadotropin (SSSSKAPPPSLPSPSRLPGPSDTPILPQ; see e.g., U.S. Patent Publication No. 2003-0120045). In another non-limiting example, additions of positively charged basic amino acids in the carboxyl terminal region of the modified EPO polypeptide provided herein can increase the biological activity of EPO (see e.g., U.S. Pat. No. 5,457,089). In one non-limiting example, one or more Arginine or Lysine residues are added to the C-terminus of the modified EPO polypeptides provided herein (e.g., R166/R167, R166/R167/A168, R166/R167/K168/R169, R166/R167/K168/R169/A170, R166/R167-176(poly Lysine), R166/R167-176(poly Lysine)/A177.

Modifications of EPO polypeptides provided herein also can be combined with other modifications that result in EPO polypeptides with improved properties, including, but not limited to, improved stability, improved serum half-life, improved purification, or altered erythropoietic or tissue protective activity. Exemplary modifications include, but are not limited to, I6A, C7A, C7S, C7H, S9A, R10A, R10I, V11S, L12A, E13A, R14A, R14L, R14E, R14Q, Y15F, Y15A, Y15I, L16A, L17A, E18A, K20A, K20E, E21A, N24Q, N38Q, N24K, C29S, C29Y, A30N, H32T, C33S, C33Y, N38K, P42N, P42A, D43A, T44I, K45A, K45D, V46A, N47A, F48A, F48I, F48S, Y49A, Y49S, Y49F, Y49A, A50S, A50S, W51F, W51N, W51S, K52A, K52S, M54L, Q59A, Q59N, E62A, E62T, W64A, Q65A, G66A, L67S, L69A, L70A, S71A, E72A, A73G, R76A, Q78A, N83K, N83Q, Q92A, L93A, H94A, V95A, D96R, D96A, K97A, S100A, S100R, S100E, S100T, G101A, G101I, L102A, R103A, R103D, R103N, R103E, R103Q, R103H, R103L, R103K, S104A, S104A, S104I, L105A, T106A, T106I, T107A, T107L, L108A, L108K, L109A, K116A, E117G, S126A, S126T, S126G, T132A, I133A, T134A, D136A, R139A, R139C, K140A, F142I, R143A, Y145F, Y145A, S146A, N147A, N147K, F148Y, L149A, R150A, R150E, G151A, K152A, K152W, L153A, K154A, L155A, Y156A, Y156F, T157A, G158A, E159A, C160S, C161A, R162A, R166G, K45D/ S100E, A30N/H32T, K45D/R150E, R103E/L108S, K140A/ K52A, K140A/K52A/K45A, K97A/K152A, K97A/K152A/ K45A, K97A/K152A/K45A/K52A, K97A/K152A/K45A/ K52A/K140A, K97A/K152A/K45A/K52A/K140A/K154A, N24K/N38K/N83K, N24K/Y15A, C33X/R139C/ΔR166, R139C/ΔR166 (see e.g., U.S. Pat. Nos. 4,703,008, 4,835,260, 5,457,089, 5,614,195, 6,048,971, 6,489,293; U.S. Patent Publication No. US 2005-0176627; International Patent Publication Nos. WO 86/03520, WO 94/25055, WO 94/24160, WO 2001/36489, WO 2004/003176, WO 2005/103076).

The additional modifications to the modified EPO polypeptide provided herein include deletions of modified EPO polypeptides that retain at least one activity of an EPO polypeptide. Such deletions include truncations at either the terminii of the polypeptide or internal deletions. Such deletions are known in the art and include, for example, truncations in the C-terminus of the EPO polypeptide (e.g., residues A160, C161, R162, T163, G164, D165, R166), N-terminus of the EPO polypeptide (e.g, residues P2, P3, R4, L5, I6) and internal deletions (e.g., T27-E55) (see e,g., U.S. Pat. Nos. 4,703,008, 5,457,089).

Any additional modifications that alter properties or activities of EPO polypeptides, such as erythropoietic and tissue protective activity, that are known in the art can be combined with the modifications provided herein. One or more properties of an EPO polypeptide can be altered as a result of a modification or combination of modifications. Non-limiting examples include modifications to interaction sites with an EPO receptor that improve erythropoietic activity, some of which are listed above.

Modifications of EPO polypeptides provided herein also can be combined with naturally occurring variants of EPO or derived from SNPs of EPO. Exemplary natural variants include, for example, C7H, Y15F, Y49F, Y145F, S126M, D43N, G77S, and S120C (see e.g., U.S. Pat. Nos. 4,703,008, 5,955,422, and 7,041,794).

E. Modifications for Increased Resistance to Proteolysis in Non-Glycosylated or Partially Glycosylated Forms of Glycosylated Therapeutic Polypeptides Provided herein are modified therapeutic polypeptides that are not glycosylated or that have a reduction in the number of glycosylation sites. The therapeutic proteins are modified in their primary sequence to exhibit increased protease resistance compared to in the absence of the modification. In addition, the therapeutic polypeptides are those that in vivo are glycosylated or that contain one or more glycosylation site(s). Reduction or elimination of glycosylation is effected by any suitable method, such as by expression in prokaryotic hosts, or by mutation, such as replacement of one or more amino acid residues at glycosylation sites to eliminate one or more glycosylation sites.

Generally, glycosylated therapeutic proteins require glycosylation for effective administration in vivo. The modified or variants of glycosylated therapeutic polypeptides, for example, can be expressed in bacteria for in vivo administration. The protease resistance confers sufficient serum stability in the absence of glycosylation. These polypeptides retain sufficient activity to be therapeutically effective. In addition, elimination of glycosylation sites or glycosylation, permits identification of sites that are protease targets that normally are masked or shielded by glycosylation. Hence provided are methods for identification of sites that are protease targets. Modification of such sites provides protease resistant mutants that may not be identified by methods that screen glycosylated polypeptides.

Thus, provided are variants of glycosylated therapeutic polypeptides that contain one or more amino acid modifications that increase the protease resistance of partially glycosylated or non-glycosylated forms of the therapeutic polypeptides. Methods for generating such proteins also are provided. The unmodified, native forms of the therapeutic polypeptides provided are normally glycosylated in vivo. Glycosylated therapeutic proteins contain one or more sites for the attachment of carbohydrate moieties to the protein at specific sites, such as asparagine (N-linked) or serine (O-linked) amino acid residues. Glycosylation typically protects the native protein from degradation by proteases of the secretory pathway during production of the protein or by extracellular proteases following secretion. In addition, glycosylation can protect a therapeutic polypeptide from degradation by proteases of the blood or digestive system following therapeutic administration. The modified therapeutic proteins provided herein exhibit increased resistance to proteases where glycosylation of the therapeutic protein is either absent (e.g., production of the protein in a prokaryotic organism such as bacteria, e.g., *E. coli*) or removed (e.g., modification of one or more glycosylation sites or carbohydrate removal in vivo).

Exemplary of modified therapeutic polypeptides are cytokines. Exemplary of the cytokines is EPO. Methods for production, expression and modification of EPO can be applied to any other therapeutic polypeptide. Methods for identifying sites for modification are known and can be employed (see, e.g., published International PCT application Nos. WO 04/022593 and WO 04/022747). Exemplary modified therapeutic polypeptides also are described elsewhere herein and are known to those of skill in the art.

A non-glycosylated modified therapeutic polypeptide provided herein exhibiting increased protease resistance can lead to an increased half-life or increased serum stability of the therapeutic polypeptide in vitro (e.g., during production, purification and storage) or in vivo (e.g., after administration to a subject) compared to the non-glycosylated form that does not have the amino acid modification(s) for protease resistance. For some therapeutic proteins, which are unstable in vivo in the absence of glycosylation, the increase is substantial, resulting in a protein that is similar in half-life to the glycosylated form of the polypeptide that has not been modified for increases in protease resistance. For example, increased half-life is exhibited following administration of the non-glycosylated modified therapeutic polypeptide to a subject, such as a human subject. The increased half-life of the non-glycosylated modified therapeutic polypeptide can be increased by an amount that is at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more compared to the half-life of the non-glycosylated unmodified therapeutic polypeptide. In some examples, the increased half-life of the non-glycosylated modified therapeutic polypeptide can be increased by an amount that is at least 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, or more times when compared to the half-life of the non-glycosylated unmodified therapeutic polypeptide. Hence, the modified non-glycosylated polypeptides provided herein offer advantages including a decrease in the frequency of injections needed to maintain a sufficient drug level in serum, thus leading to, for example, higher comfort and acceptance by subjects, lower doses necessary to achieve comparable biological effects and attenuation of secondary effects. Such advantages can be achieved without the need for glycosylation of the polypeptide.

Provided herein are non-glycosylated modified therapeutic polypeptides containing modifications that increase protease resistance. Increased protease resistance can be accomplished by direct destruction of the protease target residue or sequence. Typically, modifications include replacement (i.e., substitution), addition, deletion, or a combination thereof, of amino acid residues as described herein. Non-glycosylated modified therapeutic polypeptides include those with 1, 2, 3, 4, 5, 6, 7, 8, 9, 10, 11, 12, 13, 14, 15, 16, 17, 18, 19, 20 or more modified positions. Generally, non-glycosylated modified therapeutic polypeptides retain one or more activities of native therapeutic polypeptide.

Generally, the resulting modified therapeutic polypeptide retains one or more therapeutic activities of the unmodified polypeptide. In some cases, removal of one or more carbohydrate moieties may affect an activity of the protein (e.g., an increase or decrease protein-protein interactions, such as interaction with a receptor). In such cases, additional modifications can be introduced into the therapeutic polypeptide to compensate for these effects. Such modifications are known in the art and are provided herein (e.g., exemplary amino acid modifications that can increase EPO interactions with its receptor are provided elsewhere herein).

1. Modification of Protease Sensitive Sites

Provided herein are variants of glycosylated therapeutic polypeptides that are modified in their primary sequence to increase their resistance to proteases where therapeutic polypeptide is not glycosylated or has a reduction in the number of carbohydrate moieties attached to the polypeptide. Non-glycosylated therapeutic polypeptides are often unstable, in part due to increased proteolytic degradation in vivo. Thus, modifications for increased protease resistance are provided that compensate for removal of glycosylation. The modified therapeutic polypeptides exhibit increased protease resistance compared to the therapeutic polypeptide in the absence of the modification. The therapeutic polypeptides provided are modified by removal or replacement of one or more protease sensitive sites in the therapeutic polypeptide. The therapeutic proteins provided contain one or more amino acid modifications that increase protease resistance of the therapeutic polypeptide by modification of the one or more protease sensitive sites. The amino acid modifications of therapeutic proteins provided herein increase the resistance to proteases, such that in the absence of glycosylation, the modified protein is more resistant to proteases compared to an unmodified polypeptide.

In some instances, removal of all or part of the carbohydrate moiety increases the susceptibility of the therapeutic polypeptide to degradation by proteases by exposing protease sensitive sites to proteolytic attack. In the glycosylated form of the polypeptide, glycosylation can protect the therapeutic polypeptide from degradation by masking or shielding these protease sensitive sites. For example, glycosylation can prevent access to the protease sensitive site by physical interference by carbohydrate moiety or a change in protein conformation. Provided herein are therapeutic polypeptides modified by removal or replacement of one or more the protease sensitive sites in the therapeutic polypeptide where the one or more the protease sensitive sites are more susceptible to proteolytic attack in a non-glycosylated or partially glycosylated therapeutic polypeptide compared to a fully glycosylated polypeptide.

By engineering variants that increase the protease resistance of the non-glycosylated polypeptide or a partially glycosylated polypeptide, both the glycosylated and non-glycosylated forms of the protein are protected from degradation. If a glycosylated protein is desired, the modifications provided will protect the therapeutic protein from degradation in the event that the therapeutic protein is deglycosylated in vivo. Deglycosylation of glycosylated therapeutic proteins can occur in vivo by exposure to extracellular glucosidases (e.g., lactase, neuraminidase, amylases) of the circulatory and digestive systems. Removal of terminal sialic acid residues by sialidases, such as neuraminidase, exposes galactose residues, which are recognized and bound by galactose-specific other sugar-specific receptors (e.g., N— acetylglucosamine, mannose, fucose and phosphomannose) in hepatocytes that mediate removal of glycoproteins from circulation (reviewed in Ashwell and Harford (1982) *Ann. Rev. Biochem.* 51: 531). The amino acid modifications provided herein permit production of glycosylated therapeutic polypeptides that are resistant to degradation due to in vivo removal of one or more carbohydrate moieties following administration. In addition, the amino acid modifications provided herein allow production of non-glycosylated therapeutic polypeptides that escape degradation by clearance mechanisms which recognize carbohydrate moieties.

2. Production of Non-Glycosylated Modified Therapeutic Polypeptides

The methods provided herein for increasing protease resistance permit production of non-glycosylated forms of therapeutic polypeptides that are normally glycosylated in vivo. Production of glycosylated proteins in eukaryotic cells often results in a high degree of variability in the sugar residues. The heterogeneity in the group can contribute to unwanted production of antibodies when administered in vivo. Thus, the modifications provided that increase protease resistance of non-glycosylated therapeutic polypeptides also increase the uniformity of the therapeutic product. The ability to produce a more uniform therapeutic product can decrease the immunogenicity of the product as well as decrease the cost of production of the therapeutic polypeptide.

Production of non-glycosylated proteins can be achieved by expression of the modified therapeutic polypeptide in a system that is unable to glycosylate the protein or by further modifying the therapeutic polypeptide such that the therapeutic polypeptide cannot be glycosylated. For example, the therapeutic polypeptides can be produced in a prokaryotic organism, such as a bacterium (e.g., *E. coli*). Such systems are described in detail elsewhere herein. The therapeutic polypeptides also can modified by one or more amino acid modifications that prevents glycosylation of the protein. For example, the therapeutic polypeptide can be modified at one or more glycosylation sites, including one or more attachment sites for glycosylation in the therapeutic polypeptide (e.g., asparagine (N) or serine (S)). In one example, the modified therapeutic polypeptide is a modified EPO polypeptide, and modified EPO polypeptide is further modified by modification at one or more of N24, N38, N83 and S126. In another example, the modified therapeutic protein is a modified EPO protein and N24, N38 and N83 are modified. In another particular example, N24, N38 and N83 residues in an EPO polypeptide are replaced with histidine (H) (e.g., SEQ ID NOS: 307 or 308). In another particular example, N24, N38 and N83 residues in an EPO polypeptide are replaced with lysine (K) (e.g., SEQ ID NOS: 309 or 310). Such modified EPO polypeptides can be employed to identify protease sensitive sites for modification.

As described elsewhere herein, a variety of expression methods are known in the art and can be employed for the production of non-glycosylated therapeutic polypeptides. Such methods include introduction of nucleic acid molecules encoding the modified therapeutic polypeptides into a host cell or host animal and expression from nucleic acid molecules encoding the therapeutic polypeptides in vitro or in vivo or expression of the nucleic acid molecules encoding the therapeutic polypeptides in cell-free systems. Expression hosts include, but are not limited to, bacteria (e.g., *E. coli*), yeast, plants, insect cells, mammalian cells, including human cell lines and transgenic animals. The non-glycosylated forms of the modified therapeutic proteins can be produced in prokaryotic organisms, such as bacteria, or can be produced in eukaryotic cells, such as algae or mammalian cells, by modification of one or more glycosylation sites to prevent glycosylation.

3. Exemplary Glycosylated Therapeutic Polypeptides for Modification

Therapeutic proteins that are glycosylated in their native form can be modified for production as non-glycosylated or partially glycosylated, protease-resistant polypeptides using the methods provided. Typically, the therapeutic polypeptides that are modified using the methods provided have higher in vivo therapeutic activity in their glycosylated form. For example, the deglycosylated forms of the therapeutic proteins may be degraded faster following administration, which results in lower therapeutic activity. Exemplary glycosylated therapeutic polypeptides include, but are not limited to, hormones (e.g., insulin, thyroid hormone, catecholamines, gonadotrophines, trophic hormones, prolactin, oxytocin, dopamine, bovine somatotropin or leptins), growth hormones (e.g., human growth hormone), growth factors (e.g., epidermal growth factor, nerve growth factor or insulin-like growth factor), growth factor receptors, cytokines and immune system proteins (e.g., interleukins, colony stimulating factor (CSF), granulocyte colony stimulating factor (G-CSF), granulocyte-macrophage colony stimulating factor (GM-CSF), tumor necrosis factor (TNF), interferons such as IFNα, IFNβ, or IFNγ, erythropoietin, integrins, addressins, selectins, homing receptors, T cell receptors, immunoglobulins, soluble major histocompatability complex antigens, immunologically active antigens such as bacterial, parasitic, or viral antigens or allergens or autoantigens, enzymes (e.g., tissue plasminogen activator, streptokinase, cholesterol biosynthetic or degradative enzymes, steroidogenic enzymes, kinases, phosphodiesterases, methylases, de-methylases, dehydrogenases, cellulases, proteases, lipases, phospholipases, aromatases, cytochromes, adenylate or guanylate cyclases and neuramidases), receptors (e.g., steroid hormone receptors or peptide receptors), binding proteins (e.g., steroid binding proteins, growth hormone or growth factor binding proteins), transcription and translation factors, oncoproteins or proto-oncoproteins (e.g., cell cycle proteins), muscle proteins (e.g., myosin or tropomyosin), myeloproteins, neuroactive proteins, tumor growth suppressing proteins (e.g., angiostatin or endostatin), anti-sepsis proteins (e.g., bactericidal permeability-increasing protein), structural proteins (e.g., collagen, fibroin, fibrinogen, elastin, tubulin, actin or myosin), blood proteins (e.g., thrombin, serum albumin, Factor VII, Factor VIII, insulin, Factor IX, Factor X, tissue plasminogen activator, Protein C, von Willebrand factor, antithrombin, glucocerebrosidase, granulocyte colony stimulating factor (GCSF) or modified Factor VIII, anticoagulants, such as huridin).

Exemplary of modified therapeutic polypeptides are cytokines. Exemplary cytokine families that contain glycosylated cytokines include interferons, interleukins, hematopoietins and chemokines. Exemplary glycosylated cytokines include, but are not limited to, erythropoietin (EPO), thrombopoietin (TPO), granulocyte-colony stimulating factor (G-CSF), granulocyte macrophage-colony stimulating factor (GM-CSF), macrophage-colony stimulating factor (M-CSF), leukemia inhibitory factor (LIF), IL-1beta, IL-2, IL-3, IL-4, IL-5, IL-6, IL-9, OSM, stem cell factor (SCF), IFN-β, IFN-γ and vascular endothelial growth factor (VEGF).

a. EPO

Exemplary of glycosylated cytokines is erythropoietin (EPO). As discussed above, EPO is produced primarily by the kidney and is the main regulator of red blood cell production. The EPO gene encodes a 193 amino acid precursor protein (SEQ ID NO:1) which includes a 27 amino acid signal peptide at the N-terminus. Processing results in a glycosylated mature EPO protein that is 166 amino acids long (SEQ ID NO:2), or 165 amino acids long if the C-terminal arginine reside also is cleaved (SEQ ID NO:237). The EPO polypeptide contains three N-glycosylation sites, corresponding to N24, N38 and N83 of the mature EPO sequence set forth in SEQ ID NOS:2 and 237, and N51, N65 and N110 of the precursor polypeptide set forth in SEQ ID NO:1. There also is an O-glycosylation site located amino acid residue 136 of the mature protein set forth in SEQ ID NOS:2 and 237 (corresponding to amino acid residue 153 of the precursor polypeptide set forth in SEQ ID NO:1). One of the major functions of EPO is to promote the differentiation and development of red blood cells and to initiate the production of hemoglobin. EPO acts by binding to receptors on bone marrow erythroid precursors, stimulating them to transform into mature erythrocytes.

Provided herein are modified non-glycosylated EPO polypeptides that exhibit increased resistance to proteolysis compared to an un-modified non-glycosylated EPO polypeptide. Exemplary protease-resistant EPO polypeptides include one or more amino acid modifications set forth in Table 5 corresponding to amino acid replacements in SEQ ID NOS: 2 or 237, where the one or more amino acid replacements lead to greater resistance to proteases. The non-glycosylated modified EPO polypeptides provided herein can be produced using a prokaryotic expression system, such as expression systems using *E. coli* as the host cells. In other examples, protease-resistant EPO polypeptides can be produced as non-glycosylated proteins by modification of one or more glycosylation sites. For example, modification at one or more of amino acid positions N24, N37 and N83 of a mature EPO polypeptide (SEQ ID NOS: 2 and 237) can result in a non-glycosylated protein. The non-glycosylated protease-resistant polypeptides provided herein retain activity of a fully glycosylated EPO polypeptide that is not protease-resistant. The non-glycosylated protease-resistant EPO polypeptides, therefore, can be used to treat conditions and diseases normally treated by EPO. Recombinant EPO has been approved for the treatment of anemia associated with chronic renal failure, anemia secondary to AZT treatment of AIDS, and anemia associated with cancer. EPO also can be used in cardioprotection and neuroprotection, such in the treatment of a seizure disorder, multiple sclerosis, stroke, hypotension, cardiac arrest, ischemia, myocardial infarction, inflammation, age-related loss of cognitive function, radiation damage, cerebral palsy, a neurodegenerative disease, Alzheimer's disease, Parkinson's disease, Leigh disease, AIDS dementia, memory loss, amyotrophic lateral sclerosis, alcoholism, mood disorder, anxiety disorder, attention deficit disorder, schizophrenia, autism, Creutzfeld-Jakob disease, brain or spinal cord trauma or ischemia, heart-lung bypass, chronic head failure, macular degeneration, toxin induced neuropathy, diabetic neuropathy, diabetic retinopathy, glaucoma, retinal ischemia, or retinal trauma.

TABLE 5

EPO Modifications to Increase Resistance to Proteolysis

| | | | | | | |
|---|---|---|---|---|---|---|
| P2S | P2A | P3S | P3A | R4H | R4Q | C7S |
| C7V | D8Q | D8H | R10H | R10Q | L12V | L12I |
| E18Q | E18H | K20Q | K20T | E21Q | E21H | E23Q |
| E23H | C29S | C29V | E31Q | E31H | L35V | L35I |
| E37Q | E37H | P42S | P42A | D43Q | D43H | K45Q |
| K45T | F48I | F48V | Y49H | Y49I | W51S | W51H |
| K52Q | K52T | R53H | R53Q | M54V | M54I | E55Q |
| E55H | E62Q | E62H | W64S | W64H | L69V | L69I |
| E72Q | E72H | L75V | L75I | R76H | R76Q | L80V |
| L80I | P87S | P87A | W88S | W88H | E89Q | E89H |
| P90S | P90A | L93V | L93I | D96Q | D96H | K97Q |
| K97T | L102V | L102I | R110H | R110Q | L112V | L112I |
| K116Q | K116T | P121S | P121A | P122S | P122A | D123Q |
| D123H | P129S | P129A | L130V | L130I | R131H | R131Q |
| D136Q | D136H | R143H | R143Q | Y145H | Y145I | R150H |
| R150Q | K152Q | K152T | K154Q | K154T | L155V | L155I |
| E159Q | E159H | R162H | R162Q | C29A | C29I | C29T |
| C7A | C7I | C7T | D123N | D136N | D43N | D96N |
| E159N | E18N | E21N | E23N | E31N | E37N | E55N |
| E62N | E72N | E89N | K116N | K152N | K154N | K20N |
| K45N | K52N | K97N | D8N | D165Q | D165H | D165N |
| R166H | R166Q | L5I | L5V | E13Q | E13H | E13N |
| R14H | R14Q | Y15H | Y15I | L16I | L16V | L17I |
| L17V | L67I | L67V | L70I | L70V | L81I | L81V |
| L91I | L91V | R103H | R103Q | L105I | L105V | L108I |
| L108V | L109I | L109V | E117Q | E117H | E117N | F138I |
| F138V | R139H | R139Q | K140N | K140Q | L141I | L141V |
| F142I | F142V | F148I | F148V | L149I | L149V | L153I |
| L153V | Y156H | Y156I | | | | | b. GM-CSF

Granulocyte-macrophage colony-stimulating factor (GM-CSF) is a glycoprotein produced by a variety of cells including, but not limited to, lymphocytes, endothelial cells, mast cells, fibroblasts, monocytes and some malignant cells. The GM-CSF gene encodes a 144 amino acid precursor protein (SEQ ID NO:273) which includes a 17 amino acid signal peptide. Post-translational processing results in a glycosylated mature GM-CSF protein that is 127 amino acids long (SEQ ID NO:274). The mature GM-CSF is N-glycosylated at two sites, corresponding to N27 and N37 of the mature GM-CSF sequence set forth in SEQ ID NO:274 and N44 and N54 of the precursor polypeptide set forth in SEQ ID NO:273. There also are four O-glycosylation sites located at the N-terminus of the mature protein, at amino acid positions S5, S7, S9 and T10 of the sequence set forth in SEQ ID NO:274 (corresponding to S22, S24, S26 and T27 of the precursor polypeptide set forth in SEQ ID NO:273). GM-CSF is a multilineage colony-stimulating factor that can stimulate the proliferation and differentiation of hematopoietic progenitor cells of neutrophil, eosinophil and monocyte origin. As such, it can be used therapeutically in, for example, myeloid reconstitution following bone marrow transplant or bone marrow transplant engraftment failure or delay, following transplantation of autologous peripheral blood progenitor cells, and following induction chemotherapy in older adults with acute myelogenous leukemia.

Provided herein are modified non-glycosylated GM-CSF polypeptides that exhibit increased resistance to proteolysis compared to an un-modified non-glycosylated GM-CSF polypeptide. Exemplary protease-resistant GM-CSF polypeptides include one or more amino acid modifications set forth in Table 6 corresponding to amino acid replacements in SEQ ID NO: 274, where the one or more amino acid replacements lead to greater resistance to proteases. The non-glycosylated modified GM-CSF polypeptides provided herein can be produced using a prokaryotic expression system, such as expression systems using *E. coli* as the host cells. In other examples, protease-resistant GM-CSF polypeptides can be produced as non-glycosylated proteins by modification of one or more glycosylation sites. For example, modification at one or both of amino acid positions N27 and N37 of a mature GM-CSF polypeptide (SEQ ID NO:274) can result in a non-glycosylated protein. The non-glycosylated protease-resistant polypeptides provided herein retain activity of a fully glycosylated GM-CSF polypeptide that is not protease-resistant. The non-glycosylated protease-resistant GM-CSF polypeptides, therefore, can be used to treat conditions and diseases normally treated by GM-CSF, including, but not limited to, reconstitution of neutrophils and monocytes following chemotherapy or bone marrow transplantation.

TABLE 6

GM-CSF Modifications to Increase Resistance to Proteolysis

| | | | | |
|---|---|---|---|---|
| E38N | E38Q | E38H | E41N | E41Q |
| E41H | E45N | E45Q | E45H | M46I |
| M46V | D48N | D48Q | L49I | L49V |
| E51N | E51Q | E51H | E60N | E60Q |
| E60H | K63N | K63Q | P92A | P92S |
| E93N | E93Q | E93H | F119I | F119V |
| D120N | D120Q | E123N | E123Q | E123H |
| P124A | P124S | | | | c. M-CSF

M-CSF is a glycosylated cytokine produced by a variety of cells including lymphocytes, monocytes, fibroblasts, endothelial cells, myoblasts and osteoblasts. As a result of differential splicing, the M-CSF gene produces three different isoforms. Isoform 1 is expressed as a 554 amino acid precursor (SEQ ID NO:275), including a 32 amino acid signal sequence. The mature isoform 1 M-CSF protein is 522 amino acids long and set forth in SEQ ID NO:276). Isoform 2 is expressed as a 438 amino acid precursor (SEQ ID NO:277), including a 32 amino acid signal sequence. The mature isoform 2 M-CSF protein is 406 amino acids long and set forth in SEQ ID NO:278). Isoform 3 is expressed as a 256 amino acid precursor (SEQ ID NO:279), including a 32 amino acid signal sequence. The mature isoform 3 M-CSF protein is 224 amino acids long and set forth in SEQ ID NO:280). M-CSF has two N-glycosylation sites (corresponding to amino acid residues 154 and 172 of the precursor polypeptide set forth in each of SEQ ID NOS: 275, 277 and 279, and amino acids 122 and 140 of the mature polypeptides set forth in each of SEQ ID NOS: 276, 278 and 280). M-CSF is a key regulator of cellular proliferation, differentiation, and survival of blood monocytes, tissue macrophages and their progenitor cells. M-CSF also has been shown to play important roles in modulating dermal thickness, and male and female fertility.

Provided herein are non-glycosylated M-CSF polypeptides that are protease resistant. Such M-CSF protease-resistant polypeptides include those having one or more amino acid modification, where the one or more amino acid modification lead to a greater resistant to proteases. Amino acid positions that can be modified to effect increased resistance to proteases in an M-CSF polypeptide can be identified using the methods described in U.S. Patent Publication No. 20050202438. In one example, non-glycosylated protease-resistant M-CSF cytokines can be generated by production of protease-resistant polypeptides in host cells that are incapable of glycosylation, including, for example, prokaryotic hosts such as *E. coli*. In another example, non-glycosylated protease-resistant M-CSF cytokines can be generated by mutations of one or more, up to all, of the glycosylation sites in the polypeptide. For example, a protease-resistant polypeptide having one or more modifications that increase resistance to proteolysis can further include modification of one or more amino acid positions N122 and/or N140. The non-glycosylated protease-resistant polypeptides provided herein retain activity of a fully glycosylated M-CSF polypeptide that is not protease-resistant. Such non-glycosylated protease-resistant polypeptides can be used in the treatment of diseases or disorders for which M-CSF is normally used to treat. Exemplary of such diseases or disorders include, but are not limited to, malignancies, including hematopoietic recovery after bone marrow transplantation, atherosclerosis and fungal infection.

d. G-CSF

Exemplary of glycosylated cytokines is granulocyte colony-stimulating factor (G-CSF). G-CSF is produced by monocytes, macrophages, neutrophils, fibroblasts and endothelial cells as a 207 amino acid precursor polypeptide (SEQ ID NO:281) with a 30 amino acid signal sequence. The 177 amino acid mature protein, set forth in SEQ ID NO:282, is produced following cleavage of the signal sequence. Differential splicing of G-CSF mRNA can result in another precursor variant, isoform b, which is 204 amino acids in length (SEQ ID NO: 283). Cleavage of the signal peptide results in a 174 amino acid mature isoform b G-CSF polypeptide (SEQ ID NO:284). G-CSF is O-linked glycosylated at amino acid T136 of the mature polypeptide set forth in SEQ ID NO:282 (corresponding to T166 of the precursor polypeptide set forth in SEQ ID NO:281; T133 of the mature isoform b polypeptide set forth in SEQ ID NO:284; T163 of the precursor isoform b polypeptide set forth in SEQ ID NO:283). Granulocyte colony stimulating factor (G-CSF) is the primary extracellular regulator of granulopoiesis and regulates the production of neutrophils by stimulating proliferation and survival of specific bone marrow precursor cells and their differentiation into granulocytes.

Provided herein are modified non-glycosylated G-CSF polypeptides that exhibit increased resistance to proteolysis. Exemplary protease-resistant G-CSF polypeptides include one or more amino acid modifications set forth in Table 7 corresponding amino acid replacements in SEQ ID NO:282, where the one or more amino acid replacements lead to greater resistance to proteases. In one example, non-glycosylated protease-resistant G-CSF cytokines can be generated by production of protease-resistant polypeptides in host cells that are incapable of glycosylation, including, for example, prokaryotic hosts such as *E. coli*. In another example, non-glycosylated protease-resistant G-CSF cytokines can be generated by mutations of the O-glycosylation site in the polypeptide. For example, a protease-resistant polypeptide having one or more modifications as set forth in Table 7 corresponding to amino acid replacements in SEQ ID NO:282 can further include modification of amino acid position T136. The non-glycosylated protease-resistant polypeptides provided herein retain activity of a fully glycosylated G-CSF polypeptide that is not protease-resistant. Such non-glycosylated protease-resistant polypeptides can be used in the treatment of diseases or disorders for which G-CSF is normally used to treat. Exemplary of such diseases or disorders include, but are not limited to, Crohn's disease, cardiac disease, acquired neutropenias, such as that induced by chemotherapy, congenital neutropenias and asthma.

TABLE 7

G-CSF Modifications to Increase Resistance to Proteolysis

| | | | | |
|---|---|---|---|---|
| W61S | W61H | P63S | P63S | P68A |
| P68S | L72I | L72V | F86I | F86V |
| E96N | E96Q | E96H | P100A | P100S |
| E101N | E101Q | E101H | P131A | P131S |
| L133I | L133V | P135A | P135S | F147I |
| F147V | R169H | R169Q | R172H | R172Q |
| P177A | P177S | | | | e. LIF

Leukemia inhibitory factor (LIF) is a glycoprotein. The LIF gene encodes a 202 amino acid precursor protein (SEQ ID NO:285) that includes a 22 amino acid signal peptide. Post-translational processing results in a glycosylated mature LIF protein that is 180 amino acids long (SEQ ID NO:286). The mature LIF contains multiple N-glycosylated sites, corresponding to N7, N34, N63, N73, N96 and N116 of the mature LIF sequence set forth in SEQ ID NO:286 (N31, N56, N85, N95, N118 and N138 of the precursor polypeptide set forth in SEQ ID NO:285). LIF has a wide array of actions, including acting as a stimulus for platelet formation, proliferation of some hematopoietic cells, bone formation, adipocyte lipid transport, adrenocorticotropic hormone production, neuronal survival and formation, muscle satellite cell proliferation, and acute phase production by hepatocytes. LIF is essential for blastocyst implantation and the normal development of hippocampal and olfactory receptor neurons.

Provided herein are modified non-glycosylated LIF polypeptides that exhibit increased resistance to proteolysis compared to an un-modified non-glycosylated LIF polypeptide. Exemplary protease-resistant LIF polypeptides include one or more amino acid modifications set forth in Table 8 corresponding amino acid replacements in SEQ ID NO:286, where the one or more amino acid replacements lead to greater resistance to proteases. The non-glycosylated modified LIF polypeptides provided herein can be produced using a prokaryotic expression system, such as expression systems using *E. coli* as the host cells. In other examples, protease-resistant LIF polypeptides can be produced as non-glycosylated proteins by modification of one or more glycosylation sites. For example, modification at one or both of amino acid positions N7, N34, N63, N73, N96 and N116 of a mature LIF polypeptide (SEQ ID NO:286) can result in a non-glycosylated protein. The non-glycosylated protease-resistant polypeptides provided herein retain activity of a fully glycosylated LIF polypeptide that is not protease-resistant. The non-glycosylated protease-resistant LIF polypeptides, therefore, can be used to treat conditions and diseases normally treated by LIF, including, but not limited to, reconstitution of neutrophils and monocytes following chemotherapy or bone marrow transplantation.

TABLE 8

Leukemia Inhibitory Factor (LIF)
Modifications to Increase Resistance to Proteolysis

| P69A | P69S | F70I | F70V | R85H |
|---|---|---|---|---|
| R85Q | R99H | R99Q | K102N | K102Q |
| L104I | L104V | P106A | P106S | L109I |
| L109V | Y137H | Y137I | D143N | D143Q |
| Y146H | Y146I | P148A | P148S | D149N |
| D149Q | K153N | K153Q | D154N | D154Q |
| F156I | F156V | | | | f. Interleukin 1β

Interleukin 1β (IL-1β) is synthesized as a precursor of 268 amino acids (SEQ ID NO:287), including a 116 amino acid propeptide. The sequence of mature IL-1β is set forth in SEQ ID NO:288 and is 152 amino acids in length. IL-1β has one N-linked glycosylation site, corresponding to amino 123 of the precursor polypeptide set forth in SEQ ID NO:287 and amino acid 7 of the mature polypeptide set forth in SEQ ID NO:288). IL-1β is a proinflammatory cytokine produced in a variety of cells including monocytes, tissue macrophages, keratinocytes and other epithelial cells. Both IL-1 alpha and IL-1β bind to the same receptor and have similar if not identical biological properties. These cytokines have a broad range of activities including, stimulation of thymocyte proliferation, by inducing IL-2 release, B-cell maturation and proliferation, mitogenic FGF-like activity and the ability to stimulate the release of prostaglandin and collagenase from synovial cells.

Provided herein are non-glycosylated IL-1β polypeptides that are protease resistant. Such IL-1β protease-resistant polypeptides include those having one or more amino acid modification, where the one or more amino acid modification lead to a greater resistant to proteases. Amino acid positions that can be modified to effect increased resistance to proteases in an M-CSF polypeptide can be identified using the methods described in U.S. Patent Publication No. 2005-0202438. In one example, non-glycosylated protease-resistant IL-1β cytokines can be generated by production of protease-resistant polypeptides in host cells that are incapable of glycosylation, including, for example, prokaryotic hosts such as E. coli. In another example, non-glycosylated protease-resistant IL-1β cytokines can be generated by mutation of one or more, up to all, of the glycosylation sites in the polypeptide. For example, a protease-resistant polypeptide having one or more modifications that increase protease-resistance corresponding to amino acid replacements in SEQ ID NO:288 can further include modification of amino acid position N7. The non-glycosylated protease-resistant polypeptides provided herein retain activity of a fully glycosylated IL-1β polypeptide that is not protease-resistant. Such non-glycosylated protease-resistant polypeptides can be used in the treatment of diseases or disorders for which IL-1β is normally used to treat. Exemplary of such diseases or disorders include, but are not limited to, cancers, including use of IL-1β to restore the immune system following chemotherapy, ischemia/reperfusion injury and acquired and congenic neutropenia.

g. Interleukin 2

Interleukin-2 (IL-2) is a glycoprotein produced by T-cells in response to antigenic or mitogenic stimulation. The IL-2 gene encodes a 153 amino acid precursor protein (SEQ ID NO:289) that includes a 20 amino acid signal peptide. Post-translational processing results in a glycosylated mature IL-2 protein that is 133 amino acids long (SEQ ID NO:290). The mature IL-2 is O-glycosylated at a site corresponding to T3 of the mature IL-2 sequence set forth in SEQ ID NO:290 and T23 of the precursor polypeptide set forth in SEQ ID NO:289. IL-2 is required for T-cell proliferation and other activities crucial to regulation of the immune response. It can stimulate B-cells, monocytes, lymphokine-activated killer cells, natural killer cells, and glioma cells.

Provided herein are modified non-glycosylated IL-2 polypeptides that exhibit increased resistance to proteolysis compared to an un-modified non-glycosylated IL-2 polypeptide. Exemplary protease-resistant IL-2 polypeptides include one or more amino acid modifications set forth in Table 9 corresponding amino acid replacements in SEQ ID NO:290, where the one or more amino acid replacements lead to greater resistance to proteases. The non-glycosylated modified IL-2 polypeptides provided herein can be produced using a prokaryotic expression system, such as expression systems using E. coli as the host cells. In other examples, protease-resistant IL-2 polypeptides can be produced as non-glycosylated proteins by modification of one or more glycosylation sites. For example, modification at T3 of a mature IL-2 polypeptide (SEQ ID NO:290) can result in a non-glycosylated protein. The non-glycosylated protease-resistant polypeptides provided herein retain activity of a fully glycosylated IL-2 polypeptide that is not protease-resistant. The non-glycosylated protease-resistant IL-2 polypeptides, therefore, can be used to treat conditions and diseases normally treated by IL-2, including, infections, such as HIV and cytomegalovirus infection, lymphocytopenia, and cancers, including metastatic melanoma and metastatic kidney cancer.

TABLE 9

Interleukin-2 (IL-2) Modifications to Increase Resistance to Proteolysis

| K43N | K43Q | Y45H | Y45I | K48N |
|---|---|---|---|---|
| K48Q | K49N | K49Q | E52N | E52Q |
| E52H | L53I | L53V | E60N | E60Q |
| E60H | E61N | E61Q | E61H | P65A |
| P65S | E67N | E67Q | E67H | E68N |
| E68Q | E68H | L72I | L72V | E100N |
| E100Q | E100H | F103I | F103V | M104I |
| M104V | E106N | E106Q | E106H | Y107H |
| Y107I | D109N | D109Q | E110N | E110Q |
| E110H | L132I | L132V | | | h. Interleukin 3

Exemplary of glycosylated cytokines is interleukin-3 (IL-3). IL-3 is produced by activated T cells, monocytes/macrophages and stroma cells as a 152 amino acid precursor polypeptide (SEQ ID NO:291) with a 19 amino acid signal sequence. The 133 amino acid mature protein, set forth in SEQ ID NO:292, is produced following cleavage of the signal sequence. The IL-3 polypeptide contains N-linked glycosylation sites at N15 and N70 of the mature polypeptide set forth in SEQ ID NO:292 (corresponding to N34 and N89 of the precursor polypeptide set forth in SEQ ID NO:291). IL3 is multipotent hematopoietic growth factor that regulates the growth and differentiation of hematopoietic progenitor cells of the myeloid, erythroid and megakaryocytic lineages and functionally activates mature neutrophils and macrophages. As such, IL-3 can be used to expand haemopoietic cell populations.

Provided herein are modified non-glycosylated IL-3 polypeptides that exhibit increased resistance to proteolysis. Exemplary protease-resistant IL-3 polypeptides include one or more amino acid modifications set forth in Table 10 corresponding amino acid replacements in SEQ ID NO:292, where the one or more amino acid replacements lead to greater resistance to proteases. In one example, non-glycosylated protease-resistant IL-3 cytokines can be generated by production of protease-resistant polypeptides in host cells that are incapable of glycosylation, including, for example, prokaryotic hosts such as E. coli. In another example, non-glycosylated protease-resistant IL-3 cytokines can be generated by mutation of one or both of the N-glycosylation sites in the polypeptide. For example, a protease-resistant polypeptide having one or more modifications as set forth in Table 10 corresponding to amino acid replacements in SEQ ID NO:292 can further include modification of amino acid positions N15 and/or N70. The non-glycosylated protease-resistant polypeptides provided herein retain activity of a fully glycosylated IL-3 polypeptide that is not protease-resistant. Such non-glycosylated protease-resistant polypeptides can be used in the treatment of diseases or disorders for which IL-3 is normally used to treat. Exemplary of such diseases or disorders include, but are not limited to, congenital or acquired neutropenias and thrombocytopenias, such as those induced by chemotherapy.

TABLE 10

Interleukin-3 (IL-3) Modifications to Increase Resistance to Proteolysis

| F37I | F37V | E43N | E43Q | E43H |
|------|------|------|------|------|
| D46N | D46Q | E59N | E59Q | E59H |
| R63H | R63Q | K66N | K66Q | P96A |
| P96S | K100N | K100Q | D101N | D101Q |
| D103N | D103Q | | | | i. Interleukin 4

Exemplary of a glycosylated cytokine is Interleukin 4 (IL-4). IL-4 is synthesized as a precursor of 153 amino acids (SEQ ID NO:293), including a 24 amino acid signal peptide. The sequence of mature IL-4 is set forth in SEQ ID NO:294 (UniProt No. P05112) and is 129 amino acids in length. IL-4 has 2 N-linked glycosylation sites (corresponding to amino 62 and 129 of the precursor polypeptide set forth in SEQ ID NO:293 and amino acids 38 and 105 of the mature polypeptide set forth in SEQ ID NO:294). IL-4 also contains six cysteine residues involved in disulfide bond formation. IL-4 induces the differentiation of naïve helper T cells to Th2 cells. IL-4 also plays a role in the stimulation of activated B-cells and proliferation of T cells. Thus, IL-4 is a regulator of humor and adaptive immunity.

Provided herein are non-glycosylated IL-4 polypeptides that are protease resistant. Such IL-4 protease-resistant polypeptides include those having one or more amino acid modification, where the one or more amino acid modification lead to a greater resistant to proteases. Exemplary of such modifications include, but are not limited to, modifications shown in Table 11 below, corresponding to amino acid replacements in a sequence of amino acids set forth in SEQ ID NO:294. In one example, non-glycosylated protease-resistant IL-4 cytokines can be generated by production of protease-resistant polypeptides in host cells that are incapable of glycosylation, including, for example, prokaryotic hosts such as E. coli. In another example, non-glycosylated protease-resistant IL-4 cytokines can be generated by mutations of one or more, up to all, of the glycosylation sites in the polypeptide. For example, a protease-resistant polypeptide having one or more modifications as set forth in Table 11 corresponding to amino acid replacements in SEQ ID NO:294 can further include modification of one or more amino acid positions N38 and/or N105. The non-glycosylated protease-resistant polypeptides provided herein retain activity of a fully glycosylated IL-4 polypeptide that is not protease-resistant. Such non-glycosylated protease-resistant polypeptides can be used in the treatment of diseases or disorders for which IL-4 is normally used to treat. Exemplary of such diseases or disorders include, but are not limited to, inflammatory and autoimmune diseases such as collagen-induced arthritis, autoimmune diabetes, multiple sclerosis and inflammatory bowel disease; and cancer, including but not limited to colon and mammary carcinomas.

TABLE 11

Interleukin-4 (IL-4) Modifications to Increase Resistance to Proteolysis

| E26N | E26Q | E26H | K37N | K37Q |
|------|------|------|------|------|
| R53H | R53Q | E60N | E60Q | E60H |
| K61N | K61Q | R64H | R64Q | L66I |
| L66V | P100A | P100S | K102N | K102Q |
| E103N | E103Q | E103H | K126N | K126Q | j. Interleukin 5

Exemplary of a glycosylated cytokine is IL-5. IL-5 is a homodimeric glycoprotein that promotes the proliferation, differentiation and activation of eosinophils. IL-5 also functions to stimulate B cell growth and increases immunoglobulin secretion. IL-5 is synthesized as a precursor of 134 amino acids (SEQ ID NO:295), including a 19 amino acid signal peptide. The sequence of mature IL-5 is set forth in SEQ ID NO:296 and is 115 amino acids in length. IL-5 is an antiparallel dimer linked by two cysteines (corresponding to C44 and C86 of the sequence of amino acids set forth in SEQ ID NO:296). IL-5 also is glycosylated by O-linked and N-linked glycosylation. at T3 and N28, respectively, corresponding to the sequence of amino acids set forth in SEQ ID NO:296 (Minamitake et al. (1990): J. Biochem., 107:2:292-297). Provided herein are non-glycosylated IL-5 polypeptides that are protease resistant. Such IL-5 protease-resistant polypeptides include those having one or more amino acid modification, where the one or more amino acid modification lead to a greater resistant to proteases. Exemplary of such modifications include, but are not limited to, modifications shown in Table 12 below, corresponding to amino acid replacements in a sequence of amino acids set forth in SEQ ID NO:296. In one example, non-glycosylated protease-resistant IL-5 cytokines can be generated by production of protease-resistant polypeptides in host cells that are incapable of glycosylation, including, for example, prokaryotic hosts such as E. coli. In another example, non-glycosylated protease-resistant IL-5 cytokines can be generated by mutation of one or more, up to all, of the glycosylation sites in the polypeptide. For example, a protease-resistant polypeptide having one or more modifications as set forth in Table 12 corresponding to amino acid replacements in SEQ ID NO:296 can further include modification of one or more amino acid positions T3 and/or N28. The non-glycosylated protease-resistant polypeptides provided herein retain activity of a fully glycosylated IL-5 polypeptide that is not protease-resistant. Such non-glycosylated protease-resistant polypeptides can be used in the treatment of diseases or disorders for which IL-5 is normally used to treat, including, for example, any where eosinophilia contributes to prognosis. Exemplary of such diseases include, but are not limited to, cancers such as colonic, gastric, and carcinomas of the lung, urinary bladder, uterine cervix and head and neck; and graft rejection.

TABLE 12

Interleukin-5 (IL-5) Modifications to Increase Resistance to Proteolysis

| R32H | R32Q | P34A | P34S | K39N |
|------|------|------|------|------|
| K39Q | E46N | E46Q | E46H | E47N |

TABLE 12-continued

| Interleukin-5 (IL-5) Modifications to Increase Resistance to Proteolysis | | | | |
|---|---|---|---|---|
| E47Q | E47H | E56N | E56Q | E56H |
| K84N | K84Q | K85N | K85Q | E88N |
| E88Q | E88H | E89N | E89Q | E89H |
| R90H | R90Q | E102N | E102Q | E102H |
| E110N | E110Q | E110H | W111S | W111H | k. Interleukin 6

Exemplary of a glycosylated cytokine is Interleukin 6 (IL-6). IL-6 is a pleiotropic cytokine and can stimulate the development, proliferation and maturation of a number of hematopoietic cells. IL-6 also is required for B cell maturation into immunoglobulin-secreting cells. IL-6 also plays a role in the differentiation of nerve cells, metabolism of bone and induction of acute phase proteins in hepatocytes. IL-6 is synthesized as a precursor of 212 amino acids (SEQ ID NO:297), including a 29 amino acid signal peptide. The sequence of mature IL-6 is set forth in SEQ ID NO:298 and is 183 amino acids in length. IL-6 is expressed by T cells, macrophages, fibroblasts, endothelial cells and keratinocytes. Depending on its source of expression, the mature secreted human IL-6 contains 183 to 186 residues. For example, the amino terminus of fibroblast-derived IL-6 is Ala28 of the sequence of amino acids set forth in SEQ ID NO:297. IL-6 is modified post-translationally by N-linked and O-linked glycosylation. For example, Thr166 is an O-linked glycosylation site and Asn73 and Asn172 are N-linked glycosylation sites corresponding to residues in the precursor sequence set forth in SEQ ID NO:297 (and corresponding to residues 137, 44 and 143, respectively, in SEQ ID NO:298).

Provided herein are non-glycosylated IL-6 polypeptides that are protease resistant. Such IL-6 protease-resistant polypeptides include those having one or more amino acid modification, where the one or more amino acid modification lead to a greater resistant to proteases. Exemplary of such modifications include, but are not limited to, modifications shown in Table 13 below, corresponding to amino acid replacements in a sequence of amino acids set forth in SEQ ID NO:298. In one example, non-glycosylated protease-resistant IL-6 cytokines can be generated by production of protease-resistant polypeptides in host cells that are incapable of glycosylation, including, for example, prokaryotic hosts such as *E. coli*. In another example, non-glycosylated protease-resistant IL-6 cytokines can be generated by mutations of one or more, up to all, of the glycosylation sites in the polypeptide. For example, a protease-resistant polypeptide having one or more modifications as set forth in Table 13 corresponding to amino acid replacements in SEQ ID NO:298 can further include modification of one or more amino acid positions T137, N44 and/or N143. The non-glycosylated protease-resistant polypeptides provided herein retain activity of a fully glycosylated IL-6 polypeptide that is not protease-resistant. Such non-glycosylated protease-resistant polypeptides can be used in the treatment of diseases or disorders for which IL-6 is normally used to treat. Exemplary of such diseases include, but are not limited to, cancer, thrombocytopenia and neutropenia, such as induced by chemotherapy, inflammatory diseases (other than glomerulonephritis), such as multiple sclerosis, septic shock, arthritic conditions, particularly pathogen-induced arthritic conditions, for example, Lyme disease arthritis, bacterially induced arthritis, and polioarthritis; multiple sclerosis and other demyelinating diseases (i.e., diseases characterized by demyelination in the nerves, brain, and/or spinal cord, including, e.g., multiple sclerosis, acute disseminated encephalomyelitis or postinfectuous encephalitis, optic neuromyelitis, tinnitus, diffuse cerebral sclerosis, Schilder's disease, adrenoleukodystrophy, tertiary Lyme disease, tropical spastic parapoesis, and other diseases wherein demyelination especially autoimmune-mediated demyelination, is a major symptom); acute severe inflammatory conditions such as burns, septic shock, meningitis, and pneumonia; and autoimmune diseases including polychondritis, scleroderma, Wegener granulamatosis, dermatomyositis, chronic active hepatitis, myasthenia gravis, psoriasis, psoriatic arthritis, Steven-Johnson syndrome, idiopathic sprue, autoimmune inflammatory bowel disease (including e.g. ulcerative colitis and Crohn's disease), endocrine opthalmopathy, Graves disease, sarcoidosis, primary billiary cirrhosis, juvenile diabetes (diabetes mellitus type I), uveitis (anterior and posterior), keratoconjunctivitis sicca and vernal keratoconjunctivitis, and interstitial lung fibrosis.

TABLE 13

| Interleukin-6 (IL-6) Modifications to Increase Resistance to Proteolysis | | | | |
|---|---|---|---|---|
| P64A | P64S | K65N | K65Q | M66I |
| M66V | E68N | E68Q | E68H | K69N |
| K69Q | F73I | F73V | F77I | F77V |
| E92N | E92Q | E92H | E98N | E98Q |
| E98H | R103H | R103Q | E105N | E105Q |
| E105H | E108N | E108Q | E108H | D133N |
| D133Q | P138A | P138S | D139N | D139Q |
| P140A | P140S | K149N | K149Q | W156S |
| W156H | R178H | R178Q | R181H | R181Q | l. Oncostatin M

Exemplary of a glycosylated cytokine is Oncostatin M (OSM). OSM is a pleiotropic cytokine synthesized by stimulated T-cells and monocytes, and is involved in liver development, hematopoiesis, inflammation and CNS development. OSM is synthesized as a precursor of 252 amino acids (SEQ ID NO:299), including a 25 amino acid signal peptide. The sequence of mature OSM is set forth in SEQ ID NO:300 and is 227 amino acids in length. Cleavage of the 31 COOH-terminal amino acid residues at a trypsin like cleavage site yields the fully active 196 residue form of OSM. Of the five cysteine residues within the OSM sequence, four participate in disulphide bridges (i.e. between cysteines at positions C31 and C152; and C74 and C192, corresponding to residues set forth in SEQ ID NO: 299). The disulphide bond between helices A and B (C74 and C192) is necessary for OSM activity. The free cysteine residue (C105) does not mediate dimerization of OSM. OSM is further modified post-translationally by N-linked glycosylation. For example, Asn100 and Asn217 are N-linked glycosylation sites corresponding to residues in the precursor sequence set forth in SEQ ID NO:299 (and corresponding to residues 75 and 192, respectively, in SEQ ID NO:300). Provided herein are non-glycosylated OSM polypeptides that are protease resistant. Such OSM protease-resistant polypeptides include those having one or more amino acid modification, where the one or more amino acid modification lead to a greater resistant to proteases. Exemplary of such modifications include, but are not limited to, modifications shown in Table 14 below, corresponding to amino acid replacements in a sequence of amino acids set forth in SEQ ID NO: 300. In one example, non-glycosylated protease-resistant OSM cytokines can be generated by production of protease-resistant polypeptides in host cells that are incapable of glycosylation, including, for example, prokaryotic hosts such as *E. coli*. In another example, non-glycosylated protease-resistant OSM cytokines can be generated by mutations of one or more, up to all, of the glycosylation sites in the polypeptide. For example, a protease-resistant polypeptide having one or more modifications as set forth in Table 14 corresponding to amino acid replacements in SEQ ID NO: 300 can further include modification of one or more amino acid positions N75 and/or N192. The non-glycosylated protease-resistant polypeptides provided herein retain activity of a fully glycosylated OSM polypeptide that is not protease-resistant. Such non-glycosylated protease-resistant polypeptides can be used in the treatment of diseases or disorders for which OSM is normally used to treat. Exemplary of such diseases or treatments include, but are not limited to chronic inflammatory diseases, acute and chronic gastrointestinal inflammation, rheumatoid arthritis and multiple sclerosis and tissue damage suppression.

TABLE 14

Oncostatin M Modifications to Increase Resistance to Proteolysis

| | | | | |
|---|---|---|---|---|
| E59N | E59Q | E59H | E60N | E60Q |
| E60H | R63H | R63Q | L65I | L65V |
| R84H | R84Q | D87N | D87Q | E89N |
| E89Q | E89H | R91H | R91Q | K94N |
| K94Q | D97N | D97Q | E99N | E99Q |
| E99H | R100H | R100Q | L103I | L103V |
| E106N | E106Q | E106H | | | m. Stem Cell Factor

Exemplary of a glycosylated cytokine is Stem Cell Factor (SCF). SCF (also known as "steel factor" or "c-kit ligand") is a cytokine which binds CD117 (c-Kit) and is important for the survival, proliferation, and differentiation of hematopoietic stem cells and other hematopoietic progenitor cells. One of its functions, for example, is to change the BFU-E (burst-forming unit-erythroid) cells, which are the earliest erythrocyte precursors in the erythrocytic series, into CFU-E (colony-forming unit-erythroid) cells. SCF is synthesized as a precursor of 273 amino acids (SEQ ID NO:301), including a 25 amino acid signal peptide. The sequence of mature SCF is set forth in SEQ ID NO:302 and is 248 amino acids in length. SCF exists in two forms, cell surface bound SCF and soluble (or free) SCF. Soluble SCF is produced by the cleavage of surface bound SCF by metalloproteases to yield a 189 amino acid polypeptide corresponding to amino acids 26 to 214 of SEQ ID NO:301. SCF has two disulphide bridges between cysteines at positions C29 and C114; and C68 and C163, corresponding to residues in the precursor sequence set forth in SEQ ID NO:301. SCF is further modified post-translationally by N-linked glycosylation. For example, Asn90, Asn97, Asn118, Asn145, and Asn195 are N-linked glycosylation sites corresponding to residues in the precursor sequence set forth in SEQ ID NO:301 (and corresponding to residues 65, 72, 93, 120, and 170, respectively, in SEQ ID NO:302).

Provided herein are non-glycosylated SCF polypeptides that are protease resistant. Such SCF protease-resistant polypeptides include those having one or more amino acid modification, where the one or more amino acid modification lead to a greater resistant to proteases. Exemplary of such modifications include, but are not limited to, modifications shown in Table 15 below, corresponding to amino acid replacements in a sequence of amino acids set forth in SEQ ID NO:302. In one example, non-glycosylated protease-resistant SCF cytokines can be generated by production of protease-resistant polypeptides in host cells that are incapable of glycosylation, including, for example, prokaryotic hosts such as E. coli. In another example, non-glycosylated protease-resistant SCF cytokines can be generated by mutations of one or more, up to all, of the glycosylation sites in the polypeptide. For example, a protease-resistant polypeptide having one or more modifications as set forth in Table 15 corresponding to amino acid replacements in SEQ ID NO:302 can further include modification of one or more amino acid positions N65, N72, N93, N120, and/or N170. The non-glycosylated protease-resistant polypeptides provided herein retain activity of a fully glycosylated SCF polypeptide that is not protease-resistant. Such non-glycosylated protease-resistant polypeptides can be used in the treatment of diseases or disorders for which SCF is normally used to treat. Exemplary of such diseases or treatments include, but are not limited to, hepatic injury, asthma, hematopoietic engraftment.

TABLE 15

Stem Cell Factor (SCF) Modifications to Increase Resistance to Proteolysis

| | | | | |
|---|---|---|---|---|
| M27I | M27V | K31N | K31Q | P34A |
| P34S | D37N | D37Q | D54N | D54Q |
| D58N | D58Q | D61N | D61Q | K62N |
| K62Q | F63I | F63V | K96N | K96Q |
| L98I | L98V | K99N | K99Q | K100N |
| K100Q | F102I | F102V | K103N | K103Q |
| E106N | E106Q | E106H | P107A | P107S |
| R108H | R108Q | L109I | L109V | E134N |
| E134Q | E134H | D137N | D137Q | | n. Interferon β

Exemplary of a glycosylated cytokine is Interferon β (IFN-β). IFN-β, a member of the type I class of interferons, is a globular protein containing 5 alpha helices. Generally, IFN-β is an anti-inflammatory molecules whose observed effects on a variety of immune cells (e.g., T cells, NK cells, monocytes, macrophages and dendritic cells) include, for example, the following: enhancement of T cell cytotoxity; regulation of antibody production; inhibition of T cell proliferation and migration; downregulation of adhesion molecules; enhanced expression of tumor-associated surface antigens, stimulation of surface molecules such as MHC class I antigens, induction or activation of pro-apoptotic genes and proteins (e.g., tumor necrosis factor-related apoptosis-inducing ligand, caspases, Bak, Bax, and p53), repression of anti-apoptotic genes (e.g., Bcl-2, inhibitor of apoptosis protein), and inhibition of angiogenesis (Pestka et al. *Immunological Reviews* 202: 8-32 (2004); Holten et al., (2002), *Arthritis Research*, 4: 346-352).

IFN-β is synthesized as a precursor of 187 amino acids (SEQ ID NO:303), including a 21 amino acid signal peptide. Mature IFN-β polypeptides can be of variable length, typically including polypeptides of 166 amino acids (SEQ ID NO:304), 164 and 165 amino acids in length. IFN-β has one disulphide bridge between cysteines at positions C52 and C162, corresponding to residues in the precursor sequence set forth in SEQ ID NO:303. IFN-β is further modified post-translationally by N-linked glycosylation. For example, Asn101 is an N-linked glycosylation site (corresponding to residue 101 in the precursor sequence set forth in SEQ ID NO:303, and corresponding to residue 80 in SEQ ID NO:304). Commercial forms of IFN-β include those sold under the trademarks AVONEX®, BETASERON®, and Rebif®. IFN-β-1a (Avonex®, Biogen Inc, CA, USA, and Rebif®, Serono Inc., Geneva, Switzerland) is produced in CHO cells into which cDNA encoding IFN-β has been introduced. IFN-β-1a is 166 amino acids in length and is identical to fibroblast-derived human IFN-β (SEQ ID NO:304), including glycosylation at the asparagine residue on position 80 (Nelissen et al. *Brain* 126: 1371-1381 (2003)). Rebif® IFN-β-1a differs from Avonex® IFN-β-1a in that it is formulated for administration to the skin (i.e., subcutaneously) rather than intramuscular administration. IFN-β-1b (Betaseron®, Berlex laboratories, Richmond, Calif., USA) is produced in *E. coli* that bears a genetically engineered plasmid encoding human IFN-β. The resulting expressed IFN-β-1b product is not glycosylated, is lacking the amino terminal methionine (Met1), and the cysteine residue at position 17 (of SEQ ID NO:304) is mutated to a serine. IFN-β-1b is 165 amino acids in length and does not include the carbohydrate side chains that are found in natural human IFN-β (Nelissen et al. *Brain* 126: 1371-1381 (2003)).

Provided herein are non-glycosylated IFN-β polypeptides that are protease resistant. Such IFN-β protease-resistant polypeptides include those having one or more amino acid modification, where the one or more amino acid modification lead to a greater resistant to proteases. Exemplary of such modifications include, but are not limited to, modifications shown in Table 16 below, corresponding to amino acid replacements in a sequence of amino acids set forth in SEQ ID NO:304. In one example, non-glycosylated protease-resistant IFN-β cytokines can be generated by production of protease-resistant polypeptides in host cells that are incapable of glycosylation, including, for example, prokaryotic hosts such as *E. coli*. In another example, non-glycosylated protease-resistant IFN-β cytokines can be generated by mutations of one or more, up to all, of the glycosylation sites in the polypeptide. For example, a protease-resistant polypeptide having one or more modifications as set forth in Table 16 corresponding to amino acid replacements in SEQ ID NO:304 can further include modification of amino acid position N80. The non-glycosylated protease-resistant polypeptides provided herein retain activity of a fully glycosylated IFN-β polypeptide that is not protease-resistant. Such non-glycosylated protease-resistant polypeptides can be used in the treatment of diseases or disorders for which IFN-β is normally used to treat and/or are responsive to the administration of IFN-β. Exemplary of such diseases include, but are not limited to viral infection, a proliferative disorder, an autoimmune disease, and an inflammatory disorder. In such an example where the disease to be treated is an autoimmune disease, the disease or condition can be, but is not limited to, any one of multiple sclerosis, rheumatoid arthritis, chronic viral hepatitis, hepatitis A, hepatitis B, and myocardial viral infection. In such another example where the disease to be treated is a proliferative disorder, the disease or condition can be, but is not limited to, a cancer or bone disorder. Exemplary of cancers to be treated with a pharmaceutical composition provided herein include uveal, melanoma, colon cancer, liver cancer, or metastatic cancer. Exemplary of a bone disorder is osteoporosis or osteopenia. In such a further example, where the disease to be treated is an inflammatory disorder, the disease or condition can be, but is not limited to, any of asthma, Guillain-Barre syndrome, and inflammatory bowel disease such as for example, ulcerative colitis or Crohn's disease. In an additional example, where the disease is a viral infection, the infection can be, but is not limited to, chronic viral hepatitis or myocardial infection.

TABLE 16

Interferon-β (IFN-β) Modifications to Increase Resistance to Proteolysis

| | | | | |
|---|---|---|---|---|
| M1I | M1V | M1T | M1Q | M1A |
| Y3H | Y3I | L5I | L5V | L5T |
| L5Q | L5H | L5A | L6I | L6V |
| F8I | F8V | L9I | L9V | L9T |
| L9Q | L9H | L9A | R11H | R11Q |
| F15I | F15V | K19N | K19Q | K19T |
| K19S | K19H | L20I | L20V | L21I |
| L21V | W22S | W22H | L24I | L24V |

TABLE 16-continued

Interferon-β (IFN-β) Modifications to Increase Resistance to Proteolysis

| | | | | |
|---|---|---|---|---|
| N25H | N25Q | N25S | R27H | R27Q |
| L28I | L28V | L28T | L28Q | L28H |
| L28A | E29N | E29Q | E29H | Y30H |
| Y30I | L32I | L32V | L32T | L32Q |
| L32H | L32A | K33N | K33Q | K33T |
| K33S | K33H | D34N | D34Q | R35H |
| R35Q | M36I | M36V | M36T | M36Q |
| M36A | F38I | F38V | D39N | D39Q |
| D39H | D39G | P41A | P41S | E42N |
| E42Q | E42H | E43N | E43Q | E43H |
| K45N | K45Q | K45T | K45S | K45H |
| L47I | L47V | L47T | L47Q | L47H |
| L47A | F50I | F50V | K52N | K52Q |
| K52T | K52S | K52H | E53N | E53Q |
| E53H | D54N | D54Q | L57I | L57V |
| Y60H | Y60I | E61N | E61Q | E61H |
| M62I | M62V | L63I | L63V | F67I |
| F67V | F70I | F70V | R71H | R71Q |
| D73N | D73Q | D73H | D73G | W79S |
| W79H | E81N | E81Q | E81H | E85N |
| E85Q | E85H | L87I | L87V | L88I |
| L88V | Y92H | Y92I | L98I | L98V |
| K99N | K99Q | K99T | K99S | K99H |
| L102I | L102V | E103N | E103Q | E103H |
| E104N | E104Q | E104H | K105N | K105Q |
| K105T | K105S | K105H | L106I | L106V |
| E107N | E107Q | E107H | K108N | K108Q |
| K108T | K108S | K108H | E109N | E109Q |
| E109H | D110N | D110Q | D110H | D110G |
| F111I | F111V | R113H | R113Q | K115N |
| K115Q | L116I | L116V | L116T | L116Q |
| L116H | L116A | M117I | M117V | L120I |
| L120V | L120T | L120Q | L120H | L120A |
| L122I | L122V | K123N | K123Q | K123T |
| K123S | K123H | R124H | R124Q | Y125H |
| Y125I | Y126H | Y126I | R128H | R128Q |
| L130I | L130V | L130T | L130Q | L130H |
| L130A | Y132H | Y132I | L133I | L133V |
| K134N | K134Q | K134T | K134S | K134H |
| K136N | K136Q | K136T | K136S | K136H |
| E137N | E137Q | E137H | Y138H | Y138I |
| W143S | W143H | R147H | R147Q | E149N |
| E149Q | E149H | L151I | L151V | R152H |
| R152Q | F154I | F154V | Y155H | Y155I |
| F156I | F156V | R159H | R159Q | L160I |
| L160V | Y163H | Y163I | L164I | L164V |
| R165H | R165Q | M1D | M1E | M1K |
| M1N | M1R | M1S | L5D | L5E |
| L5K | L5R | L5N | L5S | L6D |
| L6E | L6K | L6N | L6Q | L6R |
| L6S | L6T | F8D | F8E | F8K |
| F8R | L9D | L9E | L9K | L9N |
| L9R | L9S | Q10D | Q10E | Q10K |
| Q10N | Q10R | Q10S | Q10T | S12D |
| S12E | S12K | S12R | S13D | S13E |
| S13K | S13N | S13Q | S13R | S13T |
| N14D | N14E | N14K | N14Q | N14R |
| N14S | N14T | F15D | F15E | F15K |
| F15R | Q16D | Q16E | Q16K | Q16N |
| Q16R | Q16S | Q16T | C17D | C17E |
| C17K | C17N | C17Q | C17R | C17S |
| C17T | L20N | L20Q | L20R | L20S |
| L20T | L20D | L20E | L20K | W22D |
| W22E | W22K | W22R | Q23D | Q23E |
| Q23K | Q23R | L24D | L24E | L24K |
| L24R | G78D | G78E | G78K | G78R |
| W79D | W79E | W79K | W79R | N80D |
| N80E | N80K | N80R | T82D | T82E |
| T82K | T82R | I83D | I83E | I83K |
| I83R | I83N | I83Q | I83S | I83T |
| N86D | N86E | N86K | N86R | N86Q |
| N86S | N86T | L87D | L87E | L87K |
| L87R | L87N | L87Q | L87S | L87T |
| A89D | A89E | A89K | A89R | N90D |
| N90E | N90K | N90Q | N90R | N90S |
| N90T | V91D | V91E | V91K | V91N |
| V91Q | V91R | V91S | V91T | Q94D |
| Q94E | Q94K | Q94N | Q94R | Q94S |

TABLE 16-continued

| Interferon-β (IFN-β) Modifications to Increase Resistance to Proteolysis | | | | |
|---|---|---|---|---|
| Q94T | I95D | I95E | I95K | I95N |
| I95Q | I95R | I95S | I95T | H97D |
| H97E | H97K | H97N | H97Q | H97R |
| H97S | H97T | L98D | L98E | L98K |
| L98N | L98Q | L98R | L98S | L98T |
| V101D | V101E | V101K | V101N | V101Q |
| V101R | V101S | V101T | M1C | L6C |
| Q10C | S13C | Q16C | N90C | V91C |
| Q94C | H97C | L98C | V101C | L5D/L6E |
| L5E/Q10D | L5Q/M36I | L6E/L47I | L5E/K108S | L5E/L6E |
| L5D/Q10D | L5N/M36I | L6Q/L47I | L5D/K108S | L5N/L6E |
| L5Q/Q10D | L6E/M36I | L5E/N86Q | L5Q/K108S | L5Q/L6E |
| L5N/Q10D | L6Q/M36I | L5D/N86Q | L5N/K108S | L5D/L6Q |
| L6E/Q10D | L5E/L47I | L5Q/N86Q | L6E/K108S | L5E/L6Q |
| L6Q/Q10D | L5D/L47I | L5N/N86Q | L6Q/K108S | L5N/L6Q |
| L5E/M36I | L5Q/L47I | L6E/N86Q | L5Q/L6Q | L5D/M36I |
| L5N/L47I | L6Q/N86Q | L6E/K108S | L6H | L6A |
| L20H | L20A | L21T | L21Q | L21H |
| L21A | L24T | L24Q | L24H | L24A |
| D 34G | D54G | L57T | L57Q | L57H |
| L57A | M62T | M62Q | M62A | L63T |
| L63Q | L63H | L63A | L87H | L87A |
| L88T | L88Q | L88H | L88A | L98H |
| L98A | L102T | L102Q | L102H | L102A |
| L106T | L106Q | L106H | L106A | K115S |
| K115H | K155N | M117T | M117Q | M117A |
| L122T | L122Q | L122H | L122A | L133T |
| L133Q | L133H | L133A | L151T | L151Q |
| L151H | L151A | L160T | L160Q | L160H |
| L160A | L164T | L164Q | L164H | L164A |
| Q18H | Q18S | Q18T | Q18N | Q23H |
| Q23S | Q23T | Q23N | Q48H | Q48S |
| Q48T | Q48N | Q49H | Q49S | Q49T |
| Q49N | Q51H | Q51S | Q51T | Q51N |
| Q64H | Q64S | Q64T | Q64N | Q72H |
| Q72S | Q72T | Q72N | | | o. Interferon γ

Exemplary of a glycosylated cytokine is Interferon γ (IFN-γ). In general, IFN-γγ is a pleiotropic cytokine produced by immune cells including activated T-cells and NK cells. IFN-γ, and the cells that produce it, play a pivotal role in host defense by exerting anti-viral, antiproliferative and immunoregulatory effects on a variety of cells types. For example, IFN-γ has the ability to enhance the functional activity of macrophages, promote T and B cell differentiation, modulate class I and II MHC antigen expression on a variety of cells, activate natural killer cells and neutrophils and prolong neutrophil survival. IFN-γ polypeptides are heterogeneous polypeptides, are made of varying amino acid sequence lengths and include, but are not limited to, recombinantly produced polypeptides, synthetically produced polypeptides and IFN-γ extracted from cells and tissues such as, for example, T lymphocyte and natural killer (NK) cells. Generally, IFN-γ is produced as a larger polypeptide that is matured to a smaller polypeptide upon cleavage of the signal sequence. Mature IFN-γ polypeptides are typically 124-146 amino acids in length after cleavage of the signal sequence. The precursor form of human IFN-γ is a 166 amino acid polypeptide (for example, SEQ ID NO:305), and includes a signal sequence (i.e. amino acids 1-20) that is cleaved, resulting in a mature polypeptide, such as for example, a mature polypeptide of 146 amino acids set forth in SEQ ID NO:306. IFN-γ is further modified post-translationally by N-linked glycosylation. For example, Asn48 and Asn120 are N-linked glycosylation sites corresponding to residues in the precursor sequence set forth in SEQ ID NO:305 (and corresponding to residues 28 and 100, respectively, in SEQ ID NO:306).

In addition, mature IFN-γ can exist in forms that are less than 146 amino acids in length such as, for example, 124, 125, 138, 139, 140, 141, 142, 143, 144, and 145 amino acids in length. The heterogeneity of IFN-γ polypeptides stems from natural truncations of IFN-γ that occur at the C-terminus, for example due to proteolytic digestion before and after secretion. For example, the truncation can be effected by endo- and/or exoprotease activity produced by the host cell. In some instances, the proteolytic degradation after secretion is due to the presence of proteolytic enzymes in the culture medium.

Deletion of amino acid residues at the N-terminus of IFN-γ also have been reported. In some instances, deletion of residues at the N-terminus is due to post-translational modification. Depending on the source of IFN-γ, post-translational modification of IFN-γ can involve the removal of the first three amino acids from the mature polypeptide set forth in SEQ ID NO:306, i.e. amino acid residues Cys-Tyr-Cys (The Cytokine FactsBook, (1994) Callard R., and Gearing A., (eds) pp. 157-158).

For purposes herein, modification of an IFN-γ polypeptide is with reference to an IFN-γ polypeptide having a length of 146 amino acids (SEQ ID NO:306). It is understood, however, that modified IFN-γ polypeptides provided herein can be produced by methods known to those of skill in the art and can be produced in varying lengths. Thus, the modified IFN-γ polypeptides provided herein include those that are 146 amino acids in length (i.e. containing amino acid modifications in a mature IFN-γ polypeptide set forth in SEQ ID NO:306), fragments thereof that are variously truncated at the N- or C-terminus, or combinations thereof. If necessary, IFN-γ polypeptides can be purified to homogeneity to be of any desired length Provided herein are non-glycosylated IFN-γ polypeptides that are protease resistant. Such IFN-γ protease-resistant polypeptides include those having one or more amino acid modification, where the one or more amino acid modification lead to a greater resistant to proteases. Exemplary of such modifications include, but are not limited to, modifications shown in Table 17 below, corresponding to amino acid replacements in a sequence of amino acids set forth in SEQ ID NO:306. In one example, non-glycosylated protease-resistant IFN-γ cytokines can be generated by production of protease-resistant polypeptides in host cells that are incapable of glycosylation, including, for example, prokaryotic hosts such as *E. coli*. In another example, non-glycosylated protease-resistant IFN-γ cytokines can be generated by mutations of one or more, up to all, of the glycosylation sites in the polypeptide. For example, a protease-resistant polypeptide having one or more modifications as set forth in Table 17 corresponding to amino acid replacements in SEQ ID NO:306 can further include modification of one or more amino acid positions N28 and N100. The non-glycosylated protease-resistant polypeptides provided herein retain activity of a fully glycosylated IFN-γ polypeptide that is not protease-resistant. Such non-glycosylated protease-resistant polypeptides can be used in the treatment of diseases or disorders for which IFN-γ is normally used to treat. Exemplary of such diseases include, but are not limited to, a viral infection (e.g., hepatitis C, acquired immunodeficiency syndrome), a bacterial infection, a fungal infection (e.g., aspergillosis, candidemia), a cancerous condition (e.g., neutropenia, hemopoietic cell transplantation), a cancer, liver disease, a pulmonary disease or condition, malignant osteopetrosis or chronic granulomatous.

TABLE 17

| Interferon-γ (IFN-γ) Modifications to Increase Resistance to Proteolysis | | | | |
|---|---|---|---|---|
| Y2H | Y2I | D5N | D5Q | P6A |
| P6S | Y7H | Y7I | K9N | K9Q |
| E10N | E10Q | E10H | E12N | E12Q |
| E12H | L14I | L14V | K15N | K15Q |
| K16N | K16Q | Y17H | Y17I | F18I |
| F18V | D24N | D24Q | D27N | D27Q |
| N28Q | N28S | L31I | L31V | F32I |
| F32V | L33I | L33V | L36I | L36V |
| K37N | K37Q | W39S | W39H | K40N |
| K40Q | E41N | E41Q | E41H | E42N |
| E42Q | E42H | D44N | D44Q | R45H |
| R45Q | F57I | F57V | K58N | K58Q |
| L59I | L59V | F60I | F60V | K61N |
| K61Q | F63I | F63V | K64N | K64Q |
| D65N | D65Q | D66N | D66Q | K71N |
| K71Q | E74N | E74Q | E74H | K77N |
| K77Q | E78N | E78Q | E78H | D79N |
| D79Q | K83N | K83Q | F84I | F84V |
| K89N | K89Q | K90N | K90Q | K91N |
| K91Q | R92H | R92Q | D93N | D93Q |
| D94N | D94Q | F95I | F95V | E96N |
| E96Q | E96H | K97N | K97Q | L98I |
| L98V | Y101H | Y101I | D105N | D105Q |
| L106I | L106V | E115N | E115Q | E115H |
| E122N | E122Q | E122H | L123I | L123V |
| P125A | P125S | K128N | K128Q | K131N |
| K131Q | R132H | R132Q | K133N | K133Q |
| R134H | R134Q | M137I | M137V | L138I |
| L138V | F139I | F139V | R142H | R142Q |
| R143H | R143Q | | | |

4. Other Modifications of Therapeutic Polypeptide

In addition to any one or more amino acid modifications for increase protease resistance provided herein, a modified therapeutic polypeptide also can contain one or more additional modifications. Generally, the modification results in increased stability without losing at least one activity of the therapeutic polypeptide. For example, other further modifications in a therapeutic polypeptide include one or more additional amino acid modifications and/or one or more chemical modifications. Such modifications include, but are not limited to, those that alter the immunogenicity, glycosylation, activity, or any other known property of a therapeutic polypeptide. In some examples the amino acid modification, alters a property of therapeutic polypeptide, which is required for its activity. For example, the amino acid modification can increase or decrease the interaction of the therapeutic polypeptide with another polypeptide, such as a receptor. In some examples, the amino acid modification compensates for a loss of a property. For example, if one amino acid modification decreases a property, such as binding to a receptor, a further amino acid modification at a different site can restore the binding.

Other further modifications in therapeutic polypeptide include one or more additional amino acid modifications and/or one or more chemical modifications or one or more additional amino acid modifications that permits additional chemical modification (e.g., creation of sites for chemical modification). Such modifications include, but are not limited to, PEGylation, deimmunization, acylation (e.g., acetylation or succinylation), methylation, phosphorylation, hasylation, carbamylation, sulfation, prenylation, oxidation, guanidination, amidination, carbamylation (i.e., carbamoylation), trinitrophenylation, nitration, others known to those of skill in the art (see e.g., U.S. Pat. No. 5,856,298; U.S. Patent Publication Nos. 2003-0120045, 2004-0063917, 2005-0220800, 2005-0107591, 2006-0035322, and 2006-0073563; and International PCT Publication No.: WO 01/81405) or combinations thereof.

While the modified therapeutic polypeptides provided are engineered to provide increased resistance to proteases in the absence of glycosylation, if glycosylation at non-native sites in the therapeutic polypeptide is desired, the modified therapeutic polypeptide can be further modified to introduce one or more non-native glycosylation sites for attachment of carbohydrate moieties. Exemplary methods for modification of EPO for introduction of additional glycosylation sites are provided elsewhere herein and can be applied the modified therapeutic polypeptides provided.

In addition, protein modifications also can include modification to facilitate the detection, purification, and assay development of a polypeptide, such as for example, modification of a polypeptide with a Sulfo-NHS-LC-biotin for covalent attachment to a primary amine on a protein, or other modifications for attachment florescent, non-isotopic, or radioactive labels. The modified therapeutic protein can also be fused to one or more polypeptides to facilitate the targeting of the polypeptide for therapeutic use, detection, purification, and assay development or to another therapeutic polypeptide for treatment.

a. Modifications to Increase Solubility

The modified therapeutic polypeptides provided can also be further modified to increase solubility of the protein. For example, polar residues on the surface of the protein that are not required for activity of the protein can be modified to prevent aggregation of the polypeptide where it is produced in bacteria (Narhi et al. (2001) *Prot. Eng.* 14(2) 135-140). Generally, the residues are modified such that the protein retains one or more activities of the unmodified therapeutic protein. Residues for modification include, but are not limited to, asparagine residues that are sites of protein glycosylation. Typically, the neutral asparagine residues can be replaced by basic amino acid residues, such as lysine or histidine. In one example, the modified therapeutic protein is a modified EPO protein and one or more asparagine residues selected from amino acids N24, N38 and N83 are modified. In a particular example, N24, N38 and N83 residues in an EPO polypeptide are replaced with lysine (e.g., SEQ ID NOS: 309 or 310).

5. Methods for Increasing Protease Resistance of a Partially Glycosylated or Non-Glycosylated Therapeutic Polypeptide by Targeted Modification Methods for identifying sites for modification of therapeutic polypeptides for increased protease resistance are described elsewhere herein and are known in the art (see, e.g., published International PCT application Nos. WO 04/022593 and WO 04/022747). Modifications that confer increased protease resistance can be generated in any glycosylated therapeutic polypeptide that is produced as a non-glycosylated or partially glycosylated polypeptide or modified to remove one or more glycosylation sites. In a non-glycosylated or partially glycosylated therapeutic polypeptide, modifications that confer increased protease resistance can compensate for increased degradation of the protein due to removal of the carbohydrate moieties. Exemplary modifications for protease resistance in modified therapeutic polypeptides are shown in Table 3, 5-17.

Methods for targeted identification and modification of protease sensitive sites in glycosylated therapeutic proteins where one or more protease sensitive sites are shielded by glycosylation also are provided. Such modifications can be generated in fully glycosylated, partially glycosylated or non-glycosylated forms of the therapeutic polypeptide. When present in glycosylated forms of the therapeutic polypeptide, the modifications also can protect the polypeptide from degradation if one or more carbohydrate moieties are removed from the protein in vivo following administration.

a. Targeted Modification of Protease Sensitive Sites Exposed by Deglycosylation Provided herein are methods for increasing protease resistance of a therapeutic protein by identification and modification of protease sensitive sites that are concealed by post-translational modifications, such as glycosylation. By employing the methods provided herein, a non-glycosylated variant of a therapeutic polypeptide with sensitivity to proteolysis comparable to the fully glycosylated native therapeutic polypeptide can be achieved.

Selection of amino acid modifications for increased protease resistance of non-glycosylated polypeptides is based on identification of protease sensitive sites that occur within a defined distance from the carbohydrate attachment site of the native polypeptide. Typically, the protease sensitive site is located within or about 0-25 of the glycosylation site. Using the three dimensional structure of the therapeutic polypeptide, potential protease sensitive sites that are within a defined distance from the glycosylation site can be identified. An initial list of potential protease sensitive sites (LEADs) can be generated by identification methods, such as the 2D- and 3D-scanning methods as described elsewhere herein. LEADs at sites that occur within the defined distance from the glycosylation site can be selected for testing.

In order to identify modifications that increase protease resistance in the non-glycosylated therapeutic polypeptide, the therapeutic polypeptide is first modified at a glycosylation site to prevent glycosylation at the site. Generally, the glycosylation site is modified by replacement of the amino acid for attachment of the carbohydrate moiety. Typically, the replacement amino acids are chosen such that the replacement does not alter that structural integrity of the protein. For example, asparagines of N-linked glycosylation sites are generally replace with histidine or lysine.

Each selected LEAD is then introduced into the polypeptide with the mutant glycosylation site. Protease resistance of each modified therapeutic polypeptide is then measured using methods as described in the Examples and elsewhere herein and compared to the protease resistance of the glycosylation site mutant and/or the fully glycosylated therapeutic polypeptide. Once the modifications that confer increased protease resistance of the deglycosylated protein have been identified, the modified therapeutic protein can be generated with the protease resistance modifications alone or in combination with the glycosylation site modification.

Where a particular therapeutic polypeptide has multiple glycosylation sites, the steps of the method can be carried for each glycosylation site separately, simultaneously or sequentially. For example, two or more glycosylation sites can be mutated at the same time, and modifications for protease resistance can be tested on the therapeutic polypeptide containing multiple glycosylation site mutations. In another example, a first glycosylation site can be mutated in the therapeutic polypeptide and a corresponding first protease resistant mutant is identified. Then, a mutation in the second glycosylation site can be introduced in the double mutant, and a corresponding second protease resistant mutant is then identified. In another example, a first glycosylation site is mutated in the therapeutic polypeptide and a corresponding first protease resistant variant is identified. Then, a second glycosylation site can be mutated in a separate therapeutic polypeptide and a corresponding second protease resistant variant is identified. Following identification of the protease resistant variants for each glycosylation site, a modified therapeutic polypeptide can be generated that contains the modifications. In some examples, a therapeutic polypeptide is generated with both the glycosylation site mutation(s) and the modification(s) for protease resistance. In other examples, a therapeutic polypeptide is generated with only the modification(s) for protease resistance.

Additional modifications that confer increased protease resistance can be identified by introduction of one or more additional modifications in modified therapeutic polypeptides. Such modifications can be selected from the list of potential protease resistant modification from methods, such as the 2D- or 3-D scanning methods as described elsewhere herein. Any of the modifications identified for increased protease resistance of a therapeutic polypeptide can also be engineered at corresponding sites in other homologous therapeutic polypeptides.

Identification of potential protease sensitive sites for an exemplary therapeutic polypeptide (EPO) is provided in the Examples herein. EPO contains three N-linked glycosylation sites, N24, N38 and N83 and one O-linked glycosylation site at S126. FIG. 1 depicts the three-dimensional structure of the EPO polypeptide and the locations of the N-linked glycosylation sites. As shown in Table 18, potential protease sensitive sites can be identified that occur less than 10Å or less than 15Å of each glycosylation site. For practicing the method, the N-linked glycosylation site of an EPO polypeptide can be modified by replacement of asparagine with an amino acid, such as histidine or lysine. Potential sites for modification of an EPO polypeptide for increased protease resistance where the EPO polypeptide is deglycosylated at position N24 include, but are not limited to, L17, K20, E21, E23, F142, R143, R14, L16, E18, E31, W88, E89, P90, L91, L93, K97, F138, R139, K140, L141 and Y145. Potential sites for modification of an EPO polypeptide for increase protease resistance where the EPO polypeptide is deglycosylated at position N38 include, but are not limited to, L35, E37, R76, L80, D136, F138, K140, P42, D43, L69, L70, E72, L75, L81, P129, L130, R131, R139, L141 and F142. Potential sites for modification of an EPO polypeptide for increase protease resistance where the EPO polypeptide is deglycosylated at position N83 include, but are not limited to, L35, L75, R76, L80, L81, E37, E72, P87, W88, P90, L91, L93 and D96. Potential sites for modification of an EPO polypeptide for increase protease resistance where the EPO polypeptide is deglycosylated at position S126 include, but are not limited to, L69, E72, P121, P122, D123, P129, L130, P42, E62, W64, L67, L70, L75, R76 and R131. Modifications for protease resistance were selected for these sites using the EPO LEADs identified by the 2-D scanning method (see e.g., Table 3). Corresponding modifications for each glycosylation site were identified as described in the Examples. An exemplary modification of an EPO polypeptide that confers protease resistance of an EPO polypeptide deglycosylated at N24 is K20Q. An exemplary modification of an EPO polypeptide that confers protease resistance of an EPO polypeptide deglycosylated at N38 is R139H. Exemplary modifications of an EPO polypeptide that confer protease resistance of an EPO polypeptide deglycosylated at N93 include L80I, L93I and L93V. The location of each of exemplary modifications for protease resistance are depicted in FIG. 1. Additional modifications for increased resistance to proteases of a modified EPO polypeptide include, but are not limited to, R4H, K52N, L153V and E159N.

TABLE 18

Identification of potential protease sensitive sites in deglycosylated EPO <10 Å and <15 Å

| | <10 Å | <15 Å |
|---|---|---|
| N24 | L17, K20, E21, E23, F142, R143 | R14, L16, E18, E31, W88, E89, P90, L91, L93, K97, F138, R139, K140, L141, Y145 |
| N38 | L35, E37, R76, L80, D136, F138, K140 | P42, D43, L69, L70, E72, L75, L81, P129, L130, R131, R139, L141, F142 |
| N83 | L35, L75, R76, L80, L81 | E37, E72, P87, W88, P90, L91, L93, D96 |
| S126 | L69, E72, P121, P122, D123, P129, L130 | P42, E62, W64, L67, L70, L75, R76, R131 |

F. Production of EPO Polypeptides and Other Therapeutic Polypeptides

1. Expression Systems

EPO polypeptides and other therapeutic polypeptides (modified and unmodified) can be produced by any methods known in the art for protein production, including the introduction of nucleic acid molecules encoding an EPO polypeptide or other therapeutic polypeptide into a host cell, host animal and expression from nucleic acid molecules encoding an EPO polypeptide or other therapeutic polypeptide in vitro. Expression hosts include *E. coli*, yeast, plants, insect cells, mammalian cells, including human cell lines and transgenic animals. Expression hosts can differ in their protein production levels as well as the types of post-translational modifications that are present on the expressed proteins. The choice of expression host can be made based on these and other factors, such as regulatory and safety considerations, production costs and the need and methods for purification.

Expression in eukaryotic hosts can include expression in yeasts such as *Saccharomyces cerevisiae* and *Pichia Pastoria*, insect cells such as *Drosophila* cells and lepidopteran cells, plants and plant cells such as tobacco, corn, rice, algae, and lemna. Eukaryotic cells for expression also include mammalian cells lines such as Chinese hamster ovary (CHO) cells or Baby hamster kidney (BHK) cells. Eukaryotic expression hosts also include production in transgenic animals, for example, including production in serum, urine, milk and eggs. Transgenic animals for the production of wild-type EPO polypeptides and other therapeutic polypeptides or EPO fusion polypeptides and other therapeutic fusion polypeptides are known in the art and can be adapted for production of modified EPO polypeptides and other modified therapeutic polypeptides provided herein (see e.g., Mikus et al. (2004) *Transgenic Res.* 13(5): 487-98; Korhonen et al. (1997) *Eur. J. Biochem.* 245: 482-489; Kwon et al. (2006) *Transgenic Res.* 15(1): 37-55).

Many expression vectors are available for the expression of EPO polypeptides and other therapeutic polypeptides. The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells.

Methods of production of EPO polypeptides and other therapeutic polypeptides can include co-expression of one or more additional heterologous polypeptides that can aid in the generation of the EPO polypeptides and other therapeutic polypeptides. For example, such polypeptides can contribute to cleavage of the signal peptide or aid in the secretion or post-translation processing of the EPO polypeptides or other therapeutic polypeptides (e.g., glycosylation). The one or more additional polypeptides can be expressed from the same expression vector as the EPO polypeptide or other therapeutic polypeptide or from a different vector.

a. Prokaryotic Expression

Prokaryotes, especially *E. coli*, provide a system for producing large amounts of EPO polypeptides and other therapeutic polypeptides (see, for example, Platis et al. (2003) *Protein Exp. Purif.* 31(2): 222-30; and Khalizzadeh et al. (2004) *J Ind. Microbiol. Biotechnol.* 31(2): 63-69). Transformation of *E. coli* is a simple and rapid technique well known to those of skill in the art. Expression vectors for *E. coli* can contain inducible promoters that are useful for inducing high levels of protein expression and for expressing proteins that exhibit some toxicity to the host cells. Examples of inducible promoters include the lac promoter, the trp promoter, the hybrid tac promoter, the T7 and SP6 RNA promoters and the temperature regulated $\lambda P_L$ promoter.

EPO polypeptides and other therapeutic polypeptides can be expressed in the cytoplasmic environment of *E. coli*. The cytoplasm is a reducing environment and for some molecules, this can result in the formation of insoluble inclusion bodies. Reducing agents such as dithiothreitol and β-mercaptoethanol and denaturants (e.g., such as guanidine-HCl and urea) can be used to resolubilize the proteins. An alternative approach is the expression of EPO polypeptides or other therapeutic polypeptides in the periplasmic space of bacteria which provides an oxidizing environment and chaperonin-like and disulfide isomerases leading to the production of soluble protein. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility. Typically, temperatures between 25° C. and 37° C. are used. Mutations also can be used to increase solubility of expressed proteins. Typically, bacteria produce aglycosylated proteins. Thus, if proteins require glycosylation for function, glycosylation can be added in vitro after purification from host cells.

b. Yeast

Yeasts such as *Saccharomyces cerevisiae, Schizosaccharomyces pombe, Yarrowia lipolytica, Kluyveromyces lactis,* and *Pichia pastoris* are useful expression hosts for EPO polypeptides and other therapeutic polypeptides (see for example, Skoko et al. (2003) *Biotechnol. Appl. Biochem.* 38(Pt3):257-65). Yeast can be transformed with episomal replicating vectors or by stable chromosomal integration by homologous recombination. Typically, inducible promoters are used to regulate gene expression. Examples of such promoters include GAL1, GAL7, and GAL5 and metallothionein promoters such as CUP1. Expression vectors often include a selectable marker such as LEU2, TRP1, HIS3, and URA3 for selection and maintenance of the transformed DNA. Proteins expressed in yeast are often soluble and co-expression with chaperonins, such as Bip and protein disulfide isomerase, can improve expression levels and solubility. Additionally, proteins expressed in yeast can be directed for secretion using secretion signal peptide fusions such as the yeast mating type alpha-factor secretion signal from *Saccharomyces cerevisiae* and fusions with yeast cell surface proteins such as the Aga2p mating adhesion receptor or the *Arxula adeninivorans* glucoamylase. A protease cleavage site (e.g., the Kex-2 protease) can be engineered to remove the fused sequences from the polypeptides as they exit the secretion pathway. Yeast also is capable of glycosylation at Asn-X-Ser/Thr motifs.

c. Insects and Insect Cells

Insects and insect cells, particularly using a baculovirus expression system, are useful for expressing polypeptides such as EPO polypeptides and other therapeutic polypeptides (see, e.g., Quelle et al. (1992) *Protein Expr. Purif* 3(6): 461-9). Insect cells and insect larvae, including expression in the haemolymph, express high levels of protein and are capable of most of the post-translational modifications used by higher eukaryotes. Baculoviruses have a restrictive host range which improves the safety and reduces regulatory concerns of eukaryotic expression. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *bombyx mori* nuclear polyhedrosis virus (BmNPV) and an insect cell line such as Sf9 derived from *Spodoptera frugiperda*, *Pseudaletia unipuncta* (A7S) and *Danaus plexippus* (DpN1). For high level expression, the nucleotide sequence of the molecule to be expressed is fused immediately downstream of the polyhedrin initiation codon of the virus. Mammalian secretion signals are accurately processed in insect cells and can be used to secrete the expressed protein into the culture medium. In addition, the cell lines *Pseudaletia unipuncta* (A7S) and *Danaus plexippus* (DpN1) produce proteins with glycosylation patterns similar to mammalian cell systems.

An alternative expression system in insect cells is the use of stably transformed cells. Cell lines such as the Schnieder 2 (S2) and Kc cells (*Drosophila melanogaster*) and C7 cells (*Aedes albopictus*) can be used for expression. The *Drosophila* metallothionein promoter can be used to induce high levels of expression in the presence of heavy metal induction with cadmium or copper. Expression vectors are typically maintained by the use of selectable markers such as neomycin and hygromycin.

d. Mammalian Cells

Mammalian expression systems can be used to express EPO polypeptides and other therapeutic polypeptides. Expression constructs can be transferred to mammalian cells by viral infection, such as adenovirus or vaccinia virus, or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the SV40 promoter-enhancer, the human cytomegalovirus (CMV) promoter, and the long terminal repeat of Rous sarcoma virus (RSV). These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha-fetoprotein, alpha 1-antitrypsin, beta-globin, myelin basic protein, myosin light chain-2, and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase and thymidine kinase. Fusion with cell surface signaling molecules such as TCR-ζ and Fc$_\epsilon$RI-γ can direct expression of the proteins in an active state on the cell surface.

Many cell lines are available for mammalian expression including mouse, rat human, monkey, and chicken and hamster cells. Exemplary cell lines include, but are not limited to, CHO, VERO, BHK, HT1080, MDCK, W138, Balb/3T3, HeLa, MT2, mouse NSO (non-secreting) and other myeloma cell lines, hybridoma and heterohybridoma cell lines, lymphocytes, RPMI 1788 cells, fibroblasts, Sp2/0, COS, NIH3T3, HEK293, 293S, 2B8, EBNA-1, and HKB cells (see e.g. U.S. Pat. Nos. 5,618,698, 6,777,205). Cell lines also are available adapted to serum-free media which facilitates purification of secreted proteins from the cell culture media (e.g., EBNA-1, Pham et al., (2003) *Biotechnol. Bioeng.* 84:332-42). Expression of recombinant wild-type EPO polypeptides exhibiting similar structure and post-translational carbohydrate modifications as urine-derived EPO are known in the art, some of which exhibit differences in sialyl moiety linkages (see, e.g., Takeuchi et al. (1988) *J. Biol. Chem.* 263(8): 3657-3663; Inoue et al. (1995) *Biotechnol. Annu. Rev.* 1: 297-313). Methods of optimizing erythropoietin expression also are known in the art (e.g., Tsao et al. (1992) *Ann N Y Acad Sci.* 665: 127-36; Wang et al. (2002) *Biotechnol Bioeng.* 77: 194-203; Sethuraman and Stadheim (2006) *Curr. Opin. Biotech.* 17:341-346; Yoon et al. (2001) *Biomed. Life Sci.* 37(2) 119-132)

e. Plants

Transgenic plant cells and plants can be used for the expression of EPO polypeptides and other therapeutic polypeptides. Expression constructs are typically transferred to plants using direct DNA transfer such as microprojectile bombardment and PEG-mediated transfer into protoplasts, and with *agrobacterium*-mediated transformation. Expression vectors can include promoter and enhancer sequences, transcriptional termination elements, and translational control elements (e.g., Ti plasmid). Expression vectors and transformation techniques are usually divided between dicot hosts, such as *Arabidopsis* and tobacco, and monocot hosts, such as corn and rice. Examples of plant promoters used for expression include the cauliflower mosaic virus promoter, the nopaline synthase promoter, the ribose bisphosphate carboxylase promoter and the ubiquitin and UBQ3 promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce proteins (see, for example, Mayfield et al. (2003) *PNAS* 100:438-442). Plant cell systems for expression also include plants infected with virus expression vectors, for example, cauliflower mosaic virus (CaMV) or tobacco mosaic virus (TMV). Because plants have different glycosylation patterns than mammalian cells, this can influence the choice to produce EPO in these hosts.

2. Purification

Methods for purification of EPO polypeptides and other therapeutic polypeptides from host cells depend on the chosen host cells and expression systems. For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary the proteins can be extracted and further purified using standard methods in the art.

EPO polypeptides and other therapeutic polypeptides can be purified using standard protein purification techniques known in the art including but not limited to, SDS-PAGE, differential precipitation, diafiltration, ultrafiltration, column electrofocusing, flat-bed electrofocusing, gel filtration, isotachophoresis, size fractionation, ammonium sulfate precipitation, high performance liquid chromatography, chelate chromatography, adsorption chromatography, ionic exchange chromatography, hydrophobic interaction chromatography, and molecular exclusion chromatography. Affinity purification techniques also can be used to improve the efficiency and purity of the preparations. For example, antibodies, receptors and other molecules that bind EPO or other therapeutic polypeptides can be used in affinity purification. Expression constructs also can be engineered to add an affinity tag such as a myc epitope, GST fusion or $His_6$ and affinity purified with myc antibody, glutathione resin, and Ni-resin, respectively, to a protein. Purity can be assessed by any method known in the art including gel electrophoresis and staining and spectrophotometric techniques. Exemplary techniques for the purification of EPO polypeptides and other therapeutic polypeptides are known in the art and can be found, for example, in U.S. Pat. Nos. 4,377,513, 4,667,016, 4,677,195, 5,733,761, 6,682,910, 7,012,130; Miyake et al. (1977) *J. Biol. Chem.* 252(15) 5558-5564; Spivak et al. (1977) Proc. Natl. Acad. Sci. USA 74(10): 4633-4635.

3. Fusion Proteins

In some embodiments, a modified EPO polypeptide or other therapeutic polypeptide further comprises a heterologous polypeptide (e.g., a fusion partner) to form a fusion protein or is linked to a polypeptide via a linker, such as by chemical means. Suitable fusion partners include peptides and polypeptides that confer enhanced stability in vivo (e.g., enhanced serum half-life); provide ease of purification, e.g., histidine tags $(HiS)_n$, (e.g., 6×His, and the like); provide for secretion of the fusion protein from a cell; provide an epitope tag (e.g., GST, hemagglutinin (HA), FLAG, c-myc, and the like); provide a detectable signal (e.g., an enzyme that generates a detectable product (e.g., β-galactosidase, luciferase)), or a protein that is itself detectable (e.g., a green fluorescent protein (GFP), etc.); provide for multimerization (e.g., a multimerization domain such as an Fc portion of an immunoglobulin); and the like.

Fusion proteins containing a targeting agent and a modified EPO polypeptide or other modified therapeutic polypeptides also are provided. Pharmaceutical compositions containing such fusion proteins formulated for administration by a suitable route also are provided, for example, in particular, for oral administration. Fusion proteins are formed by linking in any order the modified EPO polypeptide or other therapeutic polypeptide and an agent, such as an antibody or fragment thereof, growth factor, receptor, ligand, and other such agent for directing the mutant protein to a targeted cell or tissue. Linkage can be effected directly or indirectly via a linker. The fusion proteins can be produced recombinantly or chemically by chemical linkage, such as via heterobifunctional agents or thiol linkages or other such linkages. Such fusion proteins are often referred to as protein conjugates. Linkers and linkages that are suitable for chemically linked conjugates include, but are not limited to, disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Exemplary groups for use in heterobifunctional cross-linking reagents include, but are not limited to, aryl azides, maleimides, carbodiimides, N-hydroxysuccinimide (NHS)-esters, hydrazides, PFP-esters, hydroxymethyl phosphines, psoralens, imidoesters, pyridyl disulfides, isocyanates, and vinyl sulfones.

The fusion proteins can contain additional components, such as *E. coli* maltose binding protein (MBP) that aid in solubility, folding, purification, and uptake of proteins by cells. In another embodiment the modified EPO is fused to polypeptides that aid in stability, such as albumin (See e.g., U.S. Pat. Nos. 6,987,006, 6,548,653, 7,101,971; U.S. Patent Publication No. 2004-0063635, 2006-0058236; Albupoietin™ CoGenesys).

Optionally, a modified EPO polypeptide or other therapeutic polypeptide can be prepared in a multimeric form, by, for example, expressing as an Fc fusion protein or fusion with another multimerization domain. EPO fusion polypeptides and other therapeutic fusion polypeptides also can include fusion, or dimerization/multimerization, of two or more therapeutic polypeptides (see e.g., U.S. Pat. No. 5,580,853; Sytkowski (1999) *J. Biol. Chem.* 274(35): 24773-24778). Dimerization or multimerization can be effected directly (e.g., a single polypeptide with two or more EPO molecules in tandem arrangement) or indirectly via a linker (e.g., a hetero- or homo-bifunctional crosslinking agent) or fusion of the EPO polypeptides or other therapeutic polypeptides to a pair of polypeptides that have the ability to dimerize or can be dimerized via chemical means. In the latter example, the polypeptides that are fused to the EPO polypeptides or other therapeutic polypeptides can be identical polypeptides or different polypeptides (e.g., two proteins that can bind one another). Exemplary multimerization domains are known in the art and include, but are not limited to, Fc domains, or similar antibody-like fragments, leucine zipper motifs, a coiled coil domain, a hydrophobic region, a hydrophilic region, a polypeptide comprising a free thiol which forms an intermolecular disulfide bond between two or more multimerization domains, or a "protuberance-into-cavity" domain (see e.g., WO 94/10308; U.S. Pat. No. 5,731,168, Lovejoy et al. (1993), Science 259: 1288-1293; Harbury et al. (1993), Science 262: 1401-05; Harbury et al. (1994), Nature 371:80-83; Hakansson et al. (1999), Structure 7: 255-64.

Additional exemplary EPO fusion proteins and other therapeutic fusion polypeptides and methods of production are provided in the art and include, for example, but not limited to, Fc fusions and beta-lactoglobulin fusions, (U.S. Pat. Nos. 6,992,174, 6,165,476; U.S. Patent Publication No. 2003-0064480, 2005-0202538, 2005-0192211; Korhonen et al. (1997) *Eur. J. Bioch.* 245: 482-489). When constructed together with a therapeutic protein, an Fc domain can provide longer half-life or incorporate such functions as Fc receptor binding, dimerization, protein A binding, complement fixation and perhaps even placental transfer. In such fusion proteins, the properties of the EPO polypeptide and other therapeutic polypeptides can be further improved by one or more further modifications. In one non-limiting example, modifications such as H32G, C33, W88C, and P90A of an EPO polypeptide that result in rearrangement of the disulfide bonding pattern from Cys29-Cys33 to Cys29-Cys88, in the context of an Fc-Epo fusion protein, can lead to significantly improved properties (see e.g., Way et al. (2005) Protein Eng. Des. Sel. 18(3): 111-8). Furthermore, fusion proteins of modified EPO polypeptides and other therapeutic polypeptides provided herein can be combined with additional modifications of an EPO polypeptide or other therapeutic polypeptides as described herein (e.g., mutation, glycosylation, PEGylation, HASylation, etc.) or known in the art.

4. Polypeptide Modification

Modified EPO polypeptides and other therapeutic polypeptides can be prepared as naked polypeptide chains or as a complex. For some applications, it can be desirable to prepare modified EPO or other modified therapeutic polypeptides in a "naked" form without post-translational or other chemical modifications. Naked polypeptide chains can be prepared in suitable hosts that do not post-translationally modify the therapeutic polypeptide. Such polypeptides also can be prepared in vitro systems and using chemical polypeptide synthesis. For other applications, particular modifications can be desired including pegylation, albumination, glycosylation, carboxylation, hydroxylation, phosphorylation, or other known modifications. Modifications can be made in vitro or, for example, by producing the modified EPO and other therapeutic polypeptides in a suitable host that produces such modifications.

5. Nucleotide Sequences

Nucleic acid molecules encoding modified EPO polypeptides and other therapeutic polypeptides or fusion proteins thereof operationally linked to a promoter, such as an inducible promoter for expression in prokaryotic or eukaryotic cells, such as mammalian cells also are provided. Such promoters include, but are not limited to, prokaryotic, eukaryotic, or viral promoters. Selection of a promoter for expression in cells depends on the cell type employed for expression. Exemplary promoters for expression in mammalian cells include, but are not limited to, CMV and SV40 promoters; adenovirus promoters, such as the E2 gene promoter, which is responsive to the HPV E7 oncoprotein; a PV promoter, such as the PBV p89 promoter that is responsive to the PV E2 protein; and other promoters that are activated by the HIV or PV or oncogenes.

Modified EPO polypeptides and other therapeutic polypeptides provided herein also can be delivered to cells in gene transfer vectors. The transfer vectors can encode additional therapeutic agent(s) for treatment of diseases or disorders, such as treatments for hemophilia, inherited disorders and others for which EPO is administered. Transfer vectors encoding modified EPO polypeptides can be used systemically by administering the nucleic acid to a subject. For example, the transfer vector can be a viral vector, such as an adenoviral vector. Vectors encoding EPO or other therapeutic polypeptides also can be incorporated into stem cells and such stem cells administered to a subject, for example, by transplanting or engrafting the stem cells at sites for therapy. For example, mesenchymal stem cells (MSCs) can be engineered to express a modified EPO or other modified therapeutic polypeptide and such MSCs engrafted at a tumor site for therapy.

g. Assessing Modified EPO Polypeptide Properties and Activities

EPO activities and properties can be assessed in vitro and/or in vivo. Assays for such assessment are known to those of skill in the art and are known to correlate tested activities and results to therapeutic and in vivo activities. In one example, EPO variants can be assessed in comparison to unmodified and/or wild-type EPO. In other examples, a modified EPO polypeptide can be assessed for biological activity following in vitro or in vivo exposure to protein stability-altering conditions (i.e., exposure to proteases, or denaturing agents such as temperature or pH). In vitro assays include any laboratory assay known to one of skill in the art, such as for example, cell-based assays including erythropoiesis assays, cell viability assays, cell survival assays, protein assays, and molecular biology assays. In vivo assays include EPO assays in animal models as well as administration to humans. In some cases, activity of EPO in vivo can be determined by assessing blood, serum, or other bodily fluid for assay determinants. EPO variants also can be tested in vivo to assess an activity or property, such, stability (e.g., half-life) and therapeutic effect. Results of such assays can be used to assess parameters, such as, but not limited to, therapeutic effectiveness, dosage levels, administration protocols, and usefulness for the EPO-mediated disease or condition to be treated or a diagnostic assay.

Assays provided herein and known in the art for EPO properties and activities can be used to assess properties and activities of the modified EPO polypeptides provided herein in combination with one or more further modifications of the modified EPO polypeptide, including post-translational or chemical modification or amino acid substitutions, deletions, or additions in the primary amino acid sequence of the modified EPO polypeptide. Further modifications of a modified EPO polypeptide provided herein can be systematically introduced in an EPO polypeptide, and one or more activities can be empirically determined.

1. In Vitro Assays

Exemplary in vitro assays include assays to assess polypeptide stability and activity. Stability assays include assays that assess protease resistance or other physical property indicative of stability of the polypeptide in vivo or in vitro. Stability also can be assessed by protein structure and conformational assays known in the art. Assays for activity include, but are not limited to, erythrocyte cell proliferation assays.

Concentrations of modified EPO polypeptides can be assessed by methods well-known in the art, including, but not limited to, Enzyme-Linked Immunosorbent Assays (ELISA), SDS-PAGE; Bradford, Lowry, BCA methods; UV absorbance, and other quantifiable protein labeling methods, such as, but not limited to, immunological, radioactive, fluorescent, and related methods.

Assessment of degradation products of proteolysis reactions, including cleavage of EPO polypeptides can be performed using standard methods well-known in the art including but not limited to, SDS-PAGE analysis, immunohistochemistry, immunoprecipitation, $NH_2$-terminal sequencing, chromogenic substrate cleavage, HPLC, and protein labeling. EPO polypeptides that have been exposed to proteases can be subjected to $NH_2$-terminal sequencing to determine location or changes in cleavage sites of the modified EPO polypeptides.

EPO polypeptides can be tested for binding to an EPO receptor. For example, EPO can be assessed for binding to an EPO receptor or EPO receptor fragment using any binding assay known in the art, including, but not limited to, immunoprecipitation, column purification, non-reducing SDS- PAGE, surface plasmon resonance (SPR), fluorescence resonance energy transfer (FRET), fluorescence polarization (FP), isothermal titration calorimetry (ITC), circular dichroism (CD), protein fragment complementation assays (PCA), Nuclear Magnetic Resonance (NMR) spectroscopy, light scattering, sedimentation equilibrium, small-zone gel filtration chromatography, gel retardation, Far-western blotting, fluorescence polarization, hydroxyl-radical protein footprinting, phage display, and various two-hybrid systems.

EPO polypeptides can be tested for erythropoietic activity by using assays well known in the art. For example, some of the assays include, but are not limited to, cell based assays, such as a TF-1 proliferation assay. TF-1 cells are a human erythroleukemic cell line that expresses EPO receptors. The proliferation of TF-1 cells, which is determined by the incorporation of tritiated thymidine, is a function of erythropoietic activity (Hammerlling et al., (1996) *J. Pharm. Biomed. Anal.* 14: 1455; Kitamura et al., (1989) *J. Cellular Physiol.* 140: 323). A similar assay can be performed using a FDCP-1 cell lines (see, e.g., Dexter et al. (1980) *J. Exp. Med.* 152: 1036-1047). FDCP-1 is a growth factor dependent murine multipotential primitive hematopoietic progenitor cell line that can proliferate, but not differentiate, when supplemented with WEHI-3-conditioned media (a medium that contains IL-3, ATCC number TIB-68). For such experiments, the FDCP-1 cell line can be transfected with the human or murine EPO-R to produce FDCP-1-hEPO-R or FDCP-1-mEPO-R cell lines, respectively, that can proliferate, but not differentiate, in the presence of EPO. In one such assay, the cells are grown to half stationary density in the presence of the necessary growth factors (see, e.g., as described in U.S. Pat. No. 5,773,569 and U.S. Patent Publication No. 2005-0137329). The cells are then washed in PBS and starved for 16-24 hours in whole media without growth factors. After determining the viability of the cells (e.g., by trypan blue staining), stock solutions (in whole media without growth factors) are made to give about $10^5$ cells per 50 μL. Serial dilutions of the modified EPO polypeptides to be tested are made in 96-well tissue culture plates for a final volume of 50 μL per well. Cells (50 μL) are added to each well and the cells are incubated 24-48 hours, at which point the negative controls should die or be quiescent. Cell proliferation is then measured by techniques known in the art, such as an MTT assay which measures $H^3$-thymidine incorporation as an indication of cell proliferation (see e.g., Mosmann (1983) *J. Immunol. Meth.* 65: 55-63). EPO modified polypeptides are evaluated on both the EPO-R-expressing cell line and a parental non-expressing cell line. The concentration of test polypeptide necessary to yield one half of the maximal cell proliferation is recorded as the $EC_{50}$.

In another exemplary assay, the cells are grown to stationary phase in EPO-supplemented medium, collected, and then cultured for an additional 18 hr in medium without EPO. The cells are divided into three groups of equal cell density: one group with no added polypeptide (negative control), a group with EPO (positive control), and an experimental group with the test modified EPO polypeptide. The cultured cells are then collected at various time points, fixed, and stained with a DNA-binding fluorescent dye (e.g., propidium iodide or Hoechst dye, both available from Sigma). Fluorescence is then measured, for example, using a FACS Scan Flow cytometer. The percentage of cells in each phase of the cell cycle can then be determined, for example, using the SOBR model of CellFIT software (Becton Dickinson). Cells treated with EPO or an active modified EPO peptide will show a greater proportion of cells in S phase (as determined by increased fluorescence as an indicator of increased DNA content) relative to the negative control group.

In another exemplary assay, a murine pre-B-cell line expressing human EPO-R and further transfected with a fos promoter-driven luciferase reporter gene construct can be used. Upon exposure to EPO or another EPO-R agonist, such cells respond by synthesizing luciferase. Luciferase causes the emission of light upon addition of its substrate luciferin. Thus, the level of EPO-R activation in such cells can be quantitated via measurement of luciferase activity. The activity of a test polypeptide is measured by adding serial dilutions of the test polypeptide to the cells, which are then incubated for 4 hours. After incubation, luciferin substrate is added to the cells, and light emission is measured. The concentration of test polypeptide that results in a half-maximal emission of light is recorded as the $EC_{50}$.

In yet another assay, the procedure set forth in Krystal (1983) *Exp. Hematol* 11: 649-660 for a microassay based on $H^3$-thymidine incorporation into spleen cells can be employed to ascertain the ability of the modified EPO polypeptides provided herein to promote cell proliferation. In brief, B6C3 $F_1$ mice are injected daily for two days with phenylhydrazine (60 mg/kg). On the third day, spleen cells are removed and their ability to proliferate over a 24 hour period ascertained using an MTT assay.

The binding of EPO to EPO-R in an erythropoietin-responsive cell line induces tyrosine phosphorylation of both the receptor and numerous intracellular proteins, including Shc, vav and JAK2 kinase. Therefore, another in vitro assay measures the ability of modified EPO polypeptides provided herein to induce tyrosine phosphorylation of EPO-R and downstream intracellular signal transducer proteins. Active peptides, as identified by binding and proliferation assays described above, elicit a phosphorylation pattern nearly identical to that of EPO in erythropoietin-responsive cells. For this assay, FDC-P1/ER cells (Dexter, et al. (1980) *J Exp Med* 152: 1036-47) are maintained in EPO-supplemented medium and grown to stationary phase. These cells are then cultured in medium without EPO for 24 hr. A defined number of such cells is then incubated with a modified EPO polypeptide for approximately 10 min at 37° C. A control sample of cells with EPO also is run with each assay. The treated cells are then collected by centrifugation, resuspended in SDS lysis buffer, and subjected to SDS polyacrylamide gel electrophoresis. The electrophoresed proteins in the gel are transferred to nitrocellulose, and the phosphotyrosine containing proteins on the blot visualized by standard immunological techniques. For example, the blot can be probed with an anti-phosphotyrosine antibody (e.g., mouse anti-phosphotyrosine IgG from Upstate Biotechnology, Inc.), washed, and then probed with a secondary antibody (e.g., peroxidase labeled goat anti-mouse IgG from Kirkegaard & Perry Laboratories, Inc. (Washington, D.C.)). Thereafter, phosphotyrosine-containing proteins can be visualized by standard techniques including colorimetric, chemiluminescent, or fluorescent assays. For example, a chemiluminescent assay can be performed using the ECL Western Blotting System from Amersham.

Another cell-based in vitro assay that can be used to assess the activity of the modified EPO polypeptides provided herein is a colony assay, using murine bone marrow or human peripheral blood cells. Murine bone marrow can be obtained from the femurs of mice, while a sample of human peripheral blood can obtained from a healthy donor. In the case of peripheral blood, mononuclear cells are first isolated from the blood, for example, by centrifugation through a Ficoll-Hypaque gradient (Stem Cell Technologies, Inc. (Vancouver, Canada)). For this assay a nucleated cell count is performed to establish the number and concentration of nucleated cells in the original sample. A defined number of cells is plated on methyl cellulose as per manufacturer's instructions (Stem Cell Technologies, Inc. (Vancouver, Canada)). An experimental group is treated with a modified EPO polypeptide, a positive control group is treated with EPO, and a negative control group receives no treatment. The number of growing colonies for each group is then scored after defined periods of incubation, generally 10 days and 18 days. An active peptide will promote colony formation.

Other in vitro biological assays that can be used to demonstrate the activity of the modified EPO polypeptides provided herein are disclosed in Greenberger, et al. (1983) *Proc. Natl. Acad. Sci. USA* 80:2931-2935 (EPO-dependent hematopoietic progenitor cell line); Quelle and Wojchowski (1991) *J. Biol. Chem.* 266:609-614 (protein tyrosine phosphorylation in B6SUt.EP cells); Dusanter-Fourt, et al. (1992) *J. Biol. Chem.* 287:10670-10678 (tyrosine phosphorylation of EPO-receptor in human EPO-responsive cells); Quelle, et al. (1992) *J. Biol. Chem.* 267:17055-17060 (tyrosine phosphorylation of a cytosolic protein, pp 100, in FDC-ER cells); Worthington, et al. (1987) *Exp. Hematol.* 15:85-92 (colorimetric assay for hemoglobin); Kaiho and Miuno (1985) *Anal. Biochem.* 149:117-120 (detection of hemoglobin with 2,7-diaminofluorene); Patel, et al. (1992) *J. Biol. Chem.* 267: 21300-21302 (expression of c-myb); Witthuhn, et al. (1993) *Cell* 74:227-236 (association and tyrosine phosphorylation of JAK2); Leonard, et al. (1993) *Blood* 82:1071-1079 (expression of GATA transcription factors); and Ando, et al. (1993) *Proc. Natl. Acad. Sci. USA* 90:9571-9575 (regulation of GI transition by cycling D2 and D3).

An instrument designed by Molecular Devices Corp., known as a microphysiometer, can be used for measurement of the effect of agonists and antagonists on various receptors. The basis for this apparatus is the measurement of the alterations in the acidification rate of the extracellular media in response to receptor activation.

EPO polypeptides provided herein also can be assessed for presence of post-translational modifications. Such assays are known in the art and include assays to measure glycosylation, hydroxylation, oxidation, sulfation, carboxylation, and phosphorylation. In an exemplary assay for glycosylation, carbohydrate analysis can be performed, for example, with SDS page analysis of EPO polypeptides exposed to hydrazinolysis or endoglycosidase treatment. Hydrazinolysis releases N- and O-linked glycans from glycoproteins by incubation with anhydrous hydrazine, while endoglycosidase release involves PNGase F, which releases most N-glycans from glycoproteins. Hydrazinolysis or endoglycosidase treatment of EPO polypeptides generates a reducing terminus that can be tagged with a fluorophore or chromophore label. Labeled EPO polypeptides can be analyzed by fluorophore-assisted carbohydrate electrophoresis (FACE). The fluorescent tag for glycans also can be used for monosaccharide analysis, profiling or fingerprinting of complex glycosylation patterns by HPLC. Exemplary HPLC methods include hydrophilic interaction chromatography, electronic interaction, ion-exchange, hydrophobic interaction, and size-exclusion chromatography. Exemplary glycan probes include, but are not limited to, 3-(acetylamino)-6-aminoacridine (AA-Ac) and 2-aminobenzoic acid (2-AA). Carbohydrate moieties also can be detected through use of specific antibodies that recognize the glycosylated EPO polypeptide (see e.g., Mi et al. (2006) *J. Immunoassay Immunochem.* 27(2): 115-128).

Structural properties of modified EPO polypeptides also can be assessed. For example, X-ray crystallography, nuclear magnetic resonance (NMR), and cryoelectron microscopy (cryo-EM) of modified EPO polypeptides can be performed to assess three-dimensional structure of the EPO polypeptides and/or other properties of EPO polypeptides, such as receptor binding and carbohydrate modification (see e.g., Cheetham et al. (1998) *Nat. Struct. Biol.* 5: 861-866; Watson et al. (1994) *Glycobiology* 4(2): 227-237).

2. Non-Human Animal Models

Non-human animal models are can be used to assess activity and stability of modified EPO polypeptides. For example, non-human animals can be used as models for a disease or condition. Non-human animals can be injected with disease and/or phenotype-inducing substances prior to administration of EPO variants to monitor the effects on disease progression. Genetic models also are useful. Animals, such as mice, can be generated which mimic a disease or condition by the overexpression, underexpression or knock-out of one or more genes. Such animals can be generated by transgenic animal production techniques well-known in the art or using naturally-occurring or induced mutant strains. Examples of useful non-human animal models of diseases associated with EPO include, but are not limited to, models of anemia, including models of sickle cell anemia, acquired bone marrow failure syndromes, beta-thalassemia, acute anemia, aplastic anemia, pernicious anemia, and anemia induced by renal failure or cancer, in animals, such as mice, rats, rabbits, dogs, and primates (see e.g., Nagel (1998) *N. Engl J Med.* 339(3): 194-5; Chen (2005) *Clin. Med. Res.* 3:102-108; Chen et al. (2004) *Blood* 104: 1671-1678; McMullin et al. (1989) *Biochem Med Metab Biol.* 41(1): 30-5; Alderuccio et al. (2002) *Clin. Immun.* 102(1): 48-58; Kawamura et al. (1990) *Biotherapy* 2(1): 77-85; Bohl et al. (2000) *Blood* 95: 2793-2798). These non-human animal models can be used to monitor activity of EPO variants compared to a wild type EPO polypeptide.

Animal models also can be used to monitor stability, half-life, and clearance of modified EPO polypeptides. Such assays are useful for comparing modified EPO polypeptides and for calculating doses and dose regimens for further non-human animal and human trials. For example, a modified EPO polypeptide can be injected into the tail vein of mice. Blood samples are then taken at time-points after injection (such as minutes, hours and days afterwards) and then the level of the modified EPO polypeptides in bodily samples including, but not limited to, serum or plasma can be monitored at specific time-points for example by ELISA or radioimmunoassay. Blood samples also can be tested for hematopoietic activity in methods, such as an erythrocyte proliferation assay.

Examples of in vivo assays include, but are not limited to, hematocrit (HCT) assays, iron uptake, and reticulocyte assays (see e.g., Cotes et al. (1961) *Nature* 191: 1065; U.S. Pat. No. 6,099,830). HCT assays measure the volume of red blood cells from a blood sample taken from an erythropoietin-treated animal, and are performed by centrifuging blood in capillary tubes and measuring the fraction of the total volume occupied by sedimented red blood cells. Reticulocyte assays measure new red blood cells, or reticulocytes, that have recently differentiated from precursor cells and that still have remnants of nucleic acids characteristic of the precursor cells. For this assay, normal untreated mice are subcutaneously injected on three consecutive days with either EPO or modified EPO peptide provided herein. On the third day, the mice also are intraperitoneally injected with iron dextran. At day five, blood samples are collected from the mice. The percent (%) of reticulocytes in the blood is determined by staining with a nucleic acid-staining dye such as acridine orange or thiazole orange, and flow cytometer analysis (retic-count program). Reticulocytes are measured by counting the positively-stained reticulocyte fraction. In addition, hematocrits are manually determined.

Another exemplary in vivo functional assay that can be used to assess the potency of a modified EPO peptide is the polycythemic exhypoxic mouse bioassay. For this assay, mice are subjected to an alternating conditioning cycle for several days. In this cycle, the mice alternate between periods of hypobaric conditions and ambient pressure conditions. Thereafter, the mice are maintained at ambient pressure for 2-3 days prior to administration of test samples. Test modified EPO polypeptide samples, or EPO standard in the case positive control mice, are injected subcutaneously into the conditioned mice. Radiolabeled iron (e.g., $^{59}$Fe) is administered 2 days later, and blood samples are taken two days after administration of radiolabeled iron. Hematocrits and radioactivity measurements are then determined for each blood sample by standard techniques. Blood samples from mice injected with active test peptides will show greater radioactivity (due to binding of $^{59}$Fe by erythrocyte hemoglobin) than mice that did not receive modified EPO polypeptides or native EPO.

Modified EPO polypeptides also can be tested for immune tolerance using animal models. Animal models for immune tolerance, including primate and rodent models can be used to test long term expression of EPO via injection of polypeptides or gene transfer vectors. Blood samples taken at time-points after injection can be assessed for production of anti-EPO antibodies.

3. Clinical Assays

Many assays are available to assess activity of EPO for clinical use. Such assays can include assessment of erythropoietic activity, tissue protective activity, protein stability, and half-life in vivo and phenotypic assays. Phenotypic assays and assays to assess the therapeutic effect of EPO treatment include assessment of blood levels of EPO (e.g., measurement of serum EPO prior to administration and time-points following administrations including, after the first administration, immediately after last administration, and time-points in between, correcting for the body mass index (BMI)), phenotypic response to EPO treatment including amelioration of symptoms over time compared to subjects treated with an unmodified and/or wild type EPO or placebo. Examples of clinical assays to assess EPO activity can be found, for example in Marsden (2006) *Ann Clin Biochem* 43: 97-104; Gascon (2005) *Eur J Cancer* 41(17): 2601-12; ANNA J. 1989 August; 16(5):344-8. Patients can be monitored regularly over a period of time for routine or repeated administrations, following administration in response to acute events, such as hemorrhage, trauma, or surgical procedures.

H. Formulation/Packaging/Administration

Pharmaceutical compositions containing an optimized EPO variant or other therapeutic polypeptide produced using methods described herein, including EPO variant (modified) polypeptides, modified EPO fusion proteins or encoding nucleic acid molecules, can be formulated in any conventional manner by mixing a selected amount of the polypeptide with one or more physiologically acceptable carriers or excipients. Selection of the carrier or excipient is within the skill of the administering profession and can depend upon a number of parameters. These include, for example, the mode of administration (e.g., systemic (e.g., intravenous or intraperitoneal injection), oral, nasal, pulmonary, transdermal, parenteral, rectal, local, topical, or any other mode) and disorder treated. Compositions of EPO polypeptides and other therapeutic polypeptides can be formulated with additional factors, such as one or more therapeutic agents, useful in the disease or disorder to be treated. Such combinations of therapeutic agents for use in the compositions provided are described elsewhere herein. The pharmaceutical compositions provided herein can be formulated for single dosage (direct) administration or for dilution or other modification. The concentrations of the compounds in the formulations are effective for delivery of an amount, upon administration, that is effective for the intended treatment. Typically, the compositions are formulated for single dosage administration. To formulate a composition, the weight fraction of a compound or mixture thereof is dissolved, suspended, dispersed, or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

1. Administration of Modified EPO Polypeptides and Other Modified Therapeutic Polypeptides The polypeptides can be formulated as the sole pharmaceutically active ingredient in the composition or can be combined with other active ingredients. The polypeptides can be targeted for delivery, such as by conjugation to a targeting agent, such as an antibody. Liposomal suspensions, including tissue-targeted liposomes, also can be suitable as pharmaceutically acceptable carriers. These can be prepared according to methods known to those skilled in the art. For example, liposome formulations can be prepared as described, for example, in U.S. Pat. Nos. 6,645,522 or 6,726,924. Liposomal delivery also can include slow release formulations, including pharmaceutical matrices such as collagen gels and liposomes modified with fibronectin (see, for example, Weiner et al. (1985) *J Pharm Sci.* 74(9): 922-5).

The active compound is included in the pharmaceutically acceptable carrier in an amount sufficient to exert a therapeutically useful effect in the absence of undesirable side effects on the subject treated. The therapeutically effective concentration can be determined empirically by testing the compounds in known in vitro and in vivo systems, such as the assays provided herein. The active compounds can be administered by any appropriate route, for example, oral, nasal, pulmonary, parenteral, intravenous, intradermal, subcutaneous, or topical, in liquid, semi-liquid or solid form and are formulated in a manner suitable for each route of administration. In a particular embodiment, the EPO polypeptide or other therapeutic polypeptide is administered orally.

The modified EPO or other modified therapeutic polypeptide and physiologically acceptable salts and solvates can be formulated for administration by inhalation (either through the mouth or the nose), oral, transdermal, pulmonary, parenteral, or rectal administration. For administration by inhalation, the modified EPO and other modified therapeutic polypeptide can be delivered in the form of an aerosol spray presentation from pressurized packs or a nebulizer with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of e.g., gelatin for use in an inhaler or insufflator can be formulated containing a powder mix of a therapeutic compound and a suitable powder base such as lactose or starch.

For pulmonary administration to the lungs, the modified EPO and other modified therapeutic polypeptide can be delivered in the form of an aerosol spray presentation from a nebulizer, turbonebulizer, or microprocessor-controlled metered dose oral inhaler with the use of a suitable propellant.

Generally, the particle size is small, such as in the range of 0.5 to 5 microns. In the case of a pharmaceutical composition formulated for pulmonary administration, detergent surfactants are not typically used. Pulmonary drug delivery is a promising non-invasive method of systemic administration. The lungs represent an attractive route for drug delivery, mainly due to the high surface area for absorption, thin alveolar epithelium, extensive vascularization, lack of hepatic first-pass metabolism, and relatively low metabolic activity.

For oral administration, the pharmaceutical compositions can take the form of, for example, tablets, pills, liquid suspensions, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically-acceptable saline, pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations also can contain buffer salts, flavoring, coloring and sweetening agents as appropriate.

Preparations for oral administration can be suitably formulated to give controlled release of the active compound. For buccal administration the compositions can take the form of tablets or lozenges formulated in conventional manner.

The modified EPO polypeptides and other modified therapeutic polypeptides exhibit increased resistance to proteolysis and half-life in the gastrointestinal tract. Thus, preparations for oral administration can be suitably formulated without the use of protease inhibitors, such as a Bowman-Birk inhibitor, a conjugated Bowman-Birk inhibitor, aprotinin and camostat. Such compounds, however, are not excluded from use in the compositions provided.

The modified EPO polypeptides and other modified therapeutic polypeptides can be formulated as a depot preparation. Such long-acting formulations can be administered by implantation (for example, subcutaneously or intramuscularly) or by intramuscular injection. Thus, for example, the therapeutic compounds can be formulated with suitable polymeric or hydrophobic materials (for example as an emulsion in an acceptable oil) or ion exchange resins, or as sparingly soluble derivatives, for example, as a sparingly soluble salt.

The modified EPO polypeptides and other modified therapeutic polypeptides can be formulated, for example, for parenteral administration by injection (e.g., by bolus injection or continuous infusion. Formulations for injection can be presented in unit dosage form (e.g., in ampoules or in multi-dose containers) with an added preservative. The compositions can take such forms as suspensions, solutions or emulsions in oily or aqueous vehicles and can contain formulatory agents such as suspending, stabilizing and/or dispersing agents. Alternatively, the active ingredient can be in powder-lyophilized form for constitution with a suitable vehicle, e.g., sterile pyrogen free water, before use.

The active agents can be formulated for local or topical application, such as for topical application to the skin (transdermal) and mucous membranes, such as in the eye, in the form of gels, creams, and lotions and for application to the eye or for intracisternal or intraspinal application. Such solutions, particularly those intended for ophthalmic use, can be formulated as 0.01%-10% isotonic solutions and pH about 5-7 with appropriate salts. The compounds can be formulated for topical application (see, for example, U.S. Pat. Nos. 4,044,126, 4,414,209 and 4,364,923, which describe aerosols for delivery of a steroid useful for treatment inflammatory diseases, particularly asthma each of which is incorporated herein by reference in its entirety).

The concentration of active compound in the drug composition depends on absorption, inactivation and excretion rates of the active compound, the dosage schedule, and amount administered as well as other factors known to those of skill in the art. As described further herein, dosages can be determined empirically using dosages known in the art for administration of unmodified EPO or other unmodified therapeutic polypeptide, and comparisons of properties and activities (e.g., stability and activities) of the modified EPO or other modified therapeutic polypeptide compared to the unmodified and/or native EPO or other unmodified and/or native therapeutic polypeptides.

The compositions, if desired, can be presented in a package, in a kit or dispenser device, that can contain one or more unit dosage forms containing the active ingredient. The package, for example, contains metal or plastic foil, such as a blister pack. The pack or dispenser device can be accompanied by instructions for administration. The compositions containing the active agents can be packaged as articles of manufacture containing packaging material, an agent provided herein, and a label that indicates the disorder for which the agent is provided.

Among the modified EPO polypeptides and other modified therapeutic polypeptides provided herein are EPO polypeptides and other modified therapeutic polypeptides modified to increase stability to conditions amendable to oral delivery. Oral delivery can include administration to the mouth and/or gastrointestinal tract. Such modifications can include increased protein-half life under one or more conditions such as exposure to saliva, exposure to proteases in the gastrointestinal tract, and exposure to particular pH conditions, such as the low pH of the stomach and/or pH conditions in the intestine. Modifications can include resistance to one or more proteases including pepsin, trypsin, chymotrypsin, elastase, aminopeptidase, gelatinase B, gelatinase A, α-chymotrypsin, carboxypeptidase, endoproteinase Arg-C, endoproteinase Asp-N, endoproteinase Glu-C, endoproteinase Lys-C, and trypsin, luminal pepsin, microvillar endopeptidase, dipeptidyl peptidase, enteropeptidase, hydrolase, NS3, elastase, factor Xa, Granzyme B, thrombin, trypsin, plasmin, urokinase, tPA and PSA. Modifications also can include increasing overall stability to potentially denaturing or conformation-altering conditions such as thermal tolerance, and tolerance to mixing and aeration (e.g., chewing).

EPO polypeptides and other therapeutic polypeptides modified for suitability to oral delivery can be prepared using any of the methods described herein. For example, 2D- and 3D-scanning mutagenesis methods for protein rational evolution (see, co-pending U.S. Publication No. US 2005-0202438 A1 and U.S. Publication No. US-2004-0132977-A1 and published International applications WO 2004/022593 and WO 2004/022747) can be used to prepare modified EPO and other modified therapeutic polypeptides. Modification of EPO polypeptides and other modified therapeutic polypeptides for suitability for oral delivery can include removal of proteolytic digestion sites and/or increasing the overall stability of the protein structure. Such EPO variants and other modified therapeutic variants exhibit increased protein half-life compared to an unmodified and/or wild-type native EPO or other unmodified and/or wild-type native therapeutic polypeptides in one or more conditions for oral delivery. For example, a modified EPO or other therapeutic polypeptide can have increased protein half-life and/or bioavailability in the mouth, throat (e.g., through the mucosal lining), the gastrointestinal tract or systemically.

In one embodiment, the half-life of the modified EPO polypeptides provided herein is increased by an amount at least about or 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more compared to the half-life of a native EPO polypeptide exposed to one or more conditions for oral delivery. In other embodiments, the half-life of the modified EPO polypeptides provided herein is increased by an amount of at least 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, or more, compared to the half-life of native EPO exposed to one or more conditions for oral delivery.

In one example, half-life of the modified EPO polypeptide or other therapeutic polypeptides is assessed by increased half-life in the presence of one or more proteases such as pepsin, trypsin, chymotrypsin, elastase, aminopeptidase, gelatinase B, gelatinase A, α-chymotrypsin, carboxypeptidase, endoproteinase Arg-C, endoproteinase Asp-N, endoproteinase Glu-C, endoproteinase Lys-C, and trypsin, luminal pepsin, microvillar endopeptidase, dipeptidyl peptidase, enteropeptidase, hydrolase, NS3, elastase, factor Xa, Granzyme B, thrombin, trypsin, plasmin, urokinase, tPA and PSA. The modified EPO or other therapeutic polypeptides can be mixed with one or more proteases and then assessed for activity and/or protein structure after a suitable reaction time. Assessment of half-life also can include exposure to increased temperature, such as the body temperature of a subject; exposure to gastric juices and/or simulated gastric juices; exposure to particular pH conditions and/or a combination of two or more conditions. Following exposure to one or more conditions, activity and/or assessment of protein structure can be used to assess the half-life of the modified EPO or other modified therapeutic polypeptide in comparison to an appropriate control (i.e., an unmodified and/or wild-type EPO polypeptide).

The modified EPO polypeptides and other modified therapeutic polypeptides can be formulated for oral administration, such as in tablets, capsules, liquids or other suitable vehicle for oral administration. Preparation of pharmaceutical compositions containing a modified EPO or other modified therapeutic polypeptides for oral delivery can include formulating modified EPO polypeptides or other modified therapeutic polypeptides with oral formulations known in the art and described herein. The compositions as formulated do not require addition of protease inhibitors and/or other ingredients that are necessary for stabilization of unmodified and wild-type modified therapeutic polypeptides upon exposure of proteases, pH and other conditions of oral delivery. For example, such compositions exhibit stability in the absence of compounds such as actinonin or epiactinonin and derivatives thereof; Bowman-Birk inhibitor and conjugates thereof; aprotinin and camostat. Such compounds, however, are not excluded from use in the compositions provided.

Additionally, because modified EPO polypeptides and other modified therapeutic polypeptides provided herein exhibit increased protein stability, there is more flexibility in the administration of pharmaceutical compositions than their unmodified counterparts. Typically, orally ingested polypeptides are administered in the morning before eating (i.e., before digestive enzymes are activated). The modified polypeptides provided herein exhibit protease resistance to digestive enzymes and can offer the ability to administer pharmaceutical compositions containing a modified EPO polypeptide or other modified therapeutic polypeptide at other periods during the day and under conditions when digestive enzymes are present and active.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p hydroxybenzoates or sorbic acid). The preparations also can contain buffer salts, flavoring, coloring and/or sweetening agents as appropriate.

Preparations for oral administration can be formulated to give controlled or sustained release or for release after passage through the stomach or in the small intestine of the active compound. For oral administration the compositions can take the form of tablets, capsules, liquids, lozenges and other forms suitable for oral administration. Formulations suitable for oral administration include lozenges and other formulations that deliver the pharmaceutical composition to the mucosa of the mouth, throat and/or gastrointestinal tract. Lozenges can be formulated with suitable ingredients including excipients for example, anhydrous crystalline maltose and magnesium stearate. As noted, modified polypeptides described herein exhibit resistance to blood or intestinal proteases and can be formulated without additional protease inhibitors or other protective compounds. Preparations for oral administration also can include a modified EPO polypeptide or other modified therapeutic polypeptide resistant to proteolysis formulated with one or more additional ingredients that also confer proteases resistance, or confer stability in other conditions, such as particular pH conditions.

2. Administration of Nucleic Acids Encoding Modified EPO Polypeptides or Other Modified Therapeutic Polypeptides (Gene Therapy)

Also provided are compositions of nucleic acid molecules encoding the modified EPO polypeptides or other modified therapeutic polypeptides and expression vectors encoding them that are suitable for gene therapy. Rather than deliver the protein, nucleic acid can be administered in vivo, such as systemically or by other route, or ex vivo, such as by removal of cells, including lymphocytes, introduction of the nucleic therein, and reintroduction into the host or a compatible recipient.

Modified EPO polypeptides and other modified therapeutic polypeptides can be delivered to cells and tissues by expression of nucleic acid molecules. Modified EPO polypeptides and other modified therapeutic polypeptides can be administered as nucleic acid molecules encoding modified EPO polypeptides or other modified therapeutic polypeptides, including ex vivo techniques and direct in vivo expression. Nucleic acids can be delivered to cells and tissues by any method known to those of skill in the art including, for example direct injection of naked DNA into tissues, such as skeletal muscle tissue, for expression (see e.g., Rizzuto et al. (1999) *Proc Natl Acad Sci USA* 96: 6417-6422). The isolated nucleic acid sequences can be incorporated into vectors for further manipulation. As used herein, vector (or plasmid) refers to discrete elements that are used to introduce heterologous DNA into cells for either expression or replication thereof. Selection and use of such vehicles are well within the skill of the artisan.

Methods for administering modified EPO polypeptides and other modified therapeutic polypeptides by expression of encoding nucleic acid molecules include administration of recombinant vectors. The vector can be designed to remain episomal, such as by inclusion of an origin of replication or can be designed to integrate into a chromosome in the cell. Modified EPO polypeptides and other modified therapeutic polypeptides also can be used in ex vivo gene expression therapy using non-viral vectors. For example, cells can be engineered to express a modified EPO polypeptide or other modified therapeutic polypeptides, such as by integrating a modified EPO polypeptide or other modified therapeutic polypeptide encoding-nucleic acid into a genomic location, either operatively linked to regulatory sequences or such that it is placed operatively linked to regulatory sequences in a genomic location. Such cells then can be administered locally or systemically to a subject, such as a patient in need of treatment.

Viral vectors, include, for example adenoviruses, adeno-associated viruses (AAV), poxviruses, herpes viruses, retroviruses and others designed for gene therapy can be employed. The vectors can remain episomal or can integrate into chromosomes of the treated subject. A modified EPO polypeptide or other modified therapeutic polypeptide can be expressed by a virus, which is administered to a subject in need of treatment. Viral vectors suitable for gene therapy include adenovirus, adeno-associated virus (AAV), retroviruses, lentiviruses, vaccinia viruses and others noted above. For example, adenovirus expression technology is well-known in the art and adenovirus production and administration methods also are well known. Adenovirus serotypes are available, for example, from the American Type Culture Collection (ATCC, Rockville, Md.). Adenovirus can be used ex vivo, for example, cells are isolated from a patient in need of treatment, and transduced with a modified EPO polypeptide-expressing adenovirus vector. After a suitable culturing period, the transduced cells are administered to a subject, locally and/or systemically. Alternatively, modified therapeutic polypeptide-expressing adenovirus particles are isolated and formulated in a pharmaceutically-acceptable carrier for delivery of a therapeutically effective amount to prevent, treat or ameliorate a disease or condition of a subject. Typically, adenovirus particles are delivered at a dose ranging from 1 particle to 1014 particles per kilogram subject weight, generally between 106 or 108 particles to 1012 particles per kilogram subject weight. In some situations it is desirable to provide a nucleic acid source with an agent that targets cells, such as an antibody specific for a cell surface membrane protein or a target cell, or a ligand for a receptor on a target cell. EPO polypeptides and other modified therapeutic polypeptides also can be targeted for delivery into specific cell types. For example, adenoviral vectors encoding EPO polypeptides or other modified therapeutic polypeptides can be used for stable expression in nondividing cells, such as liver or skeletal muscle cells (see e.g., Tipathy et al. (1994) *Proc Natl Acad Sci USA*. 91(24): 11557-11561; Svensson et al. (1997) *Hum Gene Ther* 8: 1797; Setoguchi et al. (1994) *Blood* 84(9): 2946-2953; U.S. Pat. No. 6,613,319). In another example, viral or nonviral vectors encoding EPO polypeptides or other modified therapeutic polypeptides can be transduced into isolated cells for subsequent delivery. Additional cell types for expression and delivery of EPO and other modified therapeutic polypeptides are known in the art and include, but are not limited to, delivery to pancreatic cells, pulmonary epithelia, and mesothelial cells (Fenjves et al. (2004) *Transplantation* 77(1): 13-8; Davis et al. (2004) *Mol Ther.* 10(3): 500-6).

The nucleic acid molecules can be introduced into artificial chromosomes and other non-viral vectors. Artificial chromosomes, such as ACES (see, Lindenbaum et al. *Nucleic Acids Res.* 2004 Dec. 7; 32(21):e172) can be engineered to encode and express the isoform. Briefly, mammalian artificial chromosomes (MACs) provide a means to introduce large payloads of genetic information into the cell in an autonomously replicating, non-integrating format. Unique among MACs, the mammalian satellite DNA-based Artificial Chromosome Expression (ACE) can be reproducibly generated de novo in cell lines of different species and readily purified from the host cells' chromosomes. Purified mammalian ACEs can then be re-introduced into a variety of recipient cell lines where they have been stably maintained for extended periods in the absence of selective pressure using an ACE System. Using this approach, specific loading of one or two gene targets has been achieved in LMTK(−) and CHO cells.

Another method for introducing nucleic acids encoding the modified EPO polypeptides or other modified therapeutic polypeptides is a two-step gene replacement technique in yeast, starting with a complete adenovirus genome (Ad2; Ketner et al. (1994) *Proc. Natl. Acad. Sci. USA* 91: 6186-6190) cloned in a Yeast Artificial Chromosome (YAC) and a plasmid containing adenovirus sequences to target a specific region in the YAC clone, an expression cassette for the gene of interest and a positive and negative selectable marker. YACs are of particular interest because they permit incorporation of larger genes. This approach can be used for construction of adenovirus-based vectors bearing nucleic acids encoding any of the described modified EPO polypeptides or other modified therapeutic polypeptides for gene transfer to mammalian cells or whole animals.

The nucleic acids can be encapsulated in a vehicle, such as a liposome, or introduced into cells, such as a bacterial cell, particularly an attenuated bacterium or introduced into a viral vector. For example, when liposomes are employed, proteins that bind to a cell surface membrane protein associated with endocytosis can be used for targeting and/or to facilitate uptake, e.g., capsid proteins or fragments thereof tropic for a particular cell type, antibodies for proteins which undergo internalization in cycling, and proteins that target intracellular localization and enhance intracellular half-life.

For ex vivo and in vivo methods, nucleic acid molecules encoding the modified EPO polypeptide or other modified therapeutic polypeptide is introduced into cells that are from a suitable donor or the subject to be treated. Cells into which a nucleic acid can be introduced for purposes of therapy include, for example, any desired, available cell type appropriate for the disease or condition to be treated, including but not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., such as stem cells obtained from bone marrow, umbilical cord blood, peripheral blood, fetal liver, and other sources thereof.

For ex vivo treatment, cells from a donor compatible with the subject to be treated or the subject to be treated cells are removed, the nucleic acid is introduced into these isolated cells and the modified cells are administered to the subject. Treatment includes direct administration, such as, for example, encapsulated within porous membranes, which are implanted into the patient (see, e.g., U.S. Pat. Nos. 4,892,538 and 5,283,187 each of which is herein incorporated by reference in its entirety). Techniques suitable for the transfer of nucleic acid into mammalian cells in vitro include the use of liposomes and cationic lipids (e.g., DOTMA, DOPE and DC-Chol) electroporation, microinjection, cell fusion, DEAE-dextran, and calcium phosphate precipitation methods. Methods of DNA delivery can be used to express modified EPO polypeptides and other modified therapeutic polypeptides in vivo. Such methods include liposome delivery of nucleic acids and naked DNA delivery, including local and systemic delivery such as using electroporation, ultrasound and calcium-phosphate delivery. Other techniques include microinjection, cell fusion, chromosome-mediated gene transfer, microcell-mediated gene transfer and spheroplast fusion.

In vivo expression of a modified EPO polypeptide or other modified therapeutic polypeptides can be linked to expression of additional molecules. For example, expression of a modified EPO polypeptide or other modified therapeutic polypeptide can be linked with expression of a cytotoxic product such as in an engineered virus or expressed in a cytotoxic virus. Such viruses can be targeted to a particular cell type that is a target for a therapeutic effect. The expressed modified EPO polypeptide or other modified therapeutic polypeptides can be used to enhance the cytotoxicity of the virus.

In vivo expression of a modified EPO polypeptide or other modified therapeutic polypeptides can include operatively linking a modified therapeutic polypeptide encoding nucleic acid molecule to specific regulatory sequences such as a cell-specific or tissue-specific promoter. Modified EPO polypeptides and other modified therapeutic polypeptides also can be expressed from vectors that specifically infect and/or replicate in target cell types and/or tissues. Inducible promoters can be used to selectively regulate modified polypeptide expression. Exemplary regulatable expression systems include, but are not limited to, mifepristone, doxycycline and tetracycline gene expression systems, which have been used to regulate recombinant EPO or other modified therapeutic polypeptide expression in skeletal muscle (Serguera et al. (1999) *Human Gene Therapy* 10(3): 375-383; Bohl et al. (1998) *Blood* 2(5): 1512-1517; Rizutto et al. (1999) *Proc Natl Acad Sci USA*. 96(11): 6417-6422; Rendahl et al. (2002) *Human Gene Therapy* 13(2): 335-342).

Nucleic acid molecules, as naked nucleic acids or in vectors, artificial chromosomes, liposomes and other vehicles can be administered to the subject by systemic administration, topical, local and other routes of administration. When systemic and in vivo, the nucleic acid molecule or vehicle containing the nucleic acid molecule can be targeted to a cell.

Administration also can be direct, such as by administration of a vector or cells that typically targets a cell or tissue. For example, tumor cells and proliferating cells can be targeted cells for in vivo expression of modified EPO polypeptides and other modified therapeutic polypeptides. Cells used for in vivo expression of a modified EPO polypeptide or other modified therapeutic polypeptide also include cells autologous to the patient. Such cells can be removed from a patient, nucleic acids for expression of a modified EPO polypeptide or other modified therapeutic polypeptides introduced, and then administered to a patient such as by injection or engraftment.

Polynucleotides and expression vectors provided herein can be made by any suitable method. Further provided are nucleic acid vectors comprising nucleic acid molecules as described above, including a nucleic acid molecule comprising a sequence of nucleotides that encodes the EPO polypeptide as set forth in any of SEQ ID NOS: 3-201 or a fragment thereof. Further provided are nucleic acid vectors comprising nucleic acid molecules as described above and cells containing these vectors.

I. Therapeutic Uses

The modified EPO polypeptides and other modified therapeutic polypeptides and nucleic acid molecules provided herein can be used for treatment of any condition for which the unmodified EPO or unmodified therapeutic polypeptide is employed. Modified EPO polypeptides and other modified therapeutic polypeptides have therapeutic activity alone or in combination with other agents. The modified polypeptides provided herein are designed to retain therapeutic activity but exhibit modified properties, particularly increased stability. Such modified properties, for example, can improve the therapeutic effectiveness of the polypeptides and/or can provide for additional routes of administration, such as oral administration. The modified EPO polypeptides and other modified therapeutic polypeptides and encoding nucleic acid molecules provided herein can be used for treatment of any condition for which unmodified EPO or unmodified therapeutic protein is employed. This section provides exemplary uses of and administration methods. These described therapies are exemplary and do not limit the applications of modified EPO polypeptides or other modified therapeutic polypeptides.

The modified EPO polypeptides and other modified therapeutic polypeptides provided herein can be used in various therapeutic as well as diagnostic methods in which EPO or the therapeutic polypeptide is employed. Such methods include, but are not limited to, methods of treatment of physiological and medical conditions described and listed below. Modified EPO polypeptides and other modified therapeutic polypeptides provided herein can exhibit improvement of in vivo activities and therapeutic effects compared to corresponding wild-type therapeutic polypeptide, including lower dosage to achieve the same effect, a more sustained therapeutic effect and other improvements in administration and treatment.

The modified EPO polypeptides and other modified therapeutic polypeptides described herein exhibit increased protein stability and improved half-life. Thus, modified EPO polypeptides and other modified therapeutic polypeptides can be used to deliver longer-lasting, more stable therapies. Examples of therapeutic improvements using modified EPO polypeptides and other modified therapeutic polypeptides provided include, but are not limited to, lower dosages, fewer and/or less frequent administrations, decreased side effects and increased therapeutic effects.

In particular, modified EPO polypeptides, are intended for use in therapeutic methods in which EPO has been used for treatment. Such methods include, but are not limited to, methods of treatment of diseases and disorders, such as, but not limited to, anemias, such as anemias that accompany renal failure, AIDS, malignancy, and chronic inflammation. Additional exemplary anemias for treatment with modified EPO polypeptides include thalassemia, sickle cell anemia, the anemia of prematurity, anemia that accompanies cis-platinum chemotherapy, and anemia following intensive radiotherapy and/or chemotherapy plus bone marrow transplantation.

The modified EPO polypeptides provided herein are useful in modulating cell survival, proliferation and differentiation. For example, the modified EPO polypeptides and compositions containing the modified EPO polypeptides are useful in promoting erythroid precursor proliferation and can be used in vivo, ex vivo, in situ, or in vitro. For example, a composition containing a modified human EPO polypeptide where the modified EPO polypeptide is selected from any of SEQ ID NOS: 3-201, can be used to treat erythroid precursor cells derived from an individual ex vivo and then the increased proliferating cells can be administered back to the subject. EPO modified polypeptides provided herein that do not exhibit erythropoietic activity can still retain EPO activities useful for the treatment of EPO-mediated diseases, such as tissue protective activity, or can be used as antagonists of native erythropoietin (e.g. for treatment of polycythemias or conditions involving overproduction of erythropoietin) or in diagnostic assays.

Treatment of diseases and conditions with modified EPO polypeptides or other modified therapeutic polypeptides can be effected by any suitable route of administration using suitable formulations as described herein including, but not limited to, injection, pulmonary, oral and transdermal administration. If necessary, a particular dosage and duration and treatment protocol can be empirically determined or extrapolated. For example, exemplary doses of recombinant and native EPO polypeptides or other therapeutic polypeptides can be used as a starting point to determine appropriate dosages. Modified EPO polypeptides and other modified therapeutic polypeptides that are more stable and have an increased half-life in vivo, can be effective at reduced dosage amounts and or frequencies. For example, because of the improvement in properties such as serum stability, dosages can be lower than comparable amounts of unmodified EPO or other unmodified therapeutic polypeptide. Dosages for unmodified EPO polypeptides or other unmodified therapeutic polypeptides can be used as guidance for determining dosages for the corresponding modified polypeptides. Factors such as the level of activity and half-life of the modified polypeptide in comparison to the unmodified polypeptide can be used in making such determinations. Particular dosages and regimens can be empirically determined.

For any of the modified EPO polypeptides and other modified therapeutic polypeptides provided herein, a particular dosage that is therapeutically effective can be estimated initially using a variety of techniques well known in the art. For example, in a cell culture assay, a dose can be formulated in animal models to achieve a circulating concentration range that includes the IC50 as determined in cell culture. Dosage range appropriate for human subjects can be determined, for example using data obtained from cell culture assay and other animal studies.

Dosage levels and regimens can be determined based upon known dosages and regimens, and, if necessary can be extrapolated based upon the changes in properties of the modified polypeptides and/or can be determined empirically based on a variety of factors. Such factors include body weight of the individual, general health, age, the activity of the specific compound employed, sex, diet, time of administration, rate of excretion, drug combination, the severity and course of the disease, and the patient's disposition to the disease and the judgment of the treating physician. Other factors for determination of dosage can include the desired level of biological activity or result, such as, but not limited to, desired hematocrit levels. The active ingredient, the polypeptide, typically is combined with a pharmaceutically effective carrier. The amount of active ingredient that can be combined with the carrier materials to produce a single dosage form or multi-dosage form can vary depending upon the host treated and the particular mode of administration.

Upon improvement of a patient's condition, a maintenance dose of a compound or compositions can be administered, if necessary; and the dosage, the dosage form, or frequency of administration, or a combination thereof can be modified. In some cases, a subject can require intermittent treatment on a long-term basis upon any recurrence of disease symptoms or based upon scheduled dosages. In other cases, additional administrations can be required in response to acute events such as hemorrhage, trauma, or surgical procedures.

Selection of the preferred effective and non-toxic dose for the administration methods provided can be determined by a skilled artisan based upon factors known to one of ordinary skill in the art. Examples of these factors include the particular form of the modified EPO polypeptide or other modified therapeutic polypeptide; the pharmacokinetic parameters of the modified polypeptide, such as bioavailability, metabolism, half-life, etc. (provided to the skilled artisan); the condition or disease to be treated; the benefit to be achieved in a normal individual; the body mass of the patient; the method of administration; the frequency of administration, i.e., chronic, acute, intermittent; concomitant medications; and other factors well known to affect the efficacy of administered pharmaceutical agents. Thus the precise dosage should be decided according to the judgment of the practitioner and the circumstances of the particular patient.

Exemplary dosages for administration of an EPO polypeptide are known in the art and can be used as a basis for determination of dosages for the modified EPO polypeptides provided herein. For example, wherein a recombinant human EPO polypeptide has erythropoietic activity for the treatment of anemia, the recombinant human EPO is typically administered in an initial dose of between 50-150 units/kg body weight three times per week for about six to eight weeks either by an intravenous or subcutaneous injection in order to restore the suggested hematocrit range within the patient. After the patient achieves a desired hematocrit level, such as an amount falling within from about 30 percent to about 36 percent, that level can be sustained by maintenance doses of EPO, an amount sufficient to and administered with a frequency suitable for maintaining the normal hematocrit levels achieved by the initial doses of EPO, in the absence of iron deficiency and concurrent illnesses. While dosage requirements can vary according to the patient's individual needs, typically maintenance dosages can be administered about three times a week (less if larger doses are provided). The effective dose should be sufficient to achieve serum levels of the compound greater than about 10,000, 15,000, or 20,000 mU/ml of serum after compound administration. Such serum levels can be achieved at about 1, 2, 3, 4, 5, 6, 7, 8, 9, or 10 hours post-administration. Such dosages can be repeated as necessary. For example, administration can be repeated daily, as long as clinically necessary, or after an appropriate interval, e.g., every 1 to 12 weeks, but preferably, every 1 to 3 weeks.

The modified EPO polypeptides provided herein have an increased resistance to proteases which can result in increased serum half-life. Hence, their effectiveness in the body also is increased. As a result, modified EPO polypeptides provided herein can be administered with less frequent or smaller doses than compared to the frequency and amount of present recombinant EPO compositions.

The following are some exemplary conditions for which EPO has been used as a treatment agent alone or in combination with other agents.

1. Anemias

Among purified EPO therapeutics available for the treatment of EPO-mediated diseases, such as anemia, are: Epoietin α isoforms including products such as Epogen®, Procrit®, Eprex®, Erypo®, Epopen®, Epoxitin®, Globuren®, Epoade®, and Espo®; Epoietin β isoforms including products such as Recormon®, Neorecormon®, Epogin®, Epoch®, Eritrogen®, Erantin®, and Marogen®; Epoietin ω isoforms including products such as Epomax® and Hemax®; Epoietin δ isoforms including products such as Dynepo®; Darbepoietin α isoforms including products such as Aranesp®; R-744 Continuous erythropoietin receptor activator (CERA); and Synthetic erythropoiesis protein (SEP). All such products can be modified as described herein and/or replaced with modified EPO polypeptides provided herein. The modified EPO polypeptides provided herein and the nucleic acids encoding the modified EPO polypeptides provided herein can be used in therapies for anemia, including treatment of conditions associated with deficiencies of red blood cells. The modified EPO polypeptides provided herein can be used, for example, to promote erythropoiesis and regeneration of red blood cells. Exemplary anemias for treatment with modified EPO polypeptides provided herein include anemias caused by renal failure, AIDS, malignancy, and chronic inflammation. Additional exemplary anemias for treatment with modified EPO polypeptides provided herein include hemoglobinopathies, such as thalassemia and sickle cell disorders, anemia of prematurity, iron storage disorders, anemia caused by administration of chemotherapeutic agents, such as cis-platinum or radiation, aplitic anemias, anemia caused by administration of therapeutic agents, such as ribavirin, for the treatment of hepatitis C, anemias associated with malignant disease (e.g., any type of solid cancer, metastatic breast cancer, or hematological cancer including leukemia, lymphoma, or multiple myeloma), excessive blood cell destruction (hemolysis, hemolytic anemias, eryptosis), excessive blood loss (acutely such as a hemorrhage or chronically through low-volume loss), aging, chronic kidney disease (CDK), hepatitis, renal failure, zidovudine therapy (e.g., AZT treatment) in AIDS patients, paroxysmal nocturnal hemoglobinuria (PNH), cystic fibrosis, diabetic nephropathy, sepsis, cerebral hypoxia/ischemia, rheumatic disease, myelodysplastic syndrome, congestive heart failure (CHF), Gaucher's disease, Castleman's disease, and anemia following intensive radiotherapy and/or chemotherapy plus bone marrow transplantation (see e.g., Little et al. (2006) *Haematologica* 91(8): 1076-83; Eisenstaedt et al. (2006) *Blood Rev.* 20(4): 213-26; Rodgers and Lessin (1989) *Blood* 73(8): 2228-9; Boogaerts et al. (2005) *Oncology.* 69 Suppl 2: 22-30; Regnier et al. (1989) *AANA J.* (7): 512-3, Olsson et al. (2002) *Acta Oncol.* 41(6): 517-24; Ritz and Haxsen (2005) *Eur J Clin Invest.* 35 Suppl 3: 66-74, Nurko (2006) *Cleveland Clin. J. Med.* 73(3): 289-297; Koltwasser et al. (2001) *J Rheumatol.* 28(11): 2430-6; Kuehl and Noormohamed (1995) *Ann Pharmacother.* 29(7-8): 778-9; Singer et al. (2005) *Ann N Y Acad Sci.* 1054: 250-6). Modified EPO polypeptides provided herein also can be used in treatment of anemias associated with angina, pulmonary disease, hypotension, congestive heart failure, or cerebrovascular disease causing transient ischemic attacks. Modified EPO polypeptides provided herein also can be used in treatment of subjects undergoing surgery, either before, during, or after surgery, such as non-cardiac or non-vascular surgery, where there is a risk of excessive blood loss. Modified EPO polypeptides provided herein also can be used for the treatment of nutritional deficiency anemias, such iron deficiency anemia or folate deficiency anemia, in combination with iron or vitamin supplement therapies.

In addition to the treatment of anemia, modified EPO polypeptides provided herein and the nucleic acids encoding the modified EPO polypeptides provided herein can be used in therapies for the treatment of iron overload disorder. A subject having an iron overload disorder is administered modified EPO polypeptides to increase red blood cell production and the subject is subsequently phlebotomized to remove the excess red blood cells produced (see e.g., U.S. Pat. No. 5,013,718).

Modified EPO polypeptides provided herein and the nucleic acids encoding the modified EPO polypeptides provided herein can be used in therapies for abnormal hemostasis. For example, modified EPO polypeptide can be used to treat, control or prevent the bleeding in patients with congenital or acquired disorders of coagulation, platelets, or blood vessels, patients on therapeutic or overdose of anticoagulants or antiplatelet drugs (U.S. Pat. No. 6,274,158).

A method is provided for increasing erythrocytes in a subject by administering to the subject an effective amount of a composition that contains a modified EPO polypeptide containing an amino acid sequence selected from SEQ ID NOS: 3-201 and a pharmaceutically acceptable medium. The number of erythrocytes in an individual can be measured, for example, using a hematocrit. Further, a method is provided for increasing erythrocytes in a subject by administering to the subject an effective amount of a composition that contains a modified EPO polypeptide containing an amino acid sequence selected from SEQ ID NOS: 3-201 and a pharmaceutically acceptable medium, and where the subject is anemic. For example, a modified EPO polypeptide or composition of a modified EPO polypeptide can be administered in an amount effective to increase the hematocrit level of an anemic subject. Anemia can be caused by several factors including diet and genetic factors as well as pathologies. For example, anemia can be caused by chronic renal failure or can be induced as a side-effect of chemotherapy treatment for an individual who has cancer.

The modified EPO polypeptides herein provide increased protein stability and increased protein half-life. Of particular interest are EPO polypeptides that are resistant to proteases. Thus, modified EPO polypeptides can be used to deliver longer lasting, more stable therapies for anemia. Such polypeptides include, for example, a modified EPO polypeptide selected from any of SEQ ID NOS: 3-201. Examples of therapeutic improvements using modified EPO polypeptides include, but are not limited to, lower dosages, fewer and/or less frequent administrations, decreased side effects, and increased therapeutic effects. Modified EPO polypeptides can be tested for therapeutic effectiveness, for example, by using animal models. For example anemic mice, or any other known disease model for anemia, can be treated with modified EPO polypeptides. Progression of disease symptoms and phenotypes is monitored to assess the effects of the modified EPO polypeptides. Modified EPO polypeptides also can be administered to animal models as well as subjects such as in clinical trials to assess in vivo effectiveness in comparison to placebo controls and/or controls using unmodified EPO.

The modified EPO polypeptide can be used to deliver longer lasting, more stable anemia therapies. Thus, the modified EPO polypeptides provided herein can be administered at lower dosages and/or less frequently than unmodified or native EPO polypeptides or other recombinant forms of EPO, such as the Epoietin α, β, ω, δ, and Darbepoietin α isoform listed above, while retaining one or more therapeutic activities and/or having one or more fewer/decreased side effects.

2. Tissue Protective Therapies

The modified EPO polypeptides provided herein and the nucleic acids encoding the modified EPO polypeptides provided herein can be used in therapies for protection against an injury or restoration of function following the injury to responsive mammalian cells, tissues, or organs. Exemplary responsive mammalian cells include neuronal, brain, spinal cord, retinal, muscle, heart, lung, liver, kidney, small intestine, adrenal cortex, adrenal medulla, capillary, endothelial, testes, ovary, endometrial, or stem cells. Additional exemplary responsive mammalian cells include photoreceptor, ganglion, bipolar, horizontal, amacrine, Müller, myocardium, pace maker, sinoatrial node, sinus node, atrioventricular node, bundle of His, hepatocyte, stellate, Kupffer, mesangial, goblet, intestinal gland, enteral, endocrine, glomerulosa, fasciculate, reticularis, chromaffin, pericyte, Leydig, Sestoli, sperm, Graafian follicles, primordial follicles, endometrial stroma, and endometrial cells.

The modified EPO polypeptides provided herein and the nucleic acids encoding the modified EPO polypeptides provided herein can be used in the preparation of a pharmaceutical composition for treatment of conditions associated with diseases of the central nervous system or peripheral nervous system which have primarily neurological or psychiatric symptoms, ophthalmic diseases, cardiovascular diseases, cardiopulmonary diseases, respiratory diseases, kidney, urinary and reproductive diseases, bone diseases, skin diseases, gastrointestinal diseases, and endocrine and metabolic abnormalities. The modified EPO polypeptides provided herein and the nucleic acids encoding the modified EPO polypeptides provided herein can be used to provide for the local or systemic protection of cells, tissues and organs within a subject or restoration or regeneration of dysfunction resulting from such conditions.

In particular, such conditions and diseases include hypoxic conditions, which adversely affect excitable tissues, such as excitable tissues in the central nervous system tissue, peripheral nervous system tissue, or cardiac tissue or retinal tissue such as, for example, brain, heart, or retina/eye. Any condition which reduces the availability of oxygen to neuronal tissue, resulting in stress, damage, and finally, neuronal cell death, can be treated by administration of the modified EPO polypeptides provided herein and the nucleic acids encoding the modified EPO polypeptides provided herein. Generally referred to as hypoxia and/or ischemia, these conditions arise from or include, but are not limited to stroke, vascular occlusion, prenatal or postnatal oxygen deprivation, suffocation, choking, asthma, near drowning, carbon monoxide poisoning, smoke inhalation, trauma, including surgery and radiotherapy, asphyxia, epilepsy, hypoglycemia, chronic obstructive pulmonary disease, emphysema, adult respiratory distress syndrome, hypotensive shock, septic shock, anaphylactic shock, insulin shock, sickle cell crisis, cardiac arrest, dysrhythmia, nitrogen narcosis, and neurological deficits caused by heart-lung bypass procedures.

Hence, modified EPO polypeptides provided herein and the nucleic acids encoding the modified EPO polypeptides provided herein are useful generally for the therapeutic or prophylactic treatment of human diseases of the central nervous system or peripheral nervous system which have primarily neurological or psychiatric symptoms, ophthalmic diseases, cardiovascular diseases, cardiopulmonary diseases, respiratory diseases, kidney, urinary and reproductive diseases, bone diseases, skin diseases, gastrointestinal diseases and endocrine and metabolic abnormalities. In particular, such conditions and diseases include hypoxic conditions, which adversely affect excitable tissues, such as excitable tissues in the central nervous system tissue, peripheral nervous system tissue, or cardiac tissue or retinal tissue such as, for example, brain, heart, or retina/eye. Therefore, modified EPO polypeptides provided herein and the nucleic acids encoding the modified EPO polypeptides provided herein can be used to treat or prevent damage to excitable tissue resulting from hypoxic conditions in a variety of conditions and circumstances. Administration of modified EPO polypeptides provided herein and the nucleic acids encoding the modified EPO polypeptides provided herein can be used for protection against an injury such as a seizure disorder, multiple sclerosis, stroke, hypotension, cardiac arrest, ischemia, myocardial infarction, inflammation, age-related loss of cognitive function, cognitive decline in subjects with schizophrenia, radiation damage, cerebral palsy, neurodegenerative disease, Alzheimer's disease, Parkinson's disease, Leigh disease, AIDS dementia, memory loss, amyotrophic lateral sclerosis, alcoholism, mood disorder, anxiety disorder, attention deficit disorder, schizophrenia, autism, Creutzfeld-Jakob disease, brain or spinal cord trauma or ischemia, heart-lung bypass, chronic head failure, macular degeneration, toxin induced neuropathy, diabetic neuropathy, diabetic retinopathy, glaucoma, retinal ischemia, or retinal trauma (see e.g. Grasso et al. (2006) *J Neurosurg Spine* 4(4):310-80; Boogaert et al. (2005) *Oncology*. 69 Suppl 2:22-30; Krebs et al. (2006) *Expert Opin Pharmacother.* 7(7): 837-48).

Modified EPO polypeptides provided herein and the nucleic acids encoding the modified EPO polypeptides provided herein can be used in therapies for the treatment of a neurological condition in a subject, by administering to the subject an effective amount of a composition containing a modified EPO polypeptide provided herein having an amino acid sequence selected from SEQ ID NOS: 3-201 and a pharmaceutically acceptable medium. For example a pharmaceutical composition containing a modified EPO polypeptide provided herein can be administered prophylactically in individuals who are at risk for neurological conditions or can be used after an event such as a stroke or other neurological damage. As described above, a neurological condition can be a pathological condition affecting neuronal or glial cells in the nervous system. Pathological conditions affecting neuronal or glial cells include ischemia, apoptosis, necrosis, oxidative or free radical damage, and excitotoxicity. For example, neurological conditions include, but are not limited to, cerebral and spinal ischemia, acute brain injury, spinal cord injury, retinal disease, and neurodegenerative diseases such as Alzheimer's disease, Parkinson's disease, Huntington's disease, and ALS.

The modified EPO polypeptides herein provide increased protein stability and increased protein half-life. Of particular interest are EPO polypeptides that are resistant to proteases. Thus, modified EPO polypeptides can be used to deliver longer lasting, more stable therapies for protection against an injury or restoration of function following the injury to responsive mammalian cells, tissues, or organs. Such polypeptides include, for example, a modified EPO polypeptide selected from any of SEQ ID NOS: 3-201. Examples of therapeutic improvements using modified EPO polypeptides include, but are not limited to, lower dosages, fewer and/or less frequent administrations, decreased side effects, and increased therapeutic effects. Modified EPO polypeptides can be tested for therapeutic effectiveness, for example, by using animal models that can be treated with modified EPO polypeptides. Progression of disease symptoms and phenotypes is monitored to assess the effects of the modified EPO polypeptides. Modified EPO polypeptides also can be administered to animal models as well as subjects such as in clinical trials to assess in vivo effectiveness in comparison to placebo controls and/or controls using unmodified EPO.

The modified EPO polypeptide can be used to deliver longer lasting, more stable therapies for protection against an injury or restoration of function following the injury to responsive mammalian cells, tissues, or organs. Thus, the modified EPO polypeptides provided herein can be administered at lower dosages and/or less frequently than unmodified or native EPO polypeptides or other recombinant forms of EPO, such as the Epoietin α, β, ω, δ, and Darbepoietin α isoform listed above, while retaining one or more therapeutic activities and/or having one or more fewer/decreased side effects.

J. Diagnostic Uses

Modified EPO polypeptides provided herein also can be used for diagnostic purposes. For example, modified EPO polypeptides can be used in assay procedures for detecting the presence and determining the quantity, if desired, of an erythropoietin receptor or for comparing activities of factors that induce erythropoiesis. A modified EPO polypeptide with enhanced activity would be useful to increase the sensitivity and decrease the incubation times of assays that involve binding to a receptor, for example. Modified EPO polypeptides provided herein also can be used in in vitro binding assays to determine the effect of new drugs on the binding of erythropoietin protein to its receptor.

Modified EPO polypeptides provided herein also provide useful research reagents to further elucidate the role of erythropoietin in erythropoiesis, as well as the structure/function relationship of erythropoietin and an erythropoietin receptor. For example, modified EPO polypeptides can be useful for evaluating a substance for ability to regulate growth and differentiation of red blood cell progenitor cells. One exemplary assay to indicate the ability of a substance to regulate growth and differentiation of red blood cell progenitor cells is to compare of binding of the substance to an erythropoietin receptor with the binding of a modified EPO polypeptide to an erythropoietin receptor. If the binding to an erythropoietin receptor of the test substance (i.e., the substance to be evaluated) is comparable to the binding to the erythropoietin receptor of a modified EPO polypeptide, then the binding of the test substance is an indication that the ability of the substance to regulate growth and differentiation of red blood cell progenitor cells is of approximately the same ability as the modified secretable mutant erythropoietin. Binding to an erythropoietin receptor can be determined by using any of a number of methods familiar to those of skill in the art. For example, methods such as those described in Yonekura et al. (1991) *Proc. Natl. Acad. Sci. USA* 88: 1-5; Chem et al. (1990) *Blood* 76(11): 2204-2209; and Krystal (1983) *Exp. Hematol.* 11: 649-660, the teachings of which are incorporated herein by reference, can be used.

K. Combination Therapies

Any of the modified EPO polypeptides, and nucleic acid molecules encoding modified EPO polypeptides described herein can be administered in combination with, prior to, intermittently with, or subsequent to, other therapeutic agents or procedures including, but not limited to, other biologics, small molecule compounds and surgery. For any disease or condition, including all those exemplified above, for which EPO is indicated or has been used and for which other agents and treatments are available, EPO can be used in combination therewith. Hence, the modified EPO polypeptides provided herein similarly can be used. Depending on the disease or condition to be treated, exemplary combinations include, but are not limited to, combination with colony stimulating factors, hemoglobins, chemotherapeutic agents (e.g., cytokines, growth factors, hormones, photosensitizing agents, radionuclides, toxins, anti-metabolites, signaling modulators, anti-cancer antibiotics, anti-cancer antibodies, anti-cancer oligopeptides, angiogenesis inhibitors, radiation therapy, chemotherapeutic compounds, or a combination thereof), or iron (e.g., Tabron, Ferosol, Chromogen, Niferex, compositions of ferrous sulfate or ferrous fumarate, iron dextran).

Modified EPO polypeptides provided herein that are used to treat patients with a hemoglobinopathy, such as sickle cell anemia or hemoglobin E (Hb E)-$β^0$-thalassemia, can be co-administered with recombinant hemoglobin or agents that elevate endogenous production of fetal hemoglobin, such as, but not limited to, hydroxyurea and sodium phenylbutyrate or agents that block red blood cell dehydration, such as clotrimazole.

Modified EPO polypeptides provided herein can be co-administered or sequentially administered with one or more additional colony stimulating factors (CSF) including, cytokines, lymphokines, interleukins, hematopoietic growth factors which include but are not limited to GM-CSF (e.g., sargramostim, LEUKINE®, PROKINE®), G-CSF (e.g., filgrastim, NEUPOGEN®), c-mpl ligand (also known as thrombopoietin (TPO) or MGDF), M-CSF (also known as CSF-1), IL-1, IL-4, IL-2, IL-3, IL-5, IL 6, IL-7, IL-8, IL-9, IL-10, IL-11, IL-12, IL-13, IL-15, LIF, human growth hormone, B-cell growth factor, B-cell differentiation factor, eosinophil differentiation factor, and stem cell factor (SCF, c-kit ligand, steel factor), PIXY321 (a GMCSF/IL-3 fusion protein), or interferons, such as interferon-gamma. Modified EPO polypeptides provided herein can be used in combination with other erythropoietin forms (epoetin alfa, EPO-GEN®, PROCRIT®). Combinations of such factors with a modified EPO polypeptide provided herein can have the usual activity of each of the peptides or can have a biological or physiological activity that is greater than the additive activities of the factor and the modified EPO polypeptide alone. The combination also can provide an enhanced effect on the activity or an activity different from that expected by the presence of the EPO or the additional factor. The co-administration also can have an improved activity profile which can include reduction of undesirable biological activities associated with native human EPO. In addition to the list above, modified forms of the factors also can be used in such combinations (see e.g., IL-3 variants in WO 94/12639, WO 94/12638, WO 95/21197, and WO 95/21254; G-CSF receptor agonists in WO 97/12977; c-mpl receptor agonists in WO 97/12978; IL-3 receptor agonists in WO 97/12979; multifunctional receptor agonists in WO 97/12985). As used herein "IL-3 variants" refer to IL-3 variants taught in WO 94/12639 and WO 94/12638.

Modified EPO polypeptides provided herein also can be used in combination therapies for disease and disorders for which administration of a therapeutic compound or agent causes an anemia. For example, treatment of subjects with hepatitis C(HCV)-infection often involves administration of the combination of ribavirin (RBV) and interferon-alpha (IFN-α). Such therapy can lead to anemia (in up to 10% of individuals prescribed these medications) severe enough to warrant dose reductions or cessation of therapy, and a decrease in hemoglobin of >3 grams/dl (occurs in 54% of people treated with RBV and IFN-α). Combination treatment of ribavirin (RBV) and interferon-alpha (IFN-α) can alleviate the problems of therapy-induced anemia (U.S. Pat. No. 6,833, 351). Accordingly, modified EPO polypeptides provided herein can be used in combination therapies to treat anemia caused by ribavirin (RBV) and interferon-alpha (IFN-α) administration.

L. Articles of Manufacture and Kits

Pharmaceutical compounds of modified EPO polypeptides and other modified therapeutic polypeptides or nucleic acids encoding modified polypeptides thereof, or a derivative or a biologically active portion thereof can be packaged as articles of manufacture containing packaging material, a pharmaceutical composition which is effective for treating an EPO-mediated disease or disorder or therapeutic polypeptide-mediated disease or disorder, and a label that indicates that modified EPO polypeptide or nucleic acid molecule is to be used for treating a EPO-mediated disease or disorder or therapeutic polypeptide-mediated disease or disorder.

The articles of manufacture provided herein contain packaging materials. Packaging materials for use in packaging pharmaceutical products are well known to those of skill in the art. See, for example, U.S. Pat. Nos. 5,323,907, 5,052,558 and 5,033,352, each of which is incorporated herein in its entirety. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any EPO-mediated disease or disorder or therapeutic polypeptide-mediated disease or disorder.

Modified EPO polypeptides and other modified therapeutic polypeptides and nucleic acid molecules encoding the modified polypeptides thereof also can be provided as kits. Kits can include a pharmaceutical composition described herein and an item for administration. For example a modified EPO or other modified therapeutic polypeptide can be supplied with a device for administration, such as a syringe, an inhaler, a dosage cup, a dropper, or an applicator. The kit can, optionally, include instructions for application including dosages, dosing regimens and instructions for modes of administration. Kits also can include a pharmaceutical composition described herein and an item for diagnosis. For example, such kits can include an item for measuring the concentration, amount or activity of EPO or other therapeutic polypeptide or a EPO regulated system of a subject.

M. Antibodies to Modified EPO Polypeptides and Other Modified Therapeutic Polypeptides Antibodies can be generated that recognize the modified EPO polypeptides or other modified therapeutic polypeptides provided herein. Antibodies include, for example, monoclonal and polyclonal antibodies, single chain antibodies, chimeric antibodies, bifunctional or bispecific antibodies, humanized antibodies, human antibodies, and complementary determining region (CDR)-grafted antibodies, including compounds which include CDR or antigen-binding sequences, which specifically bind to a modified EPO polypeptide or other modified therapeutic polypeptide provided herein. Antibody fragments, including Fab, Fab', F(ab').sub.2, and Fv, also are provided. Screening assays to determine binding specificity or exclusivity of an antibody provided herein are well known in the art (see e.g., Harlow et al. (Eds), Antibodies A Laboratory Manual; Cold Spring Harbor Laboratory; Cold Spring Harbor, N.Y. (1988)).

Antibodies can be produced using any method well known in the art, using a modified EPO polypeptide and other modified therapeutic polypeptide provided, or fragment thereof that contains the modification or modifications. Immunogenic polypeptides can be isolated from natural sources, from recombinant host cells, or can be chemically synthesized. Modified EPO polypeptides and other modified therapeutic polypeptides also can be conjugated to a hapten such as keyhole limpet hemocyanin (KLH) in order to increase immunogenicity. Methods for synthesizing such peptides are known in the art, for example, as in Merrifield (1963) *J. Amer. Chem. Soc.* 85: 2149-2154; Krstenansky, et al. (1987) *FEBS Lett.* 211:10. Antibodies to a modified EPO polypeptide or other modified therapeutic polypeptide provided herein also can be prepared through immunization using a nucleic acid the encodes a modified EPO polypeptide (see e.g., Fan et al. (1999) *Nat. Biotech.* 17:870-872). DNA encoding a modified EPO polypeptide or other modified therapeutic polypeptide provide can be used to generate antibodies against the encoded polypeptide following topical administration of naked plasmid DNA or following injection, for example, intramuscular injection, of the DNA.

Non-human antibodies can be humanized by any methods known in the art. In one method, the non-human CDRs are inserted into a human antibody or consensus antibody framework sequence. Further changes can then be introduced into the antibody framework to modulate affinity or immunogenicity. Antibodies further include plastic antibodies or molecularly imprinted polymers (MIPs) (Haupt and Mosbauch (1998) *TIBTech* 16:468-475). Antibodies of this type can be useful, for example, in immunoaffinity separation, chromatography, solid phase extraction, immunoassays, for use as immunosensors, and for screening chemical or biological libraries. Advantages of antibodies of this type are that no animal immunization is required, the antibodies are relatively inexpensive to produce, they are resistant to organic solvents, and they are reusable over long period of time.

Antibodies that bind to modified EPO polypeptides or other modified therapeutic polypeptides provided herein can be used in diagnostic and therapeutic methods. For example, antibodies can be used in diagnostic assays to detect the presence, absence or amount of a modified therapeutic polypeptide in vivo, in vitro, or in situ, e.g., detecting its expression in specific cells, tissues, or serum. Various diagnostic assay techniques known in the art can be used, such as competitive binding assays, direct or indirect sandwich assays, and immunoprecipitation assays conducted in either heterogeneous or homogeneous phases (Zola (1987) Monoclonal Antibodies: A Manual of Techniques, CRC Press, Inc. 147-158).

Antibodies provided herein that recognize a modified EPO polypeptide can be specific to a modified EPO polypeptide. An antibody that is specific to a modified EPO polypeptide, as described herein, can bind to a modified EPO polypeptide with a higher affinity than a wild-type EPO polypeptide, an EPO polypeptide from another species (i.e. species variant), or other modified EPO polypeptide. An antibody that specifically recognizes a modified EPO polypeptide can be used in a diagnostic assay to distinguish a particular modified EPO polypeptide from a wild-type EPO polypeptide, an EPO polypeptide from another species (i.e. species variant), or other modified EPO polypeptide. In addition, an antibody can be labeled with a therapeutic moiety such as chemotherapeutic agent and used, for example, to reduce the number of cells that can internalize these polypeptides. Further, an antibody that recognizes a modified EPO polypeptide provided herein can act in a competitive or dominant negative fashion to interfere with or reduce an erythropoietin activity.

The antibodies used in the diagnostic assays can be labeled with a detectable moiety to facilitate detection. The detectable moiety can produce, either directly or indirectly, a detectable signal. For example, the detectable moiety can be a radioisotope, such as $^3$H, $^{14}$C, $^{32}$P, $^{35}$S, or $^{125}$I, a fluorescent, or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety can be employed, including those methods described by Hunter et al. (1962) Nature, 144: 945; David et al. (1974) Biochemistry, 13:1014; Pain et al. (1981) J. Immunol. Meth., 40: 219; and Nygren (1982) Histochem. and Cytochem. 30: 407. A moiety, such as a fluorescent molecule, can be linked to a modified therapeutic polypeptide, including an antibody that recognizes a modified EPO polypeptide, at any location within the polypeptide. Chemistries used for the linkage of various moieties to polypeptides are well known in the art. A moiety such as detection moiety can be linked to a modified therapeutic polypeptide, including an antibody, using, for example, carbodiimide conjugation (Bauminger and Wilchek (1980) Meth. Enzymol. 70:151-159). Carbodiimides comprise a group of compounds that have the general formula R—N=C=N—R', where R and R' can be aliphatic or aromatic, and are used for synthesis of polypeptide bonds. The preparative procedure is simple, relatively fast, and is carried out under mild conditions. Carbodiimide compounds attack carboxylic groups to change them into reactive sites for free amino groups. Carbodiimide conjugation has been used to conjugate a variety of compounds to carriers for the production of antibodies. The water soluble carbodiimide, 1-ethyl-3-(3-dimethylaminopropyl)carbodiimide (EDC) is useful for conjugating a moiety to a polypeptide, including an antibody provided herein.

Antibodies that bind to modified EPO polypeptides or other modified therapeutic polypeptides provided herein also are useful for the affinity purification of modified therapeutic polypeptides from recombinant cell culture or natural sources. In this process, the antibodies against the modified therapeutic polypeptide are immobilized on a suitable support, such a Sephadex resin or filter paper, using methods well known in the art. The immobilized antibody then is contacted with a sample containing the modified therapeutic polypeptide to be purified, and thereafter the support is washed with a suitable solvent that will remove substantially all the material in the sample except the modified therapeutic polypeptide, which is bound to the immobilized antibody. Finally, the support is washed with another suitable solvent that will release the modified therapeutic polypeptide from the antibody.

Antibodies specifically binding a modified EPO polypeptide or other modified therapeutic polypeptides identified herein can be administered for the treatment of various disorders in the form of pharmaceutical compositions. The formulation herein also can contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

N. Examples

The following examples are included for illustrative purposes only and are not intended to limit the scope of the embodiments provided herein.

EXAMPLE 1

Cloning and Generation EPO Mutants

1. Cloning of cDNA Encoding EPO and Insertion into a Mammalian Expression Vector The nucleotide sequence comprising the coding sequence of human erythropoietin (SEQ ID NO: 229) was amplified by polymerase chain reaction (PCR), using standard techniques known in the art, from the GeneStorm® Human Clone ID RG001720 (from ResGen ORF Expression Positive Collection—Catalog #H-K1000, Invitrogen; sequence is carried in mammalian expression plasmid pcDNA3.1/GS, Invitrogen, SEQ ID NO: 230), using the following primers:
EPO BamHI Forward Primer:

```
                                          (SEQ ID NO: 231)
5'-GGGAATTCCATATGGGGGTGCACGAATGTCCTGCCTGG-3'
and
```

EPO NdeI Reverse Primer:

```
                                          (SEQ ID NO: 232)
5'-CGGGATCCTCATCTGTCCCCTGTCCTGCAGGCCTCCC-3'.
```

The amplified sequence human erythropoietin cDNA sequence was cloned into pTOPO-TA vector (Invitrogen) to generate the plasmid pTOPO-TA-hEPO. The sequence of the EPO cDNA was checked by automatic DNA sequencing. The pTOPO-TA-hEPO plasmid was then digested with both NotI and SpeI restriction enzymes and hEPO fragment was subcloned into pNAUT digested with NotI and XbaI, to generate the construct pNAUT-hEPO (SEQ ID NO: 233). The sequence of the EPO-cDNA was confirmed by sequencing using the following primers:

```
pNAUT forward primer:
5'-TATAAGCAGAGCTCTCTG-3'       (SEQ ID NO: 234)

pNAUT reverse primer:
5'-CACAGTCGAGGCTGATCAG-3'.     (SEQ ID NO: 235)
```

The encoded mature form of the EPO polypeptide has a sequence of amino acids as set forth in SEQ ID NO: 2.

2. Generation of EPO Mutants

A collection of pre-designed, targeted mutants was generated such that each individual mutant was created and processed individually, and physically separated from each other and in addressable arrays. 2D-scanning technology, described herein and also described in published U.S. Application Nos. US-2004-0132977-A1 and US 2005-0202438 A1 was used to design and obtain hEPO mutants with improved resistance to proteolysis. Is-HITs were identified based upon (1) the protein property to be evolved (e.g., resistance to proteolysis or stability); (2) the amino acid sequence; and (3) the properties of individual amino acids.

LEADS Created for Higher Resistance to Proteolysis of EPO

Variants were designed using 2D-scanning to identify positions conferring resistance to proteolysis. Positions selected (is-HITs) on hEPO (SEQ ID NO: 2) were (numbering corresponds to amino acid positions in the mature hEPO polypeptide set forth in SEQ ID NO: 2, i.e., without the signal peptide): P2, P3, R4, L5, D8, R10, L12, E13, R14, Y15, L16, L17, E18, K20, E21, E23, E31, L35, E37, P42, D43, K45, F48, Y49, W51, K52, R53, M54, E55, E62, W64, L67, L69, L70, E72, L75, R76, L80, L81, P87, W88, E89, P90, L91, L93, D96, K97, L102, R103, L105, L108, L109, R110, L112, K116, E117, P121, P122, D123, P129, L130, R131, D136, F138, R139, K140, L141, F142, R143, Y145, F148, L149, R150, K152, L153, K154, L155, Y156, E159, R162, D165, R166.

The native amino acid at each of the is-HIT positions listed above was replaced by residues as listed in Table 19.

The EPO variants generated for testing increased resistance to proteolysis are listed in Table 20 (SEQ ID NOS: 3-201). The variants generated were as follows: P2S, P2A, P3S, P3A, R4H, R4Q, L5I, L5V, C7S, C7V, C7A, C7I, C7T, D8Q, D8H, D8N, R10H, R10Q, L12V, L12I, E13Q, E13H, E13N, R14H, R14Q, Y15H, Y15I, L16I, L16V, L17I, L17V, E18Q, E18H, E18N, K20Q, K20T, K20N, E21Q, E21H, E21N, E23Q, E23H, E23N, C29S, C29V, C29A, C29I, C29T, E31Q, E31H, E31N, L35V, L35I, E37Q, E37H, E37N, P42S, P42A, D43Q, D43H, D43N, K45Q, K45T, K45N, F48I, F48V, Y49H, Y49I, W51S, W51H, K52Q, K52T, K52N, R53H, R53Q, M54V, M54I, E55Q, E55H, E55N, E62Q, E62H, E62N, W64S, W64H, L67I, L67V, L69V, L69I, L70I, L70V, E72Q, E72H, E72N, L75V, L75I, R76H, R76Q, L80V, L80I, L81I, L81V, P87S, P87A, W88S, W88H, E89Q, E89H, E89N, P90S, P90A, L91I, L91V, L93V, L93I, D96Q, D96H, D96N, K97Q, K97T, K97N, L102V, L102I, R103H, R103Q, L105I, L105V, L108I, L108V, L109I, L109V, R110H, R110Q, L112V, L112I, K116Q, K116T, K116N, E117Q, E117H, E117N, P121S, P121A, P122S, P122A, D123Q, D123H, D123N, P129S, P129A, L130V, L130I, R131H, R131Q, D136Q, D136H, D136N, F138I, F138V, R139H, R139Q, K140N, K140Q, L141I, L141V, F142I, F142V, R143H, R143Q, Y145H, Y145I, F148I, F148V, L149I, L149V, R150H, R150Q, K152Q, K152T, K152N, L153I, L153V, K154Q, K154T, K154N, L155V, L155I, Y156H, Y156I, E159Q, E159H, E159N, R162H, R162Q, D165Q, D165H, D165N, R166H, and R166Q.

TABLE 20

List of human EPO variants for testing increased resistance to proteolysis

| | | | | | | | | | |
|---|---|---|---|---|---|---|---|---|---|
| P2S | P2A | P3S | P3A | R4H | R4Q | L5I | L5V | C7S | C7V |
| C7A | C7I | C7T | D8Q | D8H | D8N | R10H | R10Q | L12V | L12I |
| E13Q | E13H | E13N | R14H | R14Q | Y15H | Y15I | L16I | L16V | L17I |
| L17V | E18Q | E18H | E18N | K20Q | K20T | K20N | E21Q | E21H | E21N |
| E23Q | E23H | E23N | C29S | C29V | C29A | C29I | C29T | E31Q | E31H |
| E31N | L35V | L35I | E37Q | E37H | E37N | P42S | P42A | D43Q | D43H |
| D43N | K45Q | K45T | K45N | F48I | F48V | Y49H | Y49I | W51S | W51H |
| K52Q | K52T | K52N | R53H | R53Q | M54V | M54I | E55Q | E55H | E55N |
| E62Q | E62H | E62N | W64S | W64H | L67I | L67V | L69V | L69I | L70I |
| L70V | E72Q | E72H | E72N | L75V | L75I | R76H | R76Q | L80V | L80I |
| L81I | L81V | P87S | P87A | W88S | W88H | E89Q | E89H | E89N | P90S |
| P90A | L91I | L91V | L93V | L93I | D96Q | D96H | D96N | K97Q | K97T |
| K97N | L102V | L102I | R103H | R103Q | L105I | L105V | L108I | L108V | L109I |
| L109V | R110H | R110Q | L112V | L112I | K116Q | K116T | K116N | E117Q | E117H |
| E117N | P121S | P121A | P122S | P122A | D123Q | D123H | D123N | P129S | P129A |
| L130V | L130I | R131H | R131Q | D136Q | D136H | D136N | F138I | F138V | R139H |
| R139Q | K140N | K140Q | L141I | L141V | F142I | F142V | R143H | R143Q | Y145H |
| Y145I | F148I | F148V | L149I | L149V | R150H | R150Q | K152Q | K152T | K152N |
| L153I | L153V | K154Q | K154T | K154N | L155V | L155I | Y156H | Y156I | E159Q |
| E159H | E159N | R162H | R162Q | D165Q | D165H | D165N | R166H | R166Q | |

TABLE 19

| Amino acid at is-HIT | Replacing amino acids |
|---|---|
| R | H, Q |
| E | Q, H, N |
| K | Q, T, N |
| D | Q, H, N |
| M | I, V |
| P | A, S |
| Y | I, H |
| F | I, V |
| W | H, S |
| L | I, V |

EXAMPLE 2

Production of Native and Modified Human EPO Polypeptides (Proteins) in Mammalian Cells and Yield Determination Chinese Hamster Ovary (CHO) cells were grown in Dulbecco's Modified Eagle's Medium (DMEM, Invitrogen) with 10% fetal calf serum (FCS). The day before transfection, the CHO cells were plated in 6-well plates at a density of $5 \times 10^5$ cells per well in DMEM with 10% FCS (without antibiotics), at 37° C. in a humid atmosphere with a composition of 7% $CO_2$ to achieve 50-90% confluency the following day for transfection.

CHO cells were transfected with 2 μg of EPO mutant DNA using Perfectin reagent (Ozyme) according to the manufacturer instructions. Cell plates were incubated for 4 hours in Opti-MEM® reduced serum medium (Invitrogen) post-transfection at 37° C. in a humid atmosphere with a composition of 7% $CO_2$. Following incubation, the transfection medium was replaced with 1 ml of fresh DMEM medium containing 1% FCS. Cell supernatants were collected 96 hours later, aliquoted into 96-well-plates, and stored at −80° C.

Concentrations of hEPO variant polypeptides in the collected cell supernatants was determined using a human erythropoietin specific ELISA kit (IBL, Hamburg, Germany) according to manufacturer instructions. hEPO variant concentration are standardized for use protease resistance assays.

EXAMPLE 3

Determination of Specific Activity of Human EPO by TF-1 Proliferative Assay

Proliferation assays were performed for each aliquot sample undertaken at different time points of the protease degradation kinetic in the human erythroleukemia cell line TF-1 bioassay in order to determine residual proliferative activity ($EC_{50}$) contained in each kinetic point samples.

TF-1 cell line was maintained in RPMI 1640 medium (Invitrogen) supplemented with 10% FCS, 2 mM L-glutamine and 2 ng/ml of human recombinant GM-CSF at 37° C. in a humid atmosphere with a composition of 7% CO2/95% air in T175 (175 cm$^2$) polystyrene tissue culture flask and split two times per week. Twenty four hours before use in proliferation assays, cells were washed two times in ice cold PBS and re-suspended for 16 hours in GM-CSF free RPMI medium supplemented with 2 mM glutamine and 10% FCS.

TF1 cells were plated into 96-well plate at 4×10$^4$ cells per well in 70 µl of GM-CSF free RPMI medium supplemented with 2 mM glutamine and 10% FCS. Each aliquot sample was subjected to a two-fold serial dilution into 96-Deep-well plates and EPO dilutions (30 µl) were added to each well containing 70 µl of TF-1 cells with a final concentration ranging from 70000 to 34.2 pg/ml. Each EPO sample dilution was assessed in triplicate. No GM-CSF was added to the last row ("G" row) of the flat-bottomed 96-well plates in order to evaluate basal absorbance of non proliferative cells. A 2-fold serial dilution (70000 to 34.2 pg/ml) of internal positive controls including both the second international standard for EPO(NIBSC, 88/574) and the first international standard for GMCSF (NIBSC, 88/646) also were performed and added in triplicate to plate assay in order to standardize proliferation results.

The plates were incubated for 48 hours at 37° C. in a humidified, 7% CO2 atmosphere. After 48 hours of growth, 20 µl of Cell titer 96 Aqueous one solution reagent (Promega) was added to each well and incubated 3 hours at 37° C. in an atmosphere of 7% CO2. To measure the amount of colored soluble formazan produced by cellular reduction of the MTS, the absorbance of the dye was measured using an Elisa plate reader (Spectramax®) at 490 nm.

The corrected absorbances ("G" row basal value subtracted) obtained at 490 nm were plotted versus concentration of cytokine. The $EC_{50}$ value was calculated by determining the X-axis value corresponding to one-half the difference between the maximum and minimum absorbance values. ($EC_{50}$=the concentration of cytokine necessary to give one-half the maximum response).

EXAMPLE 4

Resistance to Proteolysis

EPO variants were tested for protease resistance. To evaluate the protection of EPO mutants compared to wild-type EPO, enzymatic cleavage at different time treatment at 37° C. was performed. For each of the EPO mutants and EPO native protein, a solution mixture of proteases was prepared by mixing 400 µl of serum-free RPMI medium with a 1.5% protease mixture (wt/wt) containing each of the following proteases α-chymotrypsin, endoproteinase GluC and trypsin (Sigma). For the kinetic analysis, proteolytic degradation was initiated by adding the protease mixture solution to 557.2 ng of each EPO mutants or native protein in 300 µl of DMEM medium supplemented with 1% FCS (CHOK1 culture medium). Incubation times were: 0 h, 0.5 h, 1 h, 2, 3 h, 4 h, 5 h, 6 h, and 7 h. At the different kinetic time points, for each sample, a 70 µl of aliquot was taken and mixed with 10 µl of anti-proteases mixture (mini EDTA free, Roche—one tablet was dissolved in 10 ml of RPMI supplemented with 10% FCS) in order to stop proteolysis reactions. Samples were stored at −80° C. until determination of residual proliferative activity.

Cell proliferation induction activity of the treated samples was assayed as described in Example 3 to determine residual proliferative activity at each time point. Resistance to proteases for exemplary non-limiting modified EPO polypeptides is displayed in Table 21 as either no change or increased resistance to proteases as compared to the residual proliferative activity of native EPO under the same protease treatment conditions.

The data are not meant to be representative of all proteases, but are exemplary data showing the resistance to proteolysis to an exemplary protease cocktail containing the proteases as described above. Thus, the data are not comprehensive and are not meant to be indicative that other EPO polypeptides do not exhibit protease resistance.

TABLE 21

Resistance to proteolysis of EPO native and mutant proteins

| Nemo Code # | Mutation | Resistance to proteases |
| --- | --- | --- |
| 1 | P2S | nt |
| 2 | P2A | − |
| 3 | P3S | − |
| 4 | P3A | + |
| 5 | R4H | + |
| 6 | R4Q | + |
| 7 | C7S | nt |
| 8 | C7V | nt |
| 9 | D8Q | + |
| 10 | D8H | − |
| 11 | R10H | + |
| 12 | R10Q | − |
| 13 | L12V | − |
| 14 | L12I | − |
| 15 | E18Q | + |
| 16 | E18H | − |
| 17 | K20Q | + |
| 18 | K20T | − |
| 19 | E21Q | + |
| 20 | E21H | − |
| 21 | E23Q | − |
| 22 | E23H | − |
| 23 | C29S | nt |
| 24 | C29V | nt |
| 25 | E31Q | + |
| 26 | E31H | − |
| 27 | L35V | − |
| 28 | L35I | − |
| 29 | E37Q | + |
| 30 | E37H | nt |
| 31 | P42S | nt |
| 32 | P42A | nt |
| 33 | D43Q | nt |
| 34 | D43H | nt |
| 35 | K45Q | − |
| 36 | K45T | + |
| 37 | F48I | − |
| 38 | F48V | + |
| 39 | Y49H | − |
| 40 | Y49I | + |
| 41 | W51S | − |
| 42 | W51H | nt |
| 43 | K52Q | + |
| 44 | K52T | − |

TABLE 21-continued

Resistance to proteolysis of EPO native and mutant proteins

| Nemo Code # | Mutation | Resistance to proteases |
|---|---|---|
| 45 | R53H | + |
| 46 | R53Q | nt |
| 47 | M54V | − |
| 48 | M54I | − |
| 49 | E55Q | − |
| 50 | E55H | nt |
| 51 | E62Q | − |
| 52 | E62H | − |
| 53 | W64S | + |
| 54 | W64H | − |
| 55 | L69V | − |
| 56 | L69I | + |
| 57 | E72Q | nt |
| 58 | E72H | nt |
| 59 | L75V | nt |
| 60 | L75I | + |
| 61 | R76H | − |
| 62 | R76Q | − |
| 63 | L80V | − |
| 64 | L80I | + |
| 65 | P87S | + |
| 66 | P87A | + |
| 67 | W88S | − |
| 68 | W88H | nt |
| 69 | E89Q | + |
| 70 | E89H | + |
| 71 | P90S | + |
| 72 | P90A | nt |
| 73 | L93V | + |
| 74 | L93I | + |
| 75 | D96Q | + |
| 76 | D96H | + |
| 77 | K97Q | nt |
| 78 | K97T | nt |
| 79 | L102V | + |
| 80 | L102I | + |
| 81 | R110H | + |
| 82 | R110Q | + |
| 83 | L112V | nt |
| 84 | L112I | nt |
| 85 | K116Q | + |
| 86 | K116T | + |
| 87 | P121S | nt |
| 88 | P121A | + |
| 89 | P122S | + |
| 90 | P122A | + |
| 91 | D123Q | nt |
| 92 | D123H | + |
| 93 | P129S | + |
| 94 | P129A | + |
| 95 | L130V | nt |
| 96 | L130I | + |
| 97 | R131H | + |
| 98 | R131Q | + |
| 99 | D136Q | nt |
| 100 | D136H | nt |
| 101 | R143H | + |
| 102 | R143Q | + |
| 103 | Y145H | nt |
| 104 | Y145I | nt |
| 105 | R150H | + |
| 106 | R150Q | + |
| 107 | K152Q | nt |
| 108 | K152T | nt |
| 109 | K154Q | − |
| 110 | K154T | nt |
| 111 | L155V | nt |
| 112 | L155I | nt |
| 113 | E159Q | − |
| 114 | E159H | nt |
| 115 | R162H | nt |
| 116 | R162Q | nt |
| 117 | C29A | nt |
| 118 | C29I | nt |
| 119 | C29T | nt |
| 120 | C7A | nt |
| 121 | C7I | nt |
| 122 | C7T | nt |
| 123 | D123N | + |
| 124 | D136N | + |
| 125 | D43N | nt |
| 126 | D96N | − |
| 127 | E159N | + |
| 128 | E18N | nt |
| 129 | E21N | nt |
| 130 | E23N | nt |
| 131 | E31N | nt |
| 132 | E37N | nt |
| 133 | E55N | + |
| 134 | E62N | nt |
| 135 | E72N | nt |
| 136 | E89N | nt |
| 137 | K116N | + |
| 138 | K152N | + |
| 139 | K154N | nt |
| 140 | K20N | nt |
| 141 | K45N | + |
| 142 | K52N | + |
| 143 | K97N | nt |
| 144 | D8N | nt |
| 145 | D165Q | + |
| 146 | D165H | + |
| 147 | D165N | + |
| 148 | R166H | + |
| 149 | R166Q | + |
| 354 | L5I | nt |
| 355 | L5V | − |
| 356 | E13Q | nt |
| 357 | E13H | nt |
| 358 | E13N | nt |
| 359 | R14H | nt |
| 360 | R14Q | nt |
| 361 | Y15H | nt |
| 362 | Y15I | nt |
| 363 | L16I | + |
| 364 | L16V | nt |
| 365 | L17I | nt |
| 366 | L17V | nt |
| 367 | L67I | + |
| 368 | L67V | nt |
| 369 | L70I | nt |
| 370 | L70V | nt |
| 371 | L81I | nt |
| 372 | L81V | nt |
| 373 | L91I | nt |
| 374 | L91V | + |
| 375 | R103H | nt |
| 376 | R103Q | nt |
| 377 | L105I | + |
| 378 | L105V | nt |
| 379 | L108I | nt |
| 380 | L108V | nt |
| 381 | L109I | nt |
| 382 | L109V | − |
| 383 | E117Q | nt |
| 384 | E117H | nt |
| 385 | E117N | nt |
| 386 | F138I | nt |
| 387 | F138V | nt |
| 388 | R139H | nt |
| 389 | R139Q | nt |
| 390 | K140N | nt |
| 391 | K140Q | nt |
| 392 | L141I | nt |
| 393 | L141V | nt |
| 394 | F142I | nt |
| 395 | F142V | nt |
| 396 | F148I | nt |

TABLE 21-continued

Resistance to proteolysis of EPO native and mutant proteins

| Nemo Code # | Mutation | Resistance to proteases |
|---|---|---|
| 397 | F148V | nt |
| 398 | L149I | nt |
| 399 | L149V | nt |
| 400 | L153I | nt |
| 401 | L153V | + |
| 402 | Y156H | nt |
| 403 | Y156I | nt |

− = no change;
+ = Increased resistance to proteolysis;
nt = not tested

In a second experiment, resistance to proteolysis was measured using a higher concentration of proteases. The protocol used for the assay was the same as described above except that a 3% protease mixture (wt/wt) containing each of the following proteases, α-chymotrypsin, Endoproteinase GluC and trypsin (Sigma), was used for proteolysis. Data from this experiment is presented in Table 22. The data is expressed as relative resistance to proteases among the samples tested: (+), (++), or (+++), with (+++) indicating the highest resistance to proteases.

TABLE 22

Resistance to proteolysis of EPO native and mutant proteins

| Nemo Code # | Mutation | Resistance to proteases |
|---|---|---|
| 1 | P2S | − |
| 2 | P2A | − |
| 3 | P3S | − |
| 4 | P3A | +++ |
| 5 | R4H | + |
| 6 | R4Q | + |
| 7 | C7S | nt |
| 8 | C7V | nt |
| 9 | D8Q | − |
| 10 | D8H | − |
| 11 | R10H | + |
| 12 | R10Q | − |
| 13 | L12V | − |
| 14 | L12I | − |
| 15 | E18Q | + |
| 16 | E18H | − |
| 17 | K20Q | +++ |
| 18 | K20T | − |
| 19 | E21Q | + |
| 20 | E21H | − |
| 21 | E23Q | − |
| 22 | E23H | − |
| 23 | C29S | nt |
| 24 | C29V | nt |
| 25 | E31Q | + |
| 26 | E31H | − |
| 27 | L35V | − |
| 28 | L35I | − |
| 29 | E37Q | + |
| 30 | E37H | − |
| 31 | P42S | nt |
| 32 | P42A | nt |
| 33 | D43Q | − |
| 34 | D43H | − |
| 35 | K45Q | − |
| 36 | K45T | ++ |
| 37 | F48I | ++ |
| 38 | F48V | + |
| 39 | Y49H | − |
| 40 | Y49I | + |
| 41 | W51S | − |
| 42 | W51H | − |
| 43 | K52Q | ++ |
| 44 | K52T | + |
| 45 | R53H | + |
| 46 | R53Q | nt |
| 47 | M54V | − |
| 48 | M54I | − |
| 49 | E55Q | − |
| 50 | E55H | − |
| 51 | E62Q | − |
| 52 | E62H | − |
| 53 | W64S | − |
| 54 | W64H | − |
| 55 | L69V | − |
| 56 | L69I | + |
| 57 | E72Q | nt |
| 58 | E72H | nt |
| 59 | L75V | − |
| 60 | L75I | + |
| 61 | R76H | − |
| 62 | R76Q | − |
| 63 | L80V | − |
| 64 | L80I | ++ |
| 65 | P87S | + |
| 66 | P87A | + |
| 67 | W88S | − |
| 68 | W88H | nt |
| 69 | E89Q | ++ |
| 70 | E89H | ++ |
| 71 | P90S | ++ |
| 72 | P90A | + |
| 73 | L93V | + |
| 74 | L93I | +++ |
| 75 | D96Q | +++ |
| 76 | D96H | + |
| 77 | K97Q | − |
| 78 | K97T | − |
| 79 | L102V | − |
| 80 | L102I | − |
| 81 | R110H | − |
| 82 | R110Q | + |
| 83 | L112V | − |
| 84 | L112I | nt |
| 85 | K116Q | + |
| 86 | K116T | ++ |
| 87 | P121S | − |
| 88 | P121A | + |
| 89 | P122S | + |
| 90 | P122A | + |
| 91 | D123Q | ++ |
| 92 | D123H | + |
| 93 | P129S | + |
| 94 | P129A | + |
| 95 | L130V | ++ |
| 96 | L130I | +++ |
| 97 | R131H | + |
| 98 | R131Q | ++ |
| 99 | D136Q | − |
| 100 | D136H | − |
| 101 | R143H | ++ |
| 102 | R143Q | +++ |
| 103 | Y145H | nt |
| 104 | Y145I | nt |
| 105 | R150H | +++ |
| 106 | R150Q | + |
| 107 | K152Q | − |
| 108 | K152T | − |
| 109 | K154Q | − |
| 110 | K154T | − |
| 111 | L155V | − |
| 112 | L155I | − |
| 113 | E159Q | − |
| 114 | E159H | − |

TABLE 22-continued

Resistance to proteolysis of EPO native and mutant proteins

| Nemo Code # | Mutation | Resistance to proteases |
|---|---|---|
| 115 | R162H | − |
| 116 | R162Q | − |
| 117 | C29A | nt |
| 118 | C29I | nt |
| 119 | C29T | − |
| 120 | C7A | nt |
| 121 | C7I | nt |
| 122 | C7T | nt |
| 123 | D123N | ++ |
| 124 | D136N | ++ |
| 125 | D43N | + |
| 126 | D96N | + |
| 127 | E159N | +++ |
| 128 | E18N | − |
| 129 | E21N | − |
| 130 | E23N | − |
| 131 | E31N | − |
| 132 | E37N | − |
| 133 | E55N | − |
| 134 | E62N | − |
| 135 | E72N | − |
| 136 | E89N | + |
| 137 | K116N | ++ |
| 138 | K152N | − |
| 139 | K154N | nt |
| 140 | K20N | − |
| 141 | K45N | ++ |
| 142 | K52N | ++ |
| 143 | K97N | − |
| 144 | D8N | − |
| 145 | D165Q | ++ |
| 146 | D165H | ++ |
| 147 | D165N | ++ |
| 148 | R166H | ++ |
| 149 | R166Q | + |
| 354 | L5I | − |
| 355 | L5V | − |
| 356 | E13Q | − |
| 357 | E13H | − |
| 358 | E13N | − |
| 359 | R14H | − |
| 360 | R14Q | − |
| 361 | Y15H | − |
| 362 | Y15I | − |
| 363 | L16I | ++ |
| 364 | L16V | ++ |
| 365 | L17I | ++ |
| 366 | L17V | + |
| 367 | L67I | nt |
| 368 | L67V | nt |
| 369 | L70I | nt |
| 370 | L70V | nt |
| 371 | L81I | − |
| 372 | L81V | − |
| 373 | L91I | − |
| 374 | L91V | − |
| 375 | R103H | − |
| 376 | R103Q | − |
| 377 | L105I | + |
| 378 | L105V | − |
| 379 | L108I | − |
| 380 | L108V | − |
| 381 | L109I | − |
| 382 | L109V | − |
| 383 | E117Q | − |
| 384 | E117H | − |
| 385 | E117N | − |
| 386 | F138I | nt |
| 387 | F138V | − |
| 388 | R139H | +++ |
| 389 | R139Q | +++ |
| 390 | K140N | − |
| 391 | K140Q | − |
| 392 | L141I | − |
| 393 | L141V | − |
| 394 | F142I | nt |
| 395 | F142V | nt |
| 396 | F148I | nt |
| 397 | F148V | nt |
| 398 | L149I | − |
| 399 | L149V | − |
| 400 | L153I | − |
| 401 | L153V | ++ |
| 402 | Y156H | − |
| 403 | Y156I | nt |

− = no change;
+ = Increased Resistance to proteolysis;
nt = not tested

For selection of EPO LEADS, residual proliferative activity was compared to the protein concentration of non-degraded EPO protein following exposure to proteases. EPO protein concentration for the experiment above (presented in Table 22) was determined using a human specific ELISA kit (R&D Systems) according to the manufacturer's instructions. The leads were selected by correlation of the two assays for level of residual proliferative activity relative to the amount of EPO protein in the sample to determine the EPO polypeptides with increased resistance to proteases. The data for selected EPO LEADs is presented in Table 23. The data is expressed as relative resistance to proteases among the selected EPO LEADs: (+), or (+++), with (+++) indicating the highest resistance to proteases.

TABLE 23

Selected EPO LEADs

| Nemo Code # | Mutation | Resistance to proteases |
|---|---|---|
| 5 | R4H | +++ |
| 105 | R150H | +++ |
| 102 | R143Q | +++ |
| 127 | E159N | +++ |
| 388 | R139H | +++ |
| 389 | R139Q | +++ |
| 74 | L93I | +++ |
| 75 | D96Q | +++ |
| 96 | L130I | +++ |
| 401 | L153V | +++ |
| 17 | K20Q | +++ |
| 37 | F48I | ++ |
| 98 | R131Q | ++ |
| 141 | K45N | ++ |
| 142 | K52N | ++ |
| 43 | K52Q | ++ |
| 64 | L80I | ++ |
| 86 | K116T | ++ |
| 123 | D123N | ++ |
| 124 | D136N | ++ |
| 71 | P90S | ++ |
| 145 | D165Q | ++ |
| 146 | D165H | ++ |
| 147 | D165N | ++ |
| 137 | K116N | ++ |
| 101 | R143H | ++ |
| 148 | R166H | ++ |
| 363 | L16I | ++ |
| 364 | L16V | ++ |

The data presented in the tables above are exemplary showing the resistance to proteolysis in a particular experiment with an exemplary protease cocktail containing the proteases as described above. Thus, the data are not comprehensive and are not meant to be indicative that other EPO polypeptides do not exhibit protease resistance.

EXAMPLE 5

Identification of Possible Sites for Proteolysis that are Hidden by Glycosylation To identify sensitive sites to proteolysis that could be hidden by glycosylation on native EPO, EPO variants containing the amino acid substitution N24H (SEQ ID NO:244), N38H (SEQ ID NO:245) or N83H (SEQ ID NO:246), respectively, were generated and tested for their resistance to proteolysis. Each de-glycosylated variant was expressed in CHO cells. Briefly, the day before transfection, CHO cells were plated into 6-well plates at 5×10^5 cells per well in DMEM medium (Invitrogen, CA) containing 10% FCS at 37° C. in a humid atmosphere, CHO cells were transfected with 2 µg of EPO mutant DNA using Perfectin reagent (Ozyme, France) according to the manufacturer instructions. The transfected cells were incubated for 4 hours in Optimem medium (Invitrogen, CA) post-transfection at 37° C. in a humid atmosphere. The transfection medium was then replaced with 1 ml of fresh DMEM medium containing 1% FCS and cell supernatants containing the EPO polypeptides were harvested 96 hours later, aliquoted and stored at −80° C. The concentration of each EPO variant was standardized using Quantikine IVD human EPO ELISA kit (R&D Systems, UK), according to manufacturer instructions.

To evaluate the sensitivity to proteases of each variant, compared to a fully glycosylated native EPO polypeptide, enzymatic cleavage during incubation with a set of proteases was performed. A mixture of proteases was prepared by mixing 400 µl of serum-free RPMI medium with a 1.5% protease mixture (wt/wt) containing α-chymotrypsin, Endoproteinase GluC and trypsin (Sigma). Proteolytic degradation kinetic was initiated by adding the protease mixture solution to each EPO polypeptide in DMEM medium supplemented with 1% FCS (CHOK1 culture medium). The EPO polypeptides were incubated with the proteases at 37° C. An aliquot was taken from each sample at the different kinetic time points (0 hr, 0.5 hr, 1 hr, 2 hr, 3 hr, 4 hr, 5 hr, 6 hr, and 8 hr) and mixed with an anti-protease mixture (mini EDTA free, Roche—one tablet was dissolved in 10 ml of RPMI supplemented with 10% FCS) to stop proteolysis. The samples were frozen at −80° C. before the concentration of EPO in each sample was determined by ELISA, as described above.

It was observed that mutation of the N38 glycosylation site resulted in an EPO variant that was highly susceptible to proteolysis. Mutation of the N83 and N24 glycosylation sites resulted in EPO variants that were susceptible to proteolysis at intermediate or lower levels, respectively. Thus, N38 was found to be the most sensitive site, N83 was considered the intermediate site and N24 was considered the less sensitive site.

Analysis of the distance from the N-glycosylation sites to is-HITs identified in Example 1.2 as sites that are sensitive to proteolysis was performed to determine which of the is-HITs may be "hidden" in glycosylated EPO polypeptides, but exposed to proteases upon de-glycosylation. Table 24 provides is-HITs (numbering corresponds to amino acid positions in the mature hEPO polypeptide set forth in SEQ ID NO: 2, i.e., without the signal peptide) that are within a radius of 10 Å or 15 Å from the sites of glycosylation.

TABLE 24

Distance of is-HITs from N-glycosylation sites

| N-glycosylation site | is-HITs within 10 Å from N-Glycosylation sites | is-HITs within 15 Å from N-Glycosylation sites |
| --- | --- | --- |
| N24 | L17, K20, E21, E23, F142, R143 | R14, L16, E18, E31, W88, E89, P90, L91, L93, K97, F138, R139, K140, L141, Y145 |
| N38 | L35, E37, R76, L80, D136, F138, K140 | P42, D43, L69, L70, E72, L75, L81, P129, L130, R131, R139, L141, F142 |
| N83 | L35, L75, R76, L80, L81 | E37, E72, P87, W88, P90, L91, L93, D96 |

EXAMPLE 6

Generation of De-Glycosylated EPO Variants with Increased Resistance to Proteolysis EPO polypeptides with reduced glycosylation were modified at one or more selected is-HIT positions to generate de-glycosylated EPO variants with increased resistance to proteolysis. Three initial pathways were followed to identify mutations that have a protective effect on the partially de-glycosylated EPO mutants, described in sections 1-3, below. The EPO polypeptides were incrementally de-glycosylated by serial mutation of one of N38 and N83. For each round of de-glycosylation, mutations at selected is-HIT positions also were introduced into the polypeptide to remove sites sensitive to proteolysis and determine which mutations were protective for variants de-glycosylated at N38 and N83. These mutations included the amino acid substitutions R139H, K20Q, E159N, L153V, K52N, L80I, L93I, L93V, and R4H, which are mutations carried by the LEADs identified in Examples 1-4 as having a protective effect against proteolysis. The EPO variants were assessed for protease resistance and variants that displayed increased protease resistance were used as the template into which new mutations were introduced. The final step of the process, described in section 4, below, involved mutation of the last N-glycosylation site, N24, and incorporation of mutations shown to be protective to generate EPO variants with no N-glycosylation that were protected against proteolysis.

The EPO variants were generated and expressed using the methods described in Example 1 and 2, above, and the concentrations were determined by ELISA, as described above. A fully glycosylated native EPO polypeptide also produced. A fully non-glycosylated EPO polypeptide was generated by de-glycosylation of a glycosylated EPO protein (European pharmacopeia (EP) reference standard; E1515000, Batch 3.0). De-glycosylation was effected using the GlycoPro Enzymatic Deglycosylation Kit (Prozyme, GK80110) according to the manufacturer's instructions. Briefly, 1×10^7 pg/ml of EPO was incubated overnight at 37° C. with 1× incubation buffer containing N-glycanase PNGase F, Sialidase A, O-Glycanase, Galactosidase b (1-4) and b-N-Acetyl Glucosaminidase.

To evaluate the resistance to proteolysis of the EPO mutants and control polypeptides (fully glycosylated native EPO, and fully de-glycosylated EPO), enzymatic cleavage at 37° C. over a period of time was performed. A mixture of proteases was prepared by mixing 400 µl of FCS free RPMI medium with a 1.5% protease mixture (wt/wt) containing α-chymotrypsin, Endoproteinase GluC and trypsin (Sigma). Proteolytic degradation kinetic was initiated by adding the protease mixture solution to each EPO polypeptide in DMEM medium supplemented with 1% FCS (CHOK1 culture medium). The EPO polypeptides were incubated with the proteases at 37° C. An aliquot was taken from each sample at the different kinetic time points and mixed with an anti-protease preparation (mini EDTA free, Roche—one tablet was dissolved in 10 ml of RPMI supplemented with 10% FCS) to stop proteolysis. The samples were frozen at −80° C. before the remaining concentration of EPO in each sample was determined using a Quantikine IVD human EPO ELISA kit (R&D Systems, UK). The percentage of the original concentration prior to proteolysis was then determined.

1. Generation of Partially De-Glycosylated N38H EPO Variants with Increased Resistance to Proteolysis The first experimental pathway identified protease-resistant EPO polypeptides that were partially de-glycosylated due to the N38H mutation. To reverse the sensitivity to proteolysis observed for the partially de-glycosylated EPO polypeptide containing the N38H mutation, select LEAD mutations identified in Examples 2 to 4 were serially incorporated into the N38H variant polypeptide and tested for resistance to proteolysis. EPO polypeptides with full glycosylation or no glycosylation (i.e. full de-glycosylation) also were tested.

The R139H mutation was first incorporated into the N38H variant to generate the N38H/R139H EPO variant (SEQ ID NO:247). The N38H variant, and fully glycosylated and de-glycosylated polypeptides also were assayed, as described above, for resistance to proteolysis. The EPO variant containing both the N38H and R139H mutations showed a degree of sensitivity to proteolysis similar to that of the fully glycosylated native EPO. The concentration of both the fully glycosylated EPO and the partially de-glycosylated N38H/R139H EPO variant after 1 hour of proteolysis was 48% and 44%, respectively, of the starting concentration. In comparison, only 17% of the unprotected N38H variant remained after 1 hour. Essentially all of the fully de-glycosylated EPO polypeptide was cleaved by the proteases during the 1 hour incubation. After 2 hours of proteolysis, only 2% of the unprotected N38H variant remained, compared to 15% and 14% of the of the fully glycosylated EPO and the partially de-glycosylated N38H/R139H EPO variant, respectively. These results indicated that the R139H mutation was able to replace the protective effect that glycosylation at amino acid position N38 normally affords the EPO polypeptide.

Additional mutations identified in Examples 2 to 4 and contained in LEADs were then incorporated into the EPO variant carrying the N38H and R139H mutations to generate triple mutant EPO polypeptides. EPO polypeptides containing the N38H/R139H double mutation and R4H (SEQ ID NO:248), L93I (SEQ ID NO:249), K20Q (SEQ ID NO:250), E159N (SEQ ID NO:251), K52N (SEQ ID NO:252) and L153V (SEQ ID NO:253), respectively, were generated and assessed for susceptibility to various proteases. In some instances, the incorporation of a LEAD mutation into the N38H/R139H EPO variant to remove additional protease sensitive sites resulted in increased resistance to proteolysis compared to the both the N38H/R139H double mutant, and the fully glycosylated native EPO. After 1 hour of proteolysis, approximately 46% the N38H/R139H variant and the fully-glycosylated EPO polypeptide remained. Similar or slightly better results were obtained for the variants carrying the N38H/R139H/R4H, N38H/R139H/K52N or N38H/R139H/L93I mutations. The concentration of the partially de-glycosylated N38H/R139H/L153V and N38H/R139H/E159N variants after 1 hour of proteolysis was approximately 60% of the starting concentration. The triple N38H/R139H/K20Q variant was identified as the variant with the most resistance to proteolysis, with 64% of the protein remaining after 1 hour of proteolysis. After 2 hours incubation with the proteases, 43% of the N38H/R139H/K20Q variant remained, compared to approximately 14% and 18% of the N38H/R139H mutant and the fully glycosylated native EPO, respectively.

2. Generation of Partially De-Glycosylated N38H/N83H EPO Variants with Increased Resistance to Proteolysis The second experimental pathway identified protease-resistant EPO polypeptides that were partially de-glycosylated due mutation of both the N38 and N83. The R139H mutation was incorporated into an EPO variant containing the N38H/N83H double mutation. The resulting N38H/N83H/R139H variant (SEQ ID NO: 254) was used as a template into which a further mutation, K20Q, was incorporated, generating the quadruple mutant K20Q/N38H/N83H/R139H (SEQ ID NO:255). The EPO variants were expressed in CHO cells and assayed for proteolysis resistance, as described above. EPO variants containing the single N38H mutation or the double N38H/R139H mutation, and fully glycosylated and de-glycosylated EPO polypeptides, also were assayed for protease resistance. The N38H/N83H/R139H variant exhibited reduced resistance to proteolysis compared to the N38H/R139H variant and the fully glycosylated EPO protein, with just 17% remaining after 1 hour of proteolysis, compared to 45% and 49%, respectively. This demonstrated how much protection against proteolysis glycosylation at N83 affords EPO polypeptides. This protection was restored, however, by incorporation of the K20Q mutation. The quadruple K20Q/N38H/N83H/R139H mutant exhibited a similar degree of resistance to proteolysis as that observed for the N38H/R139H variant and the fully glycosylated EPO protein. After 1 hour of proteolysis, 48% of the K20Q/N38H/N83H/R139H variant remained. After 2 hours of proteolysis, 21% remained, which was slightly more than observed for the N38H/R139H variant (16%) and slightly less than the fully glycosylated EPO protein (25%).

3. Generation of Partially De-Glycosylated N38H/N83H EPO Variants with Increased Resistance to Proteolysis The third experimental pathway utilized the N38H/N83H/R139H variant as a template into which additional mutations were incorporated to assess the ability of these mutations to increase resistance to proteolysis. EPO variants containing N38H/N83V/R139H and one of L93V (SEQ ID NO:256), L80I (SEQ ID NO:257) or L93I (SEQ ID NO:258) were generated and expressed in CHO cells. The variants were assessed for resistance to proteases, as were the N38H/N83H/R139H variant and fully glycosylated and de-glycosylated EPO polypeptides. The inclusion of any one of the L93V, L80I and L93I mutations into a N38H/N83H/R139H background conferred increased resistance to proteases compared to the N38H/N83H/R139H mutant. After 1 hour of proteolysis, 26% of the N38H/N83H/R139H remained and 46% of the fully glycosylated native EPO remained. In comparison, 30%, 37% and 45% of the N38H/N83H/R139H/L93I, N38H/N83H/R139H/L80I and N38H/N83H/R139H/L93V variants, respectively, remained after 1 hour of incubation with the proteases. After 2 hours of proteolysis, 8% of the N38H/N83H/R139H/L80I and N38H/N83H/R139H/L93V variants and 3% of the N38H/N83H/R139H/L93I variant remained, compared with 14% of the fully glycosylated protein and 4% of the N38H/N83H/R139H variant.

Each of the quadruple mutants (N38H/R139H/N83H/L80I (SEQ ID NO:257), N38H/R139H/N83H/L93I (SEQ ID NO:258) and N38H/R139H/N83H/L93V (SEQ ID NO:256)) were termed "Umbrella 83" variants, and used as templates into which the additional mutation of a K20Q substitution was introduced. This resulted in the generation of the following variants: K20Q/N38H/L80I/N83H/R139H (SEQ ID NO:259); K20Q/N38H/N83H/L93I/R139H (SEQ ID NO:260); and K20Q/N38H/N83H/L93V/R139H (SEQ ID NO:261). These variants also were assessed for protease resistance using the assays described above. Incorporation of the K20Q mutation into the Umbrella 83 variants conferred increased protease resistance to the EPO polypeptides compared to the N38H/N83H/R139H variant. After 1 hour of proteolysis, 37% of initial concentration of the N38H/N83H/R139H variant remained. In comparison, 58% of the K20Q/N38H/L80I/N83H/R139H and K20Q/N38H/N83H/L93V/R139H variants, and 71% of the K20Q/N38H/N83H/L93I/R139H variant remained. This level of protease resistance was comparable to the fully-glycosylated EPO polypeptide (71% remaining).

4. Generation of Fully De-Glycosylated N24H/N38H/N83H EPO Variants with Increased Resistance to Proteolysis The three pathways described above in parts 1-3 identified mutations that conferred signiftant protease resistance to partially de-glycosylated EPO polypeptides. In particular, the is-HIT position K20 appeared to be a key site in proteolysis, such that appropriate mutation at this position conferred increased protease resistance to the partially de-glycosylated EPO polypeptides containing mutations at N38 and/or N83. Because of its close proximity to the other N-glycosylation site, N24, it was hypothesized that the K20Q mutation also may be protective for de-glycosylation at position 24. To assess the ability of the K20Q mutation, and other LEAD mutations, to confer protease resistance to de -glycosylated EPO polypeptides, a series of variants were generated in which each of the N-glycosylation site were mutated.

The first series of variants were generated by introducing the N24H mutation into the Umbrella 83 mutants (from Example 6.3, above). The resulting fully de-glycosylated EPO variants thus contained the following mutations: N24H/N38H/N83H/R139H/L80I (SEQ ID NO:262); N24H/N38H/N83H/R139H/L93I (SEQ ID NO:263); or N24H/N38H/N83H/R139H/L93V (SEQ ID NO:264). These variants were assayed with the N38H, N38H/R139H, and N38H/N83H/R139H variants, and native fully glycosylated and de-glycosylated polypeptides for resistance to proteolysis. Removal of the N24 glycosylation site by mutagenesis reduced the resistance of the EPO variants compared to the full glycosylated EPO polypeptide and the partially de-glycosylated N38H/R139H variant, but remained markedly more resistance compared to the fully de-glycosylated control EPO polypeptide. The concentration of the fully glycosylated EPO and the partially de-glycosylated N38H/R139H and N38H EPO variants after 1 hour of proteolysis was 70%, 62% and 27%, respectively, of the starting concentration. Only 4% of the fully de-glycosylated native EPO polypeptide remained un-cleaved by the proteases after 1 hour. In comparison, 21%, 22% and % of the de-glycosylated N24H/N38H/N83H/R139H/L93I, N24H/N38H/N83H/R139H/L80I and N24H/N38H/N83H/R139H/L93V variants remained after 1 hour.

To assess the protective effect of the K20Q mutation on the fully de-glycosylated variants described above, each of the N24H/N38H/N83H/R139H/L80I, N24H/N38H/N83H/R139H/L93I, or N24H/N38H/N83H/R139H/L93V variants were used as a template into which the K20Q mutation was engineered. The resulting fully de-glycosylated EPO variants thus contained the following mutations: K20Q/N24H/N38H/N83H/R139H/L80I (SEQ ID NO:265); K20Q/N24H/N38H/N83H/R139H/L93I (SEQ ID NO:266); or K20Q/N24H/N38H/N83H/R139H/L93V (SEQ ID NO:267). These variants were assayed with the N38H, N38H/R139H, and N38H/N83H/R139H variants, and native fully glycosylated and de-glycosylated polypeptides for resistance to proteolysis. The de-glycosylated K20Q/N24H/N38H/N83H/R139H/L80I, K20Q/N24H/N38H/N83H/R139H/L93I, and K20Q/N24H/N38H/N83H/R139H/L93V variants exhibited similar resistance to proteases as observed for the N38H/N83H/R139H variant, with the amount of polypeptide remaining un-cleaved by the proteases ranging from 35% to 42%. This level of resistance was much higher than that observed for the fully de-glycosylated EPO polypeptide that contained no protective mutations (4% remaining), but less than that exhibited by the fully glycosylated native EPO polypeptide (71% remaining) and the partially de-glycosylated N38H/R139H variant (62% remaining).

Additional LEAD mutations were incorporated into the de-glycosylated variants to determine whether fully de-glycosylated EPO polypeptides could be protected from proteolysis. The resulting de-glycosylated EPO variants included: R4H/K20Q/N24H/N38H/N83H/R139H/L80I (SEQ ID NO:268); E159N/K20Q/N24H/N38H/N83H/R139H/L93I (SEQ ID NO:269); K20Q/N24H/N38H/N83H/R139H/L153V (SEQ ID NO:270); L153V/K20Q/N24H/N38H/N83H/R139H/L80I (SEQ ID NO:271) and E159N/K20Q/N24H/N38H/N83H/R139H/L80I (SEQ ID NO:272). These variants were assayed with the N38H, N38H/R139H, and N38H/N83H/R139H variants, and native fully glycosylated and de-glycosylated polypeptides for resistance to proteolysis. Each of these new variants exhibited a degree of resistance to proteolysis equal to, or slightly higher, that of the fully glycosylated native EPO polypeptide. After 1 hour of proteolysis, the percentage of the initial concentration of polypeptide remaining was 75% for E159N/K20Q/N24H/N38H/N83H/R139H/L93I, 76% for K20Q/N24H/N38H/N83H/R139H/L153V, 79% for R4H/K20Q/N24H/N38H/N83H/R139H/L80I and L153V/K20Q/N24H/N38H/N83H/R139H/L80I, and 81% for E159N/K20Q/N24H/N38H/N83H/R139H/L80I. By comparison, only 71% of the fully glycosylated EPO polypeptide remained after 1 hour of proteolysis, and just 4% of the fully de-glycosylated EPO remained. After 2.5 hours of proteolysis, the percentage of the initial concentration of EPO polypeptide still remaining was 24% for K20Q/N24H/N38H/N83H/R139H/L153V, 25% for L153V/K20Q/N24H/N38H/N83H/R139H/L80I, E159N/K20Q/N24H/N38H/N83H/R139H/L80I and E159N/K20Q/N24H/N38H/N83H/R139H/L93I, and 27% for R4H/K20Q/N24H/N38H/N83H/R139H/L80I. By comparison, 23% of the fully glycosylated EPO polypeptide remained after 2 hours of proteolysis, and none of the fully de-glycosylated EPO remained.

Since modifications will be apparent to those of skill in this art, it is intended that this invention be limited only by the scope of the appended claims.

What is claimed is:

1. A modified erythropoietin (EPO) polypeptide or an active fragment thereof, comprising the amino acid replacement K20Q or a replacement corresponding to K20Q in a mature EPO polypeptide set forth in SEQ ID NO:2 or 237, wherein:
   if the polypeptide is an active fragment, the active fragment contains the modification;
   the modified erythropoietin polypeptide or an active fragment thereof exhibits increased resistance to proteolysis compared to the unmodified erythropoietin polypeptide that does not contain the modification; and
   the modified erythropoietin polypeptide or an active fragment thereof retains one or more activities of the unmodified EPO polypeptide.

2. The modified polypeptide of claim 1 that is an active fragment that includes the K20Q modification.

3. The EPO polypeptide of claim 1 that is 160, 161, 162, 163, 164, 165 or 166 amino acids in length.

4. The modified EPO polypeptide of claim 1 that has the sequence of amino acids set forth in SEQ ID NO. 2 or 237 with the amino acid replacement K20Q and also comprising the amino acid replacement R139H, wherein the amino acid replacements correspond to amino acid replacements in a mature erythropoietin cytokine having the sequence set forth in SEQ ID NO: 2 or SEQ ID NO: 237.

5. The modified EPO polypeptide of claim 1 that comprises the sequence of amino acids set forth in any of SEQ ID NOS: 202-213, 215, 217-222 and 224-226, wherein:
   the amino acid in the modified erythropoietin polypeptide at the position corresponding to position 20 in the mature EPO polypeptide with the sequence of amino acids set forth in SEQ ID NO:2 or 237 is replaced with Q;
   the amino acid in the modified erythropoietin polypeptide at the position corresponding to position 139 in the mature EPO polypeptide whose sequence is set forth in SEQ ID NO:2 or 237 is replaced with H; and
   corresponding positions are determined by sequence alignment.

6. The EPO polypeptide of claim 1 that is 165 or 166 amino acids in length.

7. A pharmaceutical composition, comprising a polypeptide of claim 1 and a pharmaceutically acceptable carrier or excipient.

8. The modified Erythropoietin (EPO) polypeptide or active fragment thereof of claim 1, comprising K20Q and R139H, wherein the amino acid replacements correspond to amino acid replacements in a mature erythropoietin polypeptide having the sequence of amino acids set forth in SEQ ID NO: 2 or SEQ ID NO: 237.

9. The modified polypeptide of claim 8 that is a precursor form of the EPO polypeptide.

10. The modified polypeptide of claim 8 that is a mature form of the EPO polypeptide.

11. The modified EPO polypeptide of claim 8, that comprises the sequence of amino acids set forth in any of SEQ ID NOS: 2, 228, 309, 310 and 237 with the modifications K20Q and R139H or an EPO polypeptide that is an allelic or species variant thereof or is a variant that has 95% sequence identity with the sequence of amino acids set forth in any of SEQ ID NOS: 2, 228, 309, 310 and 237 and comprises the amino acid replacements Q and H at a position corresponding to K20 and R139, respectively.

12. The modified EPO polypeptide of claim 8, comprising another amino acid replacement at an amino acid position selected from among 2, 3, 4, 5, 7, 8, 10, 12, 13, 14, 15, 16, 17, 18, 21, 23, 29, 31, 35, 37, 42, 43, 45, 48, 49, 51, 52, 53, 54, 55, 62, 64, 67, 69, 70, 72, 75, 76, 80, 81, 87, 88, 89, 90, 91, 93, 96, 97, 102, 103, 105, 108, 109, 110, 112, 116, 117, 121, 122, 123, 129, 130, 131, 136, 138, 140, 141, 142, 143, 145, 148, 149, 150, 152, 153, 154, 155, 156, 159, 162, 165, and 166, wherein said amino acid positions reference the positions in a mature human EPO polypeptide having the sequence set forth in SEQ ID NO: 2 or 237.

13. The modified EPO polypeptide of claim 12, wherein the amino acid replacement(s) is/are selected from among P2S, P2A, P3S, P3A, R4H, R4Q, L5I, L5V, C7S, C7V, C7A, C7I, C7T, D8Q, D8H, D8N, R10H, R10Q, L12V, L12I, E13Q, E13H, E13N, R14H, R14Q, Y15H, Y15I, L16I, L16V, L17I, L17V, E18Q, E18H, E18N, E21Q, E21H, E21N, E23Q, E23H, E23N, C29S, C29V, C29A, C29I, C29T, E31Q, E31H, E31N, L35V, L35I, E37Q, E37H, E37N, P42S, P42A, D43Q, D43H, D43N, K45Q, K45T, K45N, F48I, F48V, Y49H, Y49I, W51S, W51H, K52Q, K52T, K52N, R53H, R53Q, M54V, M54I, E55Q, E55H, E55N, E62Q, E62H, E62N, W64S, W64H, L67I, L67V, L69V, L69I, L70I, L70V, E72Q, E72H, E72N, L75V, L75I, R76H, R76Q, L80V, L80I, L81I, L81V, P87S, P87A, W88S, W88H, E89Q, E89H, E89N, P90S, P90A, L91I, L91V, L93V, L93I, D96Q, D96H, D96N, K97Q, K97T, K97N, L102V, L102I, R103H, R103Q, L105I, L105V, L108I, L108V, L109I, L109V, R110H, R110Q, L112V, L112I, K116Q, K116T, K116N, E117Q, E117H, E117N, P121S, P121A, P122S, P122A, D123Q, D123H, D123N, P129S, P129A, L130V, L130I, R131H, R131Q, D136Q, D136H, D136N, F138I, F138V, K140N, K140Q, L141I, L141V, F142I, F142V, R143H, R143Q, Y145H, Y145I, F148I, F148V, L149I, L149V, R150H, R150Q, K152Q, K152T, K152N, L153I, L153V, K154Q, K154T, K154N, L155V, L155I, Y156H, Y156I, E159Q, E159H, E159N, R162H, R162Q, D165Q, D165H, D165N, R166H, and R166Q.

14. The modified EPO polypeptide of claim 13, wherein the amino acid replacements in the modified EPO are selected from among R139H/K20Q, K20Q/L80I/R139H, K20Q/L93I/R139H, K20Q/L93V/R139H, R4H/K20Q/R139H/L80I, E159N/K20Q/R139H/L93I, K20Q/R139H/L153V, L153V/K20Q/R139H/L80I and E159N/K20Q/R139H/L80I.

15. The modified EPO polypeptide of claim 8 that comprises one or more further amino acid replacement(s) selected from among A30N, H32T, P87V, W88N, and P90T.

16. A modified EPO polypeptide of claim 8, further comprising one or more additional amino acid modification(s) that eliminates one up to all glycosylation sites.

17. The modified EPO polypeptide of claim 16, wherein the glycosylation site is an O-glycosylation site or is an N-glycosylation site.

18. The modified EPO polypeptide of claim 17, wherein the glycosylation site is an O-glycosylation site and is S126.

19. The modified EPO polypeptide of claim 17, wherein the glycosylation site is an N-glycosylation site and is selected from among N24, N38 and N83.

20. The modified EPO polypeptide of claim 19, wherein the amino acid replacement is selected from among N24H, N38H, N83H, N24K, N38K, N83K, N38H/N83H and N24H/N38H/N83H.

21. The modified EPO polypeptide of claim 16, wherein the one or more additional amino acid modifications are selected from natural amino acids, non-natural amino acids and a combination of natural and non-natural amino acids.

22. The modified EPO polypeptide of claim 8 that is a mature form of an EPO polypeptide or that is a precursor form of an EPO polypeptide.

23. A pharmaceutical composition, comprising a polypeptide of claim 8 and a pharmaceutically acceptable carrier or excipient.

24. The pharmaceutical composition of claim 23 that is formulated as a liquid, a pill, a tablet, a lozenge or a capsule for oral administration.

25. The EPO polypeptide of claim 8 that is 165 or 166 amino acids in length.

26. A modified erythropoietin (EPO) polypeptide or an active fragment thereof, comprising the amino acid replacement K20Q or a replacement corresponding to K20Q in a mature EPO polypeptide set forth in SEQ ID NO:2 or 237, wherein:

the modified erythropoietin polypeptide or an active fragment thereof retains one or more activities of the unmodified EPO polypeptide;

if the polypeptide is an active fragment, the active fragment contains the modification; and the modified EPO polypeptide comprises amino acid replacements selected from among N38H/R139H/K20Q, K20Q/N38H/N83H/R139H, K20Q/N38H/L80I/N83H/R139H, K20Q/N38H/N83H/L93I/R139H, K20Q/N38H/N83H/L93V/R139H, K20Q/N24H/N38H/N83H/R139H/L80I, K20Q/N24H/N38H/N83H/R139H/L93I, K20Q/N24H/N38H/N83H/R139H/L93V, R4H/K20Q/N24H/N38H/N83H/R139H/L80I, E159N/K20Q/N24H/N38H/N83H/R139H/L93I, K20Q/N24H/N38H/N83H/R139H/L153V, L153V/K20Q/N24H/N38H/N83H/R139H/L80 I and E159N/K20Q/N24H/N38H/N83H/R139H/L80I.

27. The modified EPO polypeptide of claim 26 that comprises one or more further amino acid replacement(s) selected from among A30N, H32T, P87V, W88N, and P90T.

* * * * *

SEQUENCE LISTING

<160> NUMBER OF SEQ ID NOS: 310

<210> SEQ ID NO 1
<211> LENGTH: 193
<212> TYPE: PRT
<213> ORGANISM: Homo sapiens
<220> FEATURE:
<223> OTHER INFORMATION: human EPO - immature protein

<400> SEQUENCE: 1

Met Gly Val His Glu Cys Pro Ala Trp Leu Trp Leu Leu Ser Leu
 1               5                  10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 2
<211> LENGTH: 166
<212> TYPE: PRT
<213> ORGANISM: Homo sapiens
<220> FEATURE:
<223> OTHER INFORMATION: Human EPO - mature protein

<400> SEQUENCE: 2

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

```
Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 3
<211> LENGTH: 166
<212> TYPE: PRT
<213> ORGANISM: Artificial Sequence
<220> FEATURE:
<223> OTHER INFORMATION: EPO_1_P2S

<400> SEQUENCE: 3

Ala Ser Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 4
<211> LENGTH: 166
<212> TYPE: PRT
<213> ORGANISM: Artificial Sequence
<220> FEATURE:
<223> OTHER INFORMATION: EPO_2_P2A

<400> SEQUENCE: 4

Ala Ala Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60
```

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 5
<211> LENGTH: 166
<212> TYPE: PRT
<213> ORGANISM: Artificial Sequence
<220> FEATURE:
<223> OTHER INFORMATION: EPO_3_P3S

<400> SEQUENCE: 5

Ala Pro Ser Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 6
<211> LENGTH: 166
<212> TYPE: PRT
<213> ORGANISM: Artificial Sequence
<220> FEATURE:
<223> OTHER INFORMATION: EPO_4_P3A

<400> SEQUENCE: 6

Ala Pro Ala Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

```
Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 7
<211> LENGTH: 166
<212> TYPE: PRT
<213> ORGANISM: Artificial Sequence
<220> FEATURE:
<223> OTHER INFORMATION: EPO_5_R4H

<400> SEQUENCE: 7

Ala Pro Pro His Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 8
<211> LENGTH: 166
<212> TYPE: PRT
<213> ORGANISM: Artificial Sequence
<220> FEATURE:
<223> OTHER INFORMATION: EPO_6_R4Q

<400> SEQUENCE: 8
```

```
Ala Pro Pro Gln Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65              70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 9
<211> LENGTH: 166
<212> TYPE: PRT
<213> ORGANISM: Artificial Sequence
<220> FEATURE:
<223> OTHER INFORMATION: EPO_7_C7S

<400> SEQUENCE: 9

Ala Pro Pro Arg Leu Ile Ser Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65              70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 10
<211> LENGTH: 166
<212> TYPE: PRT
```

```
<213> ORGANISM: Artificial Sequence
<220> FEATURE:
<223> OTHER INFORMATION: EPO_8_C7V

<400> SEQUENCE: 10

Ala Pro Pro Arg Leu Ile Val Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65              70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 11
<211> LENGTH: 166
<212> TYPE: PRT
<213> ORGANISM: Artificial Sequence
<220> FEATURE:
<223> OTHER INFORMATION: EPO_9_D8Q

<400> SEQUENCE: 11

Ala Pro Pro Arg Leu Ile Cys Gln Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65              70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
```

```
<210> SEQ ID NO 12
<211> LENGTH: 166
<212> TYPE: PRT
<213> ORGANISM: Artificial Sequence
<220> FEATURE:
<223> OTHER INFORMATION: EPO_10_D8H

<400> SEQUENCE: 12

Ala Pro Pro Arg Leu Ile Cys His Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 13
<211> LENGTH: 166
<212> TYPE: PRT
<213> ORGANISM: Artificial Sequence
<220> FEATURE:
<223> OTHER INFORMATION: EPO_11_R10H

<400> SEQUENCE: 13

Ala Pro Pro Arg Leu Ile Cys Asp Ser His Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
```

```
            130                 135                 140
Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 14
<211> LENGTH: 166
<212> TYPE: PRT
<213> ORGANISM: Artificial Sequence
<220> FEATURE:
<223> OTHER INFORMATION: EPO_12_R10Q

<400> SEQUENCE: 14

Ala Pro Pro Arg Leu Ile Cys Asp Ser Gln Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 15
<211> LENGTH: 166
<212> TYPE: PRT
<213> ORGANISM: Artificial Sequence
<220> FEATURE:
<223> OTHER INFORMATION: EPO_13_L12V

<400> SEQUENCE: 15

Ala Pro Pro Arg Leu Ile Cys Asp Ser Arg Val Val Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
```

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 16
<211> LENGTH: 166
<212> TYPE: PRT
<213> ORGANISM: Artificial Sequence
<220> FEATURE:
<223> OTHER INFORMATION: EPO_14_L12I

<400> SEQUENCE: 16

Ala Pro Pro Arg Leu Ile Cys Asp Ser Arg Val Ile Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 17
<211> LENGTH: 166
<212> TYPE: PRT
<213> ORGANISM: Artificial Sequence
<220> FEATURE:
<223> OTHER INFORMATION: EPO_15_E18Q

<400> SEQUENCE: 17

Ala Pro Pro Arg Leu Ile Cys Asp Ser Arg Val Leu Glu Arg Tyr Leu
1               5                   10                  15

Leu Gln Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu

```
                65                  70                  75                  80
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 18
<211> LENGTH: 166
<212> TYPE: PRT
<213> ORGANISM: Artificial Sequence
<220> FEATURE:
<223> OTHER INFORMATION: EPO_16_E18H

<400> SEQUENCE: 18

Ala Pro Pro Arg Leu Ile Cys Asp Ser Arg Val Leu Glu Arg Tyr Leu
1                5                  10                  15

Leu His Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
                35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 19
<211> LENGTH: 166
<212> TYPE: PRT
<213> ORGANISM: Artificial Sequence
<220> FEATURE:
<223> OTHER INFORMATION: EPO_17_K20Q

<400> SEQUENCE: 19

Ala Pro Pro Arg Leu Ile Cys Asp Ser Arg Val Leu Glu Arg Tyr Leu
1                5                  10                  15

Leu Glu Ala Gln Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
```

```
                35                  40                  45
Tyr Ala Trp Lys Arg Met Glu Val Gly Gln Gln Ala Val Glu Val Trp
 50                  55                  60
Gln Gly Leu Ala Leu Leu Ser Glu Ala Val Leu Arg Gly Gln Ala Leu
 65                  70                  75                  80
Leu Val Asn Ser Ser Gln Pro Trp Glu Pro Leu Gln Leu His Val Asp
                 85                  90                  95
Lys Ala Val Ser Gly Leu Arg Ser Leu Thr Thr Leu Leu Arg Ala Leu
                100                 105                 110
Gly Ala Gln Lys Glu Ala Ile Ser Pro Pro Asp Ala Ala Ser Ala Ala
                115                 120                 125
Pro Leu Arg Thr Ile Thr Ala Asp Thr Phe Arg Lys Leu Phe Arg Val
                130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 20
<211> LENGTH: 166
<212> TYPE: PRT
<213> ORGANISM: Artificial Sequence
<220> FEATURE:
<223> OTHER INFORMATION: EPO_18_K20T

<400> SEQUENCE: 20

Ala Pro Pro Arg Leu Ile Cys Asp Ser Arg Val Leu Glu Arg Tyr Leu
  1               5                  10                  15
Leu Glu Ala Thr Glu Ala Glu Asn Ile Thr Thr Gly Cys Ala Glu His
                 20                  25                  30
Cys Ser Leu Asn Glu Asn Ile Thr Val Pro Asp Thr Lys Val Asn Phe
                 35                  40                  45
Tyr Ala Trp Lys Arg Met Glu Val Gly Gln Gln Ala Val Glu Val Trp
 50                  55                  60
Gln Gly Leu Ala Leu Leu Ser Glu Ala Val Leu Arg Gly Gln Ala Leu
 65                  70                  75                  80
Leu Val Asn Ser Ser Gln Pro Trp Glu Pro Leu Gln Leu His Val Asp
                 85                  90                  95
Lys Ala Val Ser Gly Leu Arg Ser Leu Thr Thr Leu Leu Arg Ala Leu
                100                 105                 110
Gly Ala Gln Lys Glu Ala Ile Ser Pro Pro Asp Ala Ala Ser Ala Ala
                115                 120                 125
Pro Leu Arg Thr Ile Thr Ala Asp Thr Phe Arg Lys Leu Phe Arg Val
                130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 21
<211> LENGTH: 166
<212> TYPE: PRT
<213> ORGANISM: Artificial Sequence
<220> FEATURE:
<223> OTHER INFORMATION: EPO_19_E21Q

<400> SEQUENCE: 21

Ala Pro Pro Arg Leu Ile Cys Asp Ser Arg Val Leu Glu Arg Tyr Leu
```

```
                1               5                  10                 15
Leu Glu Ala Lys Gln Ala Glu Asn Ile Thr Thr Gly Cys Ala Glu His
                20                 25                 30

Cys Ser Leu Asn Glu Asn Ile Thr Val Pro Asp Thr Lys Val Asn Phe
                35                 40                 45

Tyr Ala Trp Lys Arg Met Glu Val Gly Gln Gln Ala Val Glu Val Trp
                50                 55                 60

Gln Gly Leu Ala Leu Leu Ser Glu Ala Val Leu Arg Gly Gln Ala Leu
65                  70                 75                 80

Leu Val Asn Ser Ser Gln Pro Trp Glu Pro Leu Gln Leu His Val Asp
                85                 90                 95

Lys Ala Val Ser Gly Leu Arg Ser Leu Thr Thr Leu Leu Arg Ala Leu
                100                105                110

Gly Ala Gln Lys Glu Ala Ile Ser Pro Pro Asp Ala Ala Ser Ala Ala
                115                120                125

Pro Leu Arg Thr Ile Thr Ala Asp Thr Phe Arg Lys Leu Phe Arg Val
                130                135                140

Tyr Ser Asn Phe Leu Arg Gly Lys Leu Lys Leu Tyr Thr Gly Glu Ala
145                 150                155                160

Cys Arg Thr Gly Asp Arg
                165
```

<210> SEQ ID NO 22
<211> LENGTH: 166
<212> TYPE: PRT
<213> ORGANISM: Artificial Sequence
<220> FEATURE:
<223> OTHER INFORMATION: EPO_20_E21H

<400> SEQUENCE: 22

```
Ala Pro Pro Arg Leu Ile Cys Asp Ser Arg Val Leu Glu Arg Tyr Leu
1               5                  10                 15

Leu Glu Ala Lys His Ala Glu Asn Ile Thr Thr Gly Cys Ala Glu His
                20                 25                 30

Cys Ser Leu Asn Glu Asn Ile Thr Val Pro Asp Thr Lys Val Asn Phe
                35                 40                 45

Tyr Ala Trp Lys Arg Met Glu Val Gly Gln Gln Ala Val Glu Val Trp
                50                 55                 60

Gln Gly Leu Ala Leu Leu Ser Glu Ala Val Leu Arg Gly Gln Ala Leu
65                  70                 75                 80

Leu Val Asn Ser Ser Gln Pro Trp Glu Pro Leu Gln Leu His Val Asp
                85                 90                 95

Lys Ala Val Ser Gly Leu Arg Ser Leu Thr Thr Leu Leu Arg Ala Leu
                100                105                110

Gly Ala Gln Lys Glu Ala Ile Ser Pro Pro Asp Ala Ala Ser Ala Ala
                115                120                125

Pro Leu Arg Thr Ile Thr Ala Asp Thr Phe Arg Lys Leu Phe Arg Val
                130                135                140

Tyr Ser Asn Phe Leu Arg Gly Lys Leu Lys Leu Tyr Thr Gly Glu Ala
145                 150                155                160

Cys Arg Thr Gly Asp Arg
                165
```

<210> SEQ ID NO 23
<211> LENGTH: 166
<212> TYPE: PRT
<213> ORGANISM: Artificial Sequence

<220> FEATURE:
<223> OTHER INFORMATION: EPO_21_E23Q

<400> SEQUENCE: 23

Ala Pro Pro Arg Leu Ile Cys Asp Ser Arg Val Leu Glu Arg Tyr Leu
1               5                   10                  15

Leu Glu Ala Lys Glu Ala Gln Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 24
<211> LENGTH: 166
<212> TYPE: PRT
<213> ORGANISM: Artificial Sequence
<220> FEATURE:
<223> OTHER INFORMATION: EPO_22_E23H

<400> SEQUENCE: 24

Ala Pro Pro Arg Leu Ile Cys Asp Ser Arg Val Leu Glu Arg Tyr Leu
1               5                   10                  15

Leu Glu Ala Lys Glu Ala His Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 25
<211> LENGTH: 166
<212> TYPE: PRT
<213> ORGANISM: Artificial Sequence
<220> FEATURE:
<223> OTHER INFORMATION: EPO_23_C29S

<400> SEQUENCE: 25

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Ser Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 26
<211> LENGTH: 166
<212> TYPE: PRT
<213> ORGANISM: Artificial Sequence
<220> FEATURE:
<223> OTHER INFORMATION: EPO_24_C29V

<400> SEQUENCE: 26

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Val Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 27
<211> LENGTH: 166
<212> TYPE: PRT
<213> ORGANISM: Artificial Sequence
<220> FEATURE:
<223> OTHER INFORMATION: EPO_25_E31Q

<400> SEQUENCE: 27

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Gln His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 28
<211> LENGTH: 166
<212> TYPE: PRT
<213> ORGANISM: Artificial Sequence
<220> FEATURE:
<223> OTHER INFORMATION: EPO_26_E31H

<400> SEQUENCE: 28

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys His His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

```
Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 29
<211> LENGTH: 166
<212> TYPE: PRT
<213> ORGANISM: Artificial Sequence
<220> FEATURE:
<223> OTHER INFORMATION: EPO_27_L35V

<400> SEQUENCE: 29

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Val Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 30
<211> LENGTH: 166
<212> TYPE: PRT
<213> ORGANISM: Artificial Sequence
<220> FEATURE:
<223> OTHER INFORMATION: EPO_28_L35I

<400> SEQUENCE: 30

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Ile Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80
```

```
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Asp Ala Ala Ser Ala Ala
            115                 120                 125
Pro Leu Arg Thr Ile Thr Ala Asp Thr Phe Arg Lys Leu Phe Arg Val
        130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165
```

```
<210> SEQ ID NO 31
<211> LENGTH: 166
<212> TYPE: PRT
<213> ORGANISM: Artificial Sequence
<220> FEATURE:
<223> OTHER INFORMATION: EPO_29_E37Q

<400> SEQUENCE: 31

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Gln Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Asp Ala Ala Ser Ala Ala
            115                 120                 125
Pro Leu Arg Thr Ile Thr Ala Asp Thr Phe Arg Lys Leu Phe Arg Val
        130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165
```

```
<210> SEQ ID NO 32
<211> LENGTH: 166
<212> TYPE: PRT
<213> ORGANISM: Artificial Sequence
<220> FEATURE:
<223> OTHER INFORMATION: EPO_30_E37H

<400> SEQUENCE: 32

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn His Asn Ile Thr Val Pro Asp Thr Lys Val Asn Phe
        35                  40                  45
```

```
Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 33
<211> LENGTH: 166
<212> TYPE: PRT
<213> ORGANISM: Artificial Sequence
<220> FEATURE:
<223> OTHER INFORMATION: EPO_31_P42S

<400> SEQUENCE: 33

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Ser Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 34
<211> LENGTH: 166
<212> TYPE: PRT
<213> ORGANISM: Artificial Sequence
<220> FEATURE:
<223> OTHER INFORMATION: EPO_32_P42A

<400> SEQUENCE: 34

Ala Pro Pro Arg Leu Ile Cys Asp Ser Arg Val Leu Glu Arg Tyr Leu
 1               5                  10                  15
```

```
Leu Glu Ala Lys Glu Ala Glu Asn Ile Thr Thr Gly Cys Ala Glu His
            20                  25                  30

Cys Ser Leu Asn Glu Asn Ile Thr Val Ala Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 35
<211> LENGTH: 166
<212> TYPE: PRT
<213> ORGANISM: Artificial Sequence
<220> FEATURE:
<223> OTHER INFORMATION: EPO_33_D43Q

<400> SEQUENCE: 35

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Gln Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 36
<211> LENGTH: 166
<212> TYPE: PRT
<213> ORGANISM: Artificial Sequence
<220> FEATURE:
```

<223> OTHER INFORMATION: EPO_34_D43H

<400> SEQUENCE: 36

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro His Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 37
<211> LENGTH: 166
<212> TYPE: PRT
<213> ORGANISM: Artificial Sequence
<220> FEATURE:
<223> OTHER INFORMATION: EPO_35_K45Q

<400> SEQUENCE: 37

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Gln Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

```
<210> SEQ ID NO 38
<211> LENGTH: 166
<212> TYPE: PRT
<213> ORGANISM: Artificial Sequence
<220> FEATURE:
<223> OTHER INFORMATION: EPO_36_K45T

<400> SEQUENCE: 38

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Thr Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 39
<211> LENGTH: 166
<212> TYPE: PRT
<213> ORGANISM: Artificial Sequence
<220> FEATURE:
<223> OTHER INFORMATION: EPO_37_F48I

<400> SEQUENCE: 39

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Ile
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140
```

```
Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 40
<211> LENGTH: 166
<212> TYPE: PRT
<213> ORGANISM: Artificial Sequence
<220> FEATURE:
<223> OTHER INFORMATION: EPO_38_F48V

<400> SEQUENCE: 40

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Val
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 41
<211> LENGTH: 166
<212> TYPE: PRT
<213> ORGANISM: Artificial Sequence
<220> FEATURE:
<223> OTHER INFORMATION: EPO_39_Y49H

<400> SEQUENCE: 41

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

His Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110
```

```
Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 42
<211> LENGTH: 166
<212> TYPE: PRT
<213> ORGANISM: Artificial Sequence
<220> FEATURE:
<223> OTHER INFORMATION: EPO_40_Y49I

<400> SEQUENCE: 42

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Ile Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 43
<211> LENGTH: 166
<212> TYPE: PRT
<213> ORGANISM: Artificial Sequence
<220> FEATURE:
<223> OTHER INFORMATION: EPO_41_W51S

<400> SEQUENCE: 43

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Ser Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80
```

```
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 44
<211> LENGTH: 166
<212> TYPE: PRT
<213> ORGANISM: Artificial Sequence
<220> FEATURE:
<223> OTHER INFORMATION: EPO_42_W51H

<400> SEQUENCE: 44

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala His Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 45
<211> LENGTH: 166
<212> TYPE: PRT
<213> ORGANISM: Artificial Sequence
<220> FEATURE:
<223> OTHER INFORMATION: EPO_43_K52Q

<400> SEQUENCE: 45

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45
```

```
Tyr Ala Trp Gln Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 46
<211> LENGTH: 166
<212> TYPE: PRT
<213> ORGANISM: Artificial Sequence
<220> FEATURE:
<223> OTHER INFORMATION: EPO_44_K52T

<400> SEQUENCE: 46

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Thr Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 47
<211> LENGTH: 166
<212> TYPE: PRT
<213> ORGANISM: Artificial Sequence
<220> FEATURE:
<223> OTHER INFORMATION: EPO_45_R53H

<400> SEQUENCE: 47

Ala Pro Pro Arg Leu Ile Cys Asp Ser Arg Val Leu Glu Arg Tyr Leu
 1               5                  10                  15
```

```
Leu Glu Ala Lys Glu Ala Glu Asn Ile Thr Thr Gly Cys Ala Glu His
         20                  25                  30

Cys Ser Leu Asn Glu Asn Ile Thr Val Pro Asp Thr Lys Val Asn Phe
         35                  40                  45

Tyr Ala Trp Lys His Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 48
<211> LENGTH: 166
<212> TYPE: PRT
<213> ORGANISM: Artificial Sequence
<220> FEATURE:
<223> OTHER INFORMATION: EPO_46_R53Q

<400> SEQUENCE: 48

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
         20                  25                  30

Cys Ser Leu Asn Glu Asn Ile Thr Val Pro Asp Thr Lys Val Asn Phe
         35                  40                  45

Tyr Ala Trp Lys Gln Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 49
<211> LENGTH: 166
<212> TYPE: PRT
<213> ORGANISM: Artificial Sequence
<220> FEATURE:
<223> OTHER INFORMATION: EPO_47_M54V
```

<400> SEQUENCE: 49

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Val Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 50
<211> LENGTH: 166
<212> TYPE: PRT
<213> ORGANISM: Artificial Sequence
<220> FEATURE:
<223> OTHER INFORMATION: EPO_48_M54I

<400> SEQUENCE: 50

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Ile Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

```
<210> SEQ ID NO 51
<211> LENGTH: 166
<212> TYPE: PRT
<213> ORGANISM: Artificial Sequence
<220> FEATURE:
<223> OTHER INFORMATION: EPO_49_E55Q

<400> SEQUENCE: 51

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Gln Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 52
<211> LENGTH: 166
<212> TYPE: PRT
<213> ORGANISM: Artificial Sequence
<220> FEATURE:
<223> OTHER INFORMATION: EPO_50_E55H

<400> SEQUENCE: 52

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met His Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
```

```
                    145                 150                 155                 160

Cys Arg Thr Gly Asp Arg
                165

<210> SEQ ID NO 53
<211> LENGTH: 166
<212> TYPE: PRT
<213> ORGANISM: Artificial Sequence
<220> FEATURE:
<223> OTHER INFORMATION: EPO_51_E62Q

<400> SEQUENCE: 53

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Gln Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 54
<211> LENGTH: 166
<212> TYPE: PRT
<213> ORGANISM: Artificial Sequence
<220> FEATURE:
<223> OTHER INFORMATION: EPO_52_E62H

<400> SEQUENCE: 54

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val His Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
```

```
                    115                 120                 125
Pro Leu Arg Thr Ile Thr Ala Asp Thr Phe Arg Lys Leu Phe Arg Val
                130                 135                 140
Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 55
<211> LENGTH: 166
<212> TYPE: PRT
<213> ORGANISM: Artificial Sequence
<220> FEATURE:
<223> OTHER INFORMATION: EPO_53_W64S

<400> SEQUENCE: 55

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Ser
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 56
<211> LENGTH: 166
<212> TYPE: PRT
<213> ORGANISM: Artificial Sequence
<220> FEATURE:
<223> OTHER INFORMATION: EPO_54_W64H

<400> SEQUENCE: 56

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val His
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
```

85                  90                  95
Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 57
<211> LENGTH: 166
<212> TYPE: PRT
<213> ORGANISM: Artificial Sequence
<220> FEATURE:
<223> OTHER INFORMATION: EPO_55_L69V

<400> SEQUENCE: 57

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Val Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 58
<211> LENGTH: 166
<212> TYPE: PRT
<213> ORGANISM: Artificial Sequence
<220> FEATURE:
<223> OTHER INFORMATION: EPO_56_L69I

<400> SEQUENCE: 58

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

```
                    50                  55                  60
Gln Gly Leu Ala Ile Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                     85                  90                  95

Lys Ala Val Ser Gly Leu Arg Ser Leu Thr Thr Leu Leu Arg Ala Leu
                    100                 105                 110

Gly Ala Gln Lys Glu Ala Ile Ser Pro Pro Asp Ala Ala Ser Ala Ala
                    115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 59
<211> LENGTH: 166
<212> TYPE: PRT
<213> ORGANISM: Artificial Sequence
<220> FEATURE:
<223> OTHER INFORMATION: EPO_57_E72Q

<400> SEQUENCE: 59

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Gln Ala Val Leu Arg Gly Gln Ala Leu
 65                  70                  75                  80

Leu Val Asn Ser Ser Gln Pro Trp Glu Pro Leu Gln Leu His Val Asp
                     85                  90                  95

Lys Ala Val Ser Gly Leu Arg Ser Leu Thr Thr Leu Leu Arg Ala Leu
                    100                 105                 110

Gly Ala Gln Lys Glu Ala Ile Ser Pro Pro Asp Ala Ala Ser Ala Ala
                    115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 60
<211> LENGTH: 166
<212> TYPE: PRT
<213> ORGANISM: Artificial Sequence
<220> FEATURE:
<223> OTHER INFORMATION: EPO_58_E72H

<400> SEQUENCE: 60

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
```

```
                20                  25                  30
Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser His Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 61
<211> LENGTH: 166
<212> TYPE: PRT
<213> ORGANISM: Artificial Sequence
<220> FEATURE:
<223> OTHER INFORMATION: EPO_59_L75V

<400> SEQUENCE: 61

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Val Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 62
<211> LENGTH: 166
<212> TYPE: PRT
<213> ORGANISM: Artificial Sequence
<220> FEATURE:
<223> OTHER INFORMATION: EPO_60_L75I
```

<400> SEQUENCE: 62

```
Ala Pro Pro Arg Leu Ile Cys Asp Ser Arg Val Leu Glu Arg Tyr Leu
 1               5                  10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Ile Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165
```

<210> SEQ ID NO 63
<211> LENGTH: 166
<212> TYPE: PRT
<213> ORGANISM: Artificial Sequence
<220> FEATURE:
<223> OTHER INFORMATION: EPO_61_R76H

<400> SEQUENCE: 63

```
Ala Pro Pro Arg Leu Ile Cys Asp Ser Arg Val Leu Glu Arg Tyr Leu
 1               5                  10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu His Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165
```

<210> SEQ ID NO 64

```
<211> LENGTH: 166
<212> TYPE: PRT
<213> ORGANISM: Artificial Sequence
<220> FEATURE:
<223> OTHER INFORMATION: EPO_62_R76q

<400> SEQUENCE: 64

Ala Pro Pro Arg Leu Ile Cys Asp Ser Arg Val Leu Glu Arg Tyr Leu
 1               5                  10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Gln Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 65
<211> LENGTH: 166
<212> TYPE: PRT
<213> ORGANISM: Artificial Sequence
<220> FEATURE:
<223> OTHER INFORMATION: EPO_63_L80V

<400> SEQUENCE: 65

Ala Pro Pro Arg Leu Ile Cys Asp Ser Arg Val Leu Glu Arg Tyr Leu
 1               5                  10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Val
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
```

```
Cys Arg Thr Gly Asp Arg
            165

<210> SEQ ID NO 66
<211> LENGTH: 166
<212> TYPE: PRT
<213> ORGANISM: Artificial Sequence
<220> FEATURE:
<223> OTHER INFORMATION: EPO_64_L80I

<400> SEQUENCE: 66

Ala Pro Pro Arg Leu Ile Cys Asp Ser Arg Val Leu Glu Arg Tyr Leu
 1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Ile
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 67
<211> LENGTH: 166
<212> TYPE: PRT
<213> ORGANISM: Artificial Sequence
<220> FEATURE:
<223> OTHER INFORMATION: EPO_65_P87S

<400> SEQUENCE: 67

Ala Pro Pro Arg Leu Ile Cys Asp Ser Arg Val Leu Glu Arg Tyr Leu
 1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Ser Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125
```

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 68
<211> LENGTH: 166
<212> TYPE: PRT
<213> ORGANISM: Artificial Sequence
<220> FEATURE:
<223> OTHER INFORMATION: EPO_66_P87A

<400> SEQUENCE: 68

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Ala Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 69
<211> LENGTH: 166
<212> TYPE: PRT
<213> ORGANISM: Artificial Sequence
<220> FEATURE:
<223> OTHER INFORMATION: EPO_67_W88S

<400> SEQUENCE: 69

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Ser Glu Pro Leu Gln Leu His Val Asp
                85                  90                  95

```
Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 70
<211> LENGTH: 166
<212> TYPE: PRT
<213> ORGANISM: Artificial Sequence
<220> FEATURE:
<223> OTHER INFORMATION: EPO_68_W88H

<400> SEQUENCE: 70

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro His Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 71
<211> LENGTH: 166
<212> TYPE: PRT
<213> ORGANISM: Artificial Sequence
<220> FEATURE:
<223> OTHER INFORMATION: EPO_69_E89Q

<400> SEQUENCE: 71

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60
```

```
Gln Gly Leu Ala Leu Leu Ser Glu Ala Val Leu Arg Gly Gln Ala Leu
 65                  70                  75                  80

Leu Val Asn Ser Ser Gln Pro Trp Gln Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 72
<211> LENGTH: 166
<212> TYPE: PRT
<213> ORGANISM: Artificial Sequence
<220> FEATURE:
<223> OTHER INFORMATION: EPO_70_E89H

<400> SEQUENCE: 72

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp His Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 73
<211> LENGTH: 166
<212> TYPE: PRT
<213> ORGANISM: Artificial Sequence
<220> FEATURE:
<223> OTHER INFORMATION: EPO_71_P90S

<400> SEQUENCE: 73

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30
```

```
Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Ser Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 74
<211> LENGTH: 166
<212> TYPE: PRT
<213> ORGANISM: Artificial Sequence
<220> FEATURE:
<223> OTHER INFORMATION: EPO_72_P90A

<400> SEQUENCE: 74

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Ala Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 75
<211> LENGTH: 166
<212> TYPE: PRT
<213> ORGANISM: Artificial Sequence
<220> FEATURE:
<223> OTHER INFORMATION: EPO_73_L93V

<400> SEQUENCE: 75

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65              70                  75                  80

Leu Val Asn Ser Ser Gln Pro Trp Glu Pro Leu Gln Val His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 76
<211> LENGTH: 166
<212> TYPE: PRT
<213> ORGANISM: Artificial Sequence
<220> FEATURE:
<223> OTHER INFORMATION: EPO_74_L93I

<400> SEQUENCE: 76

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65              70                  75                  80

Leu Val Asn Ser Ser Gln Pro Trp Glu Pro Leu Gln Ile His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 77
<211> LENGTH: 166

```
<212> TYPE: PRT
<213> ORGANISM: Artificial Sequence
<220> FEATURE:
<223> OTHER INFORMATION: EPO_75_D96Q

<400> SEQUENCE: 77

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Gln
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 78
<211> LENGTH: 166
<212> TYPE: PRT
<213> ORGANISM: Artificial Sequence
<220> FEATURE:
<223> OTHER INFORMATION: EPO_76_D96H

<400> SEQUENCE: 78

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val His
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160
```

```
Cys Arg Thr Gly Asp Arg
                165

<210> SEQ ID NO 79
<211> LENGTH: 166
<212> TYPE: PRT
<213> ORGANISM: Artificial Sequence
<220> FEATURE:
<223> OTHER INFORMATION: EPO_77_K97Q

<400> SEQUENCE: 79

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Gln Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 80
<211> LENGTH: 166
<212> TYPE: PRT
<213> ORGANISM: Artificial Sequence
<220> FEATURE:
<223> OTHER INFORMATION: EPO_78_K97T

<400> SEQUENCE: 80

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Thr Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125
```

```
Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 81
<211> LENGTH: 166
<212> TYPE: PRT
<213> ORGANISM: Artificial Sequence
<220> FEATURE:
<223> OTHER INFORMATION: EPO_79_L102V

<400> SEQUENCE: 81

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Val Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 82
<211> LENGTH: 166
<212> TYPE: PRT
<213> ORGANISM: Artificial Sequence
<220> FEATURE:
<223> OTHER INFORMATION: EPO_80_L102I

<400> SEQUENCE: 82

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95
```

```
Lys Ala Val Ser Gly Ile Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 83
<211> LENGTH: 166
<212> TYPE: PRT
<213> ORGANISM: Artificial Sequence
<220> FEATURE:
<223> OTHER INFORMATION: EPO_81_R110H

<400> SEQUENCE: 83

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu His Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 84
<211> LENGTH: 166
<212> TYPE: PRT
<213> ORGANISM: Artificial Sequence
<220> FEATURE:
<223> OTHER INFORMATION: EPO_82_R110Q

<400> SEQUENCE: 84

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60
```

```
Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Gln Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 85
<211> LENGTH: 166
<212> TYPE: PRT
<213> ORGANISM: Artificial Sequence
<220> FEATURE:
<223> OTHER INFORMATION: EPO_83_L122V

<400> SEQUENCE: 85

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Val
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 86
<211> LENGTH: 166
<212> TYPE: PRT
<213> ORGANISM: Artificial Sequence
<220> FEATURE:
<223> OTHER INFORMATION: EPO_84_L122I

<400> SEQUENCE: 86

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30
```

```
Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Ile
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 87
<211> LENGTH: 166
<212> TYPE: PRT
<213> ORGANISM: Artificial Sequence
<220> FEATURE:
<223> OTHER INFORMATION: EPO_85_K116Q

<400> SEQUENCE: 87

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Gln Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 88
<211> LENGTH: 166
<212> TYPE: PRT
<213> ORGANISM: Artificial Sequence
<220> FEATURE:
<223> OTHER INFORMATION: EPO_86_K116T

<400> SEQUENCE: 88
```

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65              70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Thr Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 89
<211> LENGTH: 166
<212> TYPE: PRT
<213> ORGANISM: Artificial Sequence
<220> FEATURE:
<223> OTHER INFORMATION: EPO_87_P121S

<400> SEQUENCE: 89

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65              70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Ser Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 90
<211> LENGTH: 166
<212> TYPE: PRT
```

```
<213> ORGANISM: Artificial Sequence
<220> FEATURE:
<223> OTHER INFORMATION: EPO_88_P121A

<400> SEQUENCE: 90

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Ala Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 91
<211> LENGTH: 166
<212> TYPE: PRT
<213> ORGANISM: Artificial Sequence
<220> FEATURE:
<223> OTHER INFORMATION: EPO_89_P122S

<400> SEQUENCE: 91

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Ser Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
```

<210> SEQ ID NO 92
<211> LENGTH: 166
<212> TYPE: PRT
<213> ORGANISM: Artificial Sequence
<220> FEATURE:
<223> OTHER INFORMATION: EPO_90_P122A

<400> SEQUENCE: 92

```
Ala Pro Pro Arg Leu Ile Cys Asp Ser Arg Val Leu Glu Arg Tyr Leu
 1               5                  10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Ala Asp Ala Ala Ser Ala Ala
        115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165
```

<210> SEQ ID NO 93
<211> LENGTH: 166
<212> TYPE: PRT
<213> ORGANISM: Artificial Sequence
<220> FEATURE:
<223> OTHER INFORMATION: EPO_91_D123Q

<400> SEQUENCE: 93

```
Ala Pro Pro Arg Leu Ile Cys Asp Ser Arg Val Leu Glu Arg Tyr Leu
 1               5                  10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Gln Ala Ala Ser Ala Ala
        115                 120                 125
Pro Leu Arg Thr Ile Thr Ala Asp Thr Phe Arg Lys Leu Phe Arg Val
```

```
                130                 135                 140
Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 94
<211> LENGTH: 166
<212> TYPE: PRT
<213> ORGANISM: Artificial Sequence
<220> FEATURE:
<223> OTHER INFORMATION: EPO_92_D123H

<400> SEQUENCE: 94

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro His Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 95
<211> LENGTH: 166
<212> TYPE: PRT
<213> ORGANISM: Artificial Sequence
<220> FEATURE:
<223> OTHER INFORMATION: EPO_93_P129S

<400> SEQUENCE: 95

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
```

```
                100                 105                 110
Gly Ala Gln Lys Glu Ala Ile Ser Pro Pro Asp Ala Ala Ser Ala Ala
            115                 120                 125
Ser Leu Arg Thr Ile Thr Ala Asp Thr Phe Arg Lys Leu Phe Arg Val
        130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 96
<211> LENGTH: 166
<212> TYPE: PRT
<213> ORGANISM: Artificial Sequence
<220> FEATURE:
<223> OTHER INFORMATION: EPO_94_P129A

<400> SEQUENCE: 96

Ala Pro Pro Arg Leu Ile Cys Asp Ser Arg Val Leu Glu Arg Tyr Leu
 1               5                  10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Ala Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 97
<211> LENGTH: 166
<212> TYPE: PRT
<213> ORGANISM: Artificial Sequence
<220> FEATURE:
<223> OTHER INFORMATION: EPO_95_L130V

<400> SEQUENCE: 97

Ala Pro Pro Arg Leu Ile Cys Asp Ser Arg Val Leu Glu Arg Tyr Leu
 1               5                  10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
```

```
                65                  70                  75                  80
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Val Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 98
<211> LENGTH: 166
<212> TYPE: PRT
<213> ORGANISM: Artificial Sequence
<220> FEATURE:
<223> OTHER INFORMATION: EPO_96_L130I

<400> SEQUENCE: 98

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
                35                  40                  45

Tyr Ala Trp Lys Arg Met Glu Val Gly Gln Gln Ala Val Glu Val Trp
                50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Ile Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 99
<211> LENGTH: 166
<212> TYPE: PRT
<213> ORGANISM: Artificial Sequence
<220> FEATURE:
<223> OTHER INFORMATION: EPO_97_R131H

<400> SEQUENCE: 99

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
```

```
                35                  40                  45
Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu His Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 100
<211> LENGTH: 166
<212> TYPE: PRT
<213> ORGANISM: Artificial Sequence
<220> FEATURE:
<223> OTHER INFORMATION: EPO_98_R131Q

<400> SEQUENCE: 100

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Gln Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 101
<211> LENGTH: 166
<212> TYPE: PRT
<213> ORGANISM: Artificial Sequence
<220> FEATURE:
<223> OTHER INFORMATION: EPO_99_D136Q

<400> SEQUENCE: 101

Ala Pro Pro Arg Leu Ile Cys Asp Ser Arg Val Leu Glu Arg Tyr Leu
```

```
                 1               5                  10                 15
Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
                35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Gln Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 102
<211> LENGTH: 166
<212> TYPE: PRT
<213> ORGANISM: Artificial Sequence
<220> FEATURE:
<223> OTHER INFORMATION: EPO_100_D136H

<400> SEQUENCE: 102

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
                35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala His Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 103
<211> LENGTH: 166
<212> TYPE: PRT
<213> ORGANISM: Artificial Sequence
```

```
<220> FEATURE:
<223> OTHER INFORMATION: EPO_101_R143H

<400> SEQUENCE: 103

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe His Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 104
<211> LENGTH: 166
<212> TYPE: PRT
<213> ORGANISM: Artificial Sequence
<220> FEATURE:
<223> OTHER INFORMATION: EPO_102_R143Q

<400> SEQUENCE: 104

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Gln Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 105
<211> LENGTH: 166
<212> TYPE: PRT
<213> ORGANISM: Artificial Sequence
<220> FEATURE:
<223> OTHER INFORMATION: EPO_103_Y145H

<400> SEQUENCE: 105

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

His Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 106
<211> LENGTH: 166
<212> TYPE: PRT
<213> ORGANISM: Artificial Sequence
<220> FEATURE:
<223> OTHER INFORMATION: EPO_104_Y145I

<400> SEQUENCE: 106

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140
```

Ile Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 107
<211> LENGTH: 166
<212> TYPE: PRT
<213> ORGANISM: Artificial Sequence
<220> FEATURE:
<223> OTHER INFORMATION: EPO_105_R150H

<400> SEQUENCE: 107

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu His Gly Lys Leu Lys Leu Tyr Thr Gly Glu Ala
145                 150                 155                 160

Cys Arg Thr Gly Asp Arg
                165

<210> SEQ ID NO 108
<211> LENGTH: 166
<212> TYPE: PRT
<213> ORGANISM: Artificial Sequence
<220> FEATURE:
<223> OTHER INFORMATION: EPO_106_R150Q

<400> SEQUENCE: 108

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

```
Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Gln Gly Lys Leu Lys Leu Tyr Thr Gly Glu Ala
145                 150                 155                 160

Cys Arg Thr Gly Asp Arg
                165

<210> SEQ ID NO 109
<211> LENGTH: 166
<212> TYPE: PRT
<213> ORGANISM: Artificial Sequence
<220> FEATURE:
<223> OTHER INFORMATION: EPO_107_K152Q

<400> SEQUENCE: 109

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Gln Leu Lys Leu Tyr Thr Gly Glu Ala
145                 150                 155                 160

Cys Arg Thr Gly Asp Arg
                165

<210> SEQ ID NO 110
<211> LENGTH: 166
<212> TYPE: PRT
<213> ORGANISM: Artificial Sequence
<220> FEATURE:
<223> OTHER INFORMATION: EPO_108_K152T

<400> SEQUENCE: 110

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80
```

```
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Thr Leu Lys Leu Tyr Thr Gly Glu Ala
145                 150                 155                 160

Cys Arg Thr Gly Asp Arg
                165

<210> SEQ ID NO 111
<211> LENGTH: 166
<212> TYPE: PRT
<213> ORGANISM: Artificial Sequence
<220> FEATURE:
<223> OTHER INFORMATION: EPO_109_K154Q

<400> SEQUENCE: 111

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Gln Leu Tyr Thr Gly Glu Ala
145                 150                 155                 160

Cys Arg Thr Gly Asp Arg
                165

<210> SEQ ID NO 112
<211> LENGTH: 166
<212> TYPE: PRT
<213> ORGANISM: Artificial Sequence
<220> FEATURE:
<223> OTHER INFORMATION: EPO_110_K154T

<400> SEQUENCE: 112

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45
```

```
Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Thr Leu Tyr Thr Gly Glu Ala
145                 150                 155                 160

Cys Arg Thr Gly Asp Arg
                165

<210> SEQ ID NO 113
<211> LENGTH: 166
<212> TYPE: PRT
<213> ORGANISM: Artificial Sequence
<220> FEATURE:
<223> OTHER INFORMATION: EPO_111_L155V

<400> SEQUENCE: 113

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Val Tyr Thr Gly Glu Ala
145                 150                 155                 160

Cys Arg Thr Gly Asp Arg
                165

<210> SEQ ID NO 114
<211> LENGTH: 166
<212> TYPE: PRT
<213> ORGANISM: Artificial Sequence
<220> FEATURE:
<223> OTHER INFORMATION: EPO_112_L155I

<400> SEQUENCE: 114

Ala Pro Pro Arg Leu Ile Cys Asp Ser Arg Val Leu Glu Arg Tyr Leu
1               5                   10                  15
```

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 115
<211> LENGTH: 166
<212> TYPE: PRT
<213> ORGANISM: Artificial Sequence
<220> FEATURE:
<223> OTHER INFORMATION: EPO_113_E159Q

<400> SEQUENCE: 115

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Gln Ala
145                 150                 155                 160

Cys Arg Thr Gly Asp Arg
            165

<210> SEQ ID NO 116
<211> LENGTH: 166
<212> TYPE: PRT
<213> ORGANISM: Artificial Sequence
<220> FEATURE:

<223> OTHER INFORMATION: EPO_114_E159H

<400> SEQUENCE: 116

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly His Ala
145                 150                 155                 160

Cys Arg Thr Gly Asp Arg
                165
```

<210> SEQ ID NO 117
<211> LENGTH: 166
<212> TYPE: PRT
<213> ORGANISM: Artificial Sequence
<220> FEATURE:
<223> OTHER INFORMATION: EPO_115_R162H

<400> SEQUENCE: 117

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys His Thr Gly Asp Arg
                165
```

```
<210> SEQ ID NO 118
<211> LENGTH: 166
<212> TYPE: PRT
<213> ORGANISM: Artificial Sequence
<220> FEATURE:
<223> OTHER INFORMATION: EPO_116_R162Q

<400> SEQUENCE: 118

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Gln Thr Gly Asp Arg
                165

<210> SEQ ID NO 119
<211> LENGTH: 166
<212> TYPE: PRT
<213> ORGANISM: Artificial Sequence
<220> FEATURE:
<223> OTHER INFORMATION: EPO_117_C29A

<400> SEQUENCE: 119

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Ala Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140
```

Tyr Ser Asn Phe Leu Arg Gly Lys Leu Lys Leu Tyr Thr Gly Glu Ala
145                 150                 155                 160

Cys Arg Thr Gly Asp Arg
                165

```
<210> SEQ ID NO 120
<211> LENGTH: 166
<212> TYPE: PRT
<213> ORGANISM: Artificial Sequence
<220> FEATURE:
<223> OTHER INFORMATION: EPO_118_C29I

<400> SEQUENCE: 120
```

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Ile Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

```
<210> SEQ ID NO 121
<211> LENGTH: 166
<212> TYPE: PRT
<213> ORGANISM: Artificial Sequence
<220> FEATURE:
<223> OTHER INFORMATION: EPO_119_C29T

<400> SEQUENCE: 121
```

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Thr Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 122
<211> LENGTH: 166
<212> TYPE: PRT
<213> ORGANISM: Artificial Sequence
<220> FEATURE:
<223> OTHER INFORMATION: EPO_120_C7A

<400> SEQUENCE: 122

Ala Pro Pro Arg Leu Ile Ala Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 123
<211> LENGTH: 166
<212> TYPE: PRT
<213> ORGANISM: Artificial Sequence
<220> FEATURE:
<223> OTHER INFORMATION: EPO_121_C7I

<400> SEQUENCE: 123

Ala Pro Pro Arg Leu Ile Ile Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

```
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 124
<211> LENGTH: 166
<212> TYPE: PRT
<213> ORGANISM: Artificial Sequence
<220> FEATURE:
<223> OTHER INFORMATION: EPO_122_C7T

<400> SEQUENCE: 124

Ala Pro Pro Arg Leu Ile Thr Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 125
<211> LENGTH: 166
<212> TYPE: PRT
<213> ORGANISM: Artificial Sequence
<220> FEATURE:
<223> OTHER INFORMATION: EPO_123_D123N

<400> SEQUENCE: 125

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45
```

Tyr Ala Trp Lys Arg Met Glu Val Gly Gln Gln Ala Val Glu Val Trp
            50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asn Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 126
<211> LENGTH: 166
<212> TYPE: PRT
<213> ORGANISM: Artificial Sequence
<220> FEATURE:
<223> OTHER INFORMATION: EPO_124_D136N

<400> SEQUENCE: 126

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
            50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asn Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 127
<211> LENGTH: 166
<212> TYPE: PRT
<213> ORGANISM: Artificial Sequence
<220> FEATURE:
<223> OTHER INFORMATION: EPO_125_D43N

<400> SEQUENCE: 127

Ala Pro Pro Arg Leu Ile Cys Asp Ser Arg Val Leu Glu Arg Tyr Leu
 1               5                  10                  15

```
Leu Glu Ala Lys Glu Ala Glu Asn Ile Thr Thr Gly Cys Ala Glu His
         20                  25                  30

Cys Ser Leu Asn Glu Asn Ile Thr Val Pro Asn Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 128
<211> LENGTH: 166
<212> TYPE: PRT
<213> ORGANISM: Artificial Sequence
<220> FEATURE:
<223> OTHER INFORMATION: EPO_126_D96N

<400> SEQUENCE: 128

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
         20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asn
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 129
<211> LENGTH: 166
<212> TYPE: PRT
<213> ORGANISM: Artificial Sequence
<220> FEATURE:
<223> OTHER INFORMATION: EPO_127_E159N
```

<400> SEQUENCE: 129

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Asn Ala
145                 150                 155                 160

Cys Arg Thr Gly Asp Arg
                165

<210> SEQ ID NO 130
<211> LENGTH: 166
<212> TYPE: PRT
<213> ORGANISM: Artificial Sequence
<220> FEATURE:
<223> OTHER INFORMATION: EPO_128_E18N

<400> SEQUENCE: 130

Ala Pro Pro Arg Leu Ile Cys Asp Ser Arg Val Leu Glu Arg Tyr Leu
1               5                   10                  15

Leu Asn Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

```
<210> SEQ ID NO 131
<211> LENGTH: 166
<212> TYPE: PRT
<213> ORGANISM: Artificial Sequence
<220> FEATURE:
<223> OTHER INFORMATION: EPO_129_E21N

<400> SEQUENCE: 131

Ala Pro Pro Arg Leu Ile Cys Asp Ser Arg Val Leu Glu Arg Tyr Leu
 1               5                  10                  15

Leu Glu Ala Lys Asn Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 132
<211> LENGTH: 166
<212> TYPE: PRT
<213> ORGANISM: Artificial Sequence
<220> FEATURE:
<223> OTHER INFORMATION: EPO_130_E23N

<400> SEQUENCE: 132

Ala Pro Pro Arg Leu Ile Cys Asp Ser Arg Val Leu Glu Arg Tyr Leu
 1               5                  10                  15

Leu Glu Ala Lys Glu Ala Asn Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
```

```
                   145                 150                 155                 160

Cys Arg Thr Gly Asp Arg
                165

<210> SEQ ID NO 133
<211> LENGTH: 166
<212> TYPE: PRT
<213> ORGANISM: Artificial Sequence
<220> FEATURE:
<223> OTHER INFORMATION: EPO_131_E31N

<400> SEQUENCE: 133

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Asn His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 134
<211> LENGTH: 166
<212> TYPE: PRT
<213> ORGANISM: Artificial Sequence
<220> FEATURE:
<223> OTHER INFORMATION: EPO_132_E37N

<400> SEQUENCE: 134

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Asn Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
```

```
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 135
<211> LENGTH: 166
<212> TYPE: PRT
<213> ORGANISM: Artificial Sequence
<220> FEATURE:
<223> OTHER INFORMATION: EPO_133_E55N

<400> SEQUENCE: 135

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Asn Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 136
<211> LENGTH: 166
<212> TYPE: PRT
<213> ORGANISM: Artificial Sequence
<220> FEATURE:
<223> OTHER INFORMATION: EPO_134_E62N

<400> SEQUENCE: 136

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Asn Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
```

Lys Ala Val Ser Gly Leu Arg Ser Leu Thr Thr Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 137
<211> LENGTH: 166
<212> TYPE: PRT
<213> ORGANISM: Artificial Sequence
<220> FEATURE:
<223> OTHER INFORMATION: EPO_135_E72N

<400> SEQUENCE: 137

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Asn Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 138
<211> LENGTH: 166
<212> TYPE: PRT
<213> ORGANISM: Artificial Sequence
<220> FEATURE:
<223> OTHER INFORMATION: EPO_136_E89N

<400> SEQUENCE: 138

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp

```
                50                  55                  60
Gln Gly Leu Ala Leu Leu Ser Glu Ala Val Leu Arg Gly Gln Ala Leu
 65                  70                  75                  80

Leu Val Asn Ser Ser Gln Pro Trp Asn Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 139
<211> LENGTH: 166
<212> TYPE: PRT
<213> ORGANISM: Artificial Sequence
<220> FEATURE:
<223> OTHER INFORMATION: EPO_137_K116N

<400> SEQUENCE: 139

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
                 35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Asn Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 140
<211> LENGTH: 166
<212> TYPE: PRT
<213> ORGANISM: Artificial Sequence
<220> FEATURE:
<223> OTHER INFORMATION: EPO_138_K152N

<400> SEQUENCE: 140

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
```

-continued

```
                    20                  25                  30
Cys Ser Leu Asn Glu Asn Ile Thr Val Pro Asp Thr Lys Val Asn Phe
                35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Asn Leu Lys Leu Tyr Thr Gly Glu Ala
145                 150                 155                 160

Cys Arg Thr Gly Asp Arg
                165

<210> SEQ ID NO 141
<211> LENGTH: 166
<212> TYPE: PRT
<213> ORGANISM: Artificial Sequence
<220> FEATURE:
<223> OTHER INFORMATION: EPO_139_K154N

<400> SEQUENCE: 141

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
                35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Asn Leu Tyr Thr Gly Glu Ala
145                 150                 155                 160

Cys Arg Thr Gly Asp Arg
                165

<210> SEQ ID NO 142
<211> LENGTH: 166
<212> TYPE: PRT
<213> ORGANISM: Artificial Sequence
<220> FEATURE:
<223> OTHER INFORMATION: EPO_140_K20N
```

```
<400> SEQUENCE: 142

Ala Pro Pro Arg Leu Ile Cys Asp Ser Arg Val Leu Glu Arg Tyr Leu
 1               5                  10                  15

Leu Glu Ala Asn Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 143
<211> LENGTH: 166
<212> TYPE: PRT
<213> ORGANISM: Artificial Sequence
<220> FEATURE:
<223> OTHER INFORMATION: EPO_141_K45N

<400> SEQUENCE: 143

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Asn Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 144
```

```
<211> LENGTH: 166
<212> TYPE: PRT
<213> ORGANISM: Artificial Sequence
<220> FEATURE:
<223> OTHER INFORMATION: EPO_142_K52N

<400> SEQUENCE: 144

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Asn Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 145
<211> LENGTH: 166
<212> TYPE: PRT
<213> ORGANISM: Artificial Sequence
<220> FEATURE:
<223> OTHER INFORMATION: EPO_143_K97N

<400> SEQUENCE: 145

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Asn Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160
```

Cys Arg Thr Gly Asp Arg
            165

<210> SEQ ID NO 146
<211> LENGTH: 166
<212> TYPE: PRT
<213> ORGANISM: Artificial Sequence
<220> FEATURE:
<223> OTHER INFORMATION: EPO_144_D8N

<400> SEQUENCE: 146

Ala Pro Pro Arg Leu Ile Cys Asn Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 147
<211> LENGTH: 166
<212> TYPE: PRT
<213> ORGANISM: Artificial Sequence
<220> FEATURE:
<223> OTHER INFORMATION: EPO_145_D165Q

<400> SEQUENCE: 147

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Gln Arg
                165

<210> SEQ ID NO 148
<211> LENGTH: 166
<212> TYPE: PRT
<213> ORGANISM: Artificial Sequence
<220> FEATURE:
<223> OTHER INFORMATION: EPO_146_D165H

<400> SEQUENCE: 148

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly His Arg
                165

<210> SEQ ID NO 149
<211> LENGTH: 166
<212> TYPE: PRT
<213> ORGANISM: Artificial Sequence
<220> FEATURE:
<223> OTHER INFORMATION: EPO_147_D165N

<400> SEQUENCE: 149

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
              100                 105                 110

Gly Ala Gln Lys Glu Ala Ile Ser Pro Pro Asp Ala Ala Ser Ala Ala
              115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asn Arg
              165

<210> SEQ ID NO 150
<211> LENGTH: 166
<212> TYPE: PRT
<213> ORGANISM: Artificial Sequence
<220> FEATURE:
<223> OTHER INFORMATION: EPO_148_R166H

<400> SEQUENCE: 150

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
              20                  25                  30

Cys Ser Leu Asn Glu Asn Ile Thr Val Pro Asp Thr Lys Val Asn Phe
              35                  40                  45

Tyr Ala Trp Lys Arg Met Glu Val Gly Gln Gln Ala Val Glu Val Trp
          50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                  85                  90                  95

Lys Ala Val Ser Gly Leu Arg Ser Leu Thr Thr Leu Leu Arg Ala Leu
              100                 105                 110

Gly Ala Gln Lys Glu Ala Ile Ser Pro Pro Asp Ala Ala Ser Ala Ala
              115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp His
              165

<210> SEQ ID NO 151
<211> LENGTH: 166
<212> TYPE: PRT
<213> ORGANISM: Artificial Sequence
<220> FEATURE:
<223> OTHER INFORMATION: EPO_149_R166Q

<400> SEQUENCE: 151

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
              20                  25                  30

Cys Ser Leu Asn Glu Asn Ile Thr Val Pro Asp Thr Lys Val Asn Phe
              35                  40                  45

Tyr Ala Trp Lys Arg Met Glu Val Gly Gln Gln Ala Val Glu Val Trp
          50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Gln
                165

<210> SEQ ID NO 152
<211> LENGTH: 166
<212> TYPE: PRT
<213> ORGANISM: Artificial Sequence
<220> FEATURE:
<223> OTHER INFORMATION: EPO_354_L5I

<400> SEQUENCE: 152

Ala Pro Pro Arg Ile Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 153
<211> LENGTH: 166
<212> TYPE: PRT
<213> ORGANISM: Artificial Sequence
<220> FEATURE:
<223> OTHER INFORMATION: EPO_355_L5V

<400> SEQUENCE: 153

Ala Pro Pro Arg Val Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

```
Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 154
<211> LENGTH: 166
<212> TYPE: PRT
<213> ORGANISM: Artificial Sequence
<220> FEATURE:
<223> OTHER INFORMATION: EPO_356_E13Q

<400> SEQUENCE: 154

Ala Pro Pro Arg Leu Ile Cys Asp Ser Arg Val Leu Gln Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 155
<211> LENGTH: 166
<212> TYPE: PRT
<213> ORGANISM: Artificial Sequence
<220> FEATURE:
<223> OTHER INFORMATION: EPO_357_E13H

<400> SEQUENCE: 155
```

```
Ala Pro Pro Arg Leu Ile Cys Asp Ser Arg Val Leu His Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65              70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 156
<211> LENGTH: 166
<212> TYPE: PRT
<213> ORGANISM: Artificial Sequence
<220> FEATURE:
<223> OTHER INFORMATION: EPO_358_E13N

<400> SEQUENCE: 156

Ala Pro Pro Arg Leu Ile Cys Asp Ser Arg Val Leu Asn Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65              70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 157
<211> LENGTH: 166
```

```
<212> TYPE: PRT
<213> ORGANISM: Artificial Sequence
<220> FEATURE:
<223> OTHER INFORMATION: EPO_359_R14H

<400> SEQUENCE: 157

Ala Pro Pro Arg Leu Ile Cys Asp Ser Arg Val Leu Glu His Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 158
<211> LENGTH: 166
<212> TYPE: PRT
<213> ORGANISM: Artificial Sequence
<220> FEATURE:
<223> OTHER INFORMATION: EPO_360_R14Q

<400> SEQUENCE: 158

Ala Pro Pro Arg Leu Ile Cys Asp Ser Arg Val Leu Glu Gln Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160
```

```
Cys Arg Thr Gly Asp Arg
            165

<210> SEQ ID NO 159
<211> LENGTH: 166
<212> TYPE: PRT
<213> ORGANISM: Artificial Sequence
<220> FEATURE:
<223> OTHER INFORMATION: EPO_361_Y15H

<400> SEQUENCE: 159

Ala Pro Pro Arg Leu Ile Cys Asp Ser Arg Val Leu Glu Arg His Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 160
<211> LENGTH: 166
<212> TYPE: PRT
<213> ORGANISM: Artificial Sequence
<220> FEATURE:
<223> OTHER INFORMATION: EPO_362_Y15I

<400> SEQUENCE: 160

Ala Pro Pro Arg Leu Ile Cys Asp Ser Arg Val Leu Glu Arg Ile Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125
```

```
Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 161
<211> LENGTH: 166
<212> TYPE: PRT
<213> ORGANISM: Artificial Sequence
<220> FEATURE:
<223> OTHER INFORMATION: EPO_363_L16I

<400> SEQUENCE: 161

Ala Pro Pro Arg Leu Ile Cys Asp Ser Arg Val Leu Glu Arg Tyr Ile
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 162
<211> LENGTH: 166
<212> TYPE: PRT
<213> ORGANISM: Artificial Sequence
<220> FEATURE:
<223> OTHER INFORMATION: EPO_364_L16V

<400> SEQUENCE: 162

Ala Pro Pro Arg Leu Ile Cys Asp Ser Arg Val Leu Glu Arg Tyr Val
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95
```

```
Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 163
<211> LENGTH: 166
<212> TYPE: PRT
<213> ORGANISM: Artificial Sequence
<220> FEATURE:
<223> OTHER INFORMATION: EPO_365_L17I

<400> SEQUENCE: 163

Ala Pro Pro Arg Leu Ile Cys Asp Ser Arg Val Leu Glu Arg Tyr Leu
1               5                   10                  15

Ile Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 164
<211> LENGTH: 166
<212> TYPE: PRT
<213> ORGANISM: Artificial Sequence
<220> FEATURE:
<223> OTHER INFORMATION: EPO_366_L17V

<400> SEQUENCE: 164

Ala Pro Pro Arg Leu Ile Cys Asp Ser Arg Val Leu Glu Arg Tyr Leu
1               5                   10                  15

Val Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60
```

```
Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 165
<211> LENGTH: 166
<212> TYPE: PRT
<213> ORGANISM: Artificial Sequence
<220> FEATURE:
<223> OTHER INFORMATION: EPO_367_L67I

<400> SEQUENCE: 165

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Ile Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 166
<211> LENGTH: 166
<212> TYPE: PRT
<213> ORGANISM: Artificial Sequence
<220> FEATURE:
<223> OTHER INFORMATION: EPO_368_L67V

<400> SEQUENCE: 166

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30
```

```
Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Val Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 167
<211> LENGTH: 166
<212> TYPE: PRT
<213> ORGANISM: Artificial Sequence
<220> FEATURE:
<223> OTHER INFORMATION: EPO_369_L70I

<400> SEQUENCE: 167

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Ile Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 168
<211> LENGTH: 166
<212> TYPE: PRT
<213> ORGANISM: Artificial Sequence
<220> FEATURE:
<223> OTHER INFORMATION: EPO_370_L70V

<400> SEQUENCE: 168
```

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Val Ser Glu Ala Val Leu Arg Gly Gln Ala Leu
65              70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 169
<211> LENGTH: 166
<212> TYPE: PRT
<213> ORGANISM: Artificial Sequence
<220> FEATURE:
<223> OTHER INFORMATION: EPO_371_L81I

<400> SEQUENCE: 169

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65              70                  75                  80

Ile Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 170
<211> LENGTH: 166
<212> TYPE: PRT

```
<213> ORGANISM: Artificial Sequence
<220> FEATURE:
<223> OTHER INFORMATION: EPO_372_L81V

<400> SEQUENCE: 170
```

| | | | | | | | | | | | | | | |
|---|---|---|---|---|---|---|---|---|---|---|---|---|---|---|
| Ala | Pro | Pro | Arg | Leu | Ile | Cys | Asp | Ser | Arg | Val | Leu | Glu | Arg | Tyr | Leu |
| 1 | | | | 5 | | | | | 10 | | | | | 15 |
| Leu | Glu | Ala | Lys | Glu | Ala | Glu | Asn | Ile | Thr | Thr | Gly | Cys | Ala | Glu | His |
| | | | 20 | | | | | 25 | | | | | 30 | |
| Cys | Ser | Leu | Asn | Glu | Asn | Ile | Thr | Val | Pro | Asp | Thr | Lys | Val | Asn | Phe |
| | | | 35 | | | | 40 | | | | | 45 | | |
| Tyr | Ala | Trp | Lys | Arg | Met | Glu | Val | Gly | Gln | Gln | Ala | Val | Glu | Val | Trp |
| | 50 | | | | | 55 | | | | | 60 | | | | |
| Gln | Gly | Leu | Ala | Leu | Leu | Ser | Glu | Ala | Val | Leu | Arg | Gly | Gln | Ala | Leu |
| 65 | | | | | 70 | | | | | 75 | | | | | 80 |
| Val | Val | Asn | Ser | Ser | Gln | Pro | Trp | Glu | Pro | Leu | Gln | Leu | His | Val | Asp |
| | | | | 85 | | | | | 90 | | | | | 95 | |
| Lys | Ala | Val | Ser | Gly | Leu | Arg | Ser | Leu | Thr | Thr | Leu | Leu | Arg | Ala | Leu |
| | | | 100 | | | | | 105 | | | | | 110 | | |
| Gly | Ala | Gln | Lys | Glu | Ala | Ile | Ser | Pro | Pro | Asp | Ala | Ala | Ser | Ala | Ala |
| | | | 115 | | | | | 120 | | | | | 125 | | |
| Pro | Leu | Arg | Thr | Ile | Thr | Ala | Asp | Thr | Phe | Arg | Lys | Leu | Phe | Arg | Val |
| | | | 130 | | | | 135 | | | | | 140 | | | |
| Tyr | Ser | Asn | Phe | Leu | Arg | Gly | Lys | Leu | Lys | Leu | Tyr | Thr | Gly | Glu | Ala |
| 145 | | | | | 150 | | | | | 155 | | | | | 160 |
| Cys | Arg | Thr | Gly | Asp | Arg | | | | | | | | | | |
| | | | | 165 | | | | | | | | | | | |

```
<210> SEQ ID NO 171
<211> LENGTH: 166
<212> TYPE: PRT
<213> ORGANISM: Artificial Sequence
<220> FEATURE:
<223> OTHER INFORMATION: EPO_373_L91I

<400> SEQUENCE: 171
```

| | | | | | | | | | | | | | | |
|---|---|---|---|---|---|---|---|---|---|---|---|---|---|---|
| Ala | Pro | Pro | Arg | Leu | Ile | Cys | Asp | Ser | Arg | Val | Leu | Glu | Arg | Tyr | Leu |
| 1 | | | | 5 | | | | | 10 | | | | | 15 |
| Leu | Glu | Ala | Lys | Glu | Ala | Glu | Asn | Ile | Thr | Thr | Gly | Cys | Ala | Glu | His |
| | | | 20 | | | | | 25 | | | | | 30 | |
| Cys | Ser | Leu | Asn | Glu | Asn | Ile | Thr | Val | Pro | Asp | Thr | Lys | Val | Asn | Phe |
| | | | 35 | | | | 40 | | | | | 45 | | |
| Tyr | Ala | Trp | Lys | Arg | Met | Glu | Val | Gly | Gln | Gln | Ala | Val | Glu | Val | Trp |
| | 50 | | | | | 55 | | | | | 60 | | | | |
| Gln | Gly | Leu | Ala | Leu | Leu | Ser | Glu | Ala | Val | Leu | Arg | Gly | Gln | Ala | Leu |
| 65 | | | | | 70 | | | | | 75 | | | | | 80 |
| Leu | Val | Asn | Ser | Ser | Gln | Pro | Trp | Glu | Pro | Ile | Gln | Leu | His | Val | Asp |
| | | | | 85 | | | | | 90 | | | | | 95 | |
| Lys | Ala | Val | Ser | Gly | Leu | Arg | Ser | Leu | Thr | Thr | Leu | Leu | Arg | Ala | Leu |
| | | | 100 | | | | | 105 | | | | | 110 | | |
| Gly | Ala | Gln | Lys | Glu | Ala | Ile | Ser | Pro | Pro | Asp | Ala | Ala | Ser | Ala | Ala |
| | | | 115 | | | | | 120 | | | | | 125 | | |
| Pro | Leu | Arg | Thr | Ile | Thr | Ala | Asp | Thr | Phe | Arg | Lys | Leu | Phe | Arg | Val |
| | | | 130 | | | | 135 | | | | | 140 | | | |
| Tyr | Ser | Asn | Phe | Leu | Arg | Gly | Lys | Leu | Lys | Leu | Tyr | Thr | Gly | Glu | Ala |
| 145 | | | | | 150 | | | | | 155 | | | | | 160 |
| Cys | Arg | Thr | Gly | Asp | Arg | | | | | | | | | | |

<210> SEQ ID NO 172
<211> LENGTH: 166
<212> TYPE: PRT
<213> ORGANISM: Artificial Sequence
<220> FEATURE:
<223> OTHER INFORMATION: EPO_374_L91V

<400> SEQUENCE: 172

```
Ala Pro Pro Arg Leu Ile Cys Asp Ser Arg Val Leu Glu Arg Tyr Leu
 1               5                  10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Val Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165
```

<210> SEQ ID NO 173
<211> LENGTH: 166
<212> TYPE: PRT
<213> ORGANISM: Artificial Sequence
<220> FEATURE:
<223> OTHER INFORMATION: EPO_375_R103H

<400> SEQUENCE: 173

```
Ala Pro Pro Arg Leu Ile Cys Asp Ser Arg Val Leu Glu Arg Tyr Leu
 1               5                  10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu His Ser Leu Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Pro Leu Arg Thr Ile Thr Ala Asp Thr Phe Arg Lys Leu Phe Arg Val
```

```
                130                 135                 140
Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 174
<211> LENGTH: 166
<212> TYPE: PRT
<213> ORGANISM: Artificial Sequence
<220> FEATURE:
<223> OTHER INFORMATION: EPO_376_R103Q

<400> SEQUENCE: 174

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Gln Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 175
<211> LENGTH: 166
<212> TYPE: PRT
<213> ORGANISM: Artificial Sequence
<220> FEATURE:
<223> OTHER INFORMATION: EPO_377_L105I

<400> SEQUENCE: 175

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Ile Thr Thr Leu Leu Arg Ala Leu
```

```
                100             105             110
Gly Ala Gln Lys Glu Ala Ile Ser Pro Pro Asp Ala Ser Ala Ala
            115                 120             125
Pro Leu Arg Thr Ile Thr Ala Asp Thr Phe Arg Lys Leu Phe Arg Val
        130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 176
<211> LENGTH: 166
<212> TYPE: PRT
<213> ORGANISM: Artificial Sequence
<220> FEATURE:
<223> OTHER INFORMATION: EPO_378_L105V

<400> SEQUENCE: 176

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Val Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 177
<211> LENGTH: 166
<212> TYPE: PRT
<213> ORGANISM: Artificial Sequence
<220> FEATURE:
<223> OTHER INFORMATION: EPO_379_L108I

<400> SEQUENCE: 177

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
```

```
            65                  70                  75                  80
Leu Val Asn Ser Ser Gln Pro Trp Glu Pro Leu Gln Leu His Val Asp
                85                  90                  95

Lys Ala Val Ser Gly Leu Arg Ser Leu Thr Thr Ile Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 178
<211> LENGTH: 166
<212> TYPE: PRT
<213> ORGANISM: Artificial Sequence
<220> FEATURE:
<223> OTHER INFORMATION: EPO_380_L108V

<400> SEQUENCE: 178

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65              70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Val Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 179
<211> LENGTH: 166
<212> TYPE: PRT
<213> ORGANISM: Artificial Sequence
<220> FEATURE:
<223> OTHER INFORMATION: EPO_381_L109I

<400> SEQUENCE: 179

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
```

```
                   35                  40                  45
Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Ile Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 180
<211> LENGTH: 166
<212> TYPE: PRT
<213> ORGANISM: Artificial Sequence
<220> FEATURE:
<223> OTHER INFORMATION: EPO_382_L109V

<400> SEQUENCE: 180

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
                 35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Val Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 181
<211> LENGTH: 166
<212> TYPE: PRT
<213> ORGANISM: Artificial Sequence
<220> FEATURE:
<223> OTHER INFORMATION: EPO_383_E117Q

<400> SEQUENCE: 181

Ala Pro Pro Arg Leu Ile Cys Asp Ser Arg Val Leu Glu Arg Tyr Leu
```

```
                1               5                  10                 15
Leu Glu Ala Lys Glu Ala Glu Asn Ile Thr Thr Gly Cys Ala Glu His
                20                 25                 30

Cys Ser Leu Asn Glu Asn Ile Thr Val Pro Asp Thr Lys Val Asn Phe
                35                 40                 45

Tyr Ala Trp Lys Arg Met Glu Val Gly Gln Gln Ala Val Glu Val Trp
 50                55                 60

Gln Gly Leu Ala Leu Leu Ser Glu Ala Val Leu Arg Gly Gln Ala Leu
 65                 70                 75                 80

Leu Val Asn Ser Ser Gln Pro Trp Glu Pro Leu Gln Leu His Val Asp
                85                 90                 95

Lys Ala Val Ser Gly Leu Arg Ser Leu Thr Thr Leu Leu Arg Ala Leu
                100                105                110

Gly Ala Gln Lys Gln Ala Ile Ser Pro Pro Asp Ala Ala Ser Ala Ala
                115                120                125

Pro Leu Arg Thr Ile Thr Ala Asp Thr Phe Arg Lys Leu Phe Arg Val
                130                135                140

Tyr Ser Asn Phe Leu Arg Gly Lys Leu Lys Leu Tyr Thr Gly Glu Ala
145                150                155                160

Cys Arg Thr Gly Asp Arg
                165

<210> SEQ ID NO 182
<211> LENGTH: 166
<212> TYPE: PRT
<213> ORGANISM: Artificial Sequence
<220> FEATURE:
<223> OTHER INFORMATION: EPO_384_E117H

<400> SEQUENCE: 182

Ala Pro Pro Arg Leu Ile Cys Asp Ser Arg Val Leu Glu Arg Tyr Leu
 1               5                  10                 15

Leu Glu Ala Lys Glu Ala Glu Asn Ile Thr Thr Gly Cys Ala Glu His
                20                 25                 30

Cys Ser Leu Asn Glu Asn Ile Thr Val Pro Asp Thr Lys Val Asn Phe
                35                 40                 45

Tyr Ala Trp Lys Arg Met Glu Val Gly Gln Gln Ala Val Glu Val Trp
 50                55                 60

Gln Gly Leu Ala Leu Leu Ser Glu Ala Val Leu Arg Gly Gln Ala Leu
 65                 70                 75                 80

Leu Val Asn Ser Ser Gln Pro Trp Glu Pro Leu Gln Leu His Val Asp
                85                 90                 95

Lys Ala Val Ser Gly Leu Arg Ser Leu Thr Thr Leu Leu Arg Ala Leu
                100                105                110

Gly Ala Gln Lys His Ala Ile Ser Pro Pro Asp Ala Ala Ser Ala Ala
                115                120                125

Pro Leu Arg Thr Ile Thr Ala Asp Thr Phe Arg Lys Leu Phe Arg Val
                130                135                140

Tyr Ser Asn Phe Leu Arg Gly Lys Leu Lys Leu Tyr Thr Gly Glu Ala
145                150                155                160

Cys Arg Thr Gly Asp Arg
                165

<210> SEQ ID NO 183
<211> LENGTH: 166
<212> TYPE: PRT
<213> ORGANISM: Artificial Sequence
```

<220> FEATURE:
<223> OTHER INFORMATION: EPO_385_E117N

<400> SEQUENCE: 183

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Asn Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 184
<211> LENGTH: 166
<212> TYPE: PRT
<213> ORGANISM: Artificial Sequence
<220> FEATURE:
<223> OTHER INFORMATION: EPO_386_F138I

<400> SEQUENCE: 184

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Ile Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 185
<211> LENGTH: 166
<212> TYPE: PRT
<213> ORGANISM: Artificial Sequence
<220> FEATURE:
<223> OTHER INFORMATION: EPO_387_F138V

<400> SEQUENCE: 185

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Val Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 186
<211> LENGTH: 166
<212> TYPE: PRT
<213> ORGANISM: Artificial Sequence
<220> FEATURE:
<223> OTHER INFORMATION: EPO_388_R139H

<400> SEQUENCE: 186

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe His Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 187
<211> LENGTH: 166
<212> TYPE: PRT
<213> ORGANISM: Artificial Sequence
<220> FEATURE:
<223> OTHER INFORMATION: EPO_389_R139Q

<400> SEQUENCE: 187

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Gln Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 188
<211> LENGTH: 166
<212> TYPE: PRT
<213> ORGANISM: Artificial Sequence
<220> FEATURE:
<223> OTHER INFORMATION: EPO_390_K140N

<400> SEQUENCE: 188

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Asn Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 189
<211> LENGTH: 166
<212> TYPE: PRT
<213> ORGANISM: Artificial Sequence
<220> FEATURE:
<223> OTHER INFORMATION: EPO_391_K140Q

<400> SEQUENCE: 189

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Gln Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 190
<211> LENGTH: 166
<212> TYPE: PRT
<213> ORGANISM: Artificial Sequence
<220> FEATURE:
<223> OTHER INFORMATION: EPO_392_L141I

<400> SEQUENCE: 190

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

```
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Ile Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 191
<211> LENGTH: 166
<212> TYPE: PRT
<213> ORGANISM: Artificial Sequence
<220> FEATURE:
<223> OTHER INFORMATION: EPO_393_L141V

<400> SEQUENCE: 191

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Val Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 192
<211> LENGTH: 166
<212> TYPE: PRT
<213> ORGANISM: Artificial Sequence
<220> FEATURE:
<223> OTHER INFORMATION: EPO_394_F142I

<400> SEQUENCE: 192

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45
```

```
Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Ile Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 193
<211> LENGTH: 166
<212> TYPE: PRT
<213> ORGANISM: Artificial Sequence
<220> FEATURE:
<223> OTHER INFORMATION: EPO_395_F142V

<400> SEQUENCE: 193

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Val Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 194
<211> LENGTH: 166
<212> TYPE: PRT
<213> ORGANISM: Artificial Sequence
<220> FEATURE:
<223> OTHER INFORMATION: EPO_396_F148I

<400> SEQUENCE: 194

Ala Pro Pro Arg Leu Ile Cys Asp Ser Arg Val Leu Glu Arg Tyr Leu
  1               5                  10                  15
```

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Ile Leu Arg Gly Lys Leu Lys Leu Tyr Thr Gly Glu Ala
145                 150                 155                 160

Cys Arg Thr Gly Asp Arg
                165

<210> SEQ ID NO 195
<211> LENGTH: 166
<212> TYPE: PRT
<213> ORGANISM: Artificial Sequence
<220> FEATURE:
<223> OTHER INFORMATION: EPO_397_F148V

<400> SEQUENCE: 195

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Val Leu Arg Gly Lys Leu Lys Leu Tyr Thr Gly Glu Ala
145                 150                 155                 160

Cys Arg Thr Gly Asp Arg
                165

<210> SEQ ID NO 196
<211> LENGTH: 166
<212> TYPE: PRT
<213> ORGANISM: Artificial Sequence
<220> FEATURE:

<223> OTHER INFORMATION: EPO_398_L149I

<400> SEQUENCE: 196

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Ile Arg Gly Lys Leu Lys Leu Tyr Thr Gly Glu Ala
145                 150                 155                 160

Cys Arg Thr Gly Asp Arg
                165
```

<210> SEQ ID NO 197
<211> LENGTH: 166
<212> TYPE: PRT
<213> ORGANISM: Artificial Sequence
<220> FEATURE:
<223> OTHER INFORMATION: EPO_399_L149V

<400> SEQUENCE: 197

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Val Arg Gly Lys Leu Lys Leu Tyr Thr Gly Glu Ala
145                 150                 155                 160

Cys Arg Thr Gly Asp Arg
                165
```

```
<210> SEQ ID NO 198
<211> LENGTH: 166
<212> TYPE: PRT
<213> ORGANISM: Artificial Sequence
<220> FEATURE:
<223> OTHER INFORMATION: EPO_400_L153I

<400> SEQUENCE: 198

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Ile Lys Leu Tyr Thr Gly Glu Ala
145                 150                 155                 160

Cys Arg Thr Gly Asp Arg
                165

<210> SEQ ID NO 199
<211> LENGTH: 166
<212> TYPE: PRT
<213> ORGANISM: Artificial Sequence
<220> FEATURE:
<223> OTHER INFORMATION: EPO_401_L153V

<400> SEQUENCE: 199

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140
```

Tyr Ser Asn Phe Leu Arg Gly Lys Val Lys Leu Tyr Thr Gly Glu Ala
145                 150                 155                 160

Cys Arg Thr Gly Asp Arg
                165

<210> SEQ ID NO 200
<211> LENGTH: 166
<212> TYPE: PRT
<213> ORGANISM: Artificial Sequence
<220> FEATURE:
<223> OTHER INFORMATION: EPO_402_Y156H

<400> SEQUENCE: 200

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu His Thr Gly Glu Ala
145                 150                 155                 160

Cys Arg Thr Gly Asp Arg
                165

<210> SEQ ID NO 201
<211> LENGTH: 166
<212> TYPE: PRT
<213> ORGANISM: Artificial Sequence
<220> FEATURE:
<223> OTHER INFORMATION: EPO_403_Y156I

<400> SEQUENCE: 201

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

```
Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Ile Thr Gly Glu Ala
145                 150                 155                 160

Cys Arg Thr Gly Asp Arg
                165

<210> SEQ ID NO 202
<211> LENGTH: 192
<212> TYPE: PRT
<213> ORGANISM: Macaca mulatta
<220> FEATURE:
<223> OTHER INFORMATION: Rhesus macaque EPO

<400> SEQUENCE: 202

Met Gly Val His Glu Cys Pro Ala Trp Leu Trp Leu Leu Leu Ser Leu
1               5                   10                  15

Val Ser Leu Pro Leu Gly Leu Pro Val Pro Gly Ala Pro Pro Arg Leu
            20                  25                  30

Val Cys Asp Ser Arg Val Leu Glu Arg Tyr Leu Leu Glu Ala Lys Glu
        35                  40                  45

Ala Glu Asn Val Thr Met Gly Cys Ser Glu Ser Cys Ser Leu Asn Glu
    50                  55                  60

Asn Ile Thr Val Pro Asp Thr Lys Val Asn Phe Tyr Ala Trp Lys Arg
65                  70                  75                  80

Ile Glu Val Gly Gln Gln Ala Val Glu Val Trp Gln Gly Leu Ala Leu
                85                  90                  95

Leu Ser Glu Ala Val Leu Arg Gly Gln Ala Val Leu Ala Asn Ser Ser
            100                 105                 110

Gln Pro Phe Glu Pro Leu Gln Leu His Met Asp Lys Ala Ile Ser Gly
        115                 120                 125

Leu Arg Ser Ile Thr Thr Leu Leu Arg Ala Leu Gly Ala Gln Glu Ala
    130                 135                 140

Ile Ser Leu Pro Asp Ala Ala Ser Ala Ala Pro Leu Arg Thr Ile Thr
145                 150                 155                 160

Ala Asp Thr Phe Cys Lys Leu Phe Arg Val Tyr Ser Asn Phe Leu Arg
                165                 170                 175

Gly Lys Leu Lys Leu Tyr Thr Gly Glu Ala Cys Arg Arg Gly Asp Arg
            180                 185                 190

<210> SEQ ID NO 203
<211> LENGTH: 192
<212> TYPE: PRT
<213> ORGANISM: Mus musculus
<220> FEATURE:
<223> OTHER INFORMATION: Mouse EPO

<400> SEQUENCE: 203

Met Gly Val Pro Glu Arg Pro Thr Leu Leu Leu Leu Leu Ser Leu Leu
1               5                   10                  15

Leu Ile Pro Leu Gly Leu Pro Val Leu Cys Ala Pro Pro Arg Leu Ile
            20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60
```

```
Ile Thr Val Pro Asp Thr Lys Val Asn Phe Tyr Ala Trp Lys Arg Met
 65                  70                  75                  80

Glu Val Glu Glu Gln Ala Ile Glu Val Trp Gln Gly Leu Ser Leu Leu
                 85                  90                  95

Ser Glu Ala Ile Leu Gln Ala Gln Ala Leu Leu Ala Asn Ser Ser Gln
                100                 105                 110

Pro Pro Glu Thr Leu Gln Leu His Ile Asp Lys Ala Ile Ser Gly Leu
                115                 120                 125

Arg Ser Leu Thr Ser Leu Leu Arg Val Leu Gly Ala Gln Lys Glu Leu
                130                 135                 140

Met Ser Pro Pro Asp Thr Thr Pro Pro Ala Pro Leu Arg Thr Leu Thr
145                 150                 155                 160

Val Asp Thr Phe Cys Lys Leu Phe Arg Val Tyr Ala Asn Phe Leu Arg
                165                 170                 175

Gly Lys Leu Lys Leu Tyr Thr Gly Glu Val Cys Arg Arg Gly Asp Arg
                180                 185                 190

<210> SEQ ID NO 204
<211> LENGTH: 192
<212> TYPE: PRT
<213> ORGANISM: Rattus norvegicus
<220> FEATURE:
<223> OTHER INFORMATION: Rat EPO

<400> SEQUENCE: 204

Met Gly Val Pro Glu Arg Pro Thr Leu Leu Leu Leu Ser Leu Leu
 1                   5                  10                  15

Leu Ile Pro Leu Gly Leu Pro Val Leu Cys Ala Pro Pro Arg Leu Ile
                 20                  25                  30

Cys Asp Ser Arg Val Leu Glu Arg Tyr Ile Leu Glu Ala Lys Glu Ala
                 35                  40                  45

Glu Asn Val Thr Met Gly Cys Ala Glu Gly Pro Arg Leu Ser Glu Asn
                 50                  55                  60

Ile Thr Val Pro Asp Thr Lys Val Asn Phe Tyr Ala Trp Lys Arg Met
 65                  70                  75                  80

Lys Val Glu Glu Gln Ala Val Glu Val Trp Gln Gly Leu Ser Leu Leu
                 85                  90                  95

Ser Glu Ala Ile Leu Gln Ala Gln Ala Leu Gln Ala Asn Ser Ser Gln
                100                 105                 110

Pro Pro Glu Ser Leu Gln Leu His Ile Asp Lys Ala Ile Ser Gly Leu
                115                 120                 125

Arg Ser Leu Thr Ser Leu Leu Arg Val Leu Gly Ala Gln Lys Glu Leu
                130                 135                 140

Met Ser Pro Pro Asp Ala Thr Gln Ala Ala Pro Leu Arg Thr Leu Thr
145                 150                 155                 160

Ala Asp Thr Phe Cys Lys Leu Phe Arg Val Tyr Ser Asn Phe Leu Arg
                165                 170                 175

Gly Lys Leu Lys Leu Tyr Thr Gly Glu Ala Cys Arg Arg Gly Asp Arg
                180                 185                 190

<210> SEQ ID NO 205
<211> LENGTH: 194
<212> TYPE: PRT
<213> ORGANISM: Sus scrofa
<220> FEATURE:
<223> OTHER INFORMATION: Pig EPO

<400> SEQUENCE: 205
```

```
Met Gly Ala Arg Glu Cys Pro Ala Arg Leu Leu Leu Ser Leu Leu
 1               5                  10                  15

Leu Leu Pro Leu Gly Leu Pro Val Leu Gly Ala Pro Pro Arg Leu Ile
            20                  25                  30

Cys Asp Ser Arg Val Leu Glu Arg Tyr Ile Leu Glu Ala Lys Glu Gly
            35                  40                  45

Glu Asn Ala Thr Met Gly Cys Ala Glu Ser Cys Ser Phe Ser Glu Asn
         50                  55                  60

Ile Thr Val Pro Asp Thr Lys Val Asn Phe Tyr Ala Trp Lys Arg Met
 65              70                  75                  80

Glu Val Gln Gln Gln Ala Met Glu Val Trp Gln Gly Leu Ala Leu Leu
                 85                  90                  95

Ser Glu Ala Ile Leu Gln Gly Gln Ala Leu Leu Ala Asn Ser Ser Gln
             100                 105                 110

Pro Ser Glu Ala Leu Gln Leu His Val Asp Lys Ala Val Ser Gly Leu
             115                 120                 125

Arg Ser Leu Thr Ser Leu Leu Arg Ala Leu Gly Ala Gln Lys Glu Ala
130             135                 140

Ile Pro Leu Pro Asp Ala Ser Pro Ser Ser Ala Thr Pro Leu Arg Thr
145             150                 155                 160

Phe Ala Val Asp Thr Leu Cys Lys Leu Phe Arg Asn Tyr Ser Asn Phe
                165                 170                 175

Leu Arg Gly Lys Leu Thr Leu Tyr Thr Gly Glu Ala Cys Arg Arg Arg
                180                 185                 190

Asp Arg
```

<210> SEQ ID NO 206
<211> LENGTH: 206
<212> TYPE: PRT
<213> ORGANISM: Canis familiaris
<220> FEATURE:
<223> OTHER INFORMATION: Dog EPO

<400> SEQUENCE: 206

```
Met Cys Glu Pro Ala Pro Pro Lys Pro Thr Gln Ser Ala Trp His Ser
 1               5                  10                  15

Phe Pro Glu Cys Pro Ala Leu Leu Leu Leu Ser Leu Leu Leu Leu
            20                  25                  30

Pro Leu Gly Leu Pro Val Leu Gly Ala Pro Pro Arg Leu Ile Cys Asp
            35                  40                  45

Ser Arg Val Leu Glu Arg Tyr Ile Leu Glu Ala Arg Glu Ala Glu Asn
         50                  55                  60

Val Thr Met Gly Cys Ala Gln Gly Cys Ser Phe Ser Glu Asn Ile Thr
 65              70                  75                  80

Val Pro Asp Thr Lys Val Asn Phe Tyr Thr Trp Lys Arg Met Asp Val
                 85                  90                  95

Gly Gln Gln Ala Leu Glu Val Trp Gln Gly Leu Ala Leu Leu Ser Glu
             100                 105                 110

Ala Ile Leu Arg Gly Gln Ala Leu Leu Ala Asn Ala Ser Gln Pro Ser
             115                 120                 125

Glu Thr Pro Gln Leu His Val Asp Lys Ala Val Ser Ser Leu Arg Ser
             130                 135                 140

Leu Thr Ser Leu Leu Arg Ala Leu Gly Ala Gln Lys Glu Ala Met Ser
145             150                 155                 160

Leu Pro Glu Glu Ala Ser Pro Ala Pro Leu Arg Thr Phe Thr Val Asp
                165                 170                 175
```

```
Thr Leu Cys Lys Leu Phe Arg Ile Tyr Ser Asn Phe Leu Arg Gly Lys
            180                 185                 190

Leu Thr Leu Tyr Thr Gly Glu Ala Cys Arg Arg Gly Asp Arg
        195                 200                 205

<210> SEQ ID NO 207
<211> LENGTH: 192
<212> TYPE: PRT
<213> ORGANISM: Felis catus
<220> FEATURE:
<223> OTHER INFORMATION: Cat EPO

<400> SEQUENCE: 207

Met Gly Ser Cys Glu Cys Pro Ala Leu Leu Leu Leu Ser Leu Leu
 1               5                  10                  15

Leu Leu Pro Leu Gly Leu Pro Val Leu Gly Ala Pro Pro Arg Leu Ile
            20                  25                  30

Cys Asp Ser Arg Val Leu Glu Arg Tyr Ile Leu Gly Ala Arg Glu Ala
        35                  40                  45

Glu Asn Val Thr Met Gly Cys Ala Glu Gly Cys Ser Phe Ser Glu Asn
    50                  55                  60

Ile Thr Val Pro Asp Thr Lys Val Asn Phe Tyr Thr Trp Lys Arg Met
65                  70                  75                  80

Asp Val Gly Gln Gln Ala Val Glu Val Trp Gln Gly Leu Ala Leu Leu
                85                  90                  95

Ser Glu Ala Ile Leu Arg Gly Gln Ala Leu Leu Ala Asn Ser Ser Gln
            100                 105                 110

Pro Ser Glu Thr Leu Gln Leu His Val Asp Lys Ala Val Ser Ser Leu
        115                 120                 125

Arg Ser Leu Thr Ser Leu Leu Arg Ala Leu Gly Ala Gln Lys Glu Ala
    130                 135                 140

Thr Ser Leu Pro Glu Ala Thr Ser Ala Ala Pro Leu Arg Thr Phe Thr
145                 150                 155                 160

Val Asp Thr Leu Cys Lys Leu Phe Arg Ile Tyr Ser Asn Phe Leu Arg
                165                 170                 175

Gly Lys Leu Thr Leu Tyr Thr Gly Glu Ala Cys Arg Arg Gly Asp Arg
            180                 185                 190

<210> SEQ ID NO 208
<211> LENGTH: 195
<212> TYPE: PRT
<213> ORGANISM: Oryctolagus cuniculus
<220> FEATURE:
<223> OTHER INFORMATION: Rabbit EPO

<400> SEQUENCE: 208

Met Gly Val Arg Gly Arg Leu Ala Leu Leu Pro Leu Ala Leu Leu Cys
 1               5                  10                  15

Leu Leu Val Leu Ala Leu Gly Leu Pro Val Leu Gly Ala Pro Ala Arg
            20                  25                  30

Leu Ile Cys Asp Ser Arg Val Leu Glu Arg Tyr Ile Leu Glu Ala Lys
        35                  40                  45

Glu Ala Glu Asn Val Thr Met Gly Cys Ala Glu Gly Cys Ser Leu Gly
    50                  55                  60

Glu Asn Ile Thr Val Pro Asp Thr Lys Val Asn Phe His His Trp Lys
65                  70                  75                  80

Lys Ser Glu Ala Gly Arg His Ala Val Glu Val Trp Gln Gly Leu Ala
                85                  90                  95
```

```
Leu Leu Ser Glu Ala Met Leu Arg Ser Gln Ala Leu Leu Ala Asn Ser
            100                 105                 110

Ser Gln Leu Pro Glu Thr Leu Gln Val His Val Asp Lys Ala Val Ser
        115                 120                 125

Gly Leu Arg Ser Leu Thr Ser Leu Leu Arg Ala Leu Gly Val Gln Lys
    130                 135                 140

Glu Ala Val Ser Pro Pro Glu Ala Ala Ser Ala Ala Pro Leu Arg
145                 150                 155                 160

Thr Val Ala Ala Asp Thr Leu Cys Lys Leu Phe Arg Ile Tyr Ser Asn
                165                 170                 175

Phe Leu Arg Gly Lys Leu Lys Leu Tyr Thr Gly Glu Ala Cys Arg Arg
            180                 185                 190

Gly Asp Arg
        195

<210> SEQ ID NO 209
<211> LENGTH: 192
<212> TYPE: PRT
<213> ORGANISM: Bos taurus
<220> FEATURE:
<223> OTHER INFORMATION: Bovine EPO

<400> SEQUENCE: 209

Met Gly Ala Arg Asp Cys Thr Pro Leu Leu Met Leu Ser Phe Leu Leu
1               5                   10                  15

Phe Pro Leu Gly Phe Pro Val Leu Gly Ala Pro Ala Arg Leu Ile Cys
            20                  25                  30

Asp Ser Arg Val Leu Glu Arg Tyr Ile Leu Glu Ala Arg Glu Ala Glu
        35                  40                  45

Asn Ala Thr Met Gly Cys Ala Glu Gly Cys Ser Phe Asn Glu Asn Ile
    50                  55                  60

Thr Val Pro Asp Thr Lys Val Asn Phe Tyr Ala Trp Lys Arg Met Glu
65                  70                  75                  80

Val Gln Gln Gln Ala Leu Glu Val Trp Gln Gly Leu Ala Leu Leu Ser
                85                  90                  95

Glu Ala Ile Leu Arg Gly Gln Ala Leu Leu Ala Asn Ala Ser Gln Pro
            100                 105                 110

Cys Glu Ala Leu Arg Leu His Val Asp Lys Ala Val Ser Gly Leu Arg
        115                 120                 125

Ser Leu Thr Ser Leu Leu Arg Ala Leu Gly Ala Gln Lys Glu Ala Ile
    130                 135                 140

Ser Leu Pro Asp Ala Thr Pro Ser Ala Ala Pro Leu Arg Ala Phe Thr
145                 150                 155                 160

Val Asp Ala Leu Ser Lys Leu Phe Arg Ile Tyr Ser Asn Phe Leu Arg
                165                 170                 175

Gly Lys Leu Thr Leu Tyr Thr Gly Glu Ala Cys Arg Arg Gly Asp Arg
            180                 185                 190

<210> SEQ ID NO 210
<211> LENGTH: 192
<212> TYPE: PRT
<213> ORGANISM: Equus caballus
<220> FEATURE:
<223> OTHER INFORMATION: Horse EPO

<400> SEQUENCE: 210

Met Gly Val Arg Glu Cys Pro Ala Leu Leu Leu Leu Ser Leu Leu
1               5                   10                  15
```

```
Leu Pro Pro Leu Gly Leu Pro Ala Leu Gly Ala Pro Pro Arg Leu Ile
            20                  25                  30

Cys Asp Ser Arg Val Leu Glu Arg Tyr Ile Leu Glu Ala Arg Glu Ala
            35                  40                  45

Glu Asn Val Thr Met Gly Cys Ala Glu Gly Cys Ser Phe Gly Glu Asn
        50                  55                  60

Val Thr Val Pro Asp Thr Lys Val Asn Phe Tyr Ser Trp Lys Arg Met
65                  70                  75                  80

Glu Val Glu Gln Gln Ala Val Glu Val Trp Gln Gly Leu Ala Leu Leu
                85                  90                  95

Ser Glu Ala Ile Leu Gln Gly Gln Ala Leu Leu Ala Asn Ser Ser Gln
                100                 105                 110

Pro Ser Glu Thr Leu Arg Leu His Val Asp Lys Ala Val Ser Ser Leu
            115                 120                 125

Arg Ser Leu Thr Ser Leu Leu Arg Ala Leu Gly Ala Gln Lys Glu Ala
        130                 135                 140

Ile Ser Pro Pro Asp Ala Ala Ser Ala Ala Pro Leu Arg Thr Phe Ala
145                 150                 155                 160

Val Asp Thr Leu Cys Lys Leu Phe Arg Ile Tyr Ser Asn Phe Leu Arg
                165                 170                 175

Gly Lys Leu Lys Leu Tyr Thr Gly Glu Ala Cys Arg Arg Gly Asp Arg
                180                 185                 190

<210> SEQ ID NO 211
<211> LENGTH: 194
<212> TYPE: PRT
<213> ORGANISM: Ovis aries
<220> FEATURE:
<223> OTHER INFORMATION: Sheep EPO

<400> SEQUENCE: 211

Met Gly Ala Arg Asp Cys Thr Pro Leu Leu Leu Leu Leu Ser Phe
1               5                   10                  15

Leu Leu Phe Pro Leu Gly Leu Pro Val Leu Gly Ala Pro Pro Arg Leu
            20                  25                  30

Ile Cys Asp Ser Arg Val Leu Glu Arg Tyr Ile Leu Glu Ala Arg Glu
            35                  40                  45

Ala Glu Asn Ala Thr Met Gly Cys Ala Glu Gly Cys Ser Phe Ser Glu
        50                  55                  60

Asn Ile Thr Val Pro Asp Thr Lys Val Asn Phe Tyr Ala Trp Lys Arg
65                  70                  75                  80

Met Glu Val Gln Gln Gln Ala Leu Glu Val Trp Gln Gly Leu Ala Leu
                85                  90                  95

Leu Ser Glu Ala Ile Phe Arg Gly Gln Ala Leu Leu Ala Asn Ala Ser
                100                 105                 110

Gln Pro Cys Glu Ala Leu Arg Leu His Val Asp Lys Ala Val Ser Gly
            115                 120                 125

Leu Arg Ser Leu Thr Ser Leu Leu Arg Ala Leu Gly Ala Gln Lys Glu
        130                 135                 140

Ala Ile Pro Leu Pro Asp Ala Thr Pro Ser Ala Ala Pro Leu Arg Ile
145                 150                 155                 160

Phe Thr Val Asp Ala Leu Ser Lys Leu Phe Arg Ile Tyr Ser Asn Phe
                165                 170                 175

Leu Arg Gly Lys Leu Thr Leu Tyr Thr Gly Glu Ala Cys Arg Arg Gly
                180                 185                 190
```

Asp Arg

```
<210> SEQ ID NO 212
<211> LENGTH: 133
<212> TYPE: PRT
<213> ORGANISM: Pan troglodytes
<220> FEATURE:
<223> OTHER INFORMATION: Chimpanzee EPO (fragment)

<400> SEQUENCE: 212
```

Ser Arg Val Leu Glu Arg Tyr Leu Leu Glu Ala Lys Glu Ala Glu Asn
1               5                   10                  15

Ile Thr Thr Gly Cys Ala Glu His Cys Ser Leu Asn Glu Asn Ile Thr
            20                  25                  30

Val Pro Asp Thr Lys Val Asn Phe Tyr Ala Trp Lys Arg Met Glu Val
        35                  40                  45

Gly Gln Gln Ala Val Glu Val Trp Gln Gly Leu Ala Leu Leu Ser Glu
    50                  55                  60

Ala Val Leu Arg Gly Gln Ala Leu Leu Val Asn Ser Ser Gln Pro Leu
65                  70                  75                  80

Glu Pro Leu Gln Leu His Val Asp Lys Ala Val Ser Gly Leu Arg Ser
                85                  90                  95

Leu Thr Thr Leu Leu Arg Ala Leu Gly Ala Gln Lys Glu Ala Ile Ser
            100                 105                 110

Pro Pro Asp Ala Ala Ser Ala Ala Pro Leu Arg Thr Ile Thr Ala Asp
        115                 120                 125

Thr Phe Arg Lys Leu
    130

```
<210> SEQ ID NO 213
<211> LENGTH: 183
<212> TYPE: PRT
<213> ORGANISM: Danio rerio
<220> FEATURE:
<223> OTHER INFORMATION: Zebrafish EPO

<400> SEQUENCE: 213
```

Met Phe His Gly Ser Gly Leu Phe Ala Leu Leu Met Val Leu Glu
1               5                   10                  15

Trp Thr Arg Pro Gly Leu Ser Ser Pro Leu Arg Pro Ile Cys Asp Leu
            20                  25                  30

Arg Val Leu Asp His Phe Ile Lys Glu Ala Trp Asp Ala Glu Ala Ala
        35                  40                  45

Met Arg Thr Cys Lys Asp Asp Cys Ser Ile Ala Thr Asn Val Thr Val
    50                  55                  60

Pro Leu Thr Arg Val Asp Phe Glu Val Trp Ala Met Asn Ile Glu
65                  70                  75                  80

Glu Gln Ala Gln Glu Val Gln Ser Gly Leu His Met Leu Asn Glu Ala
                85                  90                  95

Ile Gly Ser Leu Gln Ile Ser Asn Gln Thr Glu Val Leu Gln Ser His
            100                 105                 110

Ile Asp Ala Ser Ile Arg Asn Ile Ala Ser Ile Arg Gln Val Leu Arg
        115                 120                 125

Ser Leu Ser Ile Pro Glu Tyr Val Pro Pro Thr Ser Ser Gly Glu Asp
    130                 135                 140

Lys Glu Thr Gln Lys Ile Ser Ser Ile Ser Glu Leu Phe Gln Val His
145                 150                 155                 160

Val Asn Phe Leu Arg Gly Lys Ala Arg Leu Leu Leu Ala Asn Ala Pro

```
                     165                 170                 175

Val Cys Arg Gln Gly Val Ser
            180

<210> SEQ ID NO 214
<211> LENGTH: 185
<212> TYPE: PRT
<213> ORGANISM: Fugu rubripes
<220> FEATURE:
<223> OTHER INFORMATION: Japanese pufferfish EPO

<400> SEQUENCE: 214

Met Leu Gln Lys Thr Gly Arg Gly Leu Leu Ala Phe Leu Leu Ile Val
1               5                   10                  15

Leu Glu Trp Thr Gln Pro Ser Leu Pro Ser Pro Leu Arg Pro Ile Cys
            20                  25                  30

Asp Leu Arg Val Leu Asn His Phe Ile Lys Glu Ala Gln Asp Ala Glu
        35                  40                  45

Ala Ala Met Lys Leu Cys Ser Glu Gly Cys Thr Leu Ser Asp Ser Val
    50                  55                  60

Ile Val Pro Gln Thr Thr Val Glu Phe Asp Val Trp Glu Lys Lys Ser
65                  70                  75                  80

Ala Leu Ala Lys Ala Gln Glu Val Gln Ser Gly Leu Trp Leu Leu Gln
                85                  90                  95

Glu Ala Phe Asn Phe Leu Arg Thr Ser Val Thr Asn Thr Ala Leu His
            100                 105                 110

Ser His Ile Asp Asn Ser Val Arg Asn Leu Leu Ser Val Asn Ala Val
        115                 120                 125

Leu Arg Ser Leu Asn Ile Gln Glu Phe Thr Pro Pro Ala Ser Ala Ala
    130                 135                 140

Glu Ile Glu Gly Thr Trp Arg Val Ser Thr Ala Thr Glu Leu Leu Gln
145                 150                 155                 160

Val His Ile Asn Phe Leu Arg Gly Lys Val Arg Leu Ile Leu Leu Asp
                165                 170                 175

Ala Gln Ala Cys Gln Gln Asp Val Ser
            180                 185

<210> SEQ ID NO 215
<211> LENGTH: 192
<212> TYPE: PRT
<213> ORGANISM: Macaca fascicularis
<220> FEATURE:
<223> OTHER INFORMATION: Crab eating macaque (Cynomolgus monkey) EPO

<400> SEQUENCE: 215

Met Gly Val His Glu Cys Pro Ala Trp Leu Trp Leu Leu Leu Ser Leu
1               5                   10                  15

Val Ser Leu Pro Leu Gly Leu Pro Val Pro Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Val Thr Met Gly Cys Ser Glu Ser Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Val Leu Ala Asn Ser Ser
```

```
                100                 105                 110
Gln Pro Phe Glu Pro Leu Gln Leu His Met Asp Lys Ala Ile Ser Gly
            115                 120                 125

Leu Arg Ser Ile Thr Thr Leu Leu Arg Ala Leu Gly Ala Gln Glu Ala
        130                 135                 140

Ile Ser Leu Pro Asp Ala Ala Ser Ala Ala Pro Leu Arg Thr Ile Thr
145                 150                 155                 160

Ala Asp Thr Phe Cys Lys Leu Phe Arg Val Tyr Ser Asn Phe Leu Arg
                165                 170                 175

Gly Lys Leu Lys Leu Tyr Thr Gly Glu Ala Cys Arg Arg Gly Asp Arg
            180                 185                 190

<210> SEQ ID NO 216
<211> LENGTH: 152
<212> TYPE: PRT
<213> ORGANISM: Oryzias melastigma
<220> FEATURE:
<223> OTHER INFORMATION: Indian medaka EPO (fragment)

<400> SEQUENCE: 216

Pro Arg Val Leu Lys His Phe Ile Gln Glu Ala Gln Asp Ala Glu Val
1               5                   10                  15

Ala Met Arg Ser Cys Arg Glu Gly Cys Gly Leu Ser Gln Thr Val Ser
            20                  25                  30

Val Pro Gln Thr Thr Val Asn Tyr Asp Asp Trp Glu Lys Lys Asp Gly
        35                  40                  45

Leu Glu Lys Ala Gln Glu Val Gln Thr Gly Leu Trp Leu Leu Gln Gln
    50                  55                  60

Ala Leu Asp Leu Leu Gly Pro Ser Val Thr Asn Thr Ala Leu Asn Asn
65                  70                  75                  80

His Ile Asp Asn Thr Val Arg Asn Leu Val Ser Ile Asn Ala Val Leu
                85                  90                  95

Arg Ser Leu Asn Phe Gln Glu Tyr Thr Pro Pro Thr Asn Val Thr Ser
            100                 105                 110

Leu Asp Gly Thr Trp Arg Val Ser Ala Thr Glu Leu Leu Gln Val
        115                 120                 125

His Val Asn Phe Leu Arg Gly Lys Val Gly Leu Leu Leu Ser Gly Ala
    130                 135                 140

Pro Ala Cys Gln His Asn Val Ser
145                 150

<210> SEQ ID NO 217
<211> LENGTH: 182
<212> TYPE: PRT
<213> ORGANISM: Cyprinus carpio
<220> FEATURE:
<223> OTHER INFORMATION: Common carp EPO-I

<400> SEQUENCE: 217

Met Gln Ile Thr Arg Leu Phe Ala Leu Leu Leu Met Val Leu Glu Trp
1               5                   10                  15

Thr Arg Pro Gly Leu Ser Ser Pro Leu Arg Pro Ile Cys Asp Leu Arg
            20                  25                  30

Val Leu Asp His Phe Ile Lys Glu Ala Trp Asp Ala Glu Ala Ala Met
        35                  40                  45

Arg Ala Cys Lys Asp Ala Cys Ser Ile Ala Thr Asn Phe Thr Val Pro
    50                  55                  60

Leu Thr Arg Val Asp Phe Asp Val Trp Glu Ala Met Asn Ile Glu Glu
```

```
                65                  70                  75                  80
Arg Ala Gln Glu Val Gln Ser Gly Leu His Val Leu Asn Glu Ala Ile
                    85                  90                  95
Ser Ser Leu Gln Ala Ser Asn Gln Thr Asp Val Leu Gln Ser His Val
                    100                 105                 110
Asp Ala Ser Ile Ser Asn Ile Ala Ser Ile Arg Gln Val Leu Arg Ser
                115                 120                 125
Leu Ser Ile Pro Glu Tyr Val Pro Pro Thr Ser Gly Gly Glu Asp Lys
            130                 135                 140
Glu Met Gln Ile Val Ser Ser Ile Ser Glu Leu Phe Gln Val His Ile
145                 150                 155                 160
Asn Phe Leu Arg Gly Lys Val Arg Leu Leu Thr Arg Ser Ala Pro Ile
                165                 170                 175
Cys His Gln Gly Val Ser
            180

<210> SEQ ID NO 218
<211> LENGTH: 136
<212> TYPE: PRT
<213> ORGANISM: Oncorhynchus mykiss
<220> FEATURE:
<223> OTHER INFORMATION: Rainbow trout EPO (fragment)

<400> SEQUENCE: 218

Ile Cys Asp Leu Ser Val Leu Asn His Phe Ile Lys Glu Ala Trp Asp
1               5                   10                  15
Ala Glu Ala Ala Met Arg Ala Cys Lys Asp Ala Cys Ser Ile Ala Thr
                20                  25                  30
Asn Phe Thr Val Pro Leu Thr Arg Val Asp Phe Asp Val Trp Glu Ala
                35                  40                  45
Met Asn Ile Glu Glu Arg Ala Gln Glu Val Gln Ser Gly Leu His Val
            50                  55                  60
Leu Asn Glu Ala Ile Ser Ser Leu Gln Ala Ser Asn Gln Thr Asp Val
65                  70                  75                  80
Leu Gln Ser His Ile Asp Ala Ser Ile Ser Asn Ile Ala Ser Ile Arg
                85                  90                  95
Gln Val Leu Arg Ser Leu Ser Ile Pro Glu Tyr Val Pro Pro Thr Ser
                100                 105                 110
Gly Gly Glu Asp Lys Glu Met Gln Ile Val Ser Ser Ile Ser Glu Leu
            115                 120                 125
Phe Gln Val His Ile Asn Phe Leu
        130                 135

<210> SEQ ID NO 219
<211> LENGTH: 183
<212> TYPE: PRT
<213> ORGANISM: Cyprinus carpio
<220> FEATURE:
<223> OTHER INFORMATION: Common carp EPO

<400> SEQUENCE: 219

Met Phe His Gly Ser Gly Leu Phe Ala Leu Leu Ile Val Leu Glu
1               5                   10                  15
Trp Thr Arg Pro Gly Leu Ser Ser Pro Leu Arg Pro Ile Cys Asp Leu
                20                  25                  30
Arg Val Leu Asp His Phe Ile Lys Glu Ala Trp Asp Ala Glu Ala Ala
                35                  40                  45
Met Arg Ala Cys Lys Asp Ala Cys Ser Ile Ala Thr Asn Phe Thr Val
```

```
                    50                  55                  60
Pro Leu Thr Arg Val Asp Phe Asp Val Trp Glu Ala Met Asn Ile Glu
 65                  70                  75                  80

Glu Arg Ala Gln Glu Val Gln Ser Gly Leu His Val Leu Asn Glu Ala
                 85                  90                  95

Ile Ser Ser Leu Gln Ala Ser Asn Gln Thr Asp Val Leu Gln Ser His
                100                 105                 110

Ile Asp Ala Ser Ile Ser Asn Ile Ala Ser Ile Arg Gln Val Leu Arg
                115                 120                 125

Ser Leu Ser Ile Pro Glu Tyr Val Pro Pro Thr Ser Gly Gly Glu Asp
130                 135                 140

Lys Glu Met Gln Ile Val Ser Ser Ile Ser Glu Leu Phe Gln Val His
145                 150                 155                 160

Ile Asn Phe Leu Arg Gly Lys Val Arg Leu Leu Ala Asn Ala Pro
                165                 170                 175

Val Cys His Gln Gly Val Ser
                180

<210> SEQ ID NO 220
<211> LENGTH: 185
<212> TYPE: PRT
<213> ORGANISM: Epinephelus coioides
<220> FEATURE:
<223> OTHER INFORMATION: Orange-spotted grouper EPO

<400> SEQUENCE: 220

Met Leu Gln Lys Arg Gly Arg Gly Leu Leu Val Leu Leu Leu Met Leu
  1               5                  10                  15

Leu Glu Trp Thr Arg Pro Gly Leu Leu Ser Pro Leu Arg Pro Ile Cys
                 20                  25                  30

Asp Leu Arg Val Leu Asn His Phe Ile Lys Glu Ala Arg Asp Ala Glu
                 35                  40                  45

Val Ala Met Lys Ser Cys Thr Glu Gly Cys Ser Leu Ser Glu Ser Val
 50                  55                  60

Thr Val Pro Gln Thr Arg Val Asp Phe Asp Val Trp Glu Lys Lys Asn
 65                  70                  75                  80

Gly Leu Glu Gln Ala Gln Glu Val Gln Ser Gly Leu Trp Leu Leu Gln
                 85                  90                  95

Gln Ala Leu Asn Leu Leu Arg Thr Ser Val Thr Asn Thr Ala Leu His
                100                 105                 110

Ser His Ile Asp Asn Ser Ile Arg Asn Leu Leu Ser Ile Asn Ala Val
                115                 120                 125

Leu Arg Ser Leu Asn Ile Gln Glu Tyr Thr Pro Pro Ala Ser Thr Val
130                 135                 140

Ala Leu Glu Gly Thr Trp Arg Val Ser Ser Ala Thr Asp Leu Leu Gln
145                 150                 155                 160

Val His Val Asn Phe Leu Arg Gly Lys Val Arg Leu Leu Leu Leu Asp
                165                 170                 175

Ala Gln Ala Cys Gln Gln Asp Val Ser
                180                 185

<210> SEQ ID NO 221
<211> LENGTH: 192
<212> TYPE: PRT
<213> ORGANISM: Spalax galili
<220> FEATURE:
<223> OTHER INFORMATION: Mole rat EPO precursor
```

<400> SEQUENCE: 221

```
Met Gly Val Pro Asp Cys Leu Ala Leu Pro Leu Leu Val Thr Phe Leu
1               5                   10                  15

Leu Leu Ser Leu Gly Leu Pro Val Leu Gly Ala Pro Pro Arg Leu Ile
            20                  25                  30

Cys Asp Ser Arg Val Leu Glu Arg Tyr Ile Leu Glu Ala Lys Glu Ala
        35                  40                  45

Glu Asn Ile Thr Met Gly Cys Ala Glu Gly Pro Arg Phe Asn Glu Asn
    50                  55                  60

Phe Thr Val Pro Asp Thr Lys Val Asn Phe Tyr Ala Trp Lys Thr Met
65                  70                  75                  80

Gly Val Glu Glu Gln Ala Val Glu Val Trp Gln Gly Leu Ser Leu Leu
                85                  90                  95

Phe Glu Ala Ile Leu Arg Ala Gln Ala Val Leu Ala Asn Ser Ser Gln
            100                 105                 110

Pro Ser Glu Met Leu Gln Leu His Val Asp Lys Ala Ile Ser Gly Leu
        115                 120                 125

Arg Ser Leu Thr Ser Leu Leu Arg Ala Leu Gly Ala Gln Lys Glu Ala
    130                 135                 140

Ile Ser Pro Pro Asp Thr Thr Gln Val Ile Pro Leu Arg Arg Phe Thr
145                 150                 155                 160

Val Asp Thr Phe Cys Lys Leu Phe Arg Ile Tyr Ser Asn Phe Leu Arg
                165                 170                 175

Gly Lys Leu Lys Leu Tyr Thr Gly Glu Ala Cys Arg Arg Gly Asp Arg
            180                 185                 190
```

<210> SEQ ID NO 222
<211> LENGTH: 192
<212> TYPE: PRT
<213> ORGANISM: Spalax judaei
<220> FEATURE:
<223> OTHER INFORMATION: Blind subterranean mole rat EPO precursor

<400> SEQUENCE: 222

```
Met Gly Val Pro Asp Cys Leu Ala Leu Pro Leu Leu Val Thr Phe Leu
1               5                   10                  15

Leu Leu Ser Leu Gly Leu Pro Val Leu Gly Ala Pro Pro Arg Leu Ile
            20                  25                  30

Cys Asp Ser Arg Val Leu Glu Arg Tyr Ile Leu Glu Ala Lys Glu Ala
        35                  40                  45

Glu Asn Ile Thr Met Gly Cys Ala Glu Gly Pro Arg Phe Asn Glu Asn
    50                  55                  60

Phe Thr Val Pro Asp Thr Lys Val Asn Phe Tyr Ala Trp Lys Thr Met
65                  70                  75                  80

Gly Val Glu Glu Gln Ala Val Glu Val Trp Gln Gly Leu Ser Leu Leu
                85                  90                  95

Phe Glu Ala Ile Leu Arg Ala Gln Ala Val Leu Ala Asn Ser Ser Gln
            100                 105                 110

Pro Ser Glu Met Leu Gln Leu His Val Asp Lys Ala Ile Ser Gly Leu
        115                 120                 125

Arg Ser Leu Thr Ser Leu Leu Arg Ala Leu Gly Ala Gln Lys Glu Ala
    130                 135                 140

Ile Ser Pro Pro Asp Thr Thr Gln Val Ile Pro Leu Arg Arg Phe Thr
145                 150                 155                 160

Val Asp Thr Phe Cys Lys Leu Phe Arg Ile Tyr Ser Asn Phe Leu Arg
                165                 170                 175
```

```
Gly Lys Leu Lys Leu Tyr Thr Gly Glu Ala Cys Arg Arg Gly Asp Arg
            180                 185                 190

<210> SEQ ID NO 223
<211> LENGTH: 195
<212> TYPE: PRT
<213> ORGANISM: Tetraodon nigroviridis
<220> FEATURE:
<223> OTHER INFORMATION: Green puffer EPO

<400> SEQUENCE: 223

Met Gly Leu Leu Met Cys Val Cys Val Val Phe Val Ser Gly Met
 1               5                  10                  15

Thr Gly Leu Leu Ala Phe Leu Leu Ile Val Leu Glu Trp Thr Arg Pro
            20                  25                  30

Ser Leu Pro Ser Pro Leu Arg Pro Ile Cys Asp Leu Arg Val Leu Asn
            35                  40                  45

His Phe Ile Lys Glu Ala Gln Asp Ala Glu Ala Met Lys Thr Cys
     50                  55                  60

Arg Glu Gly Cys Thr Leu Ser Glu Ser Val Val Pro Gln Thr Thr
65                  70                  75                  80

Val Asp Phe Asp Val Trp Glu Lys Lys Asn Ala Ser Ala Lys Ala Glu
            85                  90                  95

Glu Val Gln Ser Gly Leu Trp Leu Gln Gln Ala Phe Asn Phe Leu
                100                 105                 110

Arg Thr Ser Val Thr Asn Ala Ala Leu His Ser His Ile Asp Asn Ala
            115                 120                 125

Val Arg Asn Leu Leu Ser Val Asn Ala Val Leu Arg Ser Leu Asn Ile
130                 135                 140

Gln Glu Phe Thr Pro Gln Ala Asn Gly Ala Glu Ile Glu Gly Thr Trp
145                 150                 155                 160

Arg Ala Ser Ser Ala Ala Glu Leu Leu Gln Val Tyr Val Asn Phe Leu
            165                 170                 175

Arg Gly Lys Ala Arg Leu Leu Leu Asp Ala Gln Ala Cys Gln Gln
                180                 185                 190

Asp Val Ser
        195

<210> SEQ ID NO 224
<211> LENGTH: 133
<212> TYPE: PRT
<213> ORGANISM: Saguinus oedipus
<220> FEATURE:
<223> OTHER INFORMATION: Cotton-top tamarin EPO (fragment)

<400> SEQUENCE: 224

Ser Gly Val Leu Glu Arg Tyr Val Leu Glu Gly Lys Glu Ala Glu Asn
 1               5                  10                  15

Val Thr Met Gly Cys Ala Glu Ser Cys Ser Leu Asn Glu Asn Ile Thr
            20                  25                  30

Val Pro Asp Thr Lys Val Asn Phe Tyr Ala Trp Lys Lys Met Glu Phe
            35                  40                  45

Gly Gln Gln Ala Val Asp Val Trp Gln Gly Leu Thr Leu Leu Ser Glu
     50                  55                  60

Ala Val Leu Arg Gly Gln Ala Leu Leu Ala Asn Ser Thr Gln Pro Arg
65                  70                  75                  80

Glu Pro Leu Gln Leu His Met Asp Arg Ala Val Ser Gly Leu Arg Ser
            85                  90                  95
```

```
Leu Thr Thr Leu Leu Arg Ala Leu Gly Ala Gln Glu Ala Thr Ser Pro
            100                 105                 110

Pro Asp Ala Ala Pro Ser Ala Val Pro Leu Gln Thr Ile Thr Ala Asp
            115                 120                 125

Thr Phe Ser Lys Leu
    130

<210> SEQ ID NO 225
<211> LENGTH: 131
<212> TYPE: PRT
<213> ORGANISM: Pongo pygmaeus
<220> FEATURE:
<223> OTHER INFORMATION: Orangutan EPO (fragment)

<400> SEQUENCE: 225

Ser Arg Val Leu Glu Arg Tyr Leu Leu Glu Ala Lys Glu Ala Glu Asn
1               5                   10                  15

Thr Gly Cys Ala Glu His Cys Ser Leu Ser Glu Asn Ile Thr Val Pro
            20                  25                  30

Asp Thr Lys Val Asn Phe Tyr Ala Trp Lys Arg Met Glu Val Gly Gln
        35                  40                  45

Gln Ala Leu Glu Val Trp Gln Gly Leu Ala Leu Leu Ser Glu Ala Val
    50                  55                  60

Leu Arg Gly Gln Ala Leu Leu Val Asn Ser Ser Gln Pro Trp Glu Pro
65                  70                  75                  80

Leu Gln Leu His Val Asp Lys Ala Val Ser Gly Leu Arg Ser Leu Thr
                85                  90                  95

Thr Leu Leu Arg Ala Leu Gly Ala Gln Lys Glu Ala Ser Ser Pro Pro
            100                 105                 110

Asp Ala Ala Leu Ala Ala Pro Leu Arg Thr Ile Thr Ala Asp Thr Phe
            115                 120                 125

Arg Lys Phe
    130

<210> SEQ ID NO 226
<211> LENGTH: 133
<212> TYPE: PRT
<213> ORGANISM: Gorilla gorilla
<220> FEATURE:
<223> OTHER INFORMATION: Gorilla EPO (fragment)

<400> SEQUENCE: 226

Ser Arg Val Leu Glu Arg Tyr Leu Leu Glu Ala Lys Glu Ala Glu Asn
1               5                   10                  15

Ile Thr Thr Gly Cys Ala Glu His Cys Ser Leu Asn Glu Asn Ile Thr
            20                  25                  30

Val Pro Asp Thr Lys Val Asn Phe Tyr Ala Trp Lys Arg Met Glu Val
            35                  40                  45

Arg Gln Gln Ala Val Glu Val Trp Gln Gly Leu Ala Leu Leu Ser Glu
    50                  55                  60

Ala Val Leu Arg Gly Gln Ala Leu Leu Val Asn Ser Ser Gln Pro Trp
65                  70                  75                  80

Glu Pro Leu Gln Leu His Val Asp Lys Ala Val Ser Gly Leu Arg Ser
                85                  90                  95

Leu Thr Thr Leu Leu Arg Ala Leu Gly Ala Gln Lys Glu Ala Ile Ser
            100                 105                 110

Pro Pro Asp Ala Ala Ser Ala Ala Pro Leu Arg Thr Ile Thr Ala Asp
            115                 120                 125
```

Thr Phe Arg Lys Leu
    130

<210> SEQ ID NO 227
<211> LENGTH: 193
<212> TYPE: PRT
<213> ORGANISM: Artificial Sequence
<220> FEATURE:
<223> OTHER INFORMATION: Amgen ARANESP immature

<400> SEQUENCE: 227

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Asn Glu Thr Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Val Asn Glu Thr Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 228
<211> LENGTH: 166
<212> TYPE: PRT
<213> ORGANISM: Artificial Sequence
<220> FEATURE:
<223> OTHER INFORMATION: Amgen ARANESP mature

<400> SEQUENCE: 228

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Asn Glu Thr
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Val Asn Glu Thr Leu Gln Leu His Val Asp
                85                  90                  95

```
Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 229
<211> LENGTH: 339
<212> TYPE: DNA
<213> ORGANISM: Homo sapiens
<220> FEATURE:
<223> OTHER INFORMATION: coding sequence of human erythropoietin

<400> SEQUENCE: 229
atggaggtcg ggcagcaggc cgtagaagtc tggcagggcc tggccctgct gtcggaagct    60
gtcctgcggg gccaggccct gttggtcaac tcttcccagc cgtgggagcc cctgcagctg   120
catgtggata aagccgtcag tggccttcgc agcctcacca ctctgcttcg ggctctggga   180
gcccagaagg aagccatctc ccctccagat gcggcctcag ctgctccact ccgaacaatc   240
actgctgaca ctttccgcaa actcttccga gtctactcca atttcctccg ggaaagctg    300 aagctgtaca gggggaggc ctgcaggaca ggggacaga                           339

<210> SEQ ID NO 230
<211> LENGTH: 4020
<212> TYPE: DNA
<213> ORGANISM: Artificial Sequence
<220> FEATURE:
<223> OTHER INFORMATION: pcDNA3.1/GS

<400> SEQUENCE: 230
gacggatcgg gagatctccc gatccctat ggtcgactct cagtacaatc tgctctgatg      60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagt   900
taagctcgcc cttaagggcg agcttcgagg tcacccattc gaaggtaagc ctatccctaa   960
ccctctcctc ggtctcgatt ctacgcgtac cggtcatcat caccatcacc attgagttta  1020
```

```
aacccgctga tcagcctcga ctgtgccttc tagttgccag ccatctgttg tttgcccctc    1080
ccccgtgcct tccttgaccc tggaaggtgc cactcccact gtcctttcct aataaaatga    1140
ggaaattgca tcgcattgtc tgagtaggtg tcattctatt ctgggggtg gggtggggca     1200 ggacagcaag ggggaggatt gggaagacaa tagcaggcat gctggggatg cggtgggctc    1260
tatggcttct gaggcggaaa gaaccagctg gggctctagg gggtatcccc acgcgccctg    1320
tagcggcgca ttaagcgcgg cgggtgtggt ggttacgcgc agcgtgaccg ctacacttgc    1380
cagcgcccta gcgcccgctc ctttcgcttt cttcccttcc tttctcgcca cgttcgccgg    1440
ctttccccgt caagctctaa atcggggcat ccctttaggg ttccgattta gtgctttacg    1500
gcacctcgac cccaaaaaac ttgattaggg tgatggttca cgtagtgggc catcgccctg    1560
atagacggtt tttcgccctt tgacgttgga gtccacgttc tttaatagtg gactcttgtt    1620
ccaaactgga acaacactca accctatctc ggtctattct tttgatttat aagggatttt    1680
ggggatttcg gcctattggt taaaaaatga gctgatttaa caaaaattta acgcgaatta    1740
attctgtgga atgtgtgtca gttagggtgt ggaaagtccc caggctcccc aggcaggcag    1800
aagtatgcaa agcatgcatc tcaattagtc agcaaccagg tgtggaaagt ccccaggctc    1860
cccagcaggc agaagtatgc aaagcatgca tctcaattag tcagcaacca tagtcccgcc    1920
cctaactccg cccatcccgc ccctaactcc gcccagttcc gcccattctc cgccccatgg    1980
ctgactaatt tttttatt atgcagaggc cgaggccgcc tctgcctctg agctattcca     2040
gaagtagtga ggaggctttt ttggaggcct aggcttttgc aaaaagctcc cgggagcttg    2100
tatatccatt ttcggatctg atcagcacgt gttgacaatt aatcatcggc atagtatatc    2160
ggcatagtat aatacgacaa ggtgaggaac taaaccatgg ccaagttgac cagtgccgtt    2220
ccggtgctca ccgcgcgcga cgtcgccgga gcggtcgagt tctggaccga ccggctcggg    2280
ttctcccggg acttcgtgga ggacgacttc gccggtgtgg tccgggacga cgtgaccctg    2340
ttcatcagcg cggtccagga ccaggtggtg ccggacaaca ccctggcctg ggtgtgggtg    2400
cgcggcctgg acgagctgta cgccgagtgg tcggaggtcg tgtccacgaa cttccgggac    2460
gcctccgggc cggccatgac cgagatcggc gagcagccgt ggggcggga gttcgccctg     2520 cgcgacccgg ccggcaactg cgtgcacttc gtggccgagg agcaggactg acacgtgcta    2580
cgagatttcg attccaccgc cgccttctat gaaaggttgg gcttcggaat cgttttccgg    2640
gacgccggct ggatgatcct ccagcgcggg gatctcatgc tggagttctt cgcccacccc    2700
aacttgttta ttgcagctta taatggttac aaataaagca atagcatcac aaatttcaca    2760
aataaagcat ttttttcact gcattctagt tgtggtttgt ccaaactcat caatgtatct    2820
tatcatgtct gtataccgtc gacctctagc tagagcttgg cgtaatcatg gtcatagctg    2880
tttcctgtgt gaaattgtta tccgctcaca attccacaca acatacgagc cggaagcata    2940
aagtgtaaag cctggggtgc ctaatgagtg agctaactca cattaattgc gttgcgctca    3000
ctgcccgctt tccagtcggg aaacctgtcg tgccagctgc attaatgaat cggccaacgc    3060
gcggggagag gcggtttgcg tattgggcgc tcttccgctt cctcgctcac tgactcgctg    3120
cgctcggtcg ttcggctgcg gcgagcggta tcagctcact caaaggcggt aatacggtta    3180
tccacagaat caggggataa cgcaggaaag aacatgtgag caaaaggcca gcaaaaggcc    3240
aggaaccgta aaaaggccgc gttgctggcg ttttccata ggctccgccc cctgacgag      3300 catcacaaaa atcgacgctc aagtcagagg tggcgaaacc cgacaggact ataaagatac    3360
caggcgtttc ccctggaag ctccctcgtg cgctctcctg ttccgaccct gccgcttacc     3420
```

-continued

```
ggatacctgt ccgcctttct cccttcggga agcgtggcgc tttctcaatg ctcacgctgt    3480
aggtatctca gttcggtgta ggtcgttcgc tccaagctgg gctgtgtgca cgaaccccc     3540 gttcagcccg accgctgcgc cttatccggt aactatcgtc ttgagtccaa cccggtaaga    3600
cacgacttat cgccactggc agcagccact ggtaacagga ttagcagagc gaggtatgta    3660
ggcggtgcta cagagttctt gaagtggtgg cctaactacg gctacactag aaggacagta    3720
tttggtatct gcgctctgct gaagccagtt accttcggaa aaagagttgg tagctcttga    3780
tccggcaaac aaaccaccgc tggtagcggt ggtttttttg tttgcaagca gcagattacg    3840
cgcagaaaaa aaggatctca agaagatcct ttgatctttt ctacggggtc tgacgctcag    3900
tggaacgaaa actcacgtta agggattttg gtcatgagcg gatacatatt tgaatgtatt    3960
tagaaaaata aacaaatagg ggttccgcgc acatttcccc gaaagtgcc acctgacgtc     4020
```

<210> SEQ ID NO 231
<211> LENGTH: 38
<212> TYPE: DNA
<213> ORGANISM: Artificial Sequence
<220> FEATURE:
<223> OTHER INFORMATION: EPO BamHI forward primer

<400> SEQUENCE: 231

```
gggaattcca tatggggtg cacgaatgtc ctgcctgg                               38
```

<210> SEQ ID NO 232
<211> LENGTH: 37
<212> TYPE: DNA
<213> ORGANISM: Artificial Sequence
<220> FEATURE:
<223> OTHER INFORMATION: EPO NdeI reverse primer

<400> SEQUENCE: 232

```
cgggatcctc atctgtcccc tgtcctgcag gcctccc                               37
```

<210> SEQ ID NO 233
<211> LENGTH: 3889
<212> TYPE: DNA
<213> ORGANISM: Artificial Sequence
<220> FEATURE:
<223> OTHER INFORMATION: pNAUT-EPO

<400> SEQUENCE: 233

```
gcgcccaata cgcaaaccgc ctctccccgc gcgttggccg attcattaat gcagctgcta      60
ggggttcctt gtagttaatg attaacccgc catgctactt atctactatg ccaagtacgc     120
cccctattga cgtcaatgac ggtaaatggc ccgcctggca ttatgcccag tacatgacct     180
tatgggactt tcctacttgg cagtacatct acgtattagt catcgctatt accatggtga     240
tgcggttttg gcagtacatc aatgggcgtg gatagcggtt tgactcacgg ggatttccaa     300
gtctccaccc cattgacgtc aatgggagtt tgttttggca ccaaaatcaa cgggactttc     360
caaaatgtcg taacaactcc gccccattga cgcaaatggg cggtaggcgt gtacggtggg     420
aggtctatat aagcagagct ctctggctaa ctagagaacc cactgcttac tggcttatcg     480
aaattaatac gactcactat agggagaccc aagcttggta ccgagctcgg atccactagt     540
aacggccgcc agtgtgctgg aattctgcag atatccatca cactggcggc cgcgaattcg     600
cccttgggaa ttccatatgg gggtgcacga atgtcctgcc tggctgtggc ttctcctgtc     660
cctgctgtcg ctccctctgg gcctcccagt cctgggcgcc ccaccacgcc tcatctgtga     720
cagccgagtc ctggagaggt acctcttgga ggccaaggag gccgagaata tcacgacggg     780
```

```
ctgtgctgaa cactgcagct tgaatgagaa tatcactgtc ccagacacca aagttaattt    840
ctatgcctgg aagaggatgg aggtcgggca gcaggccgta gaagtctggc agggcctggc    900
cctgctgtcg gaagctgtcc tgcgggccag ggccctgttg gtcaactctt cccagccgtg    960
ggagcccctg cagctgcatg tggataaagc cgtcagtggc cttcgcagcc tcaccactct   1020
gcttcgggct ctgggagccc agaaggaagc catctcccct ccagatgcgg cctcagctgc   1080
tccactccga acaatcactg ctgacacttt ccgcaaactc ttccgagtct actccaattt   1140
cctccgggga aagctgaagc tgtacacagg ggaggcctgc aggacagggg acagatgagg   1200
atcccgaagg gcgaattcgt ttaaacctgc aggactagag ggccctattc tatagtgtca   1260
cctaaatgct agagctcgct gatcagcctc gactgtgcct tctagttgcc agccatctgt   1320
tgtttgcccc tcccccgtgc cttccttgac cctggaaggt gccactccca ctgtcctttc   1380
ctaataaaat gaggaaattg catcgcattg tctgagtagg tgtcattcta ttctgggggg   1440
tggggtgggg caggacagca agggggagga ttgggaagac aatagcaggc atgctgggga   1500
tgcggtgggc tctatggctt ctgaggcgga agaaccagg tagataagta gcatggcggg   1560
ttaatcatta actacacagc tggcgtaata gcgaagaggc ccgcaccgat cgcccttccc   1620
aacagttgcg cagcctgaat ggcgaatggc gcctgatgcg gtattttctc cttacgcatc   1680
tgtgcggtat ttcacaccgc atatggtgca ctctcagtac aatctgctct gatgccgcat   1740
agttaagcca gccccgacac ccgccaacac ccgctgacgc gccctgacgg gcttgtctgc   1800
tcccggcatc cgcttacaga caagctgtga ccgtctccgg gagctgcatg tgtcagaggt   1860
tttcaccgtc atcaccgaaa cgcgcgagac gaaagggcct cgtgatacgc ctatttttat   1920
aggttaatgt catgataata atggtttctt agacgtcagg tggcactttt cggggaaatg   1980
tgcgcggaac ccctatttgt ttatttttct aaatacattc aaatatgtat ccgctcatga   2040
gacaataacc ctgataaatg cttcaataat attgaaaaag gaagagtatg agtattcaac   2100
atttccgtgt cgcccttatt ccctttttg cggcattttg ccttcctgtt tttgctcacc   2160
cagaaacgct ggtgaaagta aaagatgctg aagatcagtt gggtgcacga gtgggttaca   2220
tcgaactgga tctcaacagc ggtaagatcc ttgagagttt tcgccccgaa gaacgttttc   2280
caatgatgag cacttttaaa gttctgctat gtggcgcggt attatcccgt attgacgccg   2340
ggcaagagca actcggtcgc cgcatacact attctcagaa tgacttggtt gagtactcac   2400
cagtcacaga aaagcatctt acggatggca tgacagtaag agaattatgc agtgctgcca   2460
taaccatgag tgataacact gcggccaact tacttctgac aacgatcgga ggaccgaagg   2520
agctaaccgc ttttttgcac aacatggggg atcatgtaac tcgccttgat cgttgggaac   2580
cggagctgaa tgaagccata ccaaacgacg agcgtgacac cacgatgcct gtagcaatgg   2640
caacaacgtt gcgcaaacta ttaactggcg aactacttac tctagcttcc cggcaacaat   2700
taatagactg gatggaggcg gataaagttg caggaccact tctgcgctcg gcccttccgg   2760
ctggctggtt tattgctgat aaatctggag ccggtgagcg tgggtctcgc ggtatcattg   2820
cagcactggg gccagatggt aagccctccc gtatcgtagt tatctacacg acggggagtc   2880
aggcaactat ggatgaacga atagacaga tcgctgagat aggtgcctca ctgattaagc   2940
attggtaact gtcagaccaa gtttactcat atatacttta gattgattta aaacttcatt   3000
tttaatttaa aaggatctag gtgaagatcc ttttttgataa tctcatgacc aaaatccctt   3060
aacgtgagtt ttcgttccac tgagcgtcag accccgtaga aagatcaaa ggatcttctt   3120
gagatccttt ttttctgcgc gtaatctgct gcttgcaaac aaaaaaacca ccgctaccag   3180
```

```
cggtggtttg tttgccggat caagagctac caactcttt tccgaaggta actggcttca    3240
gcagagcgca gataccaaat actgtccttc tagtgtagcc gtagttaggc caccacttca    3300
agaactctgt agcaccgcct acatacctcg ctctgctaat cctgttacca gtggctgctg    3360
ccagtggcga taagtcgtgt cttaccgggt tggactcaag acgatagtta ccggataagg    3420
cgcagcggtc gggctgaacg ggggttcgt gcacacagcc cagcttggag cgaacgacct    3480
acaccgaact gagataccta cagcgtgagc tatgagaaag cgccacgctt cccgaaggga    3540
gaaaggcgga caggtatccg gtaagcggca gggtcggaac aggagagcgc acgagggagc    3600
ttccaggggg aaacgcctgg tatctttata gtcctgtcgg gtttcgccac ctctgacttg    3660
agcgtcgatt tttgtgatgc tcgtcagggg ggcggagcct atggaaaaac gccagcaacg    3720
cggccttttt acggttcctg gccttttgct ggccttttgc tcacatgttc tttcctgcgt    3780
tatcccctga ttctgtggat aaccgtatta ccgcctttga gtgagctgat accgctcgcc    3840
gcagccgaac gaccgagcgc agcgagtcag tgagcgagga agcggaaga              3889
```

<210> SEQ ID NO 234  
<211> LENGTH: 18  
<212> TYPE: DNA  
<213> ORGANISM: Artificial Sequence  
<220> FEATURE:  
<223> OTHER INFORMATION: pNAUT forward primer
<400> SEQUENCE: 234

```
tataagcaga gctctctg                                                   18
```

<210> SEQ ID NO 235  
<211> LENGTH: 19  
<212> TYPE: DNA  
<213> ORGANISM: Artificial Sequence  
<220> FEATURE:  
<223> OTHER INFORMATION: pNAUT reverse primer
<400> SEQUENCE: 235

```
cacagtcgag gctgatcag                                                  19
```

<210> SEQ ID NO 236  
<211> LENGTH: 192  
<212> TYPE: PRT  
<213> ORGANISM: Homo sapiens  
<220> FEATURE:  
<223> OTHER INFORMATION: EPO immature form deltaR193

<400> SEQUENCE: 236

```
Met Gly Val His Glu Cys Pro Ala Trp Leu Trp Leu Leu Ser Leu
 1               5                  10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110
```

```
Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

<210> SEQ ID NO 237
<211> LENGTH: 165
<212> TYPE: PRT
<213> ORGANISM: Homo sapiens
<220> FEATURE:
<223> OTHER INFORMATION: Human EPO - mature deltaR166

<400> SEQUENCE: 237

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 238
<211> LENGTH: 193
<212> TYPE: PRT
<213> ORGANISM: Homo sapiens
<220> FEATURE:
<223> OTHER INFORMATION: Human EPO D70S variant- immature

<400> SEQUENCE: 238

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60
```

-continued

```
Asn Ile Thr Val Pro Ser Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 239
<211> LENGTH: 166
<212> TYPE: PRT
<213> ORGANISM: Homo sapiens
<220> FEATURE:
<223> OTHER INFORMATION: Human EPO D70S (D43S) - mature

<400> SEQUENCE: 239

```
Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Ser Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 240
<211> LENGTH: 193
<212> TYPE: PRT
<213> ORGANISM: Homo sapiens
<220> FEATURE:
<223> OTHER INFORMATION: Human EPO G104S - immature

<400> SEQUENCE: 240

```
Met Gly Val His Glu Cys Pro Ala Trp Leu Trp Leu Leu Leu Ser Leu
```

```
                1               5                  10                 15
        Leu Ser Leu Pro Leu Gly Leu Pro Val Leu Gly Ala Pro Pro Arg Leu
                        20                 25                 30

Ile Cys Asp Ser Arg Val Leu Glu Arg Tyr Leu Leu Glu Ala Lys Glu
                        35                 40                 45

Ala Glu Asn Ile Thr Thr Gly Cys Ala Glu His Cys Ser Leu Asn Glu
                50                 55                 60

Asn Ile Thr Val Pro Asp Thr Lys Val Asn Phe Tyr Ala Trp Lys Arg
         65                 70                 75                 80

Met Glu Val Gly Gln Gln Ala Val Glu Val Trp Gln Gly Leu Ala Leu
                        85                 90                 95

Leu Ser Glu Ala Val Leu Arg Ser Gln Ala Leu Leu Val Asn Ser Ser
                        100                105                110

Gln Pro Trp Glu Pro Leu Gln Leu His Val Asp Lys Ala Val Ser Gly
                        115                120                125

Leu Arg Ser Leu Thr Thr Leu Leu Arg Ala Leu Gly Ala Gln Lys Glu
                        130                135                140

Ala Ile Ser Pro Pro Asp Ala Ala Ser Ala Ala Pro Leu Arg Thr Ile
        145                150                155                160

Thr Ala Asp Thr Phe Arg Lys Leu Phe Arg Val Tyr Ser Asn Phe Leu
                        165                170                175

Arg Gly Lys Leu Lys Leu Tyr Thr Gly Glu Ala Cys Arg Thr Gly Asp
                        180                185                190

Arg

<210> SEQ ID NO 241
<211> LENGTH: 166
<212> TYPE: PRT
<213> ORGANISM: Homo sapiens
<220> FEATURE:
<223> OTHER INFORMATION: Human EPO G104S(G77S) - mature

<400> SEQUENCE: 241

Ala Pro Pro Arg Leu Ile Cys Asp Ser Arg Val Leu Glu Arg Tyr Leu
         1               5                  10                 15

Leu Glu Ala Lys Glu Ala Glu Asn Ile Thr Thr Gly Cys Ala Glu His
                        20                 25                 30

Cys Ser Leu Asn Glu Asn Ile Thr Val Pro Asp Thr Lys Val Asn Phe
                        35                 40                 45

Tyr Ala Trp Lys Arg Met Glu Val Gly Gln Gln Ala Val Glu Val Trp
                50                 55                 60

Gln Gly Leu Ala Leu Leu Ser Glu Ala Val Leu Arg Ser Gln Ala Leu
         65                 70                 75                 80

Leu Val Asn Ser Ser Gln Pro Trp Glu Pro Leu Gln Leu His Val Asp
                        85                 90                 95

Lys Ala Val Ser Gly Leu Arg Ser Leu Thr Thr Leu Leu Arg Ala Leu
                        100                105                110

Gly Ala Gln Lys Glu Ala Ile Ser Pro Pro Asp Ala Ala Ser Ala Ala
                        115                120                125

Pro Leu Arg Thr Ile Thr Ala Asp Thr Phe Arg Lys Leu Phe Arg Val
                        130                135                140

Tyr Ser Asn Phe Leu Arg Gly Lys Leu Lys Leu Tyr Thr Gly Glu Ala
        145                150                155                160

Cys Arg Thr Gly Asp Arg
                        165
```

```
<210> SEQ ID NO 242
<211> LENGTH: 193
<212> TYPE: PRT
<213> ORGANISM: Homo sapiens
<220> FEATURE:
<223> OTHER INFORMATION: Human EPO S147C - immature

<400> SEQUENCE: 242

Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Cys Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 243
<211> LENGTH: 166
<212> TYPE: PRT
<213> ORGANISM: Homo sapiens
<220> FEATURE:
<223> OTHER INFORMATION: Human EPO S147C(S120C) - mature

<400> SEQUENCE: 243

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Cys Pro Pro Asp Ala Ala Ser Ala Ala
```

-continued

```
                115                 120                 125
Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 244
<211> LENGTH: 166
<212> TYPE: PRT
<213> ORGANISM: Homo sapiens
<220> FEATURE:
<223> OTHER INFORMATION: EPO N24H

<400> SEQUENCE: 244

Ala Pro Pro Arg Leu Ile Cys Asp Ser Arg Val Leu Glu Arg Tyr Leu
1               5                   10                  15

Leu Glu Ala Lys Glu Ala Glu His Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 245
<211> LENGTH: 166
<212> TYPE: PRT
<213> ORGANISM: Homo sapiens
<220> FEATURE:
<223> OTHER INFORMATION: EPO N38H

<400> SEQUENCE: 245

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu His Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
```

```
                    85                  90                  95
Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 246
<211> LENGTH: 166
<212> TYPE: PRT
<213> ORGANISM: Homo sapiens
<220> FEATURE:
<223> OTHER INFORMATION: EPO N83H

<400> SEQUENCE: 246

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val His Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 247
<211> LENGTH: 166
<212> TYPE: PRT
<213> ORGANISM: Homo sapiens
<220> FEATURE:
<223> OTHER INFORMATION: EPO N38H/R139H

<400> SEQUENCE: 247

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu His Ile Thr Val Pro Asp Thr Lys Val Asn Phe
            35                  40                  45

Tyr Ala Trp Lys Arg Met Glu Val Gly Gln Gln Ala Val Glu Val Trp
```

```
                50                  55                  60
Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe His Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 248
<211> LENGTH: 166
<212> TYPE: PRT
<213> ORGANISM: Homo sapiens
<220> FEATURE:
<223> OTHER INFORMATION: EPO N38H/R139H/R4H

<400> SEQUENCE: 248

Ala Pro Pro His Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu His Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe His Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 249
<211> LENGTH: 166
<212> TYPE: PRT
<213> ORGANISM: Homo sapiens
<220> FEATURE:
<223> OTHER INFORMATION: EPO N38H/R139H/L93I

<400> SEQUENCE: 249

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
```

```
                    20                  25                  30
Cys Ser Leu Asn Glu His Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Ile His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 250
<211> LENGTH: 166
<212> TYPE: PRT
<213> ORGANISM: Homo sapiens
<220> FEATURE:
<223> OTHER INFORMATION: EPO N38H/R139H/K20Q

<400> SEQUENCE: 250

Ala Pro Pro Arg Leu Ile Cys Asp Ser Arg Val Leu Glu Arg Tyr Leu
 1               5                  10                  15

Leu Glu Ala Gln Glu Ala Glu Asn Ile Thr Thr Gly Cys Ala Glu His
            20                  25                  30

Cys Ser Leu Asn Glu His Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 251
<211> LENGTH: 166
<212> TYPE: PRT
<213> ORGANISM: Homo sapiens
<220> FEATURE:
<223> OTHER INFORMATION: EPO N38H/R139H/E159N
```

<400> SEQUENCE: 251

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe His Lys Leu Phe Arg Val
    130                 135                 140

Tyr Ser Asn Phe Leu Arg Gly Lys Leu Lys Leu Tyr Thr Gly Asn Ala
145                 150                 155                 160

Cys Arg Thr Gly Asp Arg
                165

<210> SEQ ID NO 252
<211> LENGTH: 166
<212> TYPE: PRT
<213> ORGANISM: Homo sapiens
<220> FEATURE:
<223> OTHER INFORMATION: EPO N38H/R139H/K52N

<400> SEQUENCE: 252

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Asn Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe His Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 253

<211> LENGTH: 166
<212> TYPE: PRT
<213> ORGANISM: Homo sapiens
<220> FEATURE:
<223> OTHER INFORMATION: EPO N38H/R139H/L153V

<400> SEQUENCE: 253

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe His Lys Leu Phe Arg Val
    130                 135                 140

Tyr Ser Asn Phe Leu Arg Gly Lys Val Lys Leu Tyr Thr Gly Glu Ala
145                 150                 155                 160

Cys Arg Thr Gly Asp Arg
                165
```

<210> SEQ ID NO 254
<211> LENGTH: 166
<212> TYPE: PRT
<213> ORGANISM: Homo sapiens
<220> FEATURE:
<223> OTHER INFORMATION: EPO N38H/N83H/R139H

<400> SEQUENCE: 254

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val His Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe His Lys Leu Phe Arg Val
    130                 135                 140

Tyr Ser Asn Phe Leu Arg Gly Lys Leu Lys Leu Tyr Thr Gly Glu Ala
145                 150                 155                 160
```

Cys Arg Thr Gly Asp Arg
                165

<210> SEQ ID NO 255
<211> LENGTH: 166
<212> TYPE: PRT
<213> ORGANISM: Homo sapiens
<220> FEATURE:
<223> OTHER INFORMATION: EPO K20Q/N38H/N83H/R139H

<400> SEQUENCE: 255

Ala Pro Pro Arg Leu Ile Cys Asp Ser Arg Val Leu Glu Arg Tyr Leu
 1               5                  10                  15

Leu Glu Ala Gln Glu Ala Glu Asn Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val His Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe His Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 256
<211> LENGTH: 166
<212> TYPE: PRT
<213> ORGANISM: Homo sapiens
<220> FEATURE:
<223> OTHER INFORMATION: EPO N38H/N83H/R139H/L93V

<400> SEQUENCE: 256

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val His Ser Ser Gln Pro Trp Glu Pro Leu Gln Val His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

```
Pro Leu Arg Thr Ile Thr Ala Asp Thr Phe His Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 257
<211> LENGTH: 166
<212> TYPE: PRT
<213> ORGANISM: Homo sapiens
<220> FEATURE:
<223> OTHER INFORMATION: EPO N38H/N83H/R139H/L80I

<400> SEQUENCE: 257

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
                 20                  25                  30

Cys Ser Leu Asn Glu His Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Ile
 65                  70                  75                  80

Leu Val His Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 258
<211> LENGTH: 166
<212> TYPE: PRT
<213> ORGANISM: Homo sapiens
<220> FEATURE:
<223> OTHER INFORMATION: EPO N38H/N83H/R139H/L93I

<400> SEQUENCE: 258

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
                 20                  25                  30

Cys Ser Leu Asn Glu His Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val His Ser Ser Gln Pro Trp Glu Pro Leu Gln Ile His Val Asp
                 85                  90                  95
```

```
Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 259
<211> LENGTH: 166
<212> TYPE: PRT
<213> ORGANISM: Homo sapiens
<220> FEATURE:
<223> OTHER INFORMATION: EPO K20Q/N38H/L80I/N83H/R139H

<400> SEQUENCE: 259

Ala Pro Pro Arg Leu Ile Cys Asp Ser Arg Val Leu Glu Arg Tyr Leu
1               5                   10                  15

Leu Glu Ala Gln Glu Ala Glu Asn Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Ile
65                  70                  75                  80

Leu Val His Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 260
<211> LENGTH: 166
<212> TYPE: PRT
<213> ORGANISM: Homo sapiens
<220> FEATURE:
<223> OTHER INFORMATION: K20Q/N38H/N83H/L93I/R139H

<400> SEQUENCE: 260

Ala Pro Pro Arg Leu Ile Cys Asp Ser Arg Val Leu Glu Arg Tyr Leu
1               5                   10                  15

Leu Glu Ala Gln Glu Ala Glu Asn Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60
```

Gln Gly Leu Ala Leu Leu Ser Glu Ala Val Leu Arg Gly Gln Ala Leu
65                  70                  75                  80

Leu Val His Ser Ser Gln Pro Trp Glu Pro Leu Gln Ile His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 261
<211> LENGTH: 166
<212> TYPE: PRT
<213> ORGANISM: Homo sapiens
<220> FEATURE:
<223> OTHER INFORMATION: EPO K20Q/N38H/N83H/L93V/R139H

<400> SEQUENCE: 261

Ala Pro Pro Arg Leu Ile Cys Asp Ser Arg Val Leu Glu Arg Tyr Leu
1               5                   10                  15

Leu Glu Ala Gln Glu Ala Glu Asn Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val His Ser Ser Gln Pro Trp Glu Pro Leu Gln Val His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 262
<211> LENGTH: 166
<212> TYPE: PRT
<213> ORGANISM: Homo sapiens
<220> FEATURE:
<223> OTHER INFORMATION: EPO N24H/N38H/N83H/R139H/L80I

<400> SEQUENCE: 262

Ala Pro Pro Arg Leu Ile Cys Asp Ser Arg Val Leu Glu Arg Tyr Leu
1               5                   10                  15

Leu Glu Ala Lys Glu Ala Glu His Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Ile
 65                  70                  75                  80

Leu Val His Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe His Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 263
<211> LENGTH: 166
<212> TYPE: PRT
<213> ORGANISM: Homo sapiens
<220> FEATURE:
<223> OTHER INFORMATION: EPO N24H/N38H/N83H/R139H/L93I

<400> SEQUENCE: 263

Ala Pro Pro Arg Leu Ile Cys Asp Ser Arg Val Leu Glu Arg Tyr Leu
 1               5                  10                  15

Leu Glu Ala Lys Glu Ala Glu His Ile Thr Thr Gly Cys Ala Glu His
                 20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val His Ser Ser Gln Pro Trp Glu Pro Leu Gln Ile His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe His Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 264
<211> LENGTH: 166
<212> TYPE: PRT
<213> ORGANISM: Homo sapiens
<220> FEATURE:
<223> OTHER INFORMATION: EPO N24H/N38H/N83H/R139H/L93V

<400> SEQUENCE: 264

```
Ala Pro Pro Arg Leu Ile Cys Asp Ser Arg Val Leu Glu Arg Tyr Leu
  1               5                  10                  15

Leu Glu Ala Lys Glu Ala Glu His Ile Thr Thr Gly Cys Ala Glu His
             20                  25                  30

Cys Ser Leu Asn Glu His Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val His Ser Ser Gln Pro Trp Glu Pro Leu Gln Val His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 265
<211> LENGTH: 166
<212> TYPE: PRT
<213> ORGANISM: Homo sapiens
<220> FEATURE:
<223> OTHER INFORMATION: EPO K20Q/N24H/N38H/N83H/R139H/L80I

<400> SEQUENCE: 265

Ala Pro Pro Arg Leu Ile Cys Asp Ser Arg Val Leu Glu Arg Tyr Leu
  1               5                  10                  15

Leu Glu Ala Gln Glu Ala Glu His Ile Thr Thr Gly Cys Ala Glu His
             20                  25                  30

Cys Ser Leu Asn Glu His Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Ile
 65                  70                  75                  80

Leu Val His Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 266
<211> LENGTH: 166
```

```
<212> TYPE: PRT
<213> ORGANISM: Homo sapiens
<220> FEATURE:
<223> OTHER INFORMATION: EPO K20Q/N24H/N38H/N83H/R139H/L93I

<400> SEQUENCE: 266

Ala Pro Pro Arg Leu Ile Cys Asp Ser Arg Val Leu Glu Arg Tyr Leu
 1               5                  10                  15

Leu Glu Ala Gln Glu Ala Glu His Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val His Ser Ser Gln Pro Trp Glu Pro Leu Gln Ile His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe His Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 267
<211> LENGTH: 166
<212> TYPE: PRT
<213> ORGANISM: Homo sapiens
<220> FEATURE:
<223> OTHER INFORMATION: EPO K20Q/N24H/N38H/N83H/R139H/L93V

<400> SEQUENCE: 267

Ala Pro Pro Arg Leu Ile Cys Asp Ser Arg Val Leu Glu Arg Tyr Leu
 1               5                  10                  15

Leu Glu Ala Gln Glu Ala Glu His Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val His Ser Ser Gln Pro Trp Glu Pro Leu Gln Val His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe His Lys Leu Phe Arg Val
130                 135                 140

Tyr Ser Asn Phe Leu Arg Gly Lys Leu Lys Leu Tyr Thr Gly Glu Ala
145                 150                 155                 160
```

-continued

```
Cys Arg Thr Gly Asp Arg
            165

<210> SEQ ID NO 268
<211> LENGTH: 166
<212> TYPE: PRT
<213> ORGANISM: Homo sapiens
<220> FEATURE:
<223> OTHER INFORMATION: EPO R4H/K20Q/N24H/N38H/N83H/R139H/L80I

<400> SEQUENCE: 268

Ala Pro Pro His Leu Ile Cys Asp Ser Arg Val Leu Glu Arg Tyr Leu
 1               5                  10                  15

Leu Glu Ala Gln Glu Ala Glu His Ile Thr Thr Gly Cys Ala Glu His
             20                  25                  30

Cys Ser Leu Asn Glu His Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Ile
 65                  70                  75                  80

Leu Val His Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe His Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 269
<211> LENGTH: 166
<212> TYPE: PRT
<213> ORGANISM: Homo sapiens
<220> FEATURE:
<223> OTHER INFORMATION: EPO E159H/K20Q/N24H/N38H/N83H/R139H/L93I

<400> SEQUENCE: 269

Ala Pro Pro Arg Leu Ile Cys Asp Ser Arg Val Leu Glu Arg Tyr Leu
 1               5                  10                  15

Leu Glu Ala Gln Glu Ala Glu His Ile Thr Thr Gly Cys Ala Glu His
             20                  25                  30

Cys Ser Leu Asn Glu His Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val His Ser Ser Gln Pro Trp Glu Pro Leu Gln Ile His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125
```

Pro Leu Arg Thr Ile Thr Ala Asp Thr Phe His Lys Leu Phe Arg Val
        130                 135                 140

Tyr Ser Asn Phe Leu Arg Gly Lys Leu Lys Leu Tyr Thr Gly Asn Ala
145                 150                 155                 160

Cys Arg Thr Gly Asp Arg
                165

<210> SEQ ID NO 270
<211> LENGTH: 166
<212> TYPE: PRT
<213> ORGANISM: Homo sapiens
<220> FEATURE:
<223> OTHER INFORMATION: EPO K20Q/N24H/N38H/N83H/R139H/L153V

<400> SEQUENCE: 270

Ala Pro Pro Arg Leu Ile Cys Asp Ser Arg Val Leu Glu Arg Tyr Leu
1               5                   10                  15

Leu Glu Ala Gln Glu Ala Glu His Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val His Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe His Lys Leu Phe Arg Val
    130                 135                 140

Tyr Ser Asn Phe Leu Arg Gly Lys Val Lys Leu Tyr Thr Gly Glu Ala
145                 150                 155                 160

Cys Arg Thr Gly Asp Arg
                165

<210> SEQ ID NO 271
<211> LENGTH: 166
<212> TYPE: PRT
<213> ORGANISM: Homo sapiens
<220> FEATURE:
<223> OTHER INFORMATION: EPO L153V/K20Q/N24H/N38H/N83H/R139H/L80I

<400> SEQUENCE: 271

Ala Pro Pro Arg Leu Ile Cys Asp Ser Arg Val Leu Glu Arg Tyr Leu
1               5                   10                  15

Leu Glu Ala Gln Glu Ala Glu His Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Ile
65                  70                  75                  80

Leu Val His Ser Ser Gln Pro Trp Glu Pro Leu Gln Leu His Val Asp
                85                  90                  95

```
Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
            130                 135                 140

Tyr Ser Asn Phe Leu Arg Gly Lys Val Lys Leu Tyr Thr Gly Glu Ala
145                 150                 155                 160

Cys Arg Thr Gly Asp Arg
                165

<210> SEQ ID NO 272
<211> LENGTH: 166
<212> TYPE: PRT
<213> ORGANISM: Homo sapiens
<220> FEATURE:
<223> OTHER INFORMATION: EPO E159N/K20Q/N24H/N38H/N83H/R139H/L80I

<400> SEQUENCE: 272

Ala Pro Pro Arg Leu Ile Cys Asp Ser Arg Val Leu Glu Arg Tyr Leu
1               5                   10                  15

Leu Glu Ala Gln Glu Ala Glu His Ile Thr Thr Gly Cys Ala Glu His
            20                  25                  30

Cys Ser Leu Asn Glu His Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Ile
65                  70                  75                  80

Leu Val His Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
            130                 135                 140

Tyr Ser Asn Phe Leu Arg Gly Lys Leu Lys Leu Tyr Thr Gly Asn Ala
145                 150                 155                 160

Cys Arg Thr Gly Asp Arg
                165

<210> SEQ ID NO 273
<211> LENGTH: 144
<212> TYPE: PRT
<213> ORGANISM: Homo sapiens
<220> FEATURE:
<223> OTHER INFORMATION: GM-CSF precursor

<400> SEQUENCE: 273

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60
```

-continued

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 274
<211> LENGTH: 127
<212> TYPE: PRT
<213> ORGANISM: Homo sapiens
<220> FEATURE:
<223> OTHER INFORMATION: GM-CSF mature

<400> SEQUENCE: 274

Ala Pro Ala Arg Ser Pro Ser Pro Ser Thr Gln Pro Trp Glu His Val
  1               5                  10                  15

Asn Ala Ile Gln Glu Ala Arg Arg Leu Leu Asn Leu Ser Arg Asp Thr
             20                  25                  30

Ala Ala Glu Met Asn Glu Thr Val Glu Val Ile Ser Glu Met Phe Asp
         35                  40                  45

Leu Gln Glu Pro Thr Cys Leu Gln Thr Arg Leu Glu Leu Tyr Lys Gln
     50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 275
<211> LENGTH: 554
<212> TYPE: PRT
<213> ORGANISM: Homo sapiens
<220> FEATURE:
<223> OTHER INFORMATION: M-CSF Isoform 1 precursor

<400> SEQUENCE: 275

Met Thr Ala Pro Gly Ala Ala Gly Arg Cys Pro Pro Thr Thr Trp Leu
  1               5                  10                  15

Gly Ser Leu Leu Leu Leu Val Cys Leu Leu Ala Ser Arg Ser Ile Thr
             20                  25                  30

Glu Glu Val Ser Glu Tyr Cys Ser His Met Ile Gly Ser Gly His Leu
         35                  40                  45

Gln Ser Leu Gln Arg Leu Ile Asp Ser Gln Met Glu Thr Ser Cys Gln
     50                  55                  60

Ile Thr Phe Glu Phe Val Asp Gln Glu Gln Leu Lys Asp Pro Val Cys
 65                  70                  75                  80

Tyr Leu Lys Lys Ala Phe Leu Leu Val Gln Asp Ile Met Glu Asp Thr
                 85                  90                  95

Met Arg Phe Arg Asp Asn Thr Pro Asn Ala Ile Ala Ile Val Gln Leu
            100                 105                 110

```
Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
        130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
                180                 185                 190

Tyr Pro Lys Ala Ile Pro Ser Ser Asp Pro Ala Ser Val Ser Pro His
                195                 200                 205

Gln Pro Leu Ala Pro Ser Met Ala Pro Val Ala Gly Leu Thr Trp Glu
        210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
        260                 265                 270

Thr Ile Gly Gly Ser Pro Gln Pro Arg Pro Ser Val Gly Ala Phe Asn
            275                 280                 285

Pro Gly Met Glu Asp Ile Leu Asp Ser Ala Met Gly Thr Asn Trp Val
        290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
                340                 345                 350

Ser Ala Lys Gly Gln Gln Pro Ala Asp Val Thr Gly Thr Ala Leu Pro
            355                 360                 365

Arg Val Gly Pro Val Arg Pro Thr Gly Gln Asp Trp Asn His Thr Pro
    370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415

Ser Thr Leu Ser Ala Gln Pro Gln Leu Ser Arg Ser His Ser Ser Gly
            420                 425                 430

Ser Val Leu Pro Leu Gly Glu Leu Glu Gly Arg Arg Ser Thr Arg Asp
        435                 440                 445

Arg Arg Ser Pro Ala Glu Pro Glu Gly Gly Pro Ala Ser Glu Gly Ala
    450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Ser Ser Pro Gln Leu Gln Glu Ser
                485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Arg Ser His Gln Glu Pro
        515                 520                 525

Gln Arg Ala Asp Ser Pro Leu Glu Gln Pro Glu Gly Ser Pro Leu Thr
            530                 535                 540
```

```
Gln Asp Asp Arg Gln Val Glu Leu Pro Val
545                 550

<210> SEQ ID NO 276
<211> LENGTH: 522
<212> TYPE: PRT
<213> ORGANISM: Homo sapiens
<220> FEATURE:
<223> OTHER INFORMATION: M-CSF Isoform 1 mature

<400> SEQUENCE: 276

Glu Glu Val Ser Glu Tyr Cys Ser His Met Ile Gly Ser Gly His Leu
 1               5                  10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140

Glu Cys Ser Ser Gln Asp Val Val Thr Lys Pro Asp Cys Asn Cys Leu
145                 150                 155                 160

Tyr Pro Lys Ala Ile Pro Ser Ser Asp Pro Ala Ser Val Ser Pro His
                165                 170                 175

Gln Pro Leu Ala Pro Ser Met Ala Pro Val Ala Gly Leu Thr Trp Glu
            180                 185                 190

Asp Ser Glu Gly Thr Glu Gly Ser Ser Leu Leu Pro Gly Glu Gln Pro
        195                 200                 205

Leu His Thr Val Asp Pro Gly Ser Ala Lys Gln Arg Pro Pro Arg Ser
    210                 215                 220

Thr Cys Gln Ser Phe Glu Pro Pro Glu Thr Pro Val Val Lys Asp Ser
225                 230                 235                 240

Thr Ile Gly Gly Ser Pro Gln Pro Arg Pro Ser Val Gly Ala Phe Asn
                245                 250                 255

Pro Gly Met Glu Asp Ile Leu Asp Ser Ala Met Gly Thr Asn Trp Val
            260                 265                 270

Pro Glu Glu Ala Ser Gly Glu Ala Ser Glu Ile Pro Val Pro Gln Gly
        275                 280                 285

Thr Glu Leu Ser Pro Ser Arg Pro Gly Gly Gly Ser Met Gln Thr Glu
    290                 295                 300

Pro Ala Arg Pro Ser Asn Phe Leu Ser Ala Ser Ser Pro Leu Pro Ala
305                 310                 315                 320

Ser Ala Lys Gly Gln Gln Pro Ala Asp Val Thr Gly Thr Ala Leu Pro
                325                 330                 335

Arg Val Gly Pro Val Arg Pro Thr Gly Gln Asp Trp Asn His Thr Pro
            340                 345                 350
```

-continued

```
Gln Lys Thr Asp His Pro Ser Ala Leu Leu Arg Asp Pro Pro Glu Pro
        355                 360                 365

Gly Ser Pro Arg Ile Ser Ser Leu Arg Pro Gln Gly Leu Ser Asn Pro
370                 375                 380

Ser Thr Leu Ser Ala Gln Pro Gln Leu Ser Arg Ser His Ser Ser Gly
385                 390                 395                 400

Ser Val Leu Pro Leu Gly Glu Leu Gly Arg Arg Ser Thr Arg Asp
            405                 410                 415

Arg Arg Ser Pro Ala Glu Pro Glu Gly Gly Pro Ala Ser Glu Gly Ala
                420                 425                 430

Ala Arg Pro Leu Pro Arg Phe Asn Ser Val Pro Leu Thr Asp Thr Gly
                435                 440                 445

His Glu Arg Gln Ser Glu Gly Ser Ser Ser Pro Gln Leu Gln Glu Ser
        450                 455                 460

Val Phe His Leu Leu Val Pro Ser Val Ile Leu Val Leu Leu Ala Val
465                 470                 475                 480

Gly Gly Leu Leu Phe Tyr Arg Trp Arg Arg Ser His Gln Glu Pro
                485                 490                 495

Gln Arg Ala Asp Ser Pro Leu Glu Gln Pro Glu Gly Ser Pro Leu Thr
                500                 505                 510

Gln Asp Asp Arg Gln Val Glu Leu Pro Val
        515                 520

<210> SEQ ID NO 277
<211> LENGTH: 438
<212> TYPE: PRT
<213> ORGANISM: Homo sapiens
<220> FEATURE:
<223> OTHER INFORMATION: M-CSF Isoform 2 precursor

<400> SEQUENCE: 277

Met Thr Ala Pro Gly Ala Ala Gly Arg Cys Pro Pro Thr Thr Trp Leu
 1               5                  10                  15

Gly Ser Leu Leu Leu Leu Val Cys Leu Leu Ala Ser Arg Ser Ile Thr
                20                  25                  30

Glu Glu Val Ser Glu Tyr Cys Ser His Met Ile Gly Ser Gly His Leu
            35                  40                  45

Gln Ser Leu Gln Arg Leu Ile Asp Ser Gln Met Glu Thr Ser Cys Gln
        50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
                100                 105                 110

Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
        130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
                180                 185                 190

Tyr Pro Lys Ala Ile Pro Ser Ser Asp Pro Ala Ser Val Ser Pro His
```

```
                195                 200                 205
Gln Pro Leu Ala Pro Ser Met Ala Pro Val Ala Gly Leu Thr Trp Glu
210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
                260                 265                 270

Thr Ile Gly Gly Ser Pro Gln Pro Arg Pro Ser Val Gly Ala Phe Asn
                275                 280                 285

Pro Gly Met Glu Asp Ile Leu Asp Ser Ala Met Gly Thr Asn Trp Val
290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
                340                 345                 350

Ser Ala Lys Gly Gln Gln Pro Ala Asp Val Thr Gly His Glu Arg Gln
                355                 360                 365

Ser Glu Gly Ser Ser Ser Pro Gln Leu Gln Glu Ser Val Phe His Leu
                370                 375                 380

Leu Val Pro Ser Val Ile Leu Val Leu Leu Ala Val Gly Gly Leu Leu
385                 390                 395                 400

Phe Tyr Arg Trp Arg Arg Arg Ser His Gln Glu Pro Gln Arg Ala Asp
                405                 410                 415

Ser Pro Leu Glu Gln Pro Glu Gly Ser Pro Leu Thr Gln Asp Asp Arg
                420                 425                 430

Gln Val Glu Leu Pro Val
                435

<210> SEQ ID NO 278
<211> LENGTH: 406
<212> TYPE: PRT
<213> ORGANISM: Homo sapiens
<220> FEATURE:
<223> OTHER INFORMATION: M-CSF Isoform 2 mature

<400> SEQUENCE: 278

Glu Glu Val Ser Glu Tyr Cys Ser His Met Ile Gly Ser Gly His Leu
 1               5                  10                  15

Gln Ser Leu Gln Arg Leu Ile Asp Ser Gln Met Glu Thr Ser Cys Gln
                20                  25                  30

Ile Thr Phe Glu Phe Val Asp Gln Glu Gln Leu Lys Asp Pro Val Cys
            35                  40                  45

Tyr Leu Lys Lys Ala Phe Leu Leu Val Gln Asp Ile Met Glu Asp Thr
        50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
                100                 105                 110

Leu Leu Glu Lys Val Lys Asn Val Phe Asn Glu Thr Lys Asn Leu Leu
            115                 120                 125
```

```
Asp Lys Asp Trp Asn Ile Phe Ser Lys Asn Cys Asn Ser Phe Ala
            130                 135                 140
Glu Cys Ser Ser Gln Asp Val Val Thr Lys Pro Asp Cys Asn Cys Leu
145                 150                 155                 160
Tyr Pro Lys Ala Ile Pro Ser Ser Asp Pro Ala Ser Val Ser Pro His
                165                 170                 175
Gln Pro Leu Ala Pro Ser Met Ala Pro Val Ala Gly Leu Thr Trp Glu
            180                 185                 190
Asp Ser Glu Gly Thr Glu Gly Ser Ser Leu Leu Pro Gly Glu Gln Pro
            195                 200                 205
Leu His Thr Val Asp Pro Gly Ser Ala Lys Gln Arg Pro Pro Arg Ser
            210                 215                 220
Thr Cys Gln Ser Phe Glu Pro Pro Glu Thr Pro Val Val Lys Asp Ser
225                 230                 235                 240
Thr Ile Gly Gly Ser Pro Gln Pro Arg Pro Ser Val Gly Ala Phe Asn
                245                 250                 255
Pro Gly Met Glu Asp Ile Leu Asp Ser Ala Met Gly Thr Asn Trp Val
            260                 265                 270
Pro Glu Glu Ala Ser Gly Glu Ala Ser Glu Ile Pro Val Pro Gln Gly
            275                 280                 285
Thr Glu Leu Ser Pro Ser Arg Pro Gly Gly Gly Ser Met Gln Thr Glu
            290                 295                 300
Pro Ala Arg Pro Ser Asn Phe Leu Ser Ala Ser Ser Pro Leu Pro Ala
305                 310                 315                 320
Ser Ala Lys Gly Gln Gln Pro Ala Asp Val Thr Gly His Glu Arg Gln
                325                 330                 335
Ser Glu Gly Ser Ser Ser Pro Gln Leu Gln Glu Ser Val Phe His Leu
            340                 345                 350
Leu Val Pro Ser Val Ile Leu Val Leu Leu Ala Val Gly Gly Leu Leu
            355                 360                 365
Phe Tyr Arg Trp Arg Arg Arg Ser His Gln Glu Pro Gln Arg Ala Asp
            370                 375                 380
Ser Pro Leu Glu Gln Pro Glu Gly Ser Pro Leu Thr Gln Asp Asp Arg
385                 390                 395                 400
Gln Val Glu Leu Pro Val
                405

<210> SEQ ID NO 279
<211> LENGTH: 256
<212> TYPE: PRT
<213> ORGANISM: Homo sapiens
<220> FEATURE:
<223> OTHER INFORMATION: M-CSF Isoform 3 precursor

<400> SEQUENCE: 279

Met Thr Ala Pro Gly Ala Ala Gly Arg Cys Pro Pro Thr Thr Trp Leu
1               5                   10                  15
Gly Ser Leu Leu Leu Leu Val Cys Leu Leu Ala Ser Arg Ser Ile Thr
            20                  25                  30
Glu Glu Val Ser Glu Tyr Cys Ser His Met Ile Gly Ser Gly His Leu
            35                  40                  45
Gln Ser Leu Gln Arg Leu Ile Asp Ser Gln Met Glu Thr Ser Cys Gln
            50                  55                  60
Ile Thr Phe Glu Phe Val Asp Gln Glu Gln Leu Lys Asp Pro Val Cys
65                  70                  75                  80
```

```
Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
            130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Gly His Glu Arg Gln Ser Glu Gly Ser Ser Ser
            180                 185                 190

Pro Gln Leu Gln Glu Ser Val Phe His Leu Leu Val Pro Ser Val Ile
            195                 200                 205

Leu Val Leu Leu Ala Val Gly Gly Leu Leu Phe Tyr Arg Trp Arg Arg
            210                 215                 220

Arg Ser His Gln Glu Pro Gln Arg Ala Asp Ser Pro Leu Glu Gln Pro
225                 230                 235                 240

Glu Gly Ser Pro Leu Thr Gln Asp Asp Arg Gln Val Glu Leu Pro Val
                245                 250                 255

<210> SEQ ID NO 280
<211> LENGTH: 224
<212> TYPE: PRT
<213> ORGANISM: Homo sapiens
<220> FEATURE:
<223> OTHER INFORMATION: M-CSF Isoform 3 mature

<400> SEQUENCE: 280

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
            115                 120                 125

Asp Lys Asp Trp Asn Ile Phe Ser Lys Asn Cys Asn Asn Ser Phe Ala
            130                 135                 140

Glu Cys Ser Ser Gln Gly His Glu Arg Gln Ser Glu Gly Ser Ser Ser
145                 150                 155                 160

Pro Gln Leu Gln Glu Ser Val Phe His Leu Leu Val Pro Ser Val Ile
                165                 170                 175

Leu Val Leu Leu Ala Val Gly Gly Leu Leu Phe Tyr Arg Trp Arg Arg
            180                 185                 190

Arg Ser His Gln Glu Pro Gln Arg Ala Asp Ser Pro Leu Glu Gln Pro
```

```
                    195                 200                 205
Glu Gly Ser Pro Leu Thr Gln Asp Asp Arg Gln Val Glu Leu Pro Val
    210                 215                 220

<210> SEQ ID NO 281
<211> LENGTH: 207
<212> TYPE: PRT
<213> ORGANISM: Homo sapiens
<220> FEATURE:
<223> OTHER INFORMATION: G-CSF precursor

<400> SEQUENCE: 281

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 282
<211> LENGTH: 177
<212> TYPE: PRT
<213> ORGANISM: Homo sapiens
<220> FEATURE:
<223> OTHER INFORMATION: G-CSF mature

<400> SEQUENCE: 282

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Val Ser Glu Cys Ala Thr Tyr Lys Leu Cys His Pro Glu
        35                  40                  45

Glu Leu Val Leu Leu Gly His Ser Leu Gly Ile Pro Trp Ala Pro Leu
    50                  55                  60

Ser Ser Cys Pro Ser Gln Ala Leu Gln Leu Ala Gly Cys Leu Ser Gln
65                  70                  75                  80

Leu His Ser Gly Leu Phe Leu Tyr Gln Gly Leu Leu Gln Ala Leu Glu
```

-continued

```
                85                  90                  95
Gly Ile Ser Pro Glu Leu Gly Pro Thr Leu Asp Thr Leu Gln Leu Asp
            100                 105                 110

Val Ala Asp Phe Ala Thr Thr Ile Trp Gln Gln Met Glu Glu Leu Gly
        115                 120                 125

Met Ala Pro Ala Leu Gln Pro Thr Gln Gly Ala Met Pro Ala Phe Ala
    130                 135                 140

Ser Ala Phe Gln Arg Arg Ala Gly Gly Val Leu Val Ala Ser His Leu
145                 150                 155                 160

Gln Ser Phe Leu Glu Val Ser Tyr Arg Val Leu Arg His Leu Ala Gln
                165                 170                 175

Pro

<210> SEQ ID NO 283
<211> LENGTH: 204
<212> TYPE: PRT
<213> ORGANISM: Homo sapiens
<220> FEATURE:
<223> OTHER INFORMATION: G-CSF Isoform b precursor

<400> SEQUENCE: 283

Met Ala Gly Pro Ala Thr Gln Ser Pro Met Lys Leu Met Ala Leu Gln
 1               5                  10                  15

Leu Leu Leu Trp His Ser Ala Leu Trp Thr Val Gln Glu Ala Thr Pro
                20                  25                  30

Leu Gly Pro Ala Ser Ser Leu Pro Gln Ser Phe Leu Leu Lys Cys Leu
            35                  40                  45

Glu Gln Val Arg Lys Ile Gln Gly Asp Gly Ala Ala Leu Gln Glu Lys
        50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200

<210> SEQ ID NO 284
<211> LENGTH: 174
<212> TYPE: PRT
<213> ORGANISM: Homo sapiens
<220> FEATURE:
<223> OTHER INFORMATION: G-CSF Isoform b mature

<400> SEQUENCE: 284

Thr Pro Leu Gly Pro Ala Ser Ser Leu Pro Gln Ser Phe Leu Leu Lys
 1               5                  10                  15
```

```
Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 285
<211> LENGTH: 202
<212> TYPE: PRT
<213> ORGANISM: Homo sapiens
<220> FEATURE:
<223> OTHER INFORMATION: LIF precursor

<400> SEQUENCE: 285

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
            115                 120                 125

Ser Ala Leu Ser Leu His Ser Lys Leu Asn Ala Thr Ala Asp Ile Leu
        130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Ile Ile Ala Val Leu Ala Gln Ala Phe
            195                 200
```

```
<210> SEQ ID NO 286
<211> LENGTH: 180
<212> TYPE: PRT
<213> ORGANISM: Homo sapiens
<220> FEATURE:
<223> OTHER INFORMATION: LIF mature

<400> SEQUENCE: 286

Ser Pro Leu Pro Ile Thr Pro Val Asn Ala Thr Cys Ala Ile Arg His
 1               5                  10                  15

Pro Cys His Asn Asn Leu Met Asn Gln Ile Arg Ser Gln Leu Ala Gln
             20                  25                  30

Leu Asn Gly Ser Ala Asn Ala Leu Phe Ile Leu Tyr Tyr Thr Ala Gln
         35                  40                  45

Gly Glu Pro Phe Pro Asn Asn Leu Asp Lys Leu Cys Gly Pro Asn Val
     50                  55                  60

Thr Asp Phe Pro Pro Phe His Ala Asn Gly Thr Glu Lys Ala Lys Leu
 65                  70                  75                  80

Val Glu Leu Tyr Arg Ile Val Val Tyr Leu Gly Thr Ser Leu Gly Asn
                 85                  90                  95

Ile Thr Arg Asp Gln Lys Ile Leu Asn Pro Ser Ala Leu Ser Leu His
            100                 105                 110

Ser Lys Leu Asn Ala Thr Ala Asp Ile Leu Arg Gly Leu Leu Ser Asn
        115                 120                 125

Val Leu Cys Arg Leu Cys Ser Lys Tyr His Val Gly His Val Asp Val
    130                 135                 140

Thr Tyr Gly Pro Asp Thr Ser Gly Lys Asp Val Phe Gln Lys Lys Lys
145                 150                 155                 160

Leu Gly Cys Gln Leu Leu Gly Lys Tyr Lys Gln Ile Ile Ala Val Leu
                165                 170                 175

Ala Gln Ala Phe
            180

<210> SEQ ID NO 287
<211> LENGTH: 269
<212> TYPE: PRT
<213> ORGANISM: Homo sapiens
<220> FEATURE:
<223> OTHER INFORMATION: IL-1beta precursor

<400> SEQUENCE: 287

Met Ala Glu Val Pro Glu Leu Ala Ser Glu Met Met Ala Tyr Tyr Ser
 1               5                  10                  15

Gly Asn Glu Asp Asp Leu Phe Phe Glu Ala Asp Gly Pro Lys Gln Met
             20                  25                  30

Lys Cys Ser Phe Gln Asp Leu Asp Leu Cys Pro Leu Asp Gly Gly Ile
         35                  40                  45

Gln Leu Arg Ile Ser Asp His His Tyr Ser Lys Gly Phe Arg Gln Ala
     50                  55                  60

Ala Ser Val Val Val Ala Met Asp Lys Leu Arg Lys Met Leu Val Pro
 65                  70                  75                  80

Cys Pro Gln Thr Phe Gln Glu Asn Asp Leu Ser Thr Phe Phe Pro Phe
                 85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125
```

```
Ser Gln Gln Lys Ser Leu Val Met Ser Gly Pro Tyr Glu Leu Lys Ala
130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265
```

<210> SEQ ID NO 288
<211> LENGTH: 153
<212> TYPE: PRT
<213> ORGANISM: Homo sapiens
<220> FEATURE:
<223> OTHER INFORMATION: IL-1beta mature

<400> SEQUENCE: 288

```
Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
                20                  25                  30

Gly Gln Asp Met Glu Gln Gln Val Val Phe Ser Met Ser Phe Val Gln
            35                  40                  45

Gly Glu Glu Ser Asn Asp Lys Ile Pro Val Ala Leu Gly Leu Lys Glu
        50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150
```

<210> SEQ ID NO 289
<211> LENGTH: 153
<212> TYPE: PRT
<213> ORGANISM: Homo sapiens
<220> FEATURE:
<223> OTHER INFORMATION: IL-2 precursor

<400> SEQUENCE: 289

```
Met Tyr Arg Met Gln Leu Leu Ser Cys Ile Ala Leu Ser Leu Ala Leu
1               5                   10                  15
```

```
Val Thr Asn Ser Ala Pro Thr Ser Ser Thr Lys Lys Thr Gln Leu
            20                  25                  30

Gln Leu Glu His Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65              70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150
```

<210> SEQ ID NO 290
<211> LENGTH: 133
<212> TYPE: PRT
<213> ORGANISM: Homo sapiens
<220> FEATURE:
<223> OTHER INFORMATION: IL-2 mature

<400> SEQUENCE: 290

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 291
<211> LENGTH: 152
<212> TYPE: PRT
<213> ORGANISM: Homo sapiens
<220> FEATURE:
<223> OTHER INFORMATION: IL-3 precursor

<400> SEQUENCE: 291

```
Met Ser Arg Leu Pro Val Leu Leu Leu Leu Gln Leu Leu Val Arg Pro
1               5                   10                  15

Gly Leu Gln Ala Pro Met Thr Gln Thr Thr Pro Leu Lys Thr Ser Trp
            20                  25                  30
```

```
Val Asn Cys Ser Asn Met Ile Asp Glu Ile Ile Thr His Leu Lys Gln
         35                  40                  45

Pro Pro Leu Pro Leu Leu Asp Phe Asn Asn Leu Asn Gly Glu Asp Gln
 50                  55                  60

Asp Ile Leu Met Glu Asn Asn Leu Arg Arg Pro Asn Leu Glu Ala Phe
 65                  70                  75                  80

Asn Arg Ala Val Lys Ser Leu Gln Asn Ala Ser Ala Ile Glu Ser Ile
                 85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 292
<211> LENGTH: 133
<212> TYPE: PRT
<213> ORGANISM: Homo sapiens
<220> FEATURE:
<223> OTHER INFORMATION: IL-3 mature

<400> SEQUENCE: 292

Ala Pro Met Thr Gln Thr Thr Pro Leu Lys Thr Ser Trp Val Asn Cys
  1               5                  10                  15

Ser Asn Met Ile Asp Glu Ile Ile Thr His Leu Lys Gln Pro Pro Leu
                 20                  25                  30

Pro Leu Leu Asp Phe Asn Asn Leu Asn Gly Glu Asp Gln Asp Ile Leu
             35                  40                  45

Met Glu Asn Asn Leu Arg Arg Pro Asn Leu Glu Ala Phe Asn Arg Ala
 50                  55                  60

Val Lys Ser Leu Gln Asn Ala Ser Ala Ile Glu Ser Ile Leu Lys Asn
 65                  70                  75                  80

Leu Leu Pro Cys Leu Pro Leu Ala Thr Ala Ala Pro Thr Arg His Pro
                 85                  90                  95

Ile His Ile Lys Asp Gly Asp Trp Asn Glu Phe Arg Arg Lys Leu Thr
            100                 105                 110

Phe Tyr Leu Lys Thr Leu Glu Asn Ala Gln Ala Gln Gln Thr Thr Leu
        115                 120                 125

Ser Leu Ala Ile Phe
    130

<210> SEQ ID NO 293
<211> LENGTH: 153
<212> TYPE: PRT
<213> ORGANISM: Homo sapiens
<220> FEATURE:
<223> OTHER INFORMATION: IL-4 precursor

<400> SEQUENCE: 293

Met Gly Leu Thr Ser Gln Leu Leu Pro Pro Leu Phe Phe Leu Leu Ala
  1               5                  10                  15

Cys Ala Gly Asn Phe Val His Gly His Lys Cys Asp Ile Thr Leu Gln
                 20                  25                  30

Glu Ile Ile Lys Thr Leu Asn Ser Leu Thr Glu Gln Lys Thr Leu Cys
             35                  40                  45
```

```
Thr Glu Leu Thr Val Thr Asp Ile Phe Ala Ala Ser Lys Asn Thr Thr
 50                  55                  60
Glu Lys Glu Thr Phe Cys Arg Ala Ala Thr Val Leu Arg Gln Phe Tyr
 65                  70                  75                  80
Ser His His Glu Lys Asp Thr Arg Cys Leu Gly Ala Thr Ala Gln Gln
                 85                  90                  95
Phe His Arg His Lys Gln Leu Ile Arg Phe Leu Lys Arg Leu Asp Arg
             100                 105                 110
Asn Leu Trp Gly Leu Ala Gly Leu Asn Ser Cys Pro Val Lys Glu Ala
         115                 120                 125
Asn Gln Ser Thr Leu Glu Asn Phe Leu Glu Arg Leu Lys Thr Ile Met
    130                 135                 140
Arg Glu Lys Tyr Ser Lys Cys Ser Ser
145                 150
```

<210> SEQ ID NO 294
<211> LENGTH: 129
<212> TYPE: PRT
<213> ORGANISM: Homo sapiens
<220> FEATURE:
<223> OTHER INFORMATION: IL-4 mature

<400> SEQUENCE: 294

```
His Lys Cys Asp Ile Thr Leu Gln Glu Ile Ile Lys Thr Leu Asn Ser
 1                   5                  10                  15
Leu Thr Glu Gln Lys Thr Leu Cys Thr Glu Leu Thr Val Thr Asp Ile
                 20                  25                  30
Phe Ala Ala Ser Lys Asn Thr Thr Glu Lys Glu Thr Phe Cys Arg Ala
             35                  40                  45
Ala Thr Val Leu Arg Gln Phe Tyr Ser His His Glu Lys Asp Thr Arg
 50                  55                  60
Cys Leu Gly Ala Thr Ala Gln Gln Phe His Arg His Lys Gln Leu Ile
 65                  70                  75                  80
Arg Phe Leu Lys Arg Leu Asp Arg Asn Leu Trp Gly Leu Ala Gly Leu
                 85                  90                  95
Asn Ser Cys Pro Val Lys Glu Ala Asn Gln Ser Thr Leu Glu Asn Phe
            100                 105                 110
Leu Glu Arg Leu Lys Thr Ile Met Arg Glu Lys Tyr Ser Lys Cys Ser
        115                 120                 125
Ser
```

<210> SEQ ID NO 295
<211> LENGTH: 134
<212> TYPE: PRT
<213> ORGANISM: Homo sapiens
<220> FEATURE:
<223> OTHER INFORMATION: IL-5 precursor

<400> SEQUENCE: 295

```
Met Arg Met Leu Leu His Leu Ser Leu Leu Ala Leu Gly Ala Ala Tyr
 1                   5                  10                  15
Val Tyr Ala Ile Pro Thr Glu Ile Pro Thr Ser Ala Leu Val Lys Glu
                 20                  25                  30
Thr Leu Ala Leu Leu Ser Thr His Arg Thr Leu Leu Ile Ala Asn Glu
             35                  40                  45
Thr Leu Arg Ile Pro Val Pro Val His Lys Asn His Gln Leu Cys Thr
 50                  55                  60
Glu Glu Ile Phe Gln Gly Ile Gly Thr Leu Glu Ser Gln Thr Val Gln
```

```
                65                  70                  75                  80
Gly Gly Thr Val Glu Arg Leu Phe Lys Asn Leu Ser Leu Ile Lys Lys
                    85                  90                  95

Tyr Ile Asp Gly Gln Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
    130

<210> SEQ ID NO 296
<211> LENGTH: 115
<212> TYPE: PRT
<213> ORGANISM: Homo sapiens
<220> FEATURE:
<223> OTHER INFORMATION: IL-5 mature

<400> SEQUENCE: 296

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Cys Gly Glu Glu Arg Arg Arg Val Asn Gln Phe
                85                  90                  95

Leu Asp Tyr Leu Gln Glu Phe Leu Gly Val Met Asn Thr Glu Trp Ile
            100                 105                 110

Ile Glu Ser
        115

<210> SEQ ID NO 297
<211> LENGTH: 212
<212> TYPE: PRT
<213> ORGANISM: Homo sapiens
<220> FEATURE:
<223> OTHER INFORMATION: IL-6 precursor

<400> SEQUENCE: 297

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
```

```
                    115                 120                 125
Leu Gln Asn Arg Phe Glu Ser Ser Glu Glu Ala Arg Ala Val Gln
                130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
                180                 185                 190

Leu Ile Leu Arg Ser Phe Lys Glu Phe Leu Gln Ser Ser Leu Arg Ala
                195                 200                 205

Leu Arg Gln Met
            210

<210> SEQ ID NO 298
<211> LENGTH: 183
<212> TYPE: PRT
<213> ORGANISM: Homo sapiens
<220> FEATURE:
<223> OTHER INFORMATION: IL-6 mature

<400> SEQUENCE: 298

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
                20                  25                  30

Asp Gly Ile Ser Ala Leu Arg Lys Glu Thr Cys Asn Lys Ser Asn Met
            35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
                100                 105                 110

Ala Val Gln Met Ser Thr Lys Val Leu Ile Gln Phe Leu Gln Lys Lys
            115                 120                 125

Ala Lys Asn Leu Asp Ala Ile Thr Thr Pro Asp Pro Thr Thr Asn Ala
        130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
            180

<210> SEQ ID NO 299
<211> LENGTH: 252
<212> TYPE: PRT
<213> ORGANISM: Homo sapiens
<220> FEATURE:
<223> OTHER INFORMATION: OSM precursor

<400> SEQUENCE: 299

Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
```

```
                    20                  25                  30
Lys Glu Tyr Arg Val Leu Leu Gly Gln Leu Gln Lys Gln Thr Asp Leu
                35                  40                  45

Met Gln Asp Thr Ser Arg Leu Leu Asp Pro Tyr Ile Arg Ile Gln Gly
             50                  55                  60

Leu Asp Val Pro Lys Leu Arg Glu His Cys Arg Glu Arg Pro Gly Ala
 65                  70                  75                  80

Phe Pro Ser Glu Glu Thr Leu Arg Gly Leu Gly Arg Arg Gly Phe Leu
                 85                  90                  95

Gln Thr Leu Asn Ala Thr Leu Gly Cys Val Leu His Arg Leu Ala Asp
                100                 105                 110

Leu Glu Gln Arg Leu Pro Lys Ala Gln Asp Leu Glu Arg Ser Gly Leu
            115                 120                 125

Asn Ile Glu Asp Leu Glu Lys Leu Gln Met Ala Arg Pro Asn Ile Leu
130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250

<210> SEQ ID NO 300
<211> LENGTH: 227
<212> TYPE: PRT
<213> ORGANISM: Homo sapiens
<220> FEATURE:
<223> OTHER INFORMATION: OSM mature

<400> SEQUENCE: 300

Ala Ala Ile Gly Ser Cys Ser Lys Glu Tyr Arg Val Leu Leu Gly Gln
  1               5                  10                  15

Leu Gln Lys Gln Thr Asp Leu Met Gln Asp Thr Ser Arg Leu Leu Asp
                 20                  25                  30

Pro Tyr Ile Arg Ile Gln Gly Leu Asp Val Pro Lys Leu Arg Glu His
             35                  40                  45

Cys Arg Glu Arg Pro Gly Ala Phe Pro Ser Glu Glu Thr Leu Arg Gly
         50                  55                  60

Leu Gly Arg Arg Gly Phe Leu Gln Thr Leu Asn Ala Thr Leu Gly Cys
 65                  70                  75                  80

Val Leu His Arg Leu Ala Asp Leu Glu Gln Arg Leu Pro Lys Ala Gln
                 85                  90                  95

Asp Leu Glu Arg Ser Gly Leu Asn Ile Glu Asp Leu Glu Lys Leu Gln
                100                 105                 110

Met Ala Arg Pro Asn Ile Leu Gly Leu Arg Asn Asn Ile Tyr Cys Met
            115                 120                 125

Ala Gln Leu Leu Asp Asn Ser Asp Thr Ala Glu Pro Thr Lys Ala Gly
130                 135                 140
```

```
Arg Gly Ala Ser Gln Pro Pro Thr Pro Thr Pro Ala Ser Asp Ala Phe
145                 150                 155                 160

Gln Arg Lys Leu Glu Gly Cys Arg Phe Leu His Gly Tyr His Arg Phe
                165                 170                 175

Met His Ser Val Gly Arg Val Phe Ser Lys Trp Gly Glu Ser Pro Asn
            180                 185                 190

Arg Ser Arg Arg His Ser Pro His Gln Ala Leu Arg Lys Gly Val Arg
        195                 200                 205

Arg Thr Arg Pro Ser Arg Lys Gly Lys Arg Leu Met Thr Arg Gly Gln
    210                 215                 220

Leu Pro Arg
225

<210> SEQ ID NO 301
<211> LENGTH: 273
<212> TYPE: PRT
<213> ORGANISM: Homo sapiens
<220> FEATURE:
<223> OTHER INFORMATION: SCF precursor

<400> SEQUENCE: 301

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
            85                  90                  95

Asn Tyr Ser Ile Ile Asp Lys Leu Val Asn Ile Val Asp Asp Leu Val
        100                 105                 110

Glu Cys Val Lys Glu Asn Ser Ser Lys Asp Leu Lys Lys Ser Phe Lys
    115                 120                 125

Ser Pro Glu Pro Arg Leu Phe Thr Pro Glu Glu Phe Arg Ile Phe
130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
            165                 170                 175

Val Ser Val Thr Lys Pro Phe Met Leu Pro Pro Val Ala Ala Ser Ser
        180                 185                 190

Leu Arg Asn Asp Ser Ser Ser Asn Arg Lys Ala Lys Asn Pro Pro
    195                 200                 205

Gly Asp Ser Ser Leu His Trp Ala Ala Met Ala Leu Pro Ala Leu Phe
210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
            245                 250                 255

Asp Asn Glu Ile Ser Met Leu Gln Glu Lys Glu Arg Glu Phe Gln Glu
        260                 265                 270
```

Val

<210> SEQ ID NO 302
<211> LENGTH: 248
<212> TYPE: PRT
<213> ORGANISM: Homo sapiens
<220> FEATURE:
<223> OTHER INFORMATION: SCF mature

<400> SEQUENCE: 302

```
Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Cys Trp Ile Ser Glu Met
        35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser Ser Thr Leu
    130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
                165                 170                 175

Arg Lys Ala Lys Asn Pro Pro Gly Asp Ser Ser Leu His Trp Ala Ala
            180                 185                 190

Met Ala Leu Pro Ala Leu Phe Ser Leu Ile Ile Gly Phe Ala Phe Gly
        195                 200                 205

Ala Leu Tyr Trp Lys Lys Arg Gln Pro Ser Leu Thr Arg Ala Val Glu
    210                 215                 220

Asn Ile Gln Ile Asn Glu Glu Asp Asn Glu Ile Ser Met Leu Gln Glu
225                 230                 235                 240

Lys Glu Arg Glu Phe Gln Glu Val
                245
```

<210> SEQ ID NO 303
<211> LENGTH: 187
<212> TYPE: PRT
<213> ORGANISM: Homo sapiens
<220> FEATURE:
<223> OTHER INFORMATION: IFN-beta precursor

<400> SEQUENCE: 303

```
Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
```

```
                 50                  55                  60
Ile Lys Gln Leu Gln Gln Phe Gln Lys Glu Asp Ala Ala Leu Thr Ile
 65                  70                  75                  80

Tyr Glu Met Leu Gln Asn Ile Phe Ala Ile Phe Arg Gln Asp Ser Ser
                     85                  90                  95

Ser Thr Gly Trp Asn Glu Thr Ile Val Glu Asn Leu Leu Ala Asn Val
                100                 105                 110

Tyr His Gln Ile Asn His Leu Lys Thr Val Leu Glu Glu Lys Leu Glu
            115                 120                 125

Lys Glu Asp Phe Thr Arg Gly Lys Leu Met Ser Ser Leu His Leu Lys
        130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 304
<211> LENGTH: 166
<212> TYPE: PRT
<213> ORGANISM: Homo sapiens
<220> FEATURE:
<223> OTHER INFORMATION: IFN-beta mature

<400> SEQUENCE: 304

Met Ser Tyr Asn Leu Leu Gly Phe Leu Gln Arg Ser Ser Asn Phe Gln
  1               5                  10                  15

Cys Gln Lys Leu Leu Trp Gln Leu Asn Gly Arg Leu Glu Tyr Cys Leu
                 20                  25                  30

Lys Asp Arg Met Asn Phe Asp Ile Pro Glu Glu Ile Lys Gln Leu Gln
             35                  40                  45

Gln Phe Gln Lys Glu Asp Ala Ala Leu Thr Ile Tyr Glu Met Leu Gln
         50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 305
<211> LENGTH: 166
<212> TYPE: PRT
<213> ORGANISM: Homo sapiens
<220> FEATURE:
<223> OTHER INFORMATION: IFN-gamma precursor

<400> SEQUENCE: 305

Met Lys Tyr Thr Ser Tyr Ile Leu Ala Phe Gln Leu Cys Ile Val Leu
```

```
                1               5                   10                  15
Gly Ser Leu Gly Cys Tyr Cys Gln Asp Pro Tyr Val Lys Glu Ala Glu
                20                  25                  30

Asn Leu Lys Lys Tyr Phe Asn Ala Gly His Ser Asp Val Ala Asp Asn
            35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
                115                 120                 125

Gln Arg Lys Ala Ile His Glu Leu Ile Gln Val Met Ala Glu Leu Ser
        130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 306
<211> LENGTH: 146
<212> TYPE: PRT
<213> ORGANISM: Homo sapiens
<220> FEATURE:
<223> OTHER INFORMATION: IFN-gamma mature

<400> SEQUENCE: 306

Cys Tyr Cys Gln Asp Pro Tyr Val Lys Glu Ala Glu Asn Leu Lys Lys
1               5                   10                  15

Tyr Phe Asn Ala Gly His Ser Asp Val Ala Asp Asn Gly Thr Leu Phe
                20                  25                  30

Leu Gly Ile Leu Lys Asn Trp Lys Glu Glu Ser Asp Arg Lys Ile Met
            35                  40                  45

Gln Ser Gln Ile Val Ser Phe Tyr Phe Lys Leu Phe Lys Asn Phe Lys
    50                  55                  60

Asp Asp Gln Ser Ile Gln Lys Ser Val Glu Thr Ile Lys Glu Asp Met
65                  70                  75                  80

Asn Val Lys Phe Phe Asn Ser Asn Lys Lys Lys Arg Asp Asp Phe Glu
                85                  90                  95

Lys Leu Thr Asn Tyr Ser Val Thr Asp Leu Asn Val Gln Arg Lys Ala
                100                 105                 110

Ile His Glu Leu Ile Gln Val Met Ala Glu Leu Ser Pro Ala Ala Lys
        115                 120                 125

Thr Gly Lys Arg Lys Arg Ser Gln Met Leu Phe Arg Gly Arg Arg Ala
    130                 135                 140

Ser Gln
145

<210> SEQ ID NO 307
<211> LENGTH: 166
<212> TYPE: PRT
<213> ORGANISM: Homo sapiens
<220> FEATURE:
<223> OTHER INFORMATION: Human EPO glycosylation variant
<220> FEATURE:
```

```
<221> NAME/KEY: VARIANT
<222> LOCATION: 24
<223> OTHER INFORMATION: Xaa= Asn, Lys or His
<220> FEATURE:
<221> NAME/KEY: VARIANT
<222> LOCATION: 38
<223> OTHER INFORMATION: Xaa= Asn, Lys or His
<220> FEATURE:
<221> NAME/KEY: VARIANT
<222> LOCATION: 83
<223> OTHER INFORMATION: Xaa= Asn, Lys or His

<400> SEQUENCE: 307

Ala Pro Pro Arg Leu Ile Cys Asp Ser Arg Val Leu Glu Arg Tyr Leu
 1               5                  10                  15

Leu Glu Ala Lys Glu Ala Glu Xaa Ile Thr Thr Gly Cys Ala Glu His
            20                  25                  30

Cys Ser Leu Asn Glu Xaa Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Xaa Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 308
<211> LENGTH: 165
<212> TYPE: PRT
<213> ORGANISM: Homo sapiens
<220> FEATURE:
<223> OTHER INFORMATION: Human EPO (deltaR166) glycosylation variant
<220> FEATURE:
<221> NAME/KEY: VARIANT
<222> LOCATION: 24
<223> OTHER INFORMATION: Xaa= Asn, Lys or His
<220> FEATURE:
<221> NAME/KEY: VARIANT
<222> LOCATION: 38
<223> OTHER INFORMATION: Xaa= Asn, Lys or His
<220> FEATURE:
<221> NAME/KEY: VARIANT
<222> LOCATION: 83
<223> OTHER INFORMATION: Xaa= Asn, Lys or His

<400> SEQUENCE: 308

Ala Pro Pro Arg Leu Ile Cys Asp Ser Arg Val Leu Glu Arg Tyr Leu
 1               5                  10                  15

Leu Glu Ala Lys Glu Ala Glu Xaa Ile Thr Thr Gly Cys Ala Glu His
            20                  25                  30

Cys Ser Leu Asn Glu Xaa Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60
```

Gln Gly Leu Ala Leu Leu Ser Glu Ala Val Leu Arg Gly Gln Ala Leu
65                  70                  75                  80

Leu Val Xaa Ser Ser Gln Pro Trp Glu Pro Leu Gln Leu His Val Asp
            85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 309
<211> LENGTH: 166
<212> TYPE: PRT
<213> ORGANISM: Homo sapiens
<220> FEATURE:
<223> OTHER INFORMATION: EPO N24K/N38K/N83K

<400> SEQUENCE: 309

Ala Pro Pro Arg Leu Ile Cys Asp Ser Arg Val Leu Glu Arg Tyr Leu
1               5                   10                  15

Leu Glu Ala Lys Glu Ala Glu Lys Ile Thr Thr Gly Cys Ala Glu His
            20                  25                  30

Cys Ser Leu Asn Glu Lys Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Lys Ser Ser Gln Pro Trp Glu Pro Leu Gln Leu His Val Asp
            85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 310
<211> LENGTH: 165
<212> TYPE: PRT
<213> ORGANISM: Homo sapiens
<220> FEATURE:
<223> OTHER INFORMATION: EPO (deltaR166) N24K/N38K/N83K

<400> SEQUENCE: 310

Ala Pro Pro Arg Leu Ile Cys Asp Ser Arg Val Leu Glu Arg Tyr Leu
1               5                   10                  15

Leu Glu Ala Lys Glu Ala Glu Lys Ile Thr Thr Gly Cys Ala Glu His
            20                  25                  30

-continued

```
Cys Ser Leu Asn Glu Lys Ile Thr Val Pro Asp Thr Lys Val Asn Phe
        35              40              45

Tyr Ala Trp Lys Arg Met Glu Val Gly Gln Gln Ala Val Glu Val Trp
    50              55              60

Gln Gly Leu Ala Leu Leu Ser Glu Ala Val Leu Arg Gly Gln Ala Leu
65              70              75              80

Leu Val Lys Ser Ser Gln Pro Trp Glu Pro Leu Gln Leu His Val Asp
            85              90              95

Lys Ala Val Ser Gly Leu Arg Ser Leu Thr Thr Leu Leu Arg Ala Leu
            100             105             110

Gly Ala Gln Lys Glu Ala Ile Ser Pro Pro Asp Ala Ala Ser Ala Ala
        115             120             125

Pro Leu Arg Thr Ile Thr Ala Asp Thr Phe Arg Lys Leu Phe Arg Val
        130             135             140

Tyr Ser Asn Phe Leu Arg Gly Lys Leu Lys Leu Tyr Thr Gly Glu Ala
145             150             155             160

Cys Arg Thr Gly Asp
                165
```